United States Patent
Fu et al.

(10) Patent No.: US 9,637,482 B2
(45) Date of Patent: May 2, 2017

(54) ISOXAZOLINE HYDROXAMIC ACID DERIVATIVES AS LPXC INHIBITORS

(71) Applicants: Jiping Fu, Danville, CA (US); Xianming Jin, San Ramon, CA (US); Subramanian Karur, Dublin, CA (US); Guillaume Lapointe, San Francisco, CA (US); Patrick Lee, Walnut Creek, CA (US); Zachary Kevin Sweeney, Redwood City, CA (US)

(72) Inventors: Jiping Fu, Danville, CA (US); Xianming Jin, San Ramon, CA (US); Subramanian Karur, Dublin, CA (US); Guillaume Lapointe, San Francisco, CA (US); Patrick Lee, Walnut Creek, CA (US); Zachary Kevin Sweeney, Redwood City, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/304,044

(22) PCT Filed: Apr. 22, 2015

(86) PCT No.: PCT/US2015/027009
§ 371 (c)(1),
(2) Date: Oct. 13, 2016

(87) PCT Pub. No.: WO2015/164458
PCT Pub. Date: Oct. 29, 2015

(65) Prior Publication Data
US 2017/0029415 A1    Feb. 2, 2017

Related U.S. Application Data

(60) Provisional application No. 61/982,467, filed on Apr. 22, 2014.

(51) Int. Cl.
| | |
|---|---|
| *C07D 417/10* | (2006.01) |
| *C07D 261/04* | (2006.01) |
| *A61K 31/421* | (2006.01) |
| *A61K 45/06* | (2006.01) |
| *C07D 413/04* | (2006.01) |
| *A61K 31/4439* | (2006.01) |
| *C07D 413/10* | (2006.01) |
| *A61K 31/422* | (2006.01) |
| *A61K 31/5377* | (2006.01) |

(52) U.S. Cl.
CPC .......... *C07D 417/10* (2013.01); *A61K 31/421* (2013.01); *A61K 31/422* (2013.01); *A61K 31/4439* (2013.01); *A61K 31/5377* (2013.01); *A61K 45/06* (2013.01); *C07D 261/04* (2013.01); *C07D 413/04* (2013.01); *C07D 413/10* (2013.01)

(58) Field of Classification Search
None
See application file for complete search history.

(56) References Cited

FOREIGN PATENT DOCUMENTS

| KP | 2012/137094 | * 10/2012 |
|---|---|---|
| WO | 2004/043349 | 5/2004 |
| WO | 2004/062601 | 7/2004 |
| WO | 2010/032147 | 3/2010 |
| WO | 2011/045703 | 4/2011 |
| WO | 2011/073845 | 6/2011 |
| WO | 2012/120397 | 9/2012 |
| WO | 2012/137094 | 10/2012 |
| WO | 2014/160649 | 10/2014 |

OTHER PUBLICATIONS

Grazia Piizzi, Global Discovery Chemistry, Novartis AG, Switzerland EFMC Meeting, Lisbon Sep. 9, 2014.

* cited by examiner

*Primary Examiner* — Karl J Puttlitz
(74) *Attorney, Agent, or Firm* — Michael G. Smith

(57) ABSTRACT

This invention pertains generally to compounds of Formula I and compositions containing such compounds, as well as methods of using such compounds to treat bacterial infections. In certain aspects, the invention pertains to methods and compositions for treating infections caused by Gram-negative bacteria.

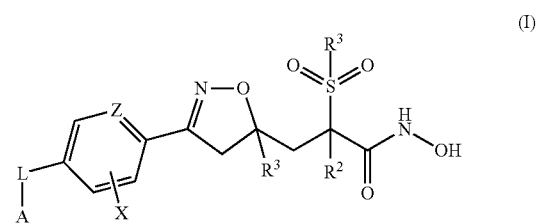

17 Claims, No Drawings

ISOXAZOLINE HYDROXAMIC ACID DERIVATIVES AS LPXC INHIBITORS

CROSS-REFERENCE TO RELATED APPLICATIONS

This application is the U.S. National Stage of International Application No. PCT/US2015/027009, filed Apr. 22, 2015, which claims the benefit of priority to U.S. Provisional Application No. 61/982,467, filed Apr. 22, 2014, the contents of which are incorporated herein by reference.

FIELD OF THE INVENTION

This invention pertains generally to compounds and compositions and methods for treating bacterial infections. In certain aspects, the invention pertains to treating infections caused by Gram-negative bacteria. More particularly, the invention pertains to treating Gram-negative infections using compounds disclosed herein. Without being bound by theory, the compounds are believed to act by inhibiting the activity of UDP-3-O—(R-3-hydroxydecanoyl)-N-acetylglucosamine deacetylase (LpxC). The invention includes compounds of Formula (I) which inhibit LpxC, pharmaceutical formulations containing such inhibitors, methods of treating patients with such compounds and pharmaceutical formulations, and methods of preparing such pharmaceutical formulations and inhibitors. The inhibitors can be used to treat Gram-negative infections of patients. These compounds may be used alone or in combination with other antibacterials.

BACKGROUND OF THE INVENTION

Over the past several decades, the frequency of antimicrobial resistance and its association with serious infectious diseases have increased at alarming rates. The increasing prevalence of resistant pathogens, especially as agents causing nosocomial infections, also called hospital-acquired infections, is particularly disconcerting. Of the over 2 million nosocomial infections occurring each year in the United States, 50 to 60% are caused by antimicrobial-resistant strains of bacteria. The high rate of resistance to commonly used antibacterial agents increases the morbidity, mortality, and costs associated with nosocomial infections. In the United States, nosocomial infections are thought to contribute to or cause more than 77,000 deaths per year and cost approximately $5 to $10 billion annually. Among Gram-positive organisms, the most important resistant pathogens are methicillin-(oxacillin-) resistant *Staphylococcus aureus* (MRSA), β-lactam-resistant and multidrug-resistant pneumococci, and vancomycin-resistant enterococci. Important causes of Gram-negative resistance include extended-spectrum β-lactamases (ESBLs) in *Klebsiella pneumoniae*, *Escherichia coli*, and *Proteus mirabilis*, high-level third-generation cephalosporin (Amp C) β-lactamase resistance among *Enterobacter* species and *Citrobacter freundii*, and multidrug-resistance genes observed in *Pseudomonas*, *Acinetobacter*, and *Stenotrophomonas*.

The problem of antibacterial resistance is compounded by the existence of bacterial strains resistant to multiple antibacterials. For example, *Pseudomonas aeruginosa* isolates resistant to fluoroquinolones are virtually all resistant to additional antibacterial medicines.

Thus there is a need for new antibacterials, particularly antibacterials with novel mechanisms of action or novel chemical structures that avoid at least some of the prevalent resistance mechanisms. Much of the antibacterial discovery effort in the pharmaceutical industry is aimed at the development of drugs effective against gram-positive bacteria. However, there is also a need for new Gram-negative antibacterials. Gram-negative bacteria are in general more resistant to a large number of antibacterials and chemotherapeutic agents than are gram-positive bacteria.

BRIEF SUMMARY OF THE INVENTION

The present invention provides novel compounds, pharmaceutical formulations including the compounds, methods of inhibiting UDP-3-O—(R-3-hydroxydecanoyl)-N-acetylglucosamine deacetylase (LpxC), and methods of treating Gram-negative bacterial infections.

In one aspect, the invention provides compounds of Formula (I), and compositions containing these compounds, and methods of using these compounds and compositions for treating infections. Compounds of the invention are generally of Formula (I),

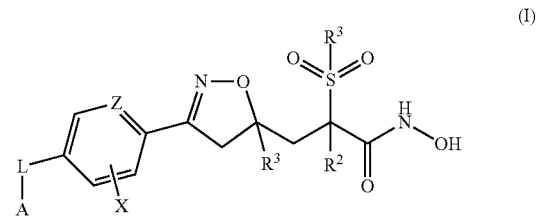

(I)

or a pharmaceutically acceptable salt thereof, wherein:
or a pharmaceutically acceptable salt thereof, wherein:

Z is N or CR$^1$, where R$^1$ is selected from H, halo, C$_{1-4}$ alkyl and C$_{1-4}$ haloalkyl;

R$^2$ and R$^3$ are independently selected from C$_{1-4}$ alkyl and C$_{1-4}$ haloalkyl, R$^4$ is H or C$_{1-4}$ alkyl;

X is selected from H, halo, C$_{1-4}$ alkyl, C$_{1-4}$ haloalkyl, and CN;

L is selected from —C≡C—, —CR$^5$=CR$^6$—, —O—, —S—, and a direct bond between A and the ring containing Z;

R$^5$ and R$^6$ are independently selected from H, halo, C$_{1-4}$ alkyl, and C$_{1-4}$ haloalkyl; and A is halo, CN, or an optionally substituted group selected from C$_{1-4}$ alkyl, C$_{3-6}$ cycloalkyl, phenyl, C$_{2-6}$ alkenyl, C$_{2-6}$ alkynyl, 5-6 membered heteroaryl containing up to four heteroatoms selected from N, O and S as ring members, and 4-6 membered heterocyclyl containing up to two heteroatoms selected from N, O and S as ring members, wherein the C$_{1-4}$ alkyl, C$_{3-6}$ cycloalkyl, phenyl, C$_{2-6}$ alkenyl, C$_{2-6}$ alkynyl, 5-6 membered heteroaryl containing up to four heteroatoms selected from N, O and S as ring members, and 4-6 membered heterocyclyl containing up to two heteroatoms selected from N, O and S as ring members are each optionally substituted with up to three groups selected from halo, hydroxy, CN, R$^{10}$, —(CH$_2$)$_{0-2}$OR$^{10}$, —SR$^{10}$, —S(O)R$^{10}$, —SO$_2$R$^{10}$, —S(O)(NH)R$^{10}$, and —(CH$_2$)$_{0-2}$N(R$^1$)$_2$;

where each R$^{10}$ is independently H or C$_{1-4}$ alkyl optionally substituted with one or two groups selected from amino, hydroxy, C$_{1-4}$ alkoxy, and CN; and —N(R$^{10}$)$_2$ can represent a 5-6 membered heterocyclic ring optionally containing an additional heteroatom selected from N, O and S as a ring member, and optionally substituted with one or two groups selected from oxo, halo, hydroxy, $C_{1-4}$ alkyl, $C_{1-4}$ alkoxy, and amino.

Various embodiments of these compounds are described further herein.

In one aspect, the invention provides a method of inhibiting a deacetylase enzyme in Gram-negative bacteria, thereby affecting bacterial growth, comprising administering to a patient in need of such inhibition a compound of formula I. In this and the following aspects of the invention, any species or subgenus of Formula I described herein can be used.

In another aspect, the invention provides a method of inhibiting LpxC, thereby modulating the virulence of a bacterial infection, comprising administering to a patient in need of such inhibition a compound of formula I.

In another aspect, the invention provides a method to interfere with biosynthesis of a bacterial outer membrane of a Gram-negative bacterium, which comprises contacting the bacterium with a compound of Formula I.

In another aspect, the invention provides a method for treating a subject with a Gram-negative bacterial infection comprising administering to the subject in need thereof an antibacterially effective amount of a compound of formula I with a pharmaceutically acceptable carrier. In certain embodiments, the subject is a mammal and in some other embodiments, the subject is a human.

In another aspect, the invention provides a method of administering an inhibitory amount of a compound of formula I to fermentative or non-fermentative Gram-negative bacteria. In certain embodiment of the method of administering an inhibitory amount of a compound of formula I to fermentative or non-fermentative Gram-negative bacteria, the Gram-negative bacteria are selected from the group consisting of *Pseudomonas aeruginosa* and other *Pseudomonas* species, *Stenotrophomonas maltophilia*, *Burkholderia cepacia* and other *Burkholderia* species, *Alcaligenes xylosoxidans*, species of *Acinetobacter*, Enterobacteriaceae, *Haemophilus, Moraxella, Bacteroides, Fransicella, Shigella, Proteus, Vibrio, Salmonella, Bordetella, Helicobactor, Legionella, Citrobactor, Serratia, Campylobactor, Yersinia* and *Neisseria*.

In another embodiment, the invention provides a method of administering an inhibitory amount of a compound of formula I to Gram-negative bacteria, such as Enterobacteriaceae which is selected from the group consisting of organisms such as *Serratia, Proteus, Klebsiella, Enterobacter, Citrobacter, Salmonella, Providencia, Morganella, Cedecea, Yersinia* and *Edwardsiella* species and *Escherichia coli*.

Another embodiment of the invention provides a pharmaceutical composition comprising a compound of Formula I admixed with a pharmaceutically acceptable carrier thereof. In some embodiments, the composition comprises an effective amount of the compound of Formula I as described herein.

Pharmaceutical formulations according to the present invention are provided which include any of the compounds described above and a pharmaceutically acceptable carrier. In some embodiments, the formulation comprises at least two pharmaceutically acceptable carriers or excipients.

Other aspects of the invention are discussed infra.

The present invention provides novel compounds, methods for inhibiting LpxC in Gram-negative bacteria, and novel methods for treating bacterial infections. The compounds provided herein can be formulated into pharmaceutical formulations and medicaments that are useful in the methods of the invention. The invention also provides for the use of the compounds in preparing medicaments and pharmaceutical formulations, for use of the compounds in inhibiting LpxC, and for use of the compounds in treating bacterial infections in a subject.

The following abbreviations and definitions are used throughout this application: "LpxC" is an abbreviation that stands for UDP-3-O—(R-3-hydroxydecan-oyl)-N-acetylglucosamine deacetylase.

This invention is directed to compounds of Formula I and subformulae thereof, and intermediates thereto, as well as pharmaceutical compositions containing the compounds for use in treatment of bacterial infections. This invention is also directed to the compounds of the invention or compositions thereof as LpxC inhibitors. The compounds are particularly useful in interfering with the life cycle of Gram-negative bacteria and in treating or preventing a Gram-negative bacterial infection or physiological conditions associated therewith. The present invention is also directed to methods of combination therapy for treating or preventing an Gram-negative bacterial infection in patients using the compounds of the invention or pharmaceutical compositions, or kits thereof in combination with at least one other therapeutic agent.

DETAILED DESCRIPTION OF THE INVENTION

For purposes of interpreting this specification, the following definitions will apply unless specified otherwise and whenever appropriate, terms used in the singular will also include the plural and vice versa.

Definitions

Terms used in the specification have the following meanings:

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "antibacterial agent" refers to agents synthesized or modified in the laboratory that have either bactericidal or bacteriostatic activity. An "active" agent in this context will inhibit the growth of *P. aeruginosa* and/or other Gram-negative bacteria. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in bacterial uptake/efflux, solubility, half-life, etc. to compounds in order to correlate enzyme inhibition with growth inhibition.

"Optionally substituted" means the group referred to can be substituted at one or more positions by any one or any combination of the radicals listed thereafter.

"Halo" or "halogen", as used herein, may be fluorine, chlorine, bromine or iodine.

"$C_1$-$C_6$-Alkyl", as used herein, denotes straight chain or branched alkyl having 1-8 carbon atoms. If a different number of carbon atoms is specified, such as $C_6$ or $C_3$, then the definition is to be amended accordingly, such as "$C_1$-$C_4$-Alkyl" will represent methyl, ethyl, propyl, isopropyl, butyl, isobutyl, sec-butyl and tert-butyl.

"$C_1$-$C_6$-Alkoxy", as used herein, denotes straight chain or branched alkoxy having 1-8 carbon atoms. If a different number of carbon atoms is specified, such as $C_6$ or $C_3$, then the edefinition is to be amended accordingly, such as "$C_1$-$C_4$-Alkoxy" will represent methoxy, ethoxy, propoxy, isopropoxy, butoxy, isobutoxy, sec-butoxy and tert-butoxy.

"$C_1$-$C_4$-Haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.

"$C_3$-$C_8$-cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, such as $C_3$-$C_6$, then the definition is to be amended accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings containing 1 to 7, 1 to 5 or 1 to 3 heteroatoms selected from the group consisting of nitrogen, oxygen and sulphur, which may be saturated, or partially saturated. The heterocyclic group can be attached at a heteroatom or a carbon atom. The term "heterocyclyl" includes single ring groups, fused ring groups and bridged groups. Examples of such heterocyclyl include, but are not limited to pyrrolidine, piperidine, piperazine, pyrrolidine, pyrrolidinone, morpholine, tetrahydrofuran, tetrahydrothiophene, tetrahydrothiopyran, tetrahydropyran, 1,4-dioxane, 1,4-oxathiane, 8-aza-bicyclo[3.2.1]octane, 3,8-diazabicyclo[3.2.1]octane, 3-Oxa-8-aza-bicyclo[3.2.1]octane, 8-Oxa-3-aza-bicyclo[3.2.1]octane, 2-Oxa-5-aza-bicyclo[2.2.1]heptane, 2,5-Diazabicyclo[2.2.1]heptane, azetidine, ethylenedioxo, oxtane or thiazole.

"Heteroaryl" is a completely unsaturated (aromatic) ring. The term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include furan, isotriazole, thiadiazole, oxadiazole, indazole, indazole, indole, quinoline, 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2, 3-triazolyl), tetrazolyl, triazine, pyrimidine, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "hydroxy" or "hydroxyl" includes groups with an —OH.

The term "a," "an," "the" and similar terms used in the context of the present invention (especially in the context of the claims) are to be construed to cover both the singular and plural unless otherwise indicated herein or clearly contradicted by the context.

Various embodiments of the invention are described herein. It will be recognized that features specified in each embodiment may be combined with other specified features to provide further embodiments.

The invention provides compounds of Formula (I) and various subgenera thereof as described herein, and methods of using these compounds to treat infections or inhibit bacterial growth or survival. The following enumerated embodiments represent certain aspects of the invention:

1. A compound of formula (I):

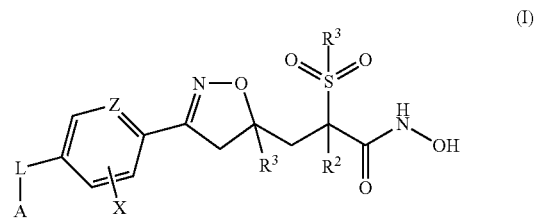

or a pharmaceutically acceptable salt thereof, wherein:
or a pharmaceutically acceptable salt thereof, wherein:
Z is N or $CR^1$, where $R^1$ is selected from H, halo, $C_{1-4}$ alkyl and $C_{1-4}$ haloalkyl;
$R^2$ and $R^3$ are independently selected from $C_{1-4}$ alkyl and $C_{1-4}$ haloalkyl,
$R^4$ is H or $C_{1-4}$ alkyl;
X is selected from H, halo, $C_{1-4}$ alkyl, $C_{1-4}$ haloalkyl, and CN;
L is selected from —C≡C—, —$CR^5$=$CR^6$—, —O—, —S—, and a direct bond between A and the ring containing Z;
$R^5$ and $R^6$ are independently selected from H, halo, $C_{1-4}$ alkyl, and $C_{1-4}$ haloalkyl; and A is halo, CN, or an optionally substituted group selected from $C_{1-4}$ alkyl, $C_{3-6}$ cycloalkyl, phenyl, $C_{2-6}$ alkenyl, $C_{2-6}$ alkynyl, 5-6 membered heteroaryl containing up to four heteroatoms selected from N, O and S as ring members, and 4-6 membered heterocyclyl containing up to two heteroatoms selected from N, O and S as ring members, wherein the $C_{1-4}$ alkyl, $C_{3-6}$ cycloalkyl, phenyl, $C_{2-6}$ alkenyl, $C_{2-6}$ alkynyl, 5-6 membered heteroaryl containing up to four heteroatoms selected from N, O and S as ring members, and 4-6 membered heterocyclyl containing up to two heteroatoms selected from N, O and S as ring members are each optionally substituted with up to three groups selected from halo, hydroxy, CN, $R^{10}$, —$(CH_2)_{0-2}OR^{10}$, —$SR^{10}$, —$S(O)R^{10}$, —$SO_2R^{10}$, —$S(O)(NH)R^{10}$, and —$(CH_2)_{0-2}N(R^1)_2$;

where each $R^{10}$ is independently H or $C_{1-4}$ alkyl optionally substituted with one or two groups selected from amino, hydroxy, $C_{1-4}$ alkoxy, and CN; and —$N(R^{10})_2$ can represent a 5-6 membered heterocyclic ring optionally containing an additional heteroatom selected from N, O and S as a ring member, and optionally substituted with one or two groups selected from oxo, halo, hydroxy, $C_{1-4}$ alkyl, $C_{1-4}$ alkoxy, and amino.

In selected embodiments of these compounds,

Z is N or $CR^1$, where $R^1$ is selected from H, halo, $C_{1-4}$ alkyl and $C_{1-4}$ haloalkyl;

$R^2$ and $R^3$ are independently selected from $C_{1-4}$ alkyl and $C_{1-4}$ haloalkyl, $R^4$ is H or $C_{1-4}$ alkyl;

X is selected from H, halo, $C_{1-4}$ alkyl, $C_{1-4}$ haloalkyl, and CN;

L is selected from —C≡C—, —$CR^5$=$CR^6$—, —O—, —S—, and a direct bond between A and the ring containing Z;

$R^5$ and $R^6$ are independently selected from H, halo, $C_{1-4}$ alkyl, and $C_{1-4}$ haloalkyl; and A is halo, CN, or an optionally substituted group selected from $C_{1-4}$ alkyl, $C_{3-6}$ cycloalkyl, phenyl, $C_{2-6}$ alkenyl, $C_{2-6}$ alkynyl, and 4-6 membered heterocyclyl containing up to three heteroatoms selected from N, O and S as ring members, wherein the $C_{1-4}$ alkyl, $C_{3-6}$ cycloalkyl, phenyl, $C_{2-6}$ alkenyl, $C_{2-6}$ alkynyl, and 4-6 membered heterocyclyl containing up to two heteroatoms selected from N, O and S as ring members are optionally substituted with up to three groups selected from halo, hydroxy, CN, —OR, and —$NR^2$ where each R is independently H or $C_{1-4}$ alkyl optionally substituted with one or two groups selected from amino, hydroxy, $C_{1-4}$ alkoxy, and CN.

In some of these embodiments, A is halo, CN, or an optionally substituted group selected from $C_{1-4}$ alkyl, $C_{3-6}$ cycloalkyl, phenyl, $C_{2-6}$ alkenyl, $C_{2-6}$ alkynyl, 5-6 membered heteroaryl such as pyridinyl, triazolyl, oxazolyl or thiazolyl, and 4-6 membered heterocyclyl containing up to two heteroatoms selected from N, O and S as ring members, such as morpholine, piperidine, pyrrolidine, and piperazine.

Each of the compounds in Table A is a specific embodiment of the invention.

2. The compound of embodiment 1 or a pharmaceutically acceptable salt thereof, wherein X is H or F.

3. The compound of embodiment 1 or 2 or a pharmaceutically acceptable salt thereof, wherein $R^2$ is methyl.

4. The compound of any of embodiments 1-3 or a pharmaceutically acceptable salt thereof, wherein $R^3$ is methyl.

5. The compound of any of embodiments 1-4 or a pharmaceutically acceptable salt thereof, wherein $R^4$ is H.

6. The compound of any of embodiments 1-5 or a pharmaceutically acceptable salt thereof, wherein Z is CH or CF.

7. The compound of any of embodiments 1-5 or a pharmaceutically acceptable salt thereof, wherein Z is N.

8. The compound of any of embodiments 1-7 or a pharmaceutically acceptable salt thereof, wherein A-L- is a group of the formula

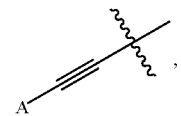

where A is an optionally substituted group selected from $C_{1-4}$ alkyl and $C_{3-6}$ cycloalkyl, wherein A is optionally substituted with up to three groups selected from halo, hydroxy, CN, —OR, and —$N(R^{10})_2$ where each $R^{10}$ is independently H or $C_{1-4}$ alkyl.

9. The compound of embodiment 8 or a pharmaceutically acceptable salt thereof, wherein A is $C_{1-4}$ alkyl or cyclopropyl and is optionally substituted with F, OH, or OMe.

10. The compound of any of embodiments 1-9, which is of the formula:

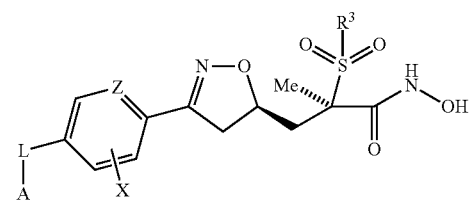

or a pharmaceutically acceptable salt thereof.

11. A pharmaceutical composition, comprising:
the compound according to any of embodiments 1 to 10 or a pharmaceutically acceptable salt thereof, and
a pharmaceutically acceptable carrier.

12. A pharmaceutical combination comprising:
a compound according to any of embodiments 1 to 10 or a pharmaceutically acceptable salt thereof,
an antibacterially effective amount of a second therapeutic agent, and
a pharmaceutically acceptable carrier.

13. The pharmaceutical combination composition according to embodiment 12, wherein the second therapeutic agent is selected from the group consisting of Ampicillin, Piperacillin, Penicillin G, Ticarcillin, Imipenem, Meropenem, Azithromycin, erythromycin, Aztreonam, Cefepime, Cefotaxime, Ceftriaxone, Cefatazidime, Ciprofloxacin, Levofloxacin, Clindamycin, Doxycycline, Gentamycin, Amikacin, Tobramycin, Tetracycline, Tegacyclin, Rifampicin, Vancomycin and Polymyxin.

14. A method of inhibiting a deacetylase enzyme in a Gram-negative bacterium, comprising:
contacting the Gram-negative bacteria with the compound according to any one of embodiments 1 to 10 or a pharmaceutically acceptable salt thereof.

15. A method for treating a subject with a Gram-negative bacterial infection, comprising:
administering to the subject an antibacterially effective amount of the compound according to any one of embodiments 1 to 10, or a pharmaceutically acceptable salt thereof, and a pharmaceutically acceptable carrier.

16. The method of embodiment 15, wherein the gram negative bacterial infection is an infection comprising at least one bacterium selected from the group consisting of *Pseudomonas, Stenotrophomonas maltophila, Burkholderia, Alcaligenes xylosoxidans, Acinetobacter,* Enterobacteriaceae, *Haemophilus, Moraxella, Bacteroides, Fransicella, Shigella, Proteus, Vibrio, Salmonella, Bordetella, Helicobactor, Legionella, Citrobactor, Serratia, Campylobactor, Yersinia* and *Neisseria.*

17. The method of embodiment 16, wherein the bacterium is a Enterobacteriaceae which is selected from the group consisting of *Serratia, Proteus, Klebsiella, Enterobacter, Citrobacter, Salmonella, Providencia, Morganella, Cedecea, Yersinia,* and *Edwardsiella* species and *Escherichia coli.*

18. A compound according to any one of embodiments 1 to 10 or a pharmaceutically acceptable salt thereof, for use as a medicament.

19. A compound according to any one of embodiments 1 to 10 or a pharmaceutically acceptable salt thereof, for use in treatment of a Gram-negative bacterial infection.

20. A compound according to any one of embodiments 1 to 10 or a pharmaceutically acceptable salt thereof, for use in treatment of a Gram-negative bacterial infection, wherein the bacterial infection is selected from *Pseudomonas aeruginosa, Stenotrophomonas maltophila, Burkholderia cepacia, Alcaligenes xylosoxidans, Acinetobacter,* Enterobacteriaceae, *Haemophilus,* and *Neisseria* species.

21. Use of the compound according to any one of embodiments 1 to 10 or a pharmaceutically acceptable salt thereof, for the preparation of a medicament for the treatment of a Gram-negative bacterial infection in a subject, wherein the bacterial infection is selected from *Pseudomonas aeruginosa, Stenotrophomonas maltophila, Burkholderia cepacia, Alcaligenes xylosoxidans, Acinetobacter,* Enterobacteriaceae, *Haemophilus,* and *Neisseria* species.

22. The use of embodiment 21, wherein the bacterial infection is caused by an Enterobacteriaceae selected from the group consisting of *Serratia, Proteus, Klebsiella, Enterobacter, Citrobacter, Salmonella, Providencia, Morganella, Cedecea,* and *Edwardsiella* species and *Escherichia coli.*

Compounds of the invention include each of the following, or any combination thereof, and their pharmaceutically acceptable salts:

3-(3-(4-bromophenyl)-4,5-dihydroisoxazol-5-yl)-N-hydroxy-2-methyl-2-(methylsulfonyl)propanamide [1-A, 1-B]

(R)-N-hydroxy-2-methyl-2-(methylsulfonyl)-3-((R)-3-(4-(prop-1-yn-1-yl)phenyl)-4,5-dihydroisoxazol-5-yl)propanamide [2-A]

3-(3-([1,1'-biphenyl]-4-yl)-4,5-dihydroisoxazol-5-yl)-N-hydroxy-2-methyl-2-(methylsulfonyl)propanamide [3-A, 3-B]

3-(3-(4-(but-2-yn-1-yloxy)phenyl)-4,5-dihydroisoxazol-5-yl)-N-hydroxy-2-methyl-2-(methylsulfonyl)propanamide [4-A, 4-B]

3-(3-(4-cyclopropylphenyl)-4,5-dihydroisoxazol-5-yl)-N-hydroxy-2-methyl-2-(methylsulfonyl)propanamide [5-A, 5-B]

(R)-3-((R)-3-(4-(cyclopropylethynyl)phenyl)-4,5-dihydroisoxazol-5-yl)-N-hydroxy-2-methyl-2-(methylsulfonyl)propanamide [6-A]

3-(3-(4-(but-1-yn-1-yl)phenyl)-4,5-dihydroisoxazol-5-yl)-N-hydroxy-2-methyl-2-(methylsulfonyl)propanamide [8-A, 8-B]

N-hydroxy-3-(3-(4-(4-hydroxybut-1-yn-1-yl)phenyl)-4,5-dihydroisoxazol-5-yl)-2-methyl-2-(methylsulfonyl)propanamide [10-A, 10-B]

3-(3-(3-fluoro-4-(prop-1-yn-1-yl)phenyl)-4,5-dihydroisoxazol-5-yl)-N-hydroxy-2-methyl-2-(methylsulfonyl)propanamide [12A, 12 B]

3-(3-(4-(cyclopropylethynyl)-3-fluorophenyl)-4,5-dihydroisoxazol-5-yl)-N-hydroxy-2-methyl-2-(methylsulfonyl)propanamide [13-A, 13-B]

N-hydroxy-2-methyl-2-(methylsulfonyl)-3-(3-(5-(prop-1-yn-1-yl)pyridin-2-yl)-4,5-dihydroisoxazol-5-yl)propanamide [14-A, 14-B]

3-(3-(5-(cyclopropylethynyl)pyridin-2-yl)-4,5-dihydroisoxazol-5-yl)-N-hydroxy-2-methyl-2-(methylsulfonyl)propanamide [15-A, 15-B]

3-(3-(2-fluoro-4-(prop-1-yn-1-yl)phenyl)-4,5-dihydroisoxazol-5-yl)-N-hydroxy-2-methyl-2-(methylsulfonyl)propanamide [16-A, 16-B]

3-(3-(4-(cyclopropylethynyl)-2-fluorophenyl)-4,5-dihydroisoxazol-5-yl)-N-hydroxy-2-methyl-2-(methylsulfonyl)propanamide [17-A, 17-B]

(R)-3-((R)-3-(4-(4-fluorobut-1-yn-1-yl)phenyl)-4,5-dihydroisoxazol-5-yl)-N-hydroxy-2-methyl-2-(methylsulfonyl)propanamide 22

(R)-N-hydroxy-2-methyl-2-(methylsulfonyl)-3-((R)-3-(4-propylphenyl)-4,5-dihydroisoxazol-5-yl)propanamide [23]

(R)-N-hydroxy-2-methyl-2-(methylsulfonyl)-3-((R)-3-(4-((E)-prop-1-en-1-yl)phenyl)-4,5-dihydroisoxazol-5-yl)propanamide [24]

(R)-3-((R)-3-(4-((Z)-1-fluoroprop-1-en-1-yl)phenyl)-4,5-dihydroisoxazol-5-yl)-N-hydroxy-2-methyl-2-(methylsulfonyl)propanamide [29]

30. (2R)-N-hydroxy-3-((5R)-3-(4-(5-hydroxyhexa-1,3-diyn-1-yl)phenyl)-4,5-dihydroisoxazol-5-yl)-2-methyl-2-(methylsulfonyl)propanamide 31. (R)-3-((R)-3-(4-ethylphenyl)-4,5-dihydroisoxazol-5-yl)-N-hydroxy-2-methyl-2-(methylsulfonyl)propanamide 32. (R)-3-((R)-3-(4-(ethylthio)phenyl)-4,5-dihydroisoxazol-5-yl)-N-hydroxy-2-methyl-2-(methylsulfonyl)propanamide 33. (R)-3-((R)-3-(4-(3-fluoropropyl) phenyl)-4, 5-dihydroisoxazol-5-yl)-N-hydroxy-2-methyl-2-(methyl sulfonyl) propanamide 34. (R)-3-((R)-3-(4-(4-fluorobutyl) phenyl)-4, 5-dihydroisoxazol-5-yl)-N-hydroxy-2-methyl-2-(methyl sulfonyl) propanamide 39A. (R)-N-hydroxy-3-((R)-3-(4-(((1r,3R)-3-(2-hydroxypropan-2-yl)cyclobutyl)ethynyl)phenyl)-4,5-dihydroisoxazol-5-yl)-2-methyl-2-(methylsulfonyl)propanamide 39B. (R)-N-hydroxy-3-((R)-3-(4-(((1s,3S)-3-(2-hydroxypropan-2-yl)cyclobutyl)ethynyl)phenyl)-4,5-dihydroisoxazol-5-yl)-2-methyl-2-(methylsulfonyl)propanamide 40. (R)-N-hydroxy-3-((R)-3-(4'-(2-hydroxyethyl)-[1,1'-biphenyl]-4-yl)-4,5-dihydroisoxazol-5-yl)-2-methyl-2-(methylsulfonyl)

41. (R)-N-hydroxy-3-((R)-3-(4'-(hydroxymethyl)-[1,1'-biphenyl]-4-yl)-4,5-dihydroisoxazol-5-yl)-2-methyl-2-(methylsulfonyl)

42. (R)-3-((R)-3-(4-(3-fluoropyridin-4-yl)phenyl)-4,5-dihydroisoxazol-5-yl)-N-hydroxy-2-methyl-2-(methylsulfonyl)propanamide 43. (R)-3-((R)-3-(4-(2H-1,2,3-triazol-2-yl)phenyl)-4,5-dihydroisoxazol-5-yl)-N-hydroxy-2-methyl-2-(methylsulfonyl)propanamide 44. (R)-N-hydroxy-3-((R)-3-(4-((3-methoxycyclobutyl)ethynyl)phenyl)-4,5-dihydroisoxazol-5-yl)-2-methyl-2-(methylsulfonyl)propanamide
45. (R)-N-hydroxy-3-((R)-3-(4'-((R)-2-hydroxypropyl)-[1,1'-biphenyl]-4-yl)-4,5-dihydroisoxazol-5-yl)-2-methyl-2-(methylsulfonyl)
46. (R)-N-hydroxy-3-((R)-3-(4'-((S)-2-hydroxypropyl)-[1,1'-biphenyl]-4-yl)-4,5-dihydroisoxazol-5-yl)-2-methyl-2-(methylsulfonyl)
47. (R)-N-hydroxy-2-methyl-2-(methylsulfonyl)-3-((R)-3-(4'-(morpholinomethyl)-[1,1'-biphenyl]-4-yl)-4,5-dihydroisoxazol-5-yl)
48. (R)-N-hydroxy-3-((R)-3-(4'-(2-methoxyethoxy)-[1,1'-biphenyl]-4-yl)-4,5-dihydroisoxazol-5-yl)-2-methyl-2-(methylsulfonyl)propanamide
49. (R)-N-hydroxy-3-((R)-3-(4'-((R)-1-hydroxyethyl)-[1,1'-biphenyl]-4-yl)-4,5-dihydroisoxazol-5-yl)-2-methyl-2-(methylsulfonyl)
50. (R)-N-hydroxy-3-((R)-3-(4'-(2-hydroxyethoxy)-[1,1'-biphenyl]-4-yl)-4,5-dihydroisoxazol-5-yl)-2-methyl-2-(methylsulfonyl)
51. (2R)-N-hydroxy-3-((5R)-3-(4'-(2-hydroxy-1-methoxypropan-2-yl)-[1,1'-biphenyl]-4-yl)-4,5-dihydroisoxazol-5-yl)-2-methyl-2-(methylsulfonyl)propanamide
52. (R)-N-hydroxy-3-((R)-3-(4-((3-(methoxymethyl)cyclobutyl)ethynyl)phenyl)-4,5-dihydroisoxazol-5-yl)-2-methyl-2-(methylsulfonyl)propanamide
53. (R)-N-hydroxy-3-((R)-3-(4-((3-(methoxymethyl)cyclobutyl)ethynyl)phenyl)-4,5-dihydroisoxazol-5-yl)-2-methyl-2-(methylsulfonyl)propanamide
54. (R)-3-((R)-3-(4-((3-fluorocyclobutyl)ethynyl)phenyl)-4,5-dihydroisoxazol-5-yl)-N-hydroxy-2-methyl-2-(methylsulfonyl)propanamide
55. (R)-3-((R)-3-(4-((3-(cyanomethyl)cyclobutyl)ethynyl)phenyl)-4,5-dihydroisoxazol-5-yl)-N-hydroxy-2-methyl-2-(methylsulfonyl)propanamide
56. (R)-N-hydroxy-3-((R)-3-(4'-((S)-1-hydroxyethyl)-[1,1'-biphenyl]-4-yl)-4,5-dihydroisoxazol-5-yl)-2-methyl-2-(methylsulfonyl)
57. (R)-N-hydroxy-3-((R)-3-(3'-(hydroxymethyl)-[1,1'-biphenyl]-4-yl)-4,5-dihydroisoxazol-5-yl)-2-methyl-2-(methylsulfonyl)
58. (R)-N-hydroxy-2-methyl-2-(methylsulfonyl)-3-((R)-3-(4'-(methylsulfonyl)-[1,1'-biphenyl]-4-yl)-4,5-dihydroisoxazol-5-yl)
59. (R)-3-((R)-3-(2'-fluoro-4'-methoxy-[1,1'-biphenyl]-4-yl)-4,5-dihydroisoxazol-5-yl)-N-hydroxy-2-methyl-2-(methylsulfonyl)
60. (R)-N-hydroxy-3-((R)-3-(4'-((R)-2-hydroxy-3-methoxypropyl)-[1,1'-biphenyl]-4-yl)-4,5-dihydroisoxazol-5-yl)-2-methyl-2-(methylsulfonyl)propanamide
61. (R)-N-hydroxy-3-((R)-3-(4'-((R)-2-hydroxypropoxy)-[1,1'-biphenyl]-4-yl)-4,5-dihydroisoxazol-5-yl)-2-methyl-2-(methylsulfonyl)propanamide
62. (R)-3-((R)-3-(4-(but-1-yn-1-yl)phenyl)-4,5-dihydroisoxazol-5-yl)-N-hydroxy-2-methyl-2-(methylsulfonyl)propanamide
64. (R)-N-hydroxy-2-methyl-2-(methylsulfonyl)-3-((R)-3-(4-(6-(trifluoromethyl)pyridin-3-yl)phenyl)-4,5-dihydroisoxazol-5-yl)propanamide
65. (R)-N-hydroxy-3-((R)-3-(4-(6-(hydroxymethyl)pyridin-3-yl)phenyl)-4,5-dihydroisoxazol-5-yl)-2-methyl-2-(methylsulfonyl)propanamide
66. (R)-N-hydroxy-3-((R)-3-(4-(6-methoxypyridin-3-yl)phenyl)-4,5-dihydroisoxazol-5-yl)-2-methyl-2-(methylsulfonyl)propanamide
67. (R)-N-hydroxy-2-methyl-3-((R)-3-(4-(6-methylpyridin-3-yl)phenyl)-4,5-dihydroisoxazol-5-yl)-2-(methylsulfonyl)propanamide
68. (R)-N-hydroxy-2-methyl-3-((R)-3-(4-(1-methyl-6-oxo-1,6-dihydropyridin-3-yl)phenyl)-4,5-dihydroisoxazol-5-yl)-2-(methylsulfonyl)propanamide
69. (R)-3-((R)-3-(4'-(2-cyanopropan-2-yl)-[1,1'-biphenyl]-4-yl)-4,5-dihydroisoxazol-5-yl)-N-hydroxy-2-methyl-2-(methylsulfonyl)propanamide
70. (R)-N-hydroxy-2-methyl-2-(methylsulfonyl)-3-((R)-3-(4-(2-(trifluoromethyl)pyridin-4-yl)phenyl)-4,5-dihydroisoxazol-5-yl)
71. (R)-3-((R)-3-(4-(2-ethylpyridin-4-yl)phenyl)-4,5-dihydroisoxazol-5-yl)-N-hydroxy-2-methyl-2-(methylsulfonyl)propanamide
72. (2R)-3-((5R)-3-(4'-(1,2-dihydroxyethyl)-[1,1'-biphenyl]-4-yl)-4,5-dihydroisoxazol-5-yl)-N-hydroxy-2-methyl-2-(methylsulfonyl)propanamide
73. (R)-N-hydroxy-3-((R)-3-(4'-(1-(hydroxymethyl)cyclopropyl)-[1,1'-biphenyl]-4-yl)-4,5-dihydroisoxazol-5-yl)-2-methyl-2-(methylsulfonyl)propanamide
74. (2R)-N-hydroxy-2-methyl-3-((5R)-3-(4'-(methylsulfinyl)-[1,1'-biphenyl]-4-yl)-4,5-dihydroisoxazol-5-yl)-2-(methylsulfonyl)propanamide
75. (2R)-N-hydroxy-3-((5R)-3-(4'-(2-hydroxy-1-methoxyethyl)-[1,1'-biphenyl]-4-yl)-4,5-dihydroisoxazol-5-yl)-2-methyl-2-(methylsulfonyl)propanamidepropanamide [
76. (2R)-N-hydroxy-2-methyl-3-((5R)-3-(4'-(S-methylsulfonimidoyl)-[1,1'-biphenyl]-4-yl)-4,5-dihydroisoxazol-5-yl)-2-(methylsulfonyl)propanamide
77. (R)-3-((R)-3-(4'-(2H-1,2,3-triazol-2-yl)-[1,1'-biphenyl]-4-yl)-4,5-dihydroisoxazol-5-yl)-N-hydroxy-2-methyl-2-(methylsulfonyl)propanamide
78. (R)-3-((R)-3-(4-(pyridin-4-yl)phenyl)-4,5-dihydroisoxazol-5-yl)-N-hydroxy-2-methyl-2-(methylsulfonyl)propanamide
79. (R)-3-((R)-3-(2',6'-difluoro-4'-methoxy-[1,1'-biphenyl]-4-yl)-4,5-dihydroisoxazol-5-yl)-N-hydroxy-2-methyl-2-(methylsulfonyl)propanamide
80. (R)-3-((R)-3-(4-(5-fluoro-2-methoxypyridin-4-yl)phenyl)-4,5-dihydroisoxazol-5-yl)-N-hydroxy-2-methyl-2-(methylsulfonyl)propanamide
81. (R)-N-hydroxy-3-((R)-3-(4-(2-(2-hydroxypropan-2-yl)pyridin-4-yl)phenyl)-4,5-dihydroisoxazol-5-yl)-2-methyl-2-(methylsulfonyl)propanamide
82. (R)-3-((R)-3-(4-(3-chloropyridin-4-yl)phenyl)-4,5-dihydroisoxazol-5-yl)-N-hydroxy-2-methyl-2-(methylsulfonyl)propanamide
83. (R)-3-((R)-3-(4-(4-fluoropyridin-3-yl)phenyl)-4,5-dihydroisoxazol-5-yl)-N-hydroxy-2-methyl-2-(methylsulfonyl)propanamide
84. (R)-N-hydroxy-3-((R)-3-(4-(6-(2-hydroxypropan-2-yl)pyridin-3-yl)phenyl)-4,5-dihydroisoxazol-5-yl)-2-methyl-2-(methylsulfonyl)propanamide
85. (R)-3-((R)-3-(4-(3-methylpyridin-4-yl)phenyl)-4,5-dihydroisoxazol-5-yl)-N-hydroxy-2-methyl-2-(methylsulfonyl)propanamide
86. (R)-N-hydroxy-3-((R)-3-(4'-((R)-3-hydroxy-2-methoxypropyl)-[1,1'-biphenyl]-4-yl)-4,5-dihydroisoxazol-5-yl)-2-methyl-2-(methylsulfonyl)propanamide
87. (R)-N-hydroxy-3-((R)-3-(4'-(hydroxymethyl)-2-methyl-[1,1'-biphenyl]-4-yl)-4,5-dihydroisoxazol-5-yl)-2-methyl-2-(methylsulfonyl)propanamide
88. (R)-3-((R)-3-(2',6'-difluoro-4'-((R)-2-hydroxypropyl)-[1,1'-biphenyl]-4-yl)-4,5-dihydroisoxazol-5-yl)-N-hydroxy-2-methyl-2-(methylsulfonyl)propanamide 89. (R)-3-((R)-3-(2-fluoro-4'-((R)-2-hydroxypropyl)-[1,1'-biphenyl]-4-yl)-4,5-dihydroisoxazol-5-yl)-N-hydroxy-2-methyl-2-(methylsulfonyl)propanamide
90. (R)-3-((R)-3-(2-methyl-4'-((R)-2-hydroxypropyl)-[1,1'-biphenyl]-4-yl)-4,5-dihydroisoxazol-5-yl)-N-hydroxy-2-methyl-2-(methylsulfonyl)propanamide
91. (R)-N-hydroxy-2-methyl-2-(methylsulfonyl)-3-((R)-3-(4-(thiophen-3-yl)phenyl)-4,5-dihydroisoxazol-5-yl)propanamide
92. (R)-N-hydroxy-3-((R)-3-(4-(isothiazol-4-yl)phenyl)-4,5-dihydroisoxazol-5-yl)-2-methyl-2-(methylsulfonyl)propanamide
93. (R)-3-((R)-3-(4'-((2S,3R)-2,3-dihydroxybutyl)-[1,1'-biphenyl]-4-yl)-4,5-dihydroisoxazol-5-yl)-N-hydroxy-2-methyl-2-(methylsulfonyl)propanamide
94. (R)-3-((R)-3-(4'-((S)-1,2-dihydroxyethyl)-[1,1'-biphenyl]-4-yl)-4,5-dihydroisoxazol-5-yl)-N-hydroxy-2-methyl-2-(methylsulfonyl)propanamide
95. (R)-3-((R)-3-(4'-((R)-1,2-dihydroxyethyl)-[1,1'-biphenyl]-4-yl)-4,5-dihydroisoxazol-5-yl)-N-hydroxy-2-methyl-2-(methylsulfonyl)propanamide
96. (2R)-3-((5R)-3-(4'-(1,3-dihydroxypropyl)-[1,1'-biphenyl]-4-yl)-4,5-dihydroisoxazol-5-yl)-N-hydroxy-2-methyl-2-(methylsulfonyl)propanamide
97. (R)-3-((R)-3-(4-((4-((R)-1,2-dihydroxyethyl)phenyl)ethynyl)phenyl)-4,5-dihydroisoxazol-5-yl)-N-hydroxy-2-methyl-2-(methylsulfonyl)propanamide
98. (R)-N-hydroxy-2-methyl-2-(methylsulfonyl)-3-((R)-3-(4-((tetrahydro-2H-pyran-4-yl)ethynyl)phenyl)-4,5-dihydroisoxazol-5-yl)propanamide
99. (R)-3-((R)-3-(4-((4-((S)-1,2-dihydroxyethyl)phenyl)ethynyl)phenyl)-4,5-dihydroisoxazol-5-yl)-N-hydroxy-2-methyl-2-(methylsulfonyl)propanamide
100. (R)-N-hydroxy-2-methyl-2-(methylsulfonyl)-3-((R)-3-(4-(3-(trifluoromethyl)pyridin-4-yl)phenyl)-4,5-dihydroisoxazol-5-yl)propanamide
101. (R)-3-((R)-3-(4-ethyl-3-fluorophenyl)-4,5-dihydroisoxazol-5-yl)-N-hydroxy-2-methyl-2-(methylsulfonyl)propanamide
102. (R)-3-((R)-3-(2-fluoro-4'-(2-hydroxyethyl)-[1,1'-biphenyl]-4-yl)-4,5-dihydroisoxazol-5-yl)-N-hydroxy-2-methyl-2-(methylsulfonyl)
103. (R)-3-((R)-3-(2-fluoro-4'-(hydroxymethyl)-[1,1'-biphenyl]-4-yl)-4,5-dihydroisoxazol-5-yl)-N-hydroxy-2-methyl-2-(methylsulfonyl)propanamide
104. (R)-3-((R)-3-(4'-(cyanomethyl)-2-fluoro-[1,1'-biphenyl]-4-yl)-4,5-dihydroisoxazol-5-yl)-N-hydroxy-2-methyl-2-(methylsulfonyl)propanamide
105. (R)-3-((R)-3-(3-fluoro-4-(6-methoxypyridin-3-yl)phenyl)-4,5-dihydroisoxazol-5-yl)-N-hydroxy-2-methyl-2-(methylsulfonyl)propanamide
107. (R)-3-((R)-3-(2-fluoro-4'-((R)-2-hydroxypropyl)-[1,1'-biphenyl]-4-yl)-4,5-dihydroisoxazol-5-yl)-N-hydroxy-2-methyl-2-(methylsulfonyl)propanamide
108. (R)-3-((R)-3-(3-fluoro-4-(1-methyl-2-oxo-1,2-dihydropyridin-4-yl)phenyl)-4,5-dihydroisoxazol-5-yl)-N-hydroxy-2-methyl-2-(methylsulfonyl)propanamide
109. (R)-3-((R)-3-(3-fluoro-4-(6-(hydroxymethyl)pyridin-3-yl)phenyl)-4,5-dihydroisoxazol-5-yl)-N-hydroxy-2-methyl-2-(methylsulfonyl)propanamide
110. (R)-3-((R)-3-(2-fluoro-4'-(2-hydroxypropan-2-yl)-[1,1'-biphenyl]-4-yl)-4,5-dihydroisoxazol-5-yl)-N-hydroxy-2-methyl-2-(methylsulfonyl)propanamide
111. (R)-N-hydroxy-2-methyl-2-(methylsulfonyl)-3-((R)-3-(4-(3-(trifluoromethyl)pyridin-4-yl)phenyl)-4,5-dihydroisoxazol-5-yl)propanamide
112. (R)-3-((R)-3-(3-fluoro-4-(2-isopropylpyridin-4-yl)phenyl)-4,5-dihydroisoxazol-5-yl)-N-hydroxy-2-methyl-2-(methylsulfonyl)propanamide
113. (R)-3-((R)-3-(2-fluoro-4'-methoxy-2-methyl-[1,1'-biphenyl]-4-yl)-4,5-dihydroisoxazol-5-yl)-N-hydroxy-2-methyl-2-(methylsulfonyl)propanamide
114. (R)-3-((R)-3-(2-fluoro-4'-(2H-tetrazol-5-yl)-[1,1'-biphenyl]-4-yl)-4,5-dihydroisoxazol-5-yl)-N-hydroxy-2-methyl-2-(methylsulfonyl)propanamide
115. (R)-3-((R)-3-(2,2'-difluoro-4'-((R)-2-hydroxypropyl)-[1,1'-biphenyl]-4-yl)-4,5-dihydroisoxazol-5-yl)-N-hydroxy-2-methyl-2-(methylsulfonyl)propanamide
116. (R)-N-hydroxy-2-methyl-2-(methylsulfonyl)-3-((R)-3-(2,2',6'-trifluoro-4'-((R)-2-hydroxypropyl)-[1,1'-biphenyl]-4-yl)-4,5-dihydroisoxazol-5-yl)propanamide
117. (R)-3-((R)-3-(3-fluoro-4-(3-fluoropyridin-4-yl)phenyl)-4,5-dihydroisoxazol-5-yl)-N-hydroxy-2-methyl-2-(methylsulfonyl)propanamide
118. (R)-3-((R)-3-(4-(2,6-dimethylpyridin-4-yl)-3-fluorophenyl)-4,5-dihydroisoxazol-5-yl)-N-hydroxy-2-methyl-2-(methylsulfonyl)propanamide
119. (R)-3-((R)-3-(2-fluoro-4-(3-fluoropyridin-4-yl)phenyl)-4,5-dihydroisoxazol-5-yl)-N-hydroxy-2-methyl-2-(methylsulfonyl)propanamide
120. (R)-3-((R)-3-(4-ethyl-2-fluorophenyl)-4,5-dihydroisoxazol-5-yl)-N-hydroxy-2-methyl-2-(methylsulfonyl)propanamide
121. (R)-N-hydroxy-3-((R)-3-(4'-((R)-2-hydroxypropyl)-2-methyl-[1,1'-biphenyl]-4-yl)-4,5-dihydroisoxazol-5-yl)-2-methyl-2-(methylsulfonyl)propanamide
122. (R)-3-((R)-3-(2,6-difluoro-4'-((R)-2-hydroxypropyl)-[1,1'-biphenyl]-4-yl)-4,5-dihydroisoxazol-5-yl)-N-hydroxy-2-methyl-2-(methylsulfonyl)propanamide
123. (R)-3-((R)-3-(2-fluoro-4-(prop-1-yn-1-yl)phenyl)-4,5-dihydroisoxazol-5-yl)-N-hydroxy-2-methyl-2-(methylsulfonyl)propanamide.

The compounds of the invention may be synthesized by the general synthetic routes below, specific examples of which are described in more detail in the Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the present invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/1, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds of the present invention, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{125}$I respectively. The invention includes various isotopically labeled compounds of the present invention, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The present invention provides novel compounds, pharmaceutical formulations including the compounds, methods of inhibiting UDP-3-O—(R-3-hydroxydecanoyl)-N-acetylglucosamine deacetylase (LpxC), and methods of treating Gram-negative bacterial infections.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. For example, deuterium substitution at non-exchangeable hydrocarbon bonds (e.g., C—H) may retard epimerization and/or metabolic oxidation in vivo.

Isotopically-labeled compounds of the invention, i.e. compounds of formula (I), can generally be prepared by conventional techniques known to those skilled in the art or by processes analogous to those described in the accompanying Examples and Preparations Sections using an appropriate isotopically-labeled reagent in place of the non-labeled reagent previously.

In another aspect, the invention provides a method of inhibiting a deacetylase enzyme in a Gram-negative bacterium, the method comprising the step of contacting the Gram-negative bacteria with a compound of the invention, e.g., a compound of Formula I or salt thereof.

In still another aspect, the invention provides a method for treating a subject with a Gram-negative bacterial infection, the method comprising the step of administering to the subject in need thereof an antibacterially effective amount of a compound of the invention, e.g., a compound of Formula I or salt thereof with a pharmaceutically acceptable carrier.

The compounds of the invention can be used for treating conditions caused by the bacterial production of endotoxin and, in particular, by Gram-negative bacteria and bacteria that use LpxC in the biosynthesis of lipopolysaccharide (LPS) or endotoxin.

The compounds of the invention also are useful in the treatment of patients suffering from or susceptible to pneumonia, sepsis, cystic fibrosis, wound, complicated diabetic foot or complicated urinary track infections and sexually transmitted diseases caused by Gram-negative pathogens. The compounds of the invention also are useful in the conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). For these conditions, treatment includes the administration of a compound of the invention, or a combination of compounds of the invention, optionally with a second agent wherein the second agent is a second antibacterial agent or a second non-antibacterial agent.

For sepsis, septic shock, systemic inflammation, localized inflammation, chronic obstructive pulmonary disease (COPD) and acute exacerbations of chronic bronchitis (AECB), preferred second non-antibacterial agents include antiendotoxins including endotoxin receptor-binding antibodies, endotoxin-binding antibodies, antiCD14-binding protein antibodies antilipopolysaccharide-binding protein antibodies and tyrosine kinase inhibitors.

In treatment of serious or chronic respiratory tract infections, the compounds of the present invention may also be used with second non-antibacterial agents administered via inhalation. Preferred non-antibacterial agents used in this treatment include anti-inflammatory steroids, non-steroidal anti-inflammatory agents, bronchiodilators, mucolytics, anti-asthma therapeutics and lung fluid surfactants. In particular, the non-antibacterial agent may be selected from a group consisting of albuterol, salbuterol, budesonide, beclomethasone, dexamethasone, nedocromil, beclomethasone, fluticasone, flunisolide, triamcinolone, ibuprofin, rofecoxib, naproxen, celecoxib, nedocromil, ipratropium, metaproterenol, pirbuterol, salneterol, bronchiodilators, mucolytics, calfactant, beractant, poractant alfa, surfaxin and pulmozyme (also called domase alfa).

The compounds of the invention can be used, alone or in combination with a second antibacterial agent for the treatment of a serious or chronic respiratory tract infection including serious lung and nosocomial infections such as those caused by *Enterobacter aerogenes, Enterobacter cloacae, Escherichia coli, Klebsiella pneumoniae, Klebsiella oxytoca, Proteus mirabilis, Serratia marcescens, Stenotrophomonas maltophilia, Pseudomonas aeruginosa, Burkholderia cepacia, Acinetobacter baumanii, Alcaligenes xylosoxidans, Flavobacterium meningosepticum, Providencia stuartii* and *Citrobacter freundi*, community lung infections such as those caused by *Haemophilus influenzae, Legionella* species, *Moraxella catarrhalis, Enterobacter* species, *Acinetobacter* species, *Klebsiella* species, and *Proteus* species, and infections caused by other bacterial species such as *Neisseria* species, *Shigella* species, *Salmonella* species, *Helicobacter pylori, Vibrionaceae* and *Bordetella* species as well as the infections is caused by a *Brucella* species, *Francisella tularensis* and/or *Yersinia Pestis*.

A compound of the present invention may also be used in combination with other agents, e.g., an additional antibiotic agent that is or is not of the formula I, for treatment of a bacterial infection in a subject.

By the term "combination", is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

When used for treating Gram-negative bacteria, the compounds of the present invention can be used to sensitize Gram-negative bacteria to the effects of a second agent.

An embodiment of the present invention is compounds of the present invention used in combination with a second antibacterial agent, non-limiting examples of antibacterial agents may be selected from the following groups:

(1) Macrolides or ketolides such as erythromycin, azithromycin, clarithromycin, and telithromycin;

(2) Beta-lactams including penicillin such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cephalosporin such as cepalothin, cephapirin, cephradine, cephaloridine, cefazolin, cefamandole, cefuroxime, cephalexin, cefprozil, cefaclor, loracarbef, cefoxitin, cefinetazole, cefotaxime, ceftizoxime, ceftriaxone, cefoperazone, ceftazidime, cefixime, cefpodoxime, ceftibuten, cefdinir, cefpirome, cefepime, and carbapenems such as carbapenem, imipenem, meropenem and PZ-601;

(3) Monobactams such as aztreonam;

(4) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin;

(5) Antibacterial sulfonanmides and antibacterial sulphanilamides, including para-aminobenzoic acid, sulfadiazine, sulfisoxazole, sulfamethoxazole and sulfathalidine;

(6) Aminoglycosides such as streptomycin, neomycin, kanamycin, paromycin, gentamicin, tobramycin, amikacin, netilmicin, spectinomycin, sisomicin, dibekalin and isepamicin;

(7) Tetracyclines such as tetracycline, chlortetracycline, demeclocycline, minocycline, oxytetracycline, methacycline, doxycycline, tegacycline;

(8) Rifamycins such as rifampicin (also called rifampin), rifapentine, rifabutin, bezoxazinorifamycin and rifaximin;

(9) Lincosamides such as lincomycin and clindamycin;

(10) Glycopeptides such as vancomycin and teicoplanin;

(11) Streptogramins such as quinupristin and daflopristin;

(12) Oxazolidinones such as linezolid;

(13) Polymyxin, colistin and colymycin;

(14) Trimethoprim and bacitracin.

(15) Efflux pump inhibitors.

The second antibacterial agent may be administered in combination with the compounds of the present inventions wherein the second antibacterial agent is administered prior to, simultaneously, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

When used for treating serious or chronic respiratory tract infections, the compounds of the invention may be used alone or in combination with a second antibacterial agent administered via inhalation. In the case of inhalation, a preferred second antibacterial agent is selected from a group consisting of tobramycin, gentamicin, aztreonam, ciprofloxacin, polymyxin, colistin, colymycin, azithromycin and clarithromycin.

The language "effective amount" of the compound is that amount necessary or sufficient to treat or prevent a bacterial infection and/or a disease or condition described herein. In an example, an effective amount of the LpxC inhibitor is the amount sufficient to treat bacterial infection in a subject. In another example, an effective amount of the LpxC inhibitor is an amount sufficient to treat a bacterial infection, such as, but not limited to *Pseudomonas aeruginosa* and the like in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a bacterial infection.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

The compounds as defined in embodiments may be synthesized by the general synthetic routes below, specific examples of which are described in more detail in the Examples.

General Synthetic Schemes

A general method to synthesize compounds of Formula (I) is depicted in Scheme A. The first step is to generate a nitrile oxide in situ from aldoxime A-1, which then undergoes cycloaddition with an alkenesulfone A-2 to provide isoxazoline A-3. The group -L-A on the phenyl/pyridinyl ring in compound A-4 could be incorporated by transition metal catalyzed reactions with a phenyl bromide or pyridyl bromide as shown in Step 2. The coupling reactions can be carried out by a variety of techniques, which will be readily apparent to those skilled in the art. The ester in A-4 can be converted to hydroxamic acid I via saponification of the ethyl ester and amidation of the free acid with O-(tetrahydro-2H-pyran-2-yl)hydroxylamine (THPONH$_2$), followed by de-protection of the THP under acidic conditions.

Scheme A

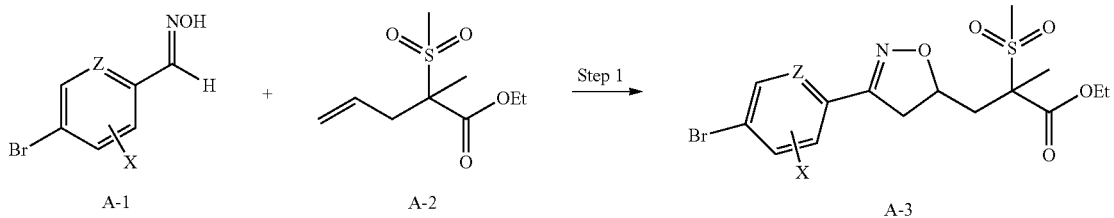

Step 2

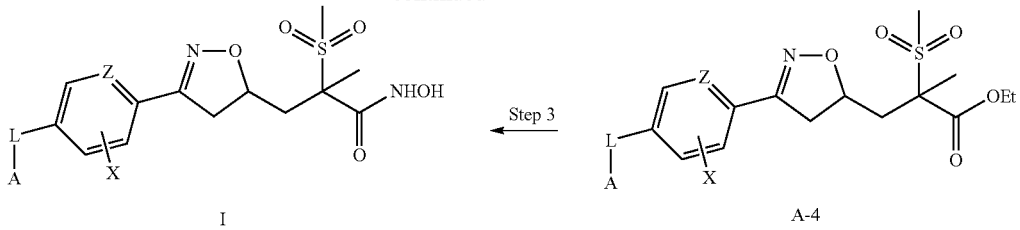

General Synthetic Procedures

Compounds of the present invention are prepared from commonly available compounds using procedures known to those skilled in the art, including any one or more of the following conditions without limitation:

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/1, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage). Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethyl hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials. Intermediates and final products can be worked up and/or purified according to standard methods, e.g., using chromatographic methods, distribution methods, (re-) crystallization, and the like.

General Process Conditions

The following applies in general to all processes mentioned throughout this disclosure. The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the H$^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

In accordance with the foregoing the present invention provides in a yet further aspect: A pharmaceutical combination comprising a) a first agent which is a compound of the invention, e.g. a compound of formula I or any subformulae thereof, and b) a co-agent, e.g. a second drug agent as defined above.

A method as defined above comprising co-administration, e.g. concomitantly or in sequence, of a therapeutically effective amount of a compound of the invention, e.g. a compound of formula I or any subformulae thereof, and a co-agent, e.g. a second drug agent as defined above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present invention. The administration of a pharmaceutical combination of the invention results in a beneficial effect, e.g. a synergistic therapeutic effect, compared to a monotherapy applying only one of its pharmaceutically active ingredients.

Each component of a combination according to this invention may be administered separately, together, or in any combination thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times. Alternatively, a composition of this invention comprises an additional agent as described herein. Each component may be present in individual compositions, combination compositions, or in a single composition.

EXAMPLES

The invention is further illustrated by the following examples, which should not be construed as further limiting.

The assays used throughout the Examples are accepted. Demonstration of efficacy in these assays is predictive of efficacy in subjects.

General Synthesis Methods

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

| LIST OF ABBREVIATIONS | |
|---|---|
| Ac | acetyl |
| ACN | Acetonitrile |
| AcOEt/EtOAc | Ethyl acetate |
| AcOH | acetic acid |
| aq | aqueous |
| Ar | aryl |
| Bn | benzyl |
| Bu | butyl (nBu = n-butyl, tBu = tert-butyl) |
| CDI | Carbonyldiimidazole |
| $CH_3CN$ | Acetonitrile |
| DBU | 1,8-Diazabicyclo[5.4.0]-undec-7-ene |
| $Boc_2O$ | di-tert-butyl dicarbonate |
| DCE | 1,2-Dichloroethane |
| DCM | Dichloromethane |
| DiBAl-H | Diisobutylaluminum Hydride |
| DIPEA | N-Ethyldiisopropylamine |
| DMAP | Dimethylaminopyridine |
| DMF | N,N'-Dimethylformamide |
| DMSO | Dimethylsulfoxide |
| EI | Electrospray ionisation |
| $Et_2O$ | Diethylether |
| $Et_3N$ | Triethylamine |
| Ether | Diethylether |
| EtOAc | Ethylacetate |
| EtOH | Ethanol |
| FC | Flash Chromatography |
| h | hour(s) |
| HATU | O-(7-Azabenzotriazole-1-yl)-N,N,N'N'-tetramethyluronium hexafluorophosphate |
| HBTU | O-(Benzotriazol-1-yl)-N,N,N',N'-tetramethyluronium hexafluorophosphate |
| HCl | Hydrochloric acid |
| HMPA | Hexamethylphosphoramide |
| HOBt | 1-Hydroxybenzotriazole |
| HPLC | High Performance Liquid Chromatography |
| $H_2O$ | Water |
| L | liter(s) |
| LC-MS | Liquid Chromatography Mass Spectrometry |
| LiHMDS | Lithium bis(trimethylsilyl)amide |
| $MgSO_4$ | Magnesium Sulfate |
| Me | methyl |
| MeI | Iodomethane |
| MeOH | Methanol |
| mg | milligram |
| min | minute(s) |
| mL | milliliter |
| MS | Mass Spectrometry |
| $NaHCO_3$ | Sodium Bicarbonate |
| $Na_2SO_4$ | Sodium Sulfate |
| $NH_2OH$ | hydroxylamine |
| Pd/C | palladium on charcoal |
| $Pd(OH)_2$ | palladium hydroxide |
| PG | protecting group |
| Ph | phenyl |
| $Ph_3P$ | triphenyl phosphine |
| Prep | Preparative |
| Rf | ratio of fronts |
| RP | reverse phase |
| Rt | Retention time |
| rt | Room temperature |
| $SiO_2$ | Silica gel |

-continued

LIST OF ABBREVIATIONS

| | |
|---|---|
| SOCl$_2$ | Thionyl Chloride |
| TBAF | Tetrabutylammonium fluoride |
| TEA | Triethylamine |
| TFA | Trifluoroacetic acid |
| THF | Tetrahydrofuran |
| TLC | Thin Layer Chromatography |

General Conditions:

Mass spectra were run on LC-MS systems using electrospray ionization and a WATERS Acquity Single Quard Detector. [M+H]$^+$ refers to mono-isotopic molecular weights. NMR spectra were run on open access Varian 400 NMR spectrometers. Spectra were measured at 298K and were referenced using the solvent peak.

If not indicated otherwise, the analytical UPLC conditions are as follows:

Method A
Column Phenonemax Kinetix C18 Column; 2.1 mm×50 mm; 2.6 u core size
Column Temperature 50° C.
Eluents solvent A: water with 0.1% TFA; solvent B: CH$_3$CN with 0.1% TFA
Flow Rate 1.2 mL/min
Gradient 2-88% solvent B in 9.5 mins Example 1

Synthesis of 3-(3-(4-bromophenyl)-4,5-dihydroisoxazol-5-yl)-N-hydroxy-2-methyl-2-(methylsulfonyl)propanamide [1-A, 1-B]

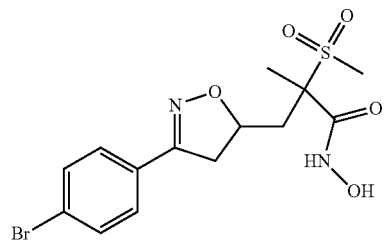

1-A, 1-B

Synthetic scheme

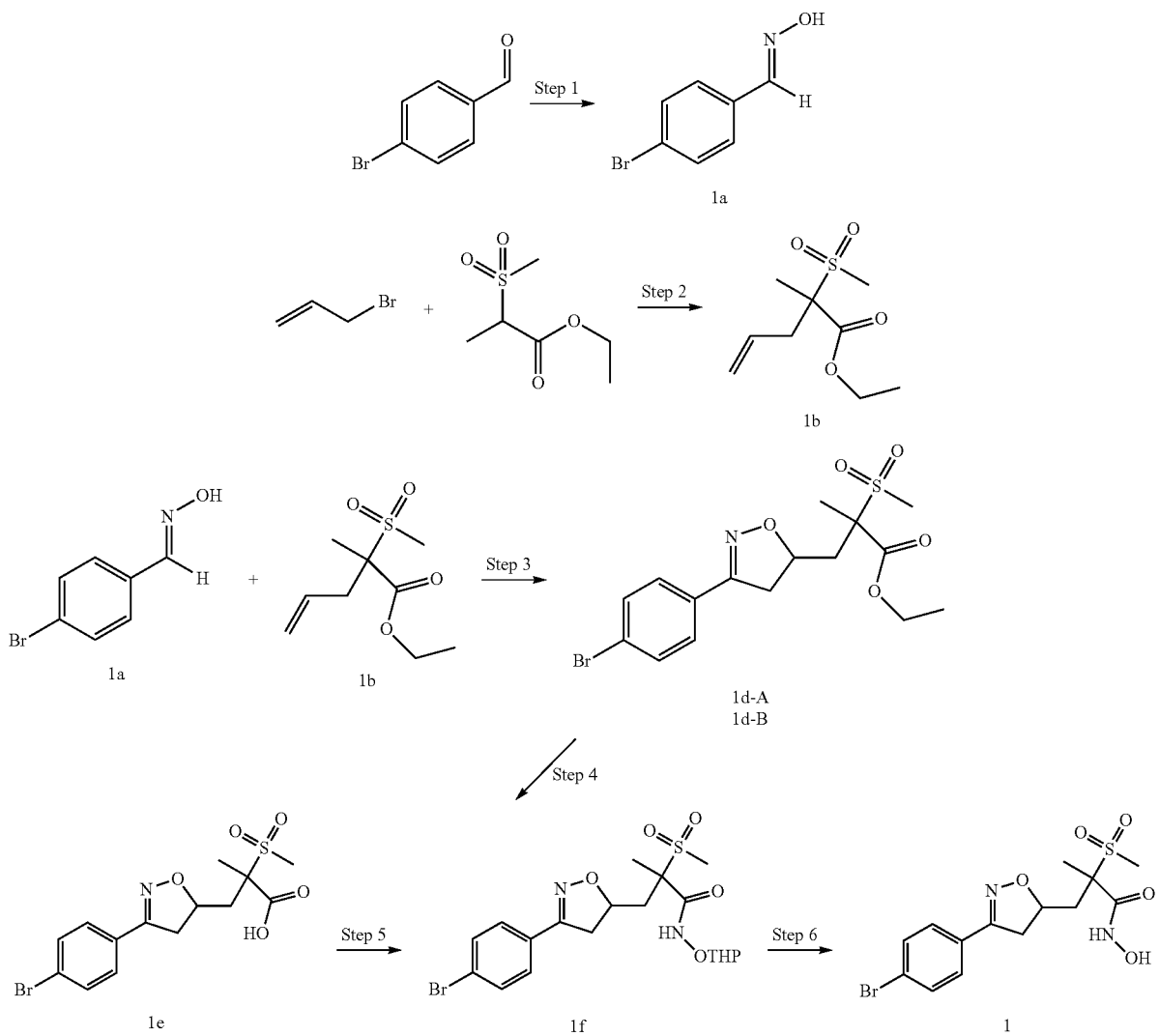

Reagents:

Step 1: NH₂OH.HCl, NaOH, water, 70° C. Step 2: NaH (60%), N,N-dimethylformamide, 0° C. to room temperature. Step 3: Et₂Zn, (R,R)-DIPT, tBuOCl, chloroform, 1,4-dioxane, 0° C. to room temperature, 3 h. Step 4: LiOH.H₂O, MeOH, water, room temperature. Step 5: NH₂O-THP, EDC.HCl, HOBT, TEA, dichloromethane, room temperature. Step 6: 35.5% aq. HCl, EtOH, room temperature.

Step 1. Synthesis of 4-bromobenzaldehyde oxime [1a]

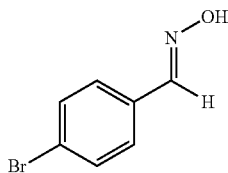

1a

4-Bromobenzaldehyde (5 g, 27.0 mmol, 1.0 equiv) was mixed with water (40 ml) and the reaction mixture was stirred at 70° C. A solution of hydroxylamine hydrochloride (2.27 g, 32.0 mmol, 1.2 equiv) and sodium hydroxide (1.29 g, 35.0 mmol, 1.3 equiv) in water (10 mL) was added to the reaction mixture at same temperature. The reaction mixture was allowed to stir for 3 hours. The white precipitate was then filtered and dried to afford product 1a (5 g, 92% yield). ¹H NMR (400 MHz, DMSO) δ 11.39 (s, 1H), 8.14 (s, 1H), 7.63-7.58 (m, 2H), 7.57-7.52 (m, 2H).

Step 2. Synthesis of ethyl 2-methyl-2-(methylsulfonyl)pent-4-enoate [1b]

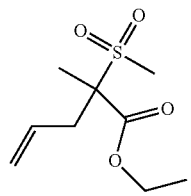

1b

Ethyl 2-(methylsulfonyl)propanoate (1 g, 5.6 mmol, 1.0 equiv) was dissolved in N,N-dimethylformamide (7 mL) and cooled to 0° C. NaH (0.3 g, 60% in mineral oil, 8.3 mmol, 1.5 equiv) was added. The reaction mixture was stirred at 0° C. for 1 hr. Allyl bromide (0.73 g, 6.1 mmol, 1.1 equiv) was added to reaction mixture and the resulting mixture was stirred at room temperature for 5 hours. The reaction mixture was then quenched with water and extracted with EtOAc. The organic layer was washed with brine, dried over sodium sulfate and concentrated. The crude product was purified by silica gel column chromatography (0-30% EtOAc in Hexane) to afford product 1b (0.7 g, 61.4% yield). LCMS (m/z): 238.2 [M+18]. ¹H NMR (400 MHz, DMSO) δ 5.75-5.60 (m, 1H), 5.28-5.16 (m, 2H), 4.27-4.16 (m, 2H), 3.14 (d, J=1.1 Hz, 3H), 2.97 (dd, J=13.4, 6.8 Hz, 1H), 2.50-2.45 (m, 1H), 1.45 (d, J=3.8 Hz, 3H), 1.26-1.19 (m, 3H).

Step 3. Synthesis of Ethyl 3-(3-(4-bromophenyl)-4,5-dihydroisoxazol-5-yl)-2-methyl-2-(methylsulfonyl)propanoate [1d-A & 1d-B]

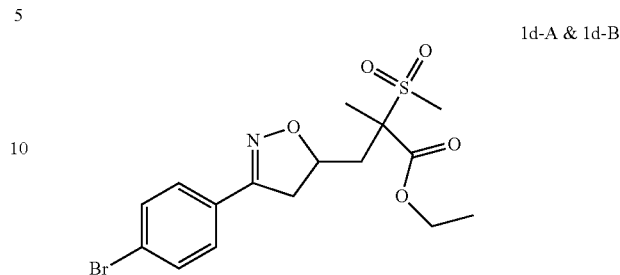

1d-A & 1d-B 1b (0.7 g, 3.4 mmol, 1.0 equiv) was dissolved in chloroform (10 ml) and cooled to 0° C. Diethyl zinc (1M in hexane) (0.94 g, 7.5 mmol, 2.2 equiv) was added and the reaction mixture was stirred 0° C. for 10 minutes. (R,R)-DIPT (0.79 g, 3.4 mmol, 1.0 equiv) was added and the reaction mixture was stirred at 0° C. for 1 hour. 1a (0.61 g, 3.1 mmol, 1.0 equiv), 1,4-dioxane (0.73 g, 6.8 mmol, 2.0 equiv) and t-BuOCl (0.45 g, 5.1 mmol, 1.5 equiv) were added. The reaction mixture was stirred at room temperature for 3 hours. The reaction mixture was quenched with saturated aqueous ammonium chloride solution and extracted with EtOAc. The organic layer was washed with brine, dried over sodium sulfate and concentrated. The crude product was purified by silica gel column chromatography (0-30% EtOAc in Hexane) to afford product 1d (0.55 g, 37.0% yield). The product was further purified by preparative HPLC purification to afford two diastereomers. 1d-A (0.2 g, 14.08%) LCMS (m/z): 418.2 [M–H]. 1d-B (0.19 g, 13.4%). LCMS (m/z): 418.2 [M–H]. ¹H NMR (400 MHz, DMSO) δ 7.72-7.65 (m, 2H), 7.64-7.58 (m, 2H), 5.01-4.87 (m, 1H), 4.27-4.11 (m, 2H), 3.57 (dd, J=17.0, 10.2 Hz, 1H), 3.25-3.12 (m, 1H), 2.63 (dd, J=13.8, 10.6 Hz, 1H), 2.06 (dd, J=13.9, 3.4 Hz, 1H), 1.58 (s, 3H), 1.28-1.16 (m, 3H).

Step 4. Synthesis of 3-(3-(4-bromophenyl)-4,5-dihydroisoxazol-5-yl)-2-methyl-2-(methylsulfonyl)propanoic acid [1e-A]

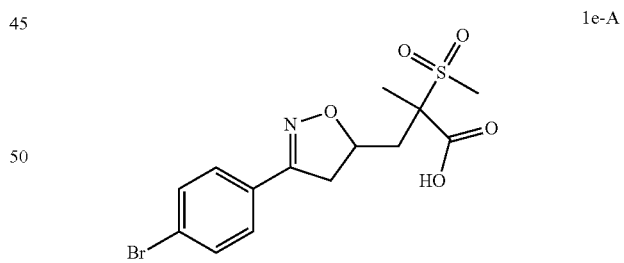

1e-A

1d-A (0.2 g, 0.5 mmol, 1.0 equiv) was dissolved in MeOH (5 ml) and water (2 ml). LiOH.H₂O (0.04 g, 1.0 mmol, 2.0 equiv) was added and the reaction mixture was stirred at room temperature for 1 hour. The reaction mixture was diluted with water, acidified by 1N HCl aqueous solution to the pH 3 to 4 and extracted with EtOAc. The organic layer was washed with brine, dried over sodium sulfate and concentrated to afford product 1e (0.18 g, 96.5% yield). LCMS (m/z): 390.2 [M–H]. ¹H NMR (400 MHz, DMSO) δ 13.58 (s, 1H), 7.73-7.65 (m, 2H), 7.64-7.55 (m, 2H), 4.96-4.87 (m, 1H), 3.58 (dd, J=17.0, 10.3 Hz, 1H), 3.19 (dd, J=17.1, 6.6 Hz, 1H), 3.09 (s, 3H), 2.62 (dd, J=13.9, 10.0 Hz, 1H), 2.08 (dd, J=13.9, 3.7 Hz, 1H), 1.54 (s, 3H).

Step 5. Synthesis of 3-(3-(4-bromophenyl)-4,5-di-hydroisoxazol-5-yl)-2-methyl-2-(methylsulfonyl)-N-((tetrahydro-2H-pyran-2-yl)oxy)propanamide [1f-A]

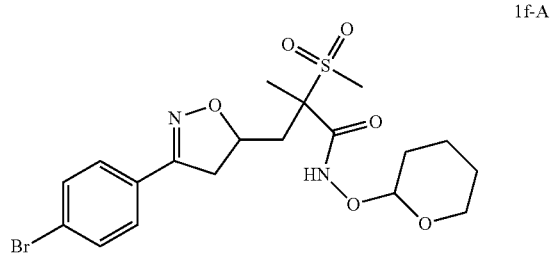 [SMILES: CC(CC1CC(c2ccc(Br)cc2)=NO1)(C(=O)NOC1CCCCO1)S(C)(=O)=O]

1f-A

1e-A (0.18 g, 0.5 mmol, 1.0 equiv) was dissolved in dichloromethane (3 mL). TEA (0.23 g, 2.3 mmol, 5.0 equiv), EDC.HCl (0.13 g, 0.7 mmol, 1.5 equiv), HOBT (0.11 g, 0.8 mmol, 1.8 equiv) and O-(tetrahydro-2H-pyran-2-yl) hydroxylamine (0.11 g, 0.9 mmol, 2.0 equiv) were added. The reaction mixture was stirred at room temperature for 20 hours. The reaction mixture was concentrated under reduced pressure and the residue was purified by silica gel column chromatography (0-5% MeOH in dichloromethane) to afford product 1f-A (0.2 g, 88.4% yield). LCMS (m/z): 489.4 [M−H]. $^1$H NMR (400 MHz, DMSO) δ 11.32 (d, J=21.4 Hz, 1H), 7.68 (d, J=8.6 Hz, 2H), 7.60 (dd, J=8.6, 1.2 Hz, 2H), 4.88-4.77 (m, 1H), 4.57 (d, J=4.9 Hz, 1H), 4.01 (d, J=12.0 Hz, 1H), 3.82-3.70 (m, 1H), 3.63-3.47 (m, 2H), 3.47-3.39 (m, 1H), 3.17 (ddd, J=17.0, 7.5, 4.5 Hz, 1H), 3.04 (d, J=5.6 Hz, 3H), 2.71 (td, J=12.9, 9.1 Hz, 1H), 2.13-1.99 (m, 1H), 1.65-1.60 (m, 1H), 1.58 (s, 3H), 1.53 (dd, J=15.2, 7.5 Hz, 3H), 1.49-1.42 (m, 3H).

Step 6. Synthesis of 3-(3-(4-bromophenyl)-4,5-di-hydroisoxazol-5-yl)-N-hydroxy-2-methyl-2-(methyl-sulfonyl)propanamide [1-A]

1f-A (0.065 g, 1.0 mmol, 1.0 equiv) was dissolved in ethanol (1 mL). 35.5% aq. HCl (1 mL) was added and the reaction mixture was stirred at room temperature for 3 hours. The reaction mixture was concentrated under reduced pressure to afford a residue. The residue was triturated with n-pentane, solvent was decanted. The reaming material product was further purified by preparative HPLC purification to afford product 1-A (0.026 g, 48.4% yield). LCMS (m/z): 405.2 [M−H]. $^1$H NMR (400 MHz, DMSO) δ 10.87 (s, 1H), 9.15 (s, 1H), 7.68 (d, J=8.6 Hz, 2H), 7.60 (d, J=8.6 Hz, 2H), 4.78 (dd, J=20.6, 10.7 Hz, 1H), 3.58 (dd, J=17.0, 10.3 Hz, 1H), 3.16 (dd, J=17.0, 7.9 Hz, 1H), 2.74 (dd, J=13.8, 8.5 Hz, 1H), 2.07 (dd, J=13.8, 4.4 Hz, 1H), 1.58 (d, J=13.7 Hz, 3H).

The diastereomer 3-(3-(4-bromophenyl)-4,5-dihydroisox-azol-5-yl)-N-hydroxy-2-methyl-2-(methylsulfonyl)propanamide [1-B] was synthesized from 1d-B following the procedures described in Step 4-6. LCMS (m/z): 405.2 [M−H]. $^1$H NMR (400 MHz, DMSO) δ 11.06 (s, 1H), 9.29 (s, 1H), 7.68 (d, J=8.6 Hz, 2H), 7.60 (d, J=8.6 Hz, 2H), 4.65 (td, J=11.5, 3.5 Hz, 1H), 3.57 (dt, J=26.4, 13.2 Hz, 1H), 3.14 (dd, J=17.1, 8.1 Hz, 1H), 3.10-3.00 (m, 3H), 2.66 (dd, J=14.0, 3.3 Hz, 1H), 2.12-1.99 (m, 1H), 1.59 (s, 3H).

Example 2

Synthesis of compound (R)-N-hydroxy-2-methyl-2-(methylsulfonyl)-3-((R)-3-(4-(prop-1-yn-1-yl)phenyl)-4,5-dihydroisoxazol-5-yl)propanamide [2-A]

1-A

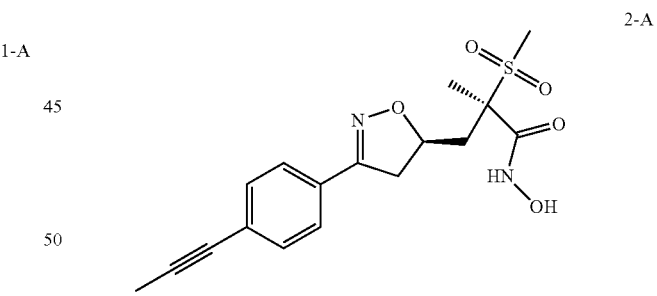

2-A

Synthetic scheme

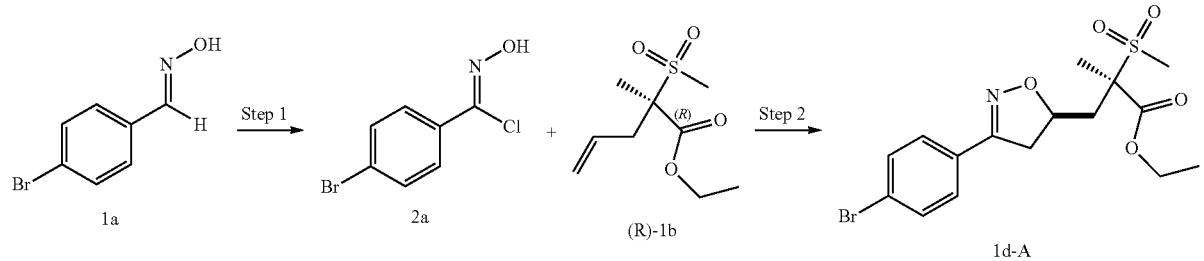

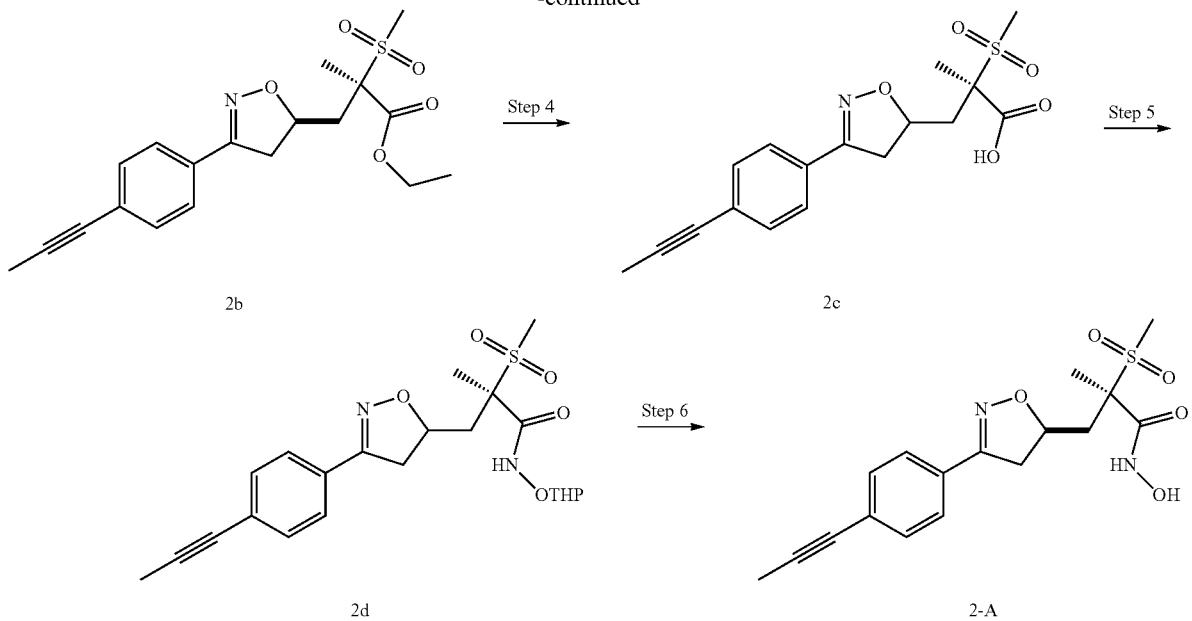

Reagents:
Step 1: NCS, DMF, 50° C. Step 2: TEA, diethyl ether, 0° C. to room temperature. Step 3: DBU, dppb, PdCl$_2$(PPh$_3$)$_2$, DMSO, 100° C. Step 4: LiOH.H$_2$O, THF, MeOH, water, room temperature. Step 5: NH$_2$OTHP, EDC.HCl, HOBT, N-methyl morpholine, THF, room temperature. Step 6: HCl (in IPA), MeOH, dichloromethane, room temperature.

Step 1. Synthesis of 4-bromo-N-hydroxybenzimidoyl chloride [1a]

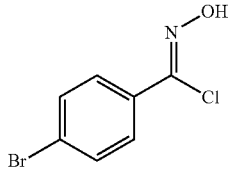

Bromobenzaldehyde oxime (2 g, 10.0 mmol, 1.0 equiv) was dissolved in DMF (20 mL). NCS (2 g, 15.0 mmol, 1.5 equiv) was added and the reaction mixture was stirred at 50° C. for 2 hours. The reaction was quenched with water and extracted with EtOAc. The organic layer was washed with brine, dried over sodium sulfate and concentrated to afford a crude residue. The crude residue was purified by silica gel column chromatography (10% Hexane) to afford the desired product 1a (2 g, 85% yield). $^1$H NMR (400 MHz, DMSO) δ 12.56 (s, 1H), 7.78-7.64 (m, 4H).

Step 2. Synthesis of (R)-ethyl 3-((R)-3-(4-bromophenyl)-4,5-dihydroisoxazol-5-yl)-2-methyl-2-(methylsulfonyl)propanoate [1d-A]

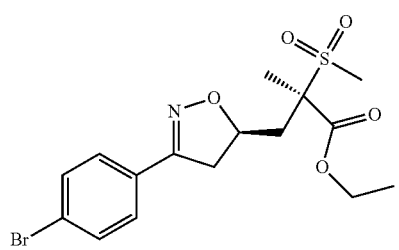

Racemic material 1b was separated into two enantiomers by chiral HPLC with following conditions. Instrumentation: VWR La Prep. HPLC system;

Mobile phase: Heptane/Ethanol 95/5;

Flow rate: 170 mL/min;

Column: Chiralpak AD 20 uM 7.65×39.3 cm+5×50 cm;

Detection UV: 210 nM.

The second fraction was determined to be (R)-ethyl 2-methyl-2-(methylsulfonyl)pent-4-enoate (R)-1b.

A flask was charged with 1a (2.04 g, 10.2 mmol, 1.5 equiv), (R)-1d-A (1.5 g, 6.8 mmol, 1.0 equiv) and diethyl ether (25 mL). At 0° C., TEA (1.37 g, 13.6 mmol, 2.0 equiv) was added and the reaction mixture was stirred at room temperature for 3 hours. The reaction mixture was quenched with water and extracted with EtOAc. The organic layer was washed with brine, dried over sodium sulfate and concentrated. The crude residue was purified by silica gel column chromatography (column packed in 50% dichloromethane/Hexane, eluent system-1 to 47% EtOAc) to afford two diastereomers (R)-1d-A and (R)-1d-B. (R)-1d-A: (1 g, 35.1% yield). LCMS (m/z): 418.3 [M+H]. $^1$H NMR (400 MHz, DMSO) δ 7.68 (d, J=8.6 Hz, 2H), 7.61 (d, J=8.6 Hz, 2H), 4.83-4.71 (m, 1H), 4.26 (q, J=7.1 Hz, 2H), 3.62 (dd, J=17.0, 10.4 Hz, 1H), 3.23-3.15 (m, 1H), 3.15 (d, J=7.1 Hz, 3H), 2.60 (dd, J=14.5, 3.3 Hz, 1H), 2.19 (dd, J=14.5, 8.5 Hz, 1H), 1.63 (s, 3H), 1.26 (t, J=7.1 Hz, 3H). (R)-1d-B: (0.8 g, 28% yield). LCMS (m/z): 418.1 [M+H]. $^1$H NMR (400 MHz, DMSO) δ 7.68 (d, J=8.6 Hz, 2H), 7.61 (d, J=8.6 Hz, 2H), 4.98-4.89 (m, 1H), 4.19 (q, J=7.1 Hz, 2H), 3.57 (dd, J=17.0, 10.2 Hz, 1H), 3.22-3.15 (m, 1H), 3.11 (d, J=13.6 Hz, 3H), 2.63 (dd, J=13.9, 10.7 Hz, 1H), 2.06 (dd, J=13.8, 3.3 Hz, 1H), 1.55 (d, J=20.4 Hz, 3H), 1.23 (t, J=7.1 Hz, 3H). The less polar diastereomer, structure shown as (R)-1d-A was used in the following step.

Step 3. Synthesis of ethyl (2R)-2-methyl-2-(methyl-sulfonyl)-3-(3-(4-(prop-1-yn-1-yl)phenyl)-4,5-dihydroisoxazol-5-yl)propanoate

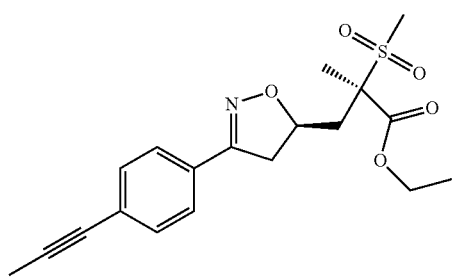

2b

A flask was charged with (R)-1d-A (1 g, 2.39 mmol, 1.0 equiv) and DMSO (10 mL). But-2-ynoic acid (0.3 g, 3.58 mmol, 1.5 equiv), 1,4-Bis (diphenylphosphino) butane (0.023 g, 0.05 mmol, 0.02 equiv), DBU (0.73 g, 4.78 mmol, 2.0 equiv) were added and the reaction mixture was degassed for 10 minutes. $PdCl_2(PPh_3)_2$ (0.018 g, 0.026 mmol, 0.01 equiv) was added and the reaction mixture was stirred at 100° C. for 3 hours. The reaction mixture was quenched with water and extracted with EtOAc. The organic layer was washed with brine, dried over sodium sulfate and concentrated. The crude residue was purified by silica gel column chromatography (35-40% EtOAc/Hexane) to afford product 2b (0.8 g, 88% yield). LCMS (m/z): 378.2 [M+H]. $^1$H NMR (400 MHz, DMSO) δ 7.62 (d, J=8.4 Hz, 2H), 7.46 (d, J=8.4 Hz, 2H), 4.76 (ddd, J=11.3, 8.3, 3.4 Hz, 1H), 4.27 (q, J=7.1 Hz, 2H), 3.61 (dd, J=17.0, 10.3 Hz, 1H), 3.22-3.06 (m, 4H), 2.59 (dd, J=14.4, 3.3 Hz, 1H), 2.19 (dd, J=14.4, 8.5 Hz, 1H), 2.07 (s, 3H), 1.63 (s, 3H), 1.26 (t, J=7.1 Hz, 3H).

Step 4. Synthesis of (R)-2-methyl-2-(methylsulfonyl)-3-((R)-3-(4-(prop-1-yn-1-yl)phenyl)-4,5-dihydroisoxazol-5-yl)propanoic acid [2c]

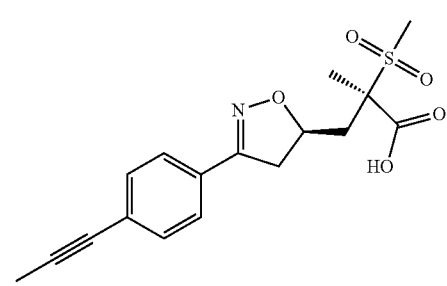

2c 2b (0.8 g, 2.12 mmol, 1.0 equiv) was dissolved in THF (16 mL), MeOH (2 mL) and water (2 mL). $LiOH·H_2O$ (0.17 g, 4.24 mmol, 2.0 equiv) was added and the reaction mixture was stirred at room temperature for 2 hours. The reaction mixture was acidified by 1.0 N HCl aqueous solution up to pH 4 to 5 and extracted with EtOAc. The organic layer was washed with brine, dried over sodium sulfate and concentrated to afford product 2c (0.62 g, 84% yield). The product was directly used in the next step with no further purification. LCMS (m/z): 350.1 [M+H]. $^1$H NMR (400 MHz, DMSO) δ 14.03 (s, 1H), 7.70-7.58 (m, 2H), 7.46 (d, J=8.3 Hz, 2H), 4.77 (dd, J=15.6, 7.8 Hz, 1H), 3.62 (dd, J=17.0, 10.4 Hz, 1H), 3.24-3.15 (m, 1H), 3.16-3.07 (m, 3H), 2.56 (d, J=3.1 Hz, 1H), 2.15 (dd, J=14.3, 8.5 Hz, 1H), 2.07 (s, 3H), 1.60 (s, 3H).

Step 5. Synthesis of (2R)-2-methyl-2-(methylsulfonyl)-3-((R)-3-(4-(prop-1-yn-1-yl)phenyl)-4,5-dihydroisoxazol-5-yl)-N-((tetrahydro-2H-pyran-2-yl)oxy)propanamide [2d]

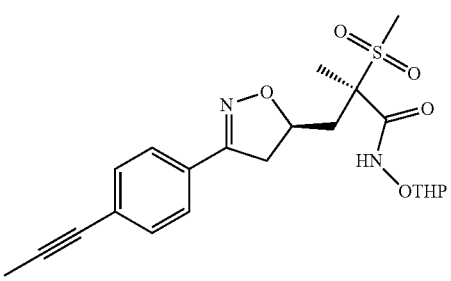

2d

A flask was charged with 2c (0.6 g, 1.7 mmol, 1.0 equiv) and THF (25 mL). N-methyl morpholine (0.87 g, 8.6 mmol, 5.0 equiv), HOBT (0.28 g, 2.0 mmol, 1.2 equiv), 0-(tetrahydro-2H-pyran-2-yl) hydroxylamine (0.4 g, 3.4 mmol, 2.0 equiv), EDC.HCl (0.49 g, 2.6 mmol, 1.5 equiv) were added and the reaction mixture was stirred at room temperature for 24 hours. The reaction mixture was quenched with water and extracted with EtOAc. The organic layer was washed with brine, dried over sodium sulfate and concentrated. The residue was purified by silica gel column chromatography (35-50% EtOAc/Hexane) to afford product 2d (0.65 g, 88% yield). LCMS (m/z): 365.0 [M−THP]. $^1$H NMR (400 MHz, DMSO) δ 11.47 (s, 1H), 7.61 (dd, J=8.4, 1.7 Hz, 2H), 7.46 (d, J=8.4 Hz, 2H), 4.97 (d, J=8.6 Hz, 1H), 4.67 (d, J=9.8 Hz, 1H), 4.07 (dd, J=18.4, 10.0 Hz, 1H), 3.64-3.43 (m, 2H), 3.14 (dd, J=17.1, 7.5 Hz, 1H), 3.06 (d, J=8.7 Hz, 3H), 2.71-2.63 (m, 1H), 2.06 (d, J=6.7 Hz, 3H), 1.70 (s, 3H), 1.61 (d, J=4.3 Hz, 3H), 1.54 (s, 3H).

Step 6. Synthesis of (R)-N-hydroxy-2-methyl-2-(methylsulfonyl)-3-((R)-3-(4-(prop-1-yn-1-yl)phenyl)-4,5-dihydroisoxazol-5-yl)propanamide [2-A]

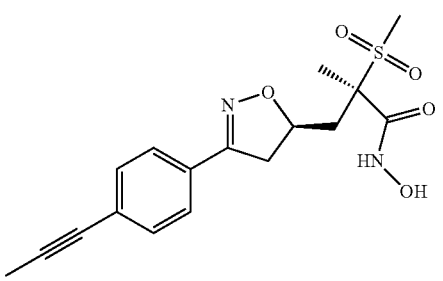

2-A 2d (0.6 g, 1.33 mmol, 1.0 equiv) was dissolved in methanol (4 mL) and dichloromethane (4 mL). 10% HCl (in IPA) (0.3 mL) was added and the reaction mixture was stirred at room temperature for 2 hours. The reaction mixture was quenched with water, neutralized by saturated aqueous sodium bicarbonate solution and extracted with EtOAc. The organic layer was washed with brine, dried over sodium sulfate and concentrated. The residue was triturated with n-pentane/diethyl ether, solvent was decanted and dried to afford product 2-A (0.48 g, 90% yield). LCMS (m/z): 365.1 [M+H]. ¹H NMR (400 MHz, DMSO) δ 11.06 (s, 1H), 9.28 (s, 1H), 7.62 (d, J=8.4 Hz, 2H), 7.46 (d, J=8.4 Hz, 2H), 4.63 (dt, J=11.6, 5.9 Hz, 1H), 3.57 (dd, J=17.0, 10.4 Hz, 1H), 3.14 (dd, J=17.1, 8.1 Hz, 1H), 3.05 (d, J=11.5 Hz, 3H), 2.66 (dd, J=14.2, 3.3 Hz, 1H), 2.07 (s, 3H), 2.02 (dd, J=14.6, 6.2 Hz, 1H), 1.59 (s, 3H).

Example 3

Synthesis of 3-(3-([1,1-biphenyl]-4-yl)-4,5-dihydroisoxazol-5-yl)-N-hydroxy-2-methyl-2-(methylsulfonyl)propanamide [3-A, 3-B]

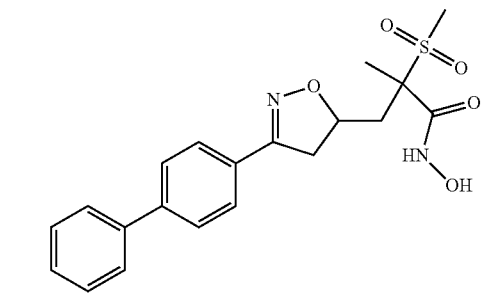

3-A, 3-B

Synthetic scheme

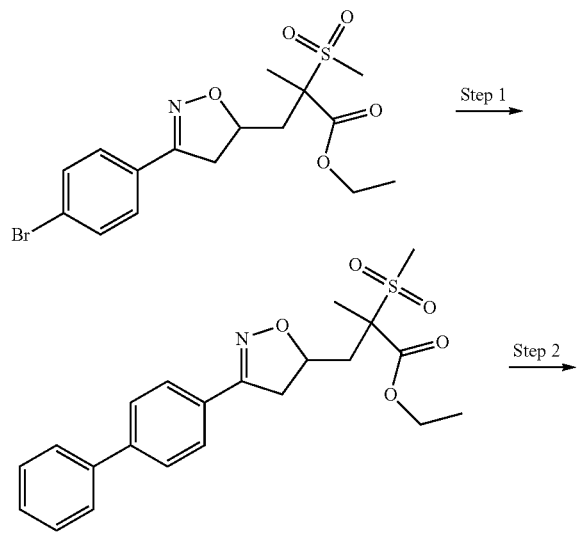

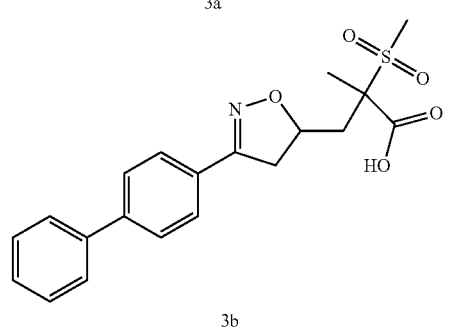

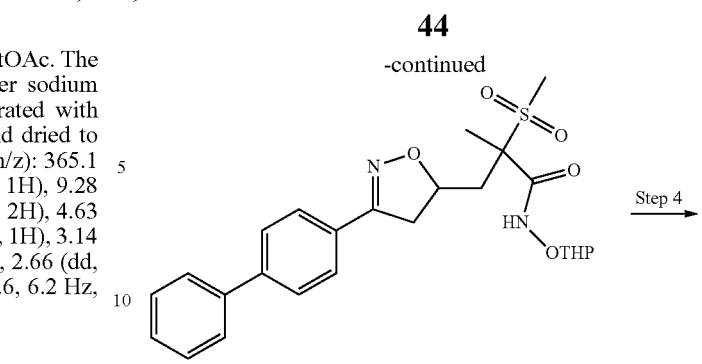

3c

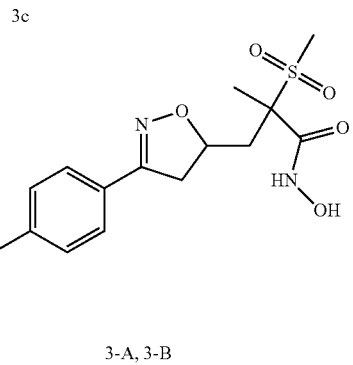

3-A, 3-B

Reagents:
Step 1: CH₃COOK, PdCl₂(dppf), 1,4-dioxane, 100° C.
Step 2: LiOH.H₂O, MeOH, water, room temperature. Step 3: NH₂O-THP, EDC.HCl, HOBT, TEA, dichloromethane, room temperature. Step 4: 35.5% aq.HCl, EtOH, room temperature.

Step 1. Synthesis of ethyl 3-(3-([1,1-biphenyl]-4-yl)-4,5-dihydroisoxazol-5-yl)-2-methyl-2-(methylsulfonyl)propanoate [3a]

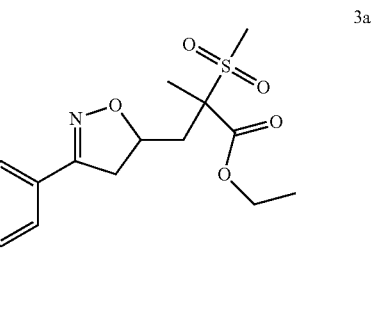

3a

1d-A & 1-d-B (0.5 g, 1.0 mmol, 1.0 equiv), phenylboronic acid (0.18 g, 1.2 mmol, 1.2 equiv) and potassium acetate (0.351 g, 2.9 mmol, 3.0 equiv) were dissolved in 1,4-dioxane (10 mL) and degassed for 5 minutes. PdCl₂(dppf) (0.087 g, 0.1 mmol, 0.1 equiv) was added to the reaction mixture. The resulting reaction mixture was stirred at 100° C. for 4 hours. The reaction mixture was quenched with water and extracted with EtOAc. The organic layer was washed with brine, dried over sodium sulfate and concentrated. The residue was purified by silica gel column chromatography (0-50% EtOAc in Hexane) to afford product 3a (0.35 g, 70.6% yield). LCMS (m/z): 416 [M+H]. ¹H NMR (400 MHz, DMSO) δ 7.75 (dt, J=8.6, 7.5 Hz, 6H), 7.49 (t, J=7.5 Hz, 2H), 7.40 (t, J=7.4 Hz, 1H), 5.01-4.87 (m, 1H), 4.35-4.15 (m, 2H), 3.64 (dd, J=17.7, 11.2 Hz, 1H), 3.29-3.16 (m, 1H), 3.11 (d, J=21.0 Hz, 3H), 2.63 (t, J=12.4 Hz, 1H), 2.19 (dd, J=14.5, 8.5 Hz, 1H), 2.07 (d, J=13.3 Hz, 1H), 1.68-1.53 (m, 3H), 1.26-1.18 (m, 3H).

Step 3. Synthesis of 3-(3-([1,1-biphenyl]-4-yl)-4,5-dihydroisoxazol-5-yl)-2-methyl-2-(methylsulfonyl) propanoic acid [3b]

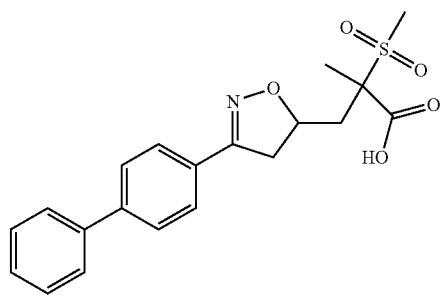

3a (0.35 g, 0.8 mmol, 1.0 equiv) was dissolved in MeOH (4 mL) and water (2 mL). LiOH.H₂O (0.070 g, 1.6 mmol, 2.0 equiv) was added and the reaction mixture was stirred at room temperature for 1 hour. The reaction mixture was diluted with water, acidified by 1N HCl aqueous solution to the pH 3 to 4 and extracted with EtOAc. The organic layer was washed with brine, dried over sodium sulfate and concentrated to afford product 3b (0.24 g, 73.6% yield). The product was used in the next step without further purification. LCMS (m/z): 388.1 [M+H]. ¹H NMR (400 MHz, DMSO) δ 13.62 (s, 1H), 7.85-7.69 (m, 6H), 7.50 (t, J=7.6 Hz, 2H), 7.45-7.38 (m, 1H), 5.02-4.70 (m, 1H), 3.76-3.57 (m, 1H), 3.23 (ddd, J=16.9, 7.3, 4.3 Hz, 1H), 3.17-3.03 (m, 3H), 2.61 (ddd, J=17.6, 13.9, 6.6 Hz, 1H), 2.14 (ddd, J=17.5, 14.0, 6.0 Hz, 1H), 1.59 (d, J=21.1 Hz, 3H).

Step 4. Synthesis of 3-(3-([1,1-biphenyl]-4-yl)-4,5-dihydroisoxazol-5-yl)-2-methyl-2-(methylsulfonyl)-N-((tetrahydro-2H-pyran-2-yl)oxy)propanamide [3c]

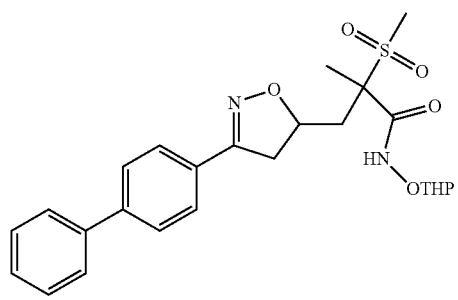

3b (0.24 g, 0.6 mmol, 1.0 equiv) was dissolved in dichloromethane (5 mL). TEA (0.31 g, 3.0 mmol, 5.0 equiv) was added. EDC.HCl (0.18 g, 0.9 mmol, 1.5 equiv), HOBt (0.15 g, 1.1 mmol, 1.8 equiv) and O-(tetrahydro-2H-pyran-2-yl) hydroxylamine (0.145 g, 1.2 mmol, 2.0 equiv) were added. The reaction mixture was stirred at room temperature for 20 hours. The reaction mixture was concentrated under reduced pressure to afford a crude product. The crude product was purified by silica gel column chromatography (0-4% MeOH in dichloromethane) to afford product 3c (0.2 g, 66.4% yield). LCMS (m/z): 487.4 [M+H]. ¹H NMR (400 MHz, DMSO) δ 7.76 (dt, J=8.6, 7.9 Hz, 6H), 7.50 (t, J=7.6 Hz, 2H), 7.41 (t, J=7.3 Hz, 1H), 4.86-4.65 (m, 1H), 4.05 (dd, J=28.6, 21.5 Hz, 1H), 3.77 (ddd, J=11.1, 7.9, 3.1 Hz, 1H), 3.62 (ddd, J=21.0, 10.3, 5.1 Hz, 1H), 3.47-3.39 (m, 2H), 3.27-3.15 (m, 1H), 3.07 (t, J=7.2 Hz, 3H), 2.79-2.65 (m, 1H), 2.10 (ddd, J=16.7, 9.9, 5.0 Hz, 1H), 1.65-1.52 (m, 6H).

Step 5. Synthesis of 3-(3-([1,1-biphenyl]-4-yl)-4,5-dihydroisoxazol-5-yl)-N-hydroxy-2-methyl-2-(methylsulfonyl)propanamide [3-A, 3-B]

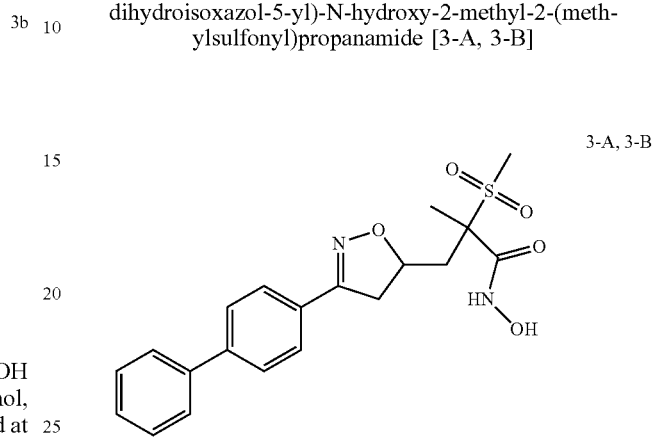

3c (0.2 g, 0.4 mmol, 1.0 equiv) was dissolved in ethanol (2 ml). 35.5% aq. HCl (1 mL) was added and the reaction mixture was stirred at room temperature for 3 hours. The reaction mixture was concentrated under reduced pressure to dryness to obtain a residue. The crude product was purified by preparative HPLC purification to afford product 3 as two diastereomers (3-A (0.027 g, 16.3% yield), LCMS (m/z): 403.2[M+H]. ¹H NMR (400 MHz, DMSO) δ 10.86 (s, 1H), 9.17 (s, 1H), 7.75 (dt, J=7.2, 6.6 Hz, 6H), 7.50 (t, J=7.6 Hz, 2H), 7.41 (t, J=7.3 Hz, 1H), 4.80 (d, J=9.9 Hz, 1H), 3.63 (dd, J=16.9, 10.3 Hz, 1H), 3.21 (dd, J=17.0, 8.0 Hz, 1H), 3.07 (s, 3H), 2.76 (dd, J=13.9, 8.6 Hz, 1H), 2.09 (dd, J=13.9, 4.5 Hz, 1H), 1.58 (s, 3H). 3-B (0.023 g, 13.9% yield), LCMS (m/z): 403.2 [M+H]. ¹H NMR (400 MHz, DMSO) δ 11.08 (s, 1H), 9.31 (s, 1H), 7.85-7.70 (m, 6H), 7.50 (t, J=7.5 Hz, 2H), 7.41 (t, J=7.3 Hz, 1H), 4.66 (d, J=7.0 Hz, 1H), 3.62 (dd, J=16.9, 10.3 Hz, 1H), 3.19 (dd, J=17.0, 8.0 Hz, 1H), 3.07 (d, J=5.9 Hz, 3H), 2.69 (dd, J=14.0, 3.5 Hz, 1H), 2.07 (dd, J=14.0, 8.5 Hz, 1H), 1.61 (s, 3H).

Example 4

Synthesis of 3-(3-(4-(but-2-yn-1-yloxy)phenyl)-4,5-dihydroisoxazol-5-yl)-N-hydroxy-2-methyl-2-(methylsulfonyl)propanamide [4-A, 4-B]

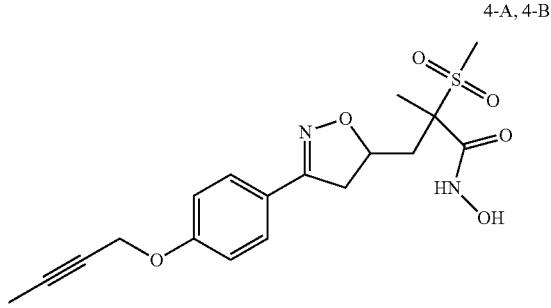 [SMILES: CC#CCOc1ccc(C2=NOC(CC(C)(C(=O)NO)S(C)(=O)=O)C2)cc1]

Synthetic scheme

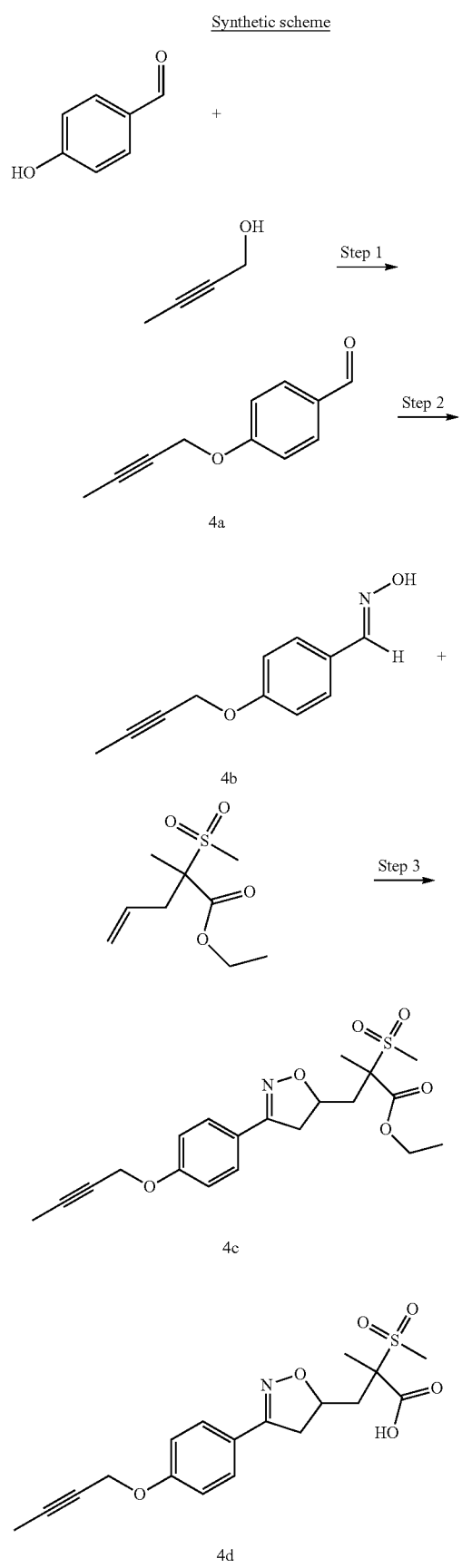

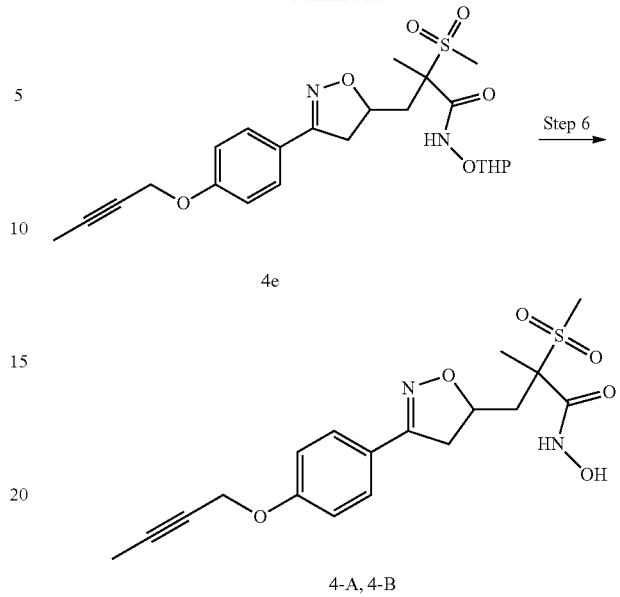

Reagents: Step 1: Triphenylphosphine, DEAD, benzene, THF, room temperature. Step 2: NH₂OH.HCl, NaOH, water, 70° C. Step 3: Et₂Zn, (R,R)-DIPT, t-BuOCl, chloroform, 1,4-dioxane, 0° C. to room temperature, 4 h. Step 4: LiOH.H₂O, MeOH, water, room temperature. Step 5: NH₂OTHP, EDC.HCl, HOBT, TEA, dichloromethane, room temperature. Step 6: 35.5% aq. HCl, EtOH, room temperature.

Step 1. Synthesis of 4-(but-2-yn-1-yloxy)benzaldehyde [4a]

But-2-yn-1-ol (2.58 g, 36.9 mmol, 1.5 equiv), triphenylphosphine (7.73 g, 29.5 mmol, 1.2 equiv) and 4-hydroxybenzaldehyde (3 g, 24.6 mmol, 1.0 equiv) were mixed with benzene:THF (2:1, 30 mL). The reaction mixture was stirred at room temperature for 10 minutes. DEAD (5.13 g, 29.5 mmol, 1.2 equiv) was added gradually and the reaction mixture was allowed to stir for 2 hours. The reaction mixture was quenched with water and extracted with EtOAc. The organic layer was washed with brine, dried over sodium sulfate and concentrated. The residue was purified by silica gel column chromatography (0-25% EtOAc in Hexane) to afford product 4a (3.5 g, 81.8% yield). LCMS (m/z): 175.2 [M+H]. ¹H NMR (400 MHz, DMSO) δ 9.92-9.84 (m, 1H), 7.95-7.83 (m, 2H), 7.24-7.10 (m, 2H), 4.89 (q, J=2.3 Hz, 2H), 1.88-1.81 (m, 3H).

Step 2. Synthesis of (E)-4-(but-2-yn-1-yloxy)benzaldehyde oxime [4h]

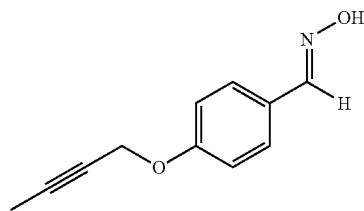

A mixture of 4a (3.5 g, 20.1 mmol, 1.0 equiv) and water (20 ml) was stirred at 70° C. A solution of hydroxylamine hydrochloride (1.68 g, 24.1 mmol, 1.2 equiv) and sodium hydroxide (1.04 g, 26.1 mmol, 1.3 equiv) in water (10 mL) was added to the reaction mixture at same temperature. The reaction mixture was allowed to stir at 70° C. for 3 hours. The reaction mixture was cooled to 0° C. and the precipitate was collected by filtration to afford product 4b (2.8 g, 73.2% yield). LCMS (m/z): 190.1 [M+H]. $^1$H NMR (400 MHz, DMSO) δ 11.01 (s, 1H), 8.07 (s, 1H), 7.53 (d, J=8.8 Hz, 2H), 7.00 (t, J=8.9 Hz, 2H), 4.78 (dq, J=4.5, 2.3 Hz, 2H), 1.89-1.79 (m, 3H).

Step 3. Synthesis of ethyl 3-(3-(4-(but-2-yn-1-yloxy)phenyl)-4,5-dihydroisoxazol-5-yl)-2-methyl-2-(methylsulfonyl)propanoate [4c]

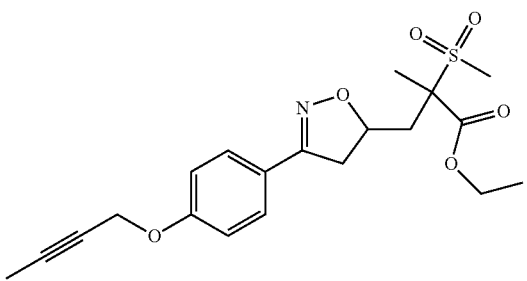

1b (1.25 g, 5.7 mmol, 1.0 equiv) was dissolved in chloroform (20 ml) and cooled to 0° C. Diethyl zinc (1.0 M in hexane) (1.57 g, 12.5 mmol, 2.2 equiv) was added and the reaction mixture was stirred 0° C. for 10 minutes. (R,R)-DIPT (1.33 g, 5.7 mmol, 1.0 equiv) was added and the reaction mixture was stirred at 0° C. for 7 hours. 4b (1.29 g, 6.8 mmol, 1.0 equiv), 1,4-dioxane (0.75 g, 8.5 mmol, 1.5 equiv) and t-BuOCl (1.22 g, 11.4 mmol, 2.0 equiv) were then added. The reaction mixture was stirred at room temperature for 4 hours. The reaction mixture was quenched with saturated aqueous ammonium chloride solution and extracted with dichloromethane. The organic layer was washed with brine, dried over sodium sulfate and concentrated. The crude product was purified by silica gel column chromatography (0-60% EtOAc in Hexane) to afford product 4c (1.6 g, 69.2% yield). LCMS (m/z): 408.3 [M+H]. $^1$H NMR (400 MHz, DMSO) δ 7.67-7.48 (m, 2H), 7.06 (t, J=12.3 Hz, 2H), 4.93 (td, J=12.2, 6.0 Hz, 1H), 4.88-4.76 (m, 2H), 4.38-4.13 (m, 3H), 3.65-3.46 (m, 1H), 3.23-3.04 (m, 4H), 2.68-2.55 (m, 1H), 2.10 (ddd, J=17.2, 14.1, 5.9 Hz, 1H), 1.84 (t, J=2.1 Hz, 3H), 1.68-1.50 (m, 3H), 1.21 (ddt, J=16.0, 9.7, 5.0 Hz, 3H).

Step 4. Synthesis of 3-(3-(4-(but-2-yn-1-yloxy)phenyl)-4,5-dihydroisoxazol-5-yl)-2-methyl-2-(methylsulfonyl)propanoic acid [4d]

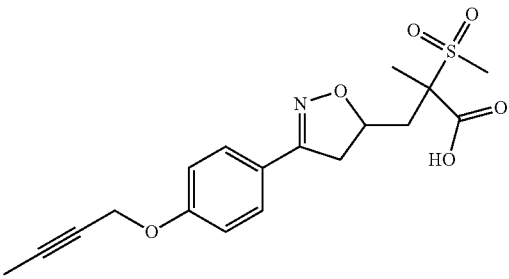

4c (1.6 g, 3.9 mmol, 1.0 equiv) was dissolved in MeOH (10 ml) and water (8 ml). LiOH.H$_2$O (0.33 g, 7.8 mmol, 2.0 equiv) was added and the reaction mixture was stirred at room temperature for 1 hour. The reaction mixture was diluted with water, acidified by 1.0 N HCl aqueous solution to the pH 3 and extracted with EtOAc. The organic layer was washed with brine, dried over sodium sulfate and concentrated. The crude product was triturated with n-pentane, the solvent was decanted to afford product 4d (1.05 g, 70.5% yield. LCMS (m/z): 380.1 [M+H]. $^1$H NMR (400 MHz, DMSO) δ 13.78 (d, J=180.1 Hz, 1H), 7.72-7.38 (m, 2H), 7.15-6.95 (m, 2H), 4.93-4.66 (m, 3H), 3.58 (ddd, J=20.6, 16.9, 10.2 Hz, 1H), 3.23-2.94 (m, 4H), 2.69-2.52 (m, 1H), 2.09 (ddd, J=17.4, 14.0, 6.0 Hz, 1H), 1.84 (t, J=2.1 Hz, 3H), 1.69-1.45 (m, 3H).

Step 5. Synthesis of 3-((R)-3-(4-(but-2-yn-1-yloxy)phenyl)-4,5-dihydroisoxazol-5-yl)-2-methyl-2-(methylsulfonyl)-N-((tetrahydro-2H-pyran-2-yl)oxy)propanamide [4e]

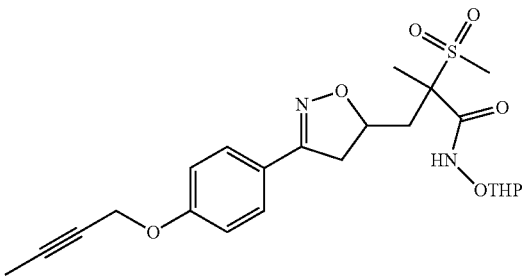

4d (0.5 g, 1.3 mmol, 1.0 equiv) was dissolved in dichloromethane (10 mL). TEA (0.66 g, 6.6 mmol, 5.0 equiv) was added. EDC.HCl (0.38 g, 2.0 mmol, 1.5 equiv), HOBT (0.32 g, 2.4 mmol, 1.8 equiv) and O-(tetrahydro-2H-pyran-2-yl) hydroxylamine (0.31 g, 2.6 mmol, 2.0 equiv) were added. The reaction mixture was stirred at room temperature for 20 hours. The reaction mixture was concentrated under reduced pressure. The crude product was purified by silica gel column chromatography (0-3% MeOH in dichloromethane) to afford product 4e (0.47 g, 74.5% yield). LCMS (m/z): 479.3 [M+H]. $^1$H NMR (400 MHz, DMSO) δ 7.68-7.56 (m, 2H), 7.04 (d, J=8.9 Hz, 2H), 4.70 (d, J=56.0 Hz, 1H), 4.07 (d, J=37.1 Hz, 1H), 3.52 (ddd, J=15.1, 10.6, 6.2 Hz, 2H), 3.20-2.97 (m, 4H), 2.75-2.61 (m, 1H), 2.12-1.95 (m, 1H), 1.56 (d, J=16.6 Hz, 6H).

Step 6. Synthesis of 3-(3-(4-(but-2-yn-1-yloxy)phenyl)-4,5-dihydroisoxazol-5-yl)-N-hydroxy-2-methyl-2-(methylsulfonyl)propanamide [4-A, 4-B]

4-A, 4-B

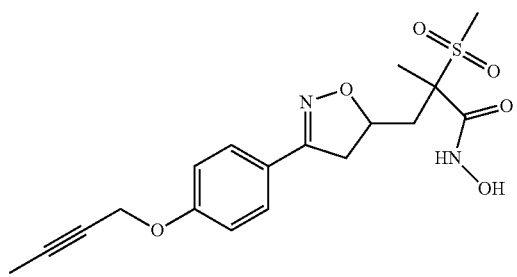

4e (0.47 g, 0.9 mmol, 1.0 equiv) was dissolved in ethanol (5 ml). 35.5% aq. HCl (2 mL) was added and the reaction mixture was stirred at room temperature for 3 hours. The reaction mixture was concentrated under reduced pressure. The crude product was purified by preparative HPLC purification to afford product 4 as two diastereomers (4-A (0.055 g, 14.5% yield), LCMS (m/z): 395.3 [M+H]. $^1$H NMR (400 MHz, DMSO) δ 10.86 (s, 1H), 9.15 (s, 1H), 7.60 (d, J=8.5 Hz, 2H), 7.04 (d, J=8.3 Hz, 2H), 4.80 (s, 2H), 4.72 (s, 1H), 3.55 (dd, J=17.0, 10.3 Hz, 1H), 3.13 (dd, J=16.8, 7.9 Hz, 1H), 3.05 (s, 3H), 2.76-2.67 (m, 1H), 2.05 (d, J=14.1 Hz, 1H), 1.84 (s, 3H), 1.56 (s, 3H). 4-B (0.050 g, 13.2% yield) LCMS (m/z): 395.3 [M+H]. $^1$H NMR (400 MHz, DMSO) δ 11.05 (s, 1H), 9.28 (s, 1H), 7.60 (d, J=8.5 Hz, 2H), 7.05 (d, J=8.6 Hz, 2H), 4.81 (s, 2H), 4.59 (d, J=7.5 Hz, 1H), 3.55 (dd, J=17.1, 10.5 Hz, 1H), 3.19-3.09 (m, 1H), 3.07 (s, 3H), 2.65 (d, J=17.1 Hz, 1H), 2.02 (dd, J=14.2, 8.4 Hz, 1H), 1.84 (s, 3H), 1.59 (s, 3H).

Example 5

Synthesis of compounds 3-(3-(4-cyclopropylphenyl)-4,5-dihydroisoxazol-5-yl)-N-hydroxy-2-methyl-2-(methylsulfonyl)propanamide [5-A, 5-B]

5-A, 5-B

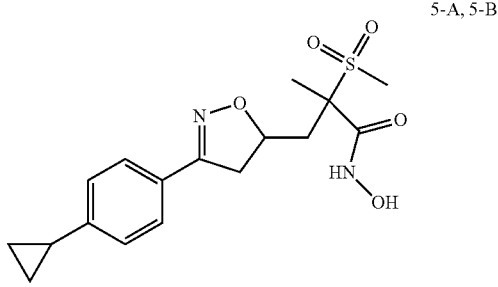 [SMILES: CC(CC1CC(c2ccc(C3CC3)cc2)=NO1)(C(=O)NO)S(C)(=O)=O]

Synthetic scheme

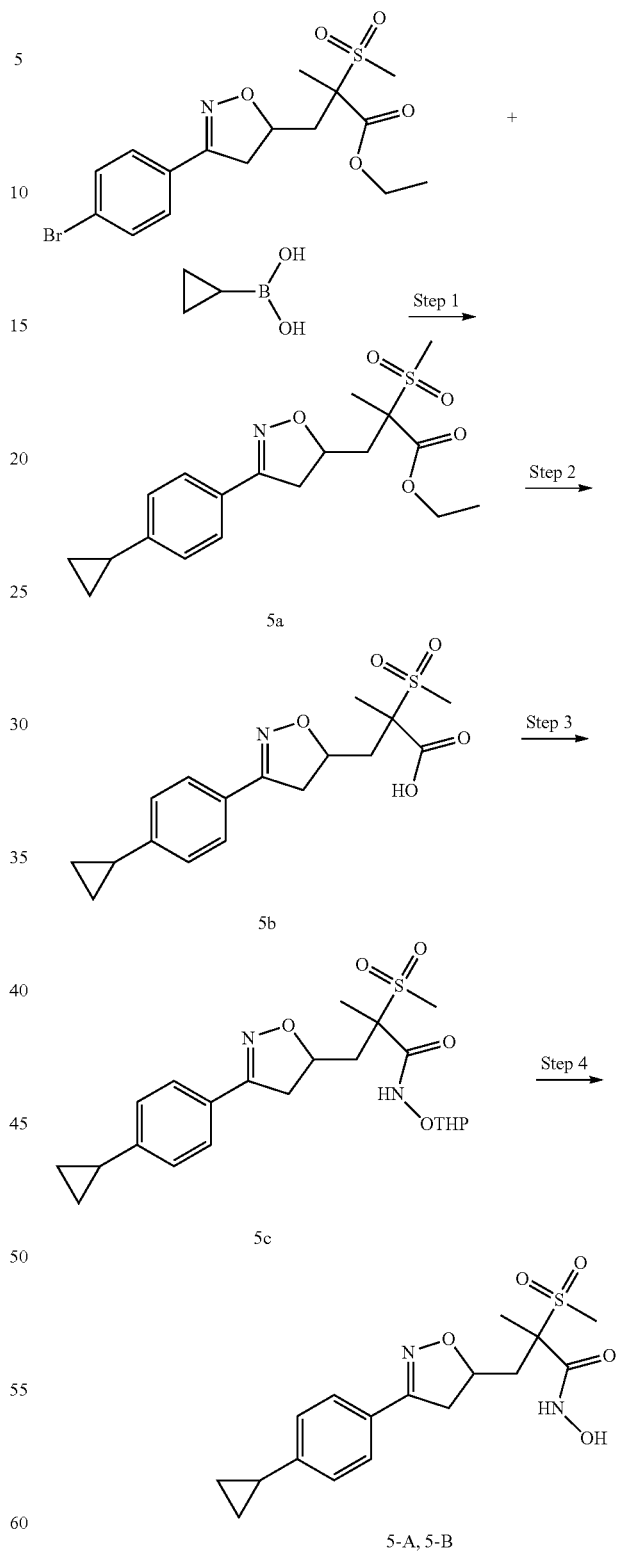

Reagents:
Step 1: Pd(OAc)$_2$, tricyclohexyl phosphine, K$_3$PO$_4$, 1,4-dioxane, Water, 130° C. Step 2: LiOH.H$_2$O, THF, MeOH, water, room temperature. Step 3: NH$_2$O-THP, EDC.HCl, HOBT, TEA, dichloromethane, room temperature. Step 4: 35.5% aq.HCl, EtOH, room temperature.

Step 1. Synthesis of ethyl 3-(3-(4-cyclopropylphenyl)-4,5-dihydroisoxazol-5-yl)-2-methyl-2-(methylsulfonyl)propanoate [5a]

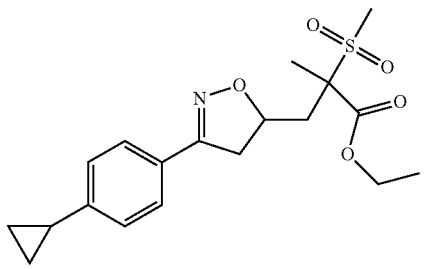

1d-A & 1d-B (0.25 g, 0.6 mmol, 1.0 equiv), cyclopropylboronic acid (0.062 g, 0.7 mmol, 1.2 equiv), $K_3PO_4$ (0.38 g, 1.8 mmol, 3.0 equiv) and tricyclohexyl phosphine (0.017 g, 0.06 mmol, 0.1 equiv) were dissolved in 1,4-dioxane:water (4:1, 15 mL) and degassed for 10 minutes. Pd(OAc)$_2$ (0.007 g, 0.02 mmol, 0.05 equiv) was added and the resulting reaction mixture was stirred at 130° C. for 1 hour. The reaction mixture was quenched with water and extracted with EtOAc. The organic layer was washed with brine, dried over sodium sulfate and concentrated. The crude product was purified by silica gel column chromatography (20-30% EtOAc in Hexane) to afford product 5a (0.19 g, 64.2% yield). LCMS (m/z): 380.2 [M+H]. $^1$H NMR (400 MHz, DMSO) δ 7.65 (d, J=20.3 Hz, 2H), 7.56-7.44 (m, 2H), 4.89 (d, J=27.7 Hz, 1H), 4.34-4.12 (m, 2H), 3.58 (dd, J=17.5, 10.5 Hz, 1H), 3.16 (ddd, J=32.2, 19.0, 4.3 Hz, 4H), 2.71-2.55 (m, 1H), 2.26-2.11 (m, 1H), 2.08 (s, 1H), 1.61 (dd, J=22.2, 3.7 Hz, 3H), 1.25-1.21 (m, 3H), 1.05-0.69 (m, 4H).

Step 2. Synthesis of 3-(3-(4-cyclopropylphenyl)-4,5-dihydroisoxazol-5-yl)-2-methyl-2-(methylsulfonyl)propanoic acid [5b]

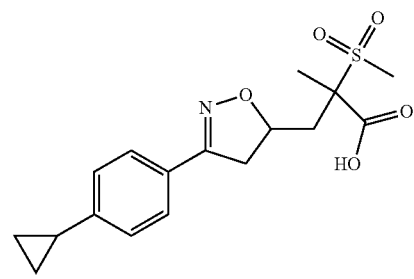

5a (0.19 g, 0.5 mmol, 1.0 equiv) was dissolved in THF (4 mL), MeOH (1 mL) and water (1 mL). LiOH.H$_2$O (0.063 g, 1.5 mmol, 3.0 equiv) was added and the reaction mixture was stirred at room temperature for 3 hours. The reaction mixture was concentrated under reduced pressure. The residue was diluted with water, acidified by 1.0 N HCl aqueous solution to the pH 3 and extracted with EtOAc. The organic layer was washed with brine, dried over sodium sulfate and concentrated to afford product 5b (0.155 g, 88.1% yield). LCMS (m/z): 352.3 [M+H]. $^1$H NMR (400 MHz, DMSO) δ 7.67 (d, J=4.4 Hz, 2H), 7.55-7.43 (m, 2H), 4.89 (s, 1H), 3.59 (dd, J=18.3, 11.3 Hz, 1H), 3.20 (d, J=13.9 Hz, 1H), 3.11 (dd, J=16.9, 2.1 Hz, 3H), 2.64 (d, J=32.5 Hz, 1H), 2.27-2.02 (m, 2H), 1.57 (dd, J=20.8, 3.8 Hz, 3H), 1.20-0.99 (m, 2H), 0.90-0.69 (m, 2H).

Step 3. Synthesis of 3-(3-(4-cyclopropylphenyl)-4,5-dihydroisoxazol-5-yl)-2-methyl-2-(methylsulfonyl)-N-((tetrahydro-2H-pyran-2-yl)oxy)propanamide [5c]

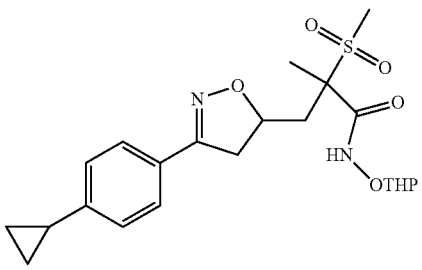

5b (0.155 g, 0.4 mmol, 1.0 equiv) was dissolved in dichloromethane (5 mL). TEA (0.22 g, 2.22 mmol, 5.0 equiv) was added. EDC.HCl (0.13 g, 0.7 mmol, 1.5 equiv), HOBT (0.107 g, 0.8 mmol, 1.8 equiv) and O-(tetrahydro-2H-pyran-2-yl) hydroxylamine (0.103 g, 0.9 mmol, 2.0 equiv) were added. The reaction mixture was stirred at room temperature for 24 hours. The reaction mixture was concentrated under reduced pressure. The crude product was purified by silica gel column chromatography (0.5-2% MeOH in dichloromethane) to afford product 5c (0.145 g, 72.5% yield). LCMS (m/z): 454.3 [M+18]. $^1$H NMR (400 MHz, DMSO) δ 7.67 (d, J=4.4 Hz, 2H), 7.55-7.43 (m, 2H), 4.89 (s, 1H), 3.59 (dd, J=18.3, 11.3 Hz, 1H), 3.20 (d, J=13.9 Hz, 1H), 3.11 (dd, J=16.9, 2.1 Hz, 3H), 2.64 (d, J=32.5 Hz, 1H), 2.27-2.02 (m, 2H), 1.57 (dd, J=20.8, 3.8 Hz, 3H), 1.20-0.99 (m, 2H), 0.90-0.69 (m, 2H).

Step 4. Synthesis of 3-(3-(4-cyclopropylphenyl)-4,5-dihydroisoxazol-5-yl)-N-hydroxy-2-methyl-2-(methylsulfonyl)propanamide [5-A, 5-B]

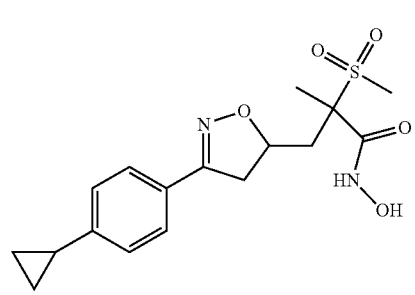

5c (0.145 g, 0.3 mmol, 1.0 equiv) was dissolved in ethanol (2 ml). 35.5% aq. HCl (0.5 mL) was added and the reaction mixture was stirred at room temperature for 6 hours. The reaction mixture was concentrated under reduced pressure to dryness. The crude product was purified by preparative HPLC purification to afford product 5 as two diastereomers. 5-A: 0.020 g, 17.1% yield, LCMS (m/z): 367.2 [M+H]. $^1$H NMR (400 MHz, DMSO) δ 10.86 (s, 1H), 9.15 (s, 1H), 7.52 (d, J=8.3 Hz, 2H), 7.15 (d, J=8.4 Hz, 2H), 4.72 (s, 1H), 3.55 (dd, J=16.9, 10.2 Hz, 2H), 3.15 (d, J=8.1 Hz, 1H), 3.05 (s, 3H), 2.74 (d, J=8.8 Hz, 1H), 2.07 (dd, J=10.3, 6.0 Hz, 1H), 1.98-1.92 (m, 1H), 1.55 (s, 3H), 1.00 (dt, J=6.2, 4.2 Hz, 2H), 0.72 (dt, J=6.5, 4.3 Hz, 2H). 5-B (0.015 g, 12.8% yield), LCMS (m/z): 367.2 [M+H]. $^1$H NMR (400 MHz, DMSO) δ 11.06 (s, 1H), 9.29 (s, 1H), 7.52 (d, J=8.3 Hz, 2H), 7.16 (d, J=8.4 Hz, 2H), 4.60 (s, 1H), 3.54 (dd, J=16.9, 10.3 Hz, 1H), 3.16-3.08 (m, 1H), 3.07 (s, 3H), 2.64 (s, 1H), 2.07-1.92 (m, 2H), 1.59 (s, 3H), 1.00 (dt, J=6.3, 4.2 Hz, 2H), 0.75-0.65 (m, 2H).

Example 6

Synthesis of (R)-3-((R)-3-(4-(cyclopropylethynyl)phenyl)-4,5-dihydroisoxazol-5-yl)-N-hydroxy-2-methyl-2-(methylsulfonyl)propanamide [6-A]

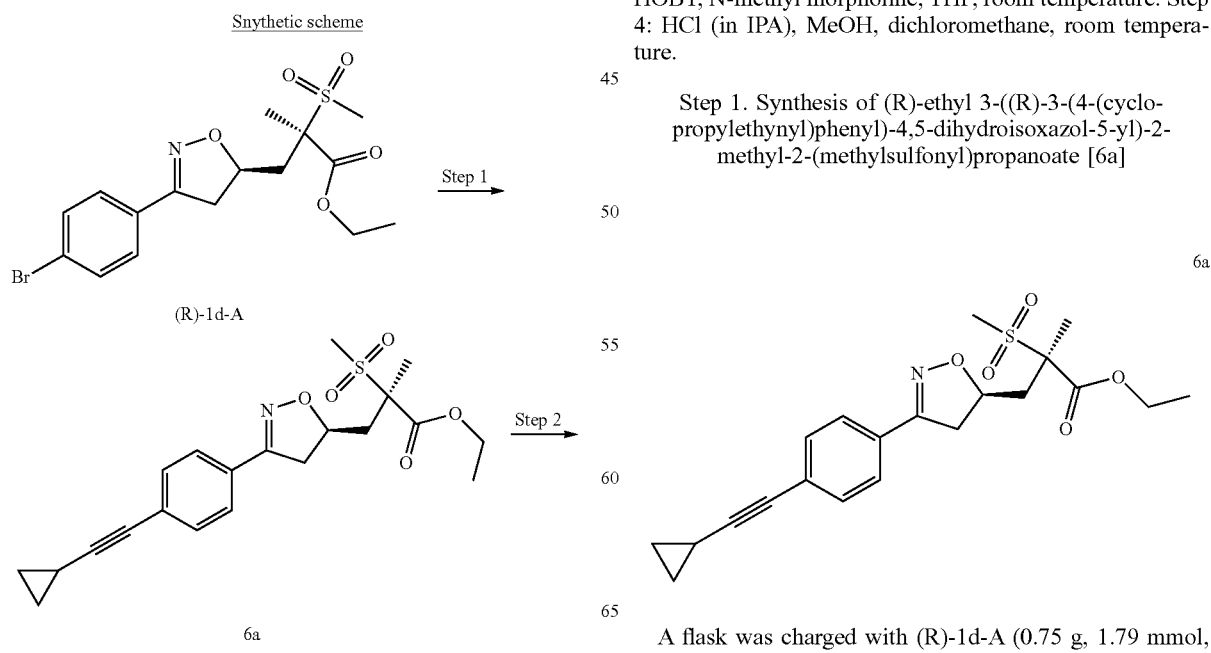

Reagents:
Step 1: Diethyl amine, triphenyl phosphine, CuI, PdCl$_2$(pph$_3$)$_2$, DMF, 100° C. Step 2: LiOH.H$_2$O, THF, MeOH, water, room temperature. Step 3: NH$_2$OTHP, EDC.HCl, HOBT, N-methyl morpholine, THF, room temperature. Step 4: HCl (in IPA), MeOH, dichloromethane, room temperature.

Step 1. Synthesis of (R)-ethyl 3-((R)-3-(4-(cyclopropylethynyl)phenyl)-4,5-dihydroisoxazol-5-yl)-2-methyl-2-(methylsulfonyl)propanoate [6a]

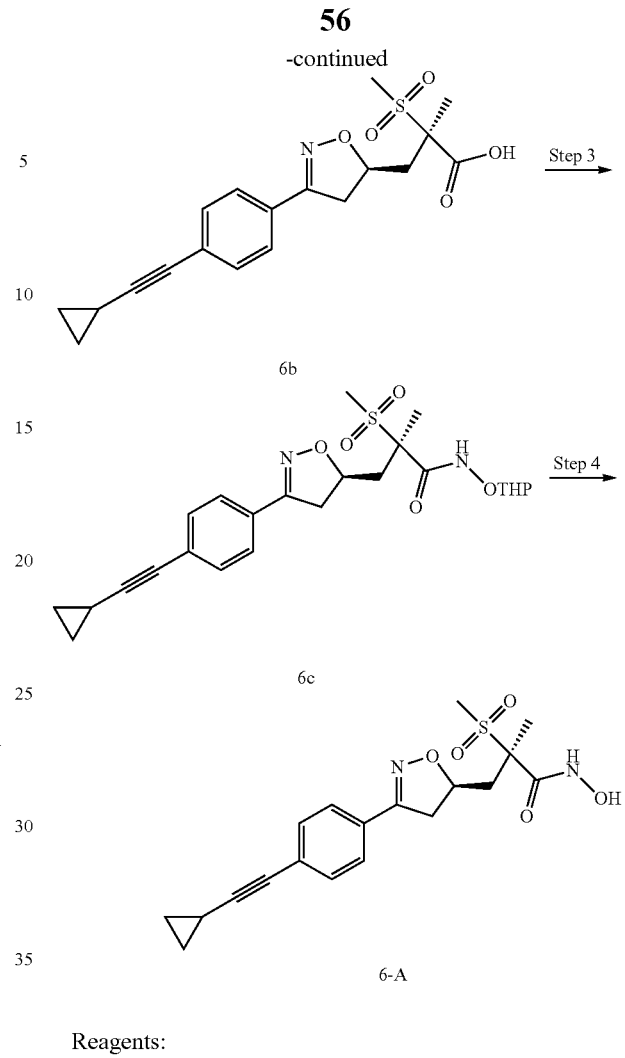

A flask was charged with (R)-1d-A (0.75 g, 1.79 mmol, 1.0 equiv), diethyl amine (10 mL) and DMF (2 mL). CuI (0.017 g, 0.089 mmol, 0.05 equiv), triphenyl phosphine (0.093 g, 0.36 mmol, 0.2 equiv) were added and the reaction mixture was degassed for 10 minutes. PdCl$_2$(PPh$_3$)$_2$ (0.062 g, 0.089 mmol, 0.05 equiv), ethynylcyclopropane (0.24 g, 3.58 mmol, 2.0 equiv) were added and the reaction mixture was stirred at 100° C. for 4 hours. The reaction mixture was quenched with water and extracted with EtOAc. The organic layer was washed with brine, dried over sodium sulfate and concentrated. The residue was purified by silica gel column chromatography (25-40% EtOAc/Hexane) to afford product 6a (0.6 g, 83% yield). LCMS (m/z): 404.2 [M+H]. $^1$H NMR (400 MHz, DMSO) δ 7.61 (d, J=8.5 Hz, 2H), 7.43 (d, J=8.5 Hz, 2H), 4.75 (d, J=7.5 Hz, 1H), 4.26 (q, J=7.1 Hz, 2H), 3.60 (dd, J=17.0, 10.3 Hz, 1H), 3.20-3.11 (m, 4H), 2.61 (s, 1H), 2.21-2.16 (m, 1H), 1.63 (s, 3H), 1.60-1.55 (m, 1H), 1.25 (t, J=7.1 Hz, 3H), 0.95-0.88 (m, 2H), 0.76 (dt, J=6.9, 3.9 Hz, 2H).

Step 2. Synthesis of (R)-3-((R)-3-(4-(cyclopropylethynyl)phenyl)-4,5-dihydroisoxazol-5-yl)-2-methyl-2-(methylsulfonyl)propanoic acid [6b]

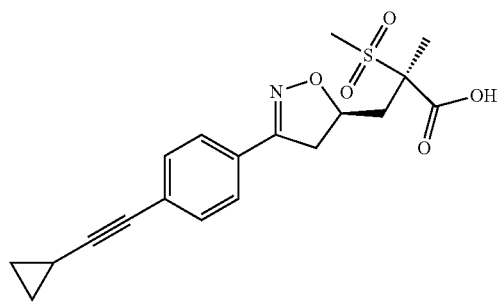

6b 6a (0.6 g, 1.49 mmol, 1.0 equiv) was dissolved in THF (12 mL), MeOH (3 mL) and water (3 mL). LiOH.H$_2$O (0.13 g, 2.97 mmol, 2.0 equiv) was added and the reaction mixture was stirred at room temperature for 2 hours. The reaction mixture was poured to water, neutralized by 2.0 N HCl aqueous solution and extracted with EtOAc. The organic layer was washed with brine, dried over sodium sulfate and concentrated to afford product 6b (0.5 g, 90% yield). LCMS (m/z): 376.2 [M+H]. The product was directly used in the next step with no further purification. $^1$H NMR (400 MHz, DMSO) δ 14.02 (s, 1H), 7.60 (d, J=8.3 Hz, 2H), 7.43 (d, J=8.3 Hz, 2H), 4.76 (d, J=7.8 Hz, 1H), 3.61 (dd, J=16.9, 10.3 Hz, 1H), 3.25-2.99 (m, 4H), 2.55 (s, 1H), 2.15 (dd, J=14.3, 8.4 Hz, 1H), 1.73-1.49 (m, 4H), 0.98-0.85 (m, 2H), 0.83-0.64 (m, 2H).

Step 3. Synthesis of (2R)-3-((R)-3-(4-(cyclopropylethynyl)phenyl)-4,5-dihydroisoxazol-5-yl)-2-methyl-2-(methylsulfonyl)-N-((tetrahydro-2H-pyran-2-yl)oxy)propanamide [6c]

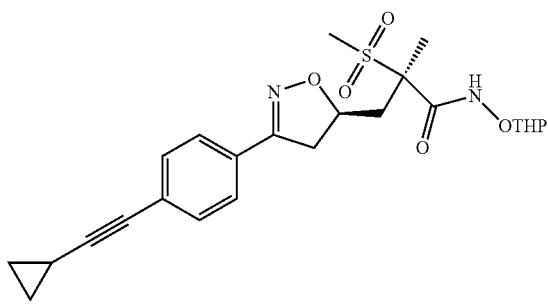

6c 6b (0.5 g, 1.34 mmol, 1.0 equiv) was dissolved in THF (35 mL). N-methyl morpholine (0.68 g, 6.68 mmol, 5.0 equiv), HOBT (0.22 g, 1.6 mmol, 1.2 equiv), O-(tetrahydro-2H-pyran-2-yl) hydroxylamine (0.32 g, 2.67 mmol, 2.0 equiv) and EDC.HCl (0.38 g, 2.0 mmol, 1.5 equiv) were added and the reaction mixture was stirred at room temperature for 24 hours. The reaction mixture was quenched with water and extracted with EtOAc. The organic layer was washed with brine, dried over sodium sulfate and concentrated. The residue was purified by silica gel column chromatography (40-60% EtOAc/Hexane) to afford product 6c (0.55 g, 87% yield). LCMS (m/z): 475.5 [M+H]. $^1$H NMR (400 MHz, DMSO) δ 11.47 (s, 1H), 7.59 (dd, J=8.4, 1.7 Hz, 2H), 7.43 (d, J=8.4 Hz, 2H), 4.97 (d, J=8.3 Hz, 1H), 4.68 (s, 1H), 4.15-4.04 (m, 1H), 3.55 (ddd, J=33.2, 16.6, 7.8 Hz, 2H), 3.14 (dd, J=17.1, 8.1 Hz, 1H), 3.06 (d, J=8.7 Hz, 3H), 2.66 (d, J=10.8 Hz, 1H), 2.06 (dd, J=13.7, 8.5 Hz, 1H), 1.69 (s, 3H), 1.64-1.38 (m, 6H), 0.96-0.85 (m, 2H), 0.81-0.64 (m, 2H).

Step 4. Synthesis of (R)-3-((R)-3-(4-(cyclopropylethynyl)phenyl)-4,5-dihydroisoxazol-5-yl)-N-hydroxy-2-methyl-2-(methylsulfonyl)propanamide [6-A]

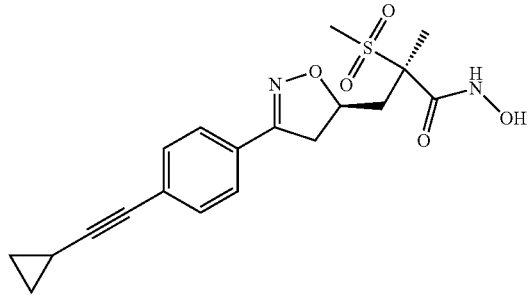

6-A 6c (0.55 g, 1.16 mmol, 1.0 equiv) was dissolved in methanol (5 mL) and dichloromethane (5 mL). 10% HCl (in IPA) (0.25 mL) was added and the reaction mixture was stirred at room temperature for 2 hours. The reaction mixture was quenched with water, neutralized by saturated aqueous sodium bicarbonate solution and extracted with EtOAc. The organic layer was washed with brine, dried over sodium sulfate and concentrated to afford crude product. The crude product was triturated with n-pentane/diethyl ether to afford product 6-A (0.43 g, 94% yield). LCMS (m/z): 391.2 [M+H]. $^1$H NMR (400 MHz, DMSO) δ 11.05 (s, 1H), 9.28 (s, 1H), 7.62 (t, J=14.4 Hz, 2H), 7.44 (d, J=8.5 Hz, 2H), 4.64 (d, J=7.4 Hz, 1H), 3.56 (dd, J=17.0, 10.4 Hz, 1H), 3.18-3.11 (m, 1H), 3.06 (s, 3H), 2.69-2.63 (m, 1H), 2.04 (dd, J=14.0, 8.5 Hz, 1H), 1.65-1.50 (m, 4H), 0.96-0.87 (m, 2H), 0.80-0.69 (m, 2H).

Example 8

Synthesis of 3-(3-(4-(but-1-yn-1-yl)phenyl)-4,5-dihydroisoxazol-5-yl)-N-hydroxy-2-methyl-2-(methylsulfonyl)propanamide [8-A, 8-B]

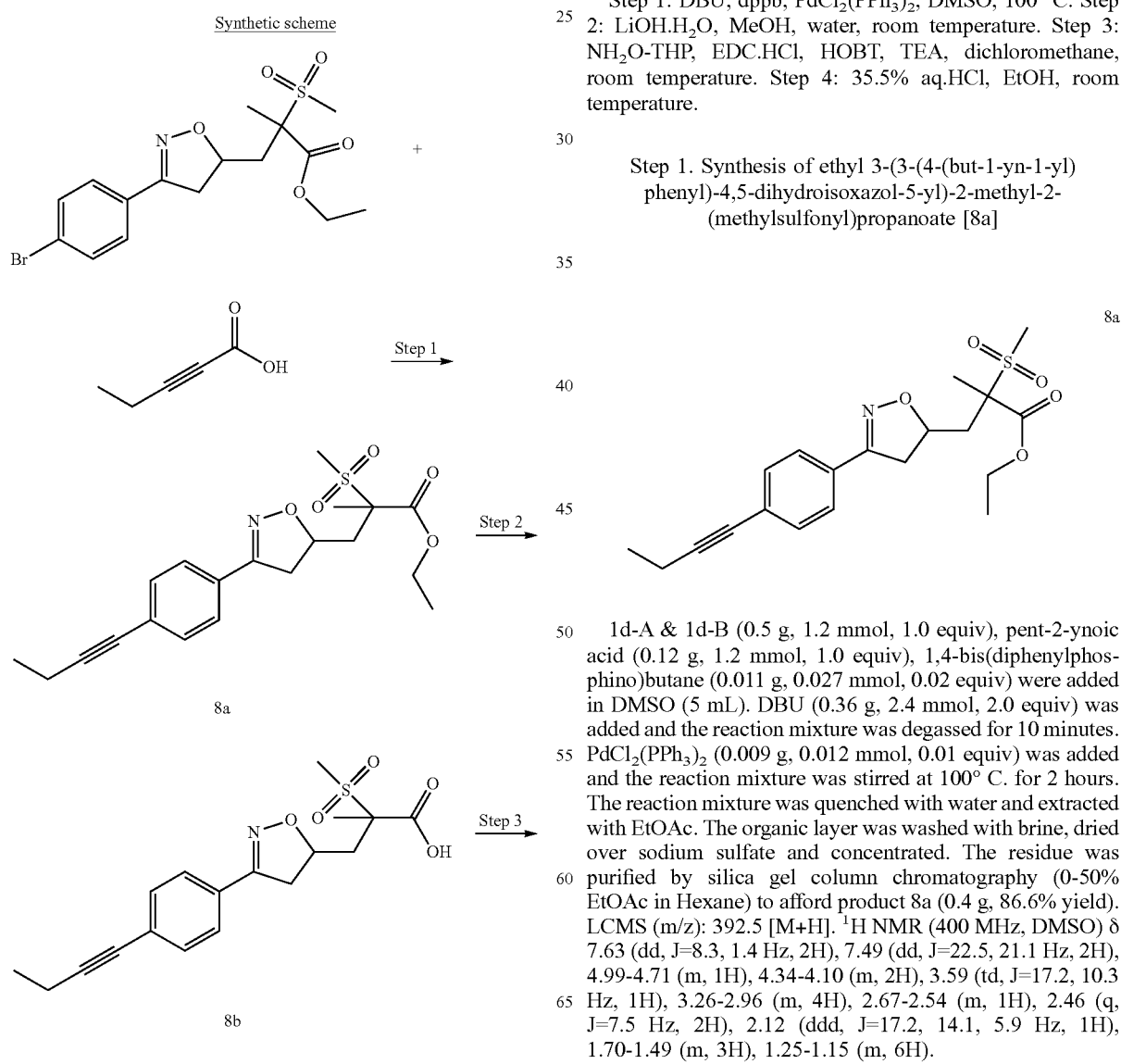

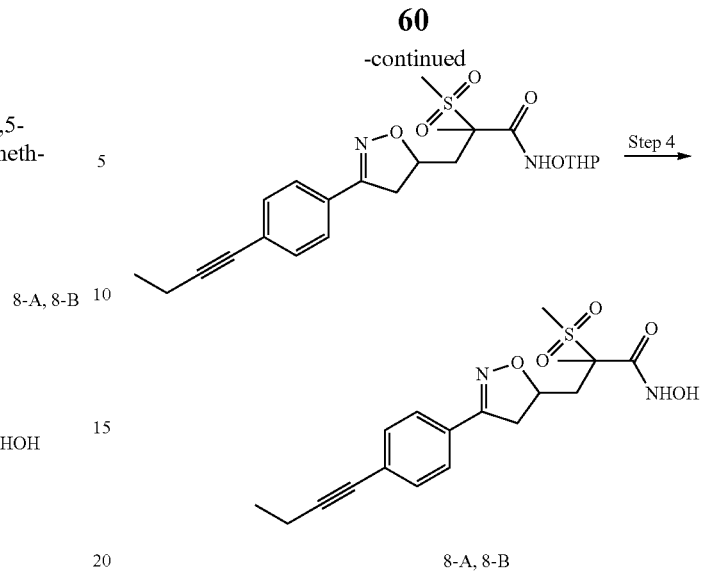

Reagents:

Step 1: DBU, dppb, PdCl$_2$(PPh$_3$)$_2$, DMSO, 100° C. Step 2: LiOH.H$_2$O, MeOH, water, room temperature. Step 3: NH$_2$O-THP, EDC.HCl, HOBT, TEA, dichloromethane, room temperature. Step 4: 35.5% aq.HCl, EtOH, room temperature.

Step 1. Synthesis of ethyl 3-(3-(4-(but-1-yn-1-yl)phenyl)-4,5-dihydroisoxazol-5-yl)-2-methyl-2-(methylsulfonyl)propanoate [8a]

1d-A & 1d-B (0.5 g, 1.2 mmol, 1.0 equiv), pent-2-ynoic acid (0.12 g, 1.2 mmol, 1.0 equiv), 1,4-bis(diphenylphosphino)butane (0.011 g, 0.027 mmol, 0.02 equiv) were added in DMSO (5 mL). DBU (0.36 g, 2.4 mmol, 2.0 equiv) was added and the reaction mixture was degassed for 10 minutes. PdCl$_2$(PPh$_3$)$_2$ (0.009 g, 0.012 mmol, 0.01 equiv) was added and the reaction mixture was stirred at 100° C. for 2 hours. The reaction mixture was quenched with water and extracted with EtOAc. The organic layer was washed with brine, dried over sodium sulfate and concentrated. The residue was purified by silica gel column chromatography (0-50% EtOAc in Hexane) to afford product 8a (0.4 g, 86.6% yield). LCMS (m/z): 392.5 [M+H]. $^1$H NMR (400 MHz, DMSO) δ 7.63 (dd, J=8.3, 1.4 Hz, 2H), 7.49 (dd, J=22.5, 21.1 Hz, 2H), 4.99-4.71 (m, 1H), 4.34-4.10 (m, 2H), 3.59 (td, J=17.2, 10.3 Hz, 1H), 3.26-2.96 (m, 4H), 2.67-2.54 (m, 1H), 2.46 (q, J=7.5 Hz, 2H), 2.12 (ddd, J=17.2, 14.1, 5.9 Hz, 1H), 1.70-1.49 (m, 3H), 1.25-1.15 (m, 6H).

Step 2. Synthesis of 3-(3-(4-(but-1-yn-1-yl)phenyl)-4,5-dihydroisoxazol-5-yl)-2-methyl-2-(methylsulfonyl)propanoic acid [8b]

Step 4. Synthesis of 3-(3-(4-(but-1-yn-1-yl)phenyl)-4,5-dihydroisoxazol-5-yl)-N-hydroxy-2-methyl-2-(methylsulfonyl)propanamide [8-A, 8-B]

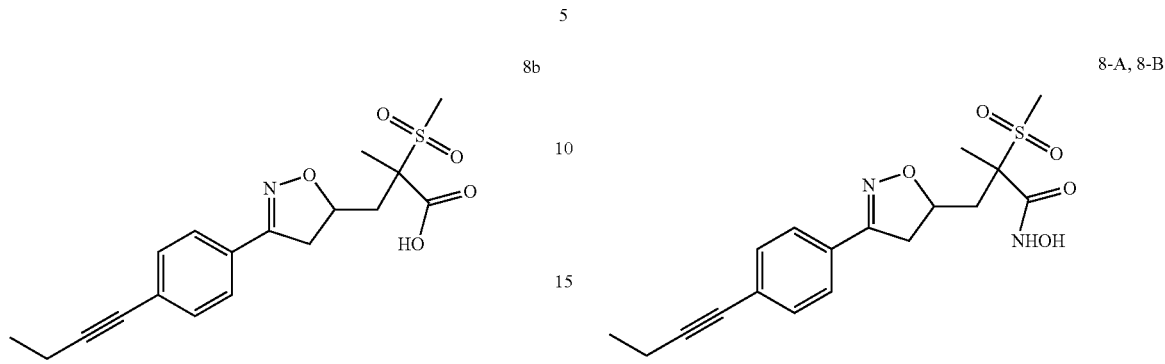

8a (0.4 g, 1.0 mmol, 1.0 equiv) was dissolved in MeOH (4 mL) and water (2 mL). LiOH.H$_2$O (0.085 g, 2.0 mmol, 2.0 equiv) was added and the reaction mixture was stirred at room temperature for 2 hours. The reaction mixture was diluted with water, acidified by 1.0 N HCl aqueous solution to the pH 4 to 5 and extracted with EtOAc. The organic layer was washed with brine, dried over sodium sulfate and concentrated to afford product 8b (0.36 g, 96.9% yield) which was used in next step without purification. LCMS (m/z): 364.3 [M+H]. $^1$H NMR (400 MHz, DMSO) δ 7.67-7.58 (m, 2H), 7.46 (d, J=8.4 Hz, 2H), 4.94-4.87 (m, 1H), 3.61 (s, 1H), 3.10 (d, J=14.7 Hz, 4H), 2.68 (s, 1H), 2.45 (s, 1H), 1.56 (d, J=17.9 Hz, 3H).

Step 3. Synthesis of 3-(3-(4-(but-1-yn-1-yl)phenyl)-4,5-dihydroisoxazol-5-yl)-2-methyl-2-(methylsulfonyl)-N-((tetrahydro-2H-pyran-2-yl)oxy)propanamide [8c]

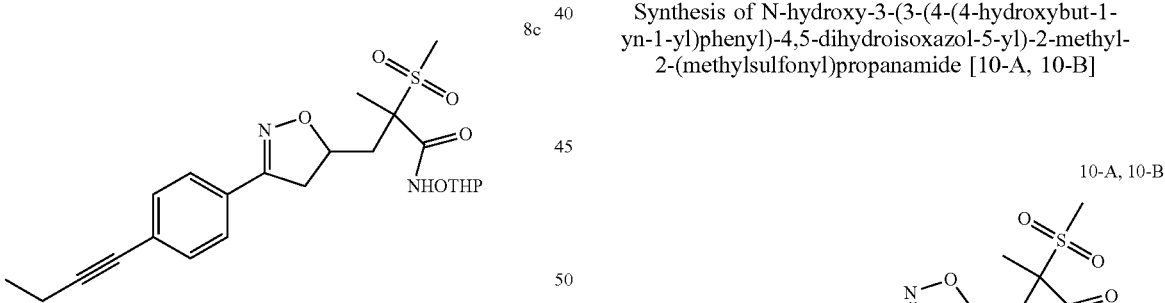

8b (0.35 g, 1.0 mmol, 1.0 equiv) was dissolved in dichloromethane (5 mL). TEA (0.49 g, 4.8 mmol, 5.0 equiv), EDC.HCl (0.28 g, 1.4 mmol, 1.5 equiv), HOBT (0.23 g, 1.7 mmol, 1.8 equiv), O-(tetrahydro-2H-pyran-2-yl) hydroxylamine (0.23 g, 1.9 mmol, 2.0 equiv) were added and the reaction mixture was stirred at room temperature for 24 hours. The reaction mixture was concentrated under reduced pressure. The residue was purified by silica gel column chromatography (0-4% MeOH in dichloromethane) to afford product 8c (0.38 g, 85.3% yield). LCMS (m/z): 463.6 [M+H]. $^1$H NMR (400 MHz, DMSO) δ 7.62 (d, J=6.9 Hz, 2H), 7.46 (d, J=8.4 Hz, 2H), 4.95 (s, 1H), 4.85-4.75 (m, 1H), 4.06-3.99 (m, 1H), 3.56 (s, 1H), 3.52 (s, 2H), 3.17-3.10 (m, 1H), 3.05 (t, J=7.3 Hz, 3H), 2.69 (s, 1H), 2.05 (s, 1H), 1.65-1.54 (m, 9H).

8c (0.38 g, 0.8 mmol, 1.0 equiv) was dissolved in ethanol (2 mL). 35.5% aq. HCl (1 mL) was added and the reaction mixture was stirred at room temperature for 4 hours. The reaction mixture was then concentrated under reduced pressure. The crude residue was purified by preparative HPLC to afford 8 as two diastereomers (8-A, 0.07 g, 22.4% yield), LCMS (m/z): 379.2 [M+H]. $^1$H NMR (400 MHz, DMSO) δ 10.86 (s, 1H), 9.15 (s, 1H), 7.62 (d, J=8.4 Hz, 2H), 7.46 (d, J=8.4 Hz, 2H), 4.79 (s, 1H), 3.57 (dd, J=16.9, 10.3 Hz, 1H), 3.16 (dd, J=17.1, 7.9 Hz, 1H), 3.11-2.95 (m, 3H), 2.77-2.65 (m, 1H), 2.45 (d, J=7.4 Hz, 2H), 2.08-2.01 (m, 1H), 1.56 (s, 3H), 1.18 (t, J=7.5 Hz, 3H). (8-B, 0.045 g, 14.4% yield), LCMS (m/z): 379.2 [M+H]. $^1$H NMR (400 MHz, DMSO) δ 11.03 (s, 1H), 9.10 (s, 1H), 7.61 (d, J=8.4 Hz, 2H), 7.46 (d, J=8.4 Hz, 2H), 3.54 (dd, J=17.0, 10.4 Hz, 1H), 3.14 (dd, J=17.1, 7.9 Hz, 1H), 3.06 (s, 3H), 2.63 (dd, J=13.9, 3.7 Hz, 1H), 2.45 (d, J=7.5 Hz, 2H), 2.02 (dd, J=13.9, 8.1 Hz, 1H), 1.56 (s, 3H), 1.18 (t, J=7.5 Hz, 3H).

Example 10

Synthesis of N-hydroxy-3-(3-(4-(4-hydroxybut-1-yn-1-yl)phenyl)-4,5-dihydroisoxazol-5-yl)-2-methyl-2-(methylsulfonyl)propanamide [10-A, 10-B]

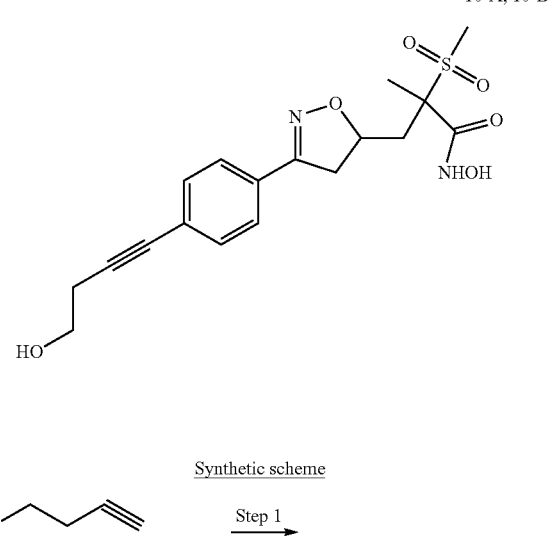

Synthetic scheme

Step 1

-continued

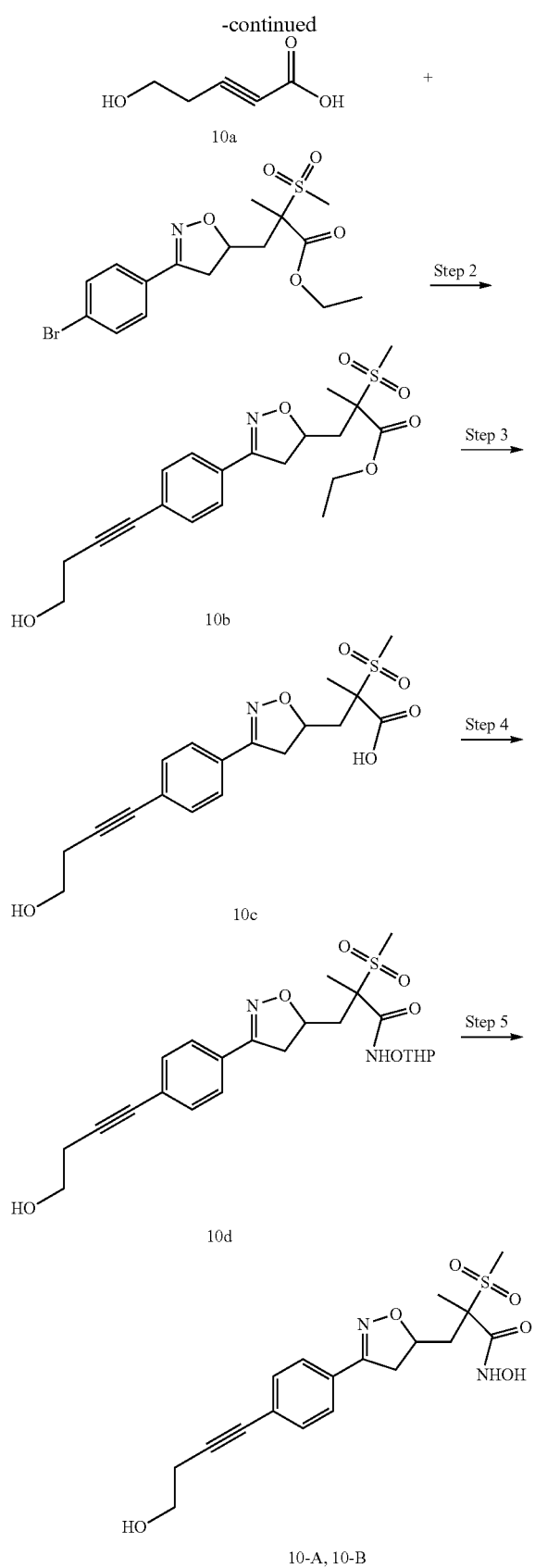

Reagents:
Step 1: n-BuLi (2.5 M in hexane), CO₂, THF, −40° C.
Step 2: DBU, dppb, PdCl₂(PPh₃)₂, DMSO, 100° C. Step 3:
LiOH.H₂O, THF, MeOH, water, room temperature. Step 4:
NH₂O-THP, EDC.HCl, HOBt, N-methyl morpholine, THF, room temperature. Step 5: 35.5% aq.HCl, EtOH, room temperature.

Step 1. Synthesis of 5-hydroxypent-2-ynoic acid [10a]

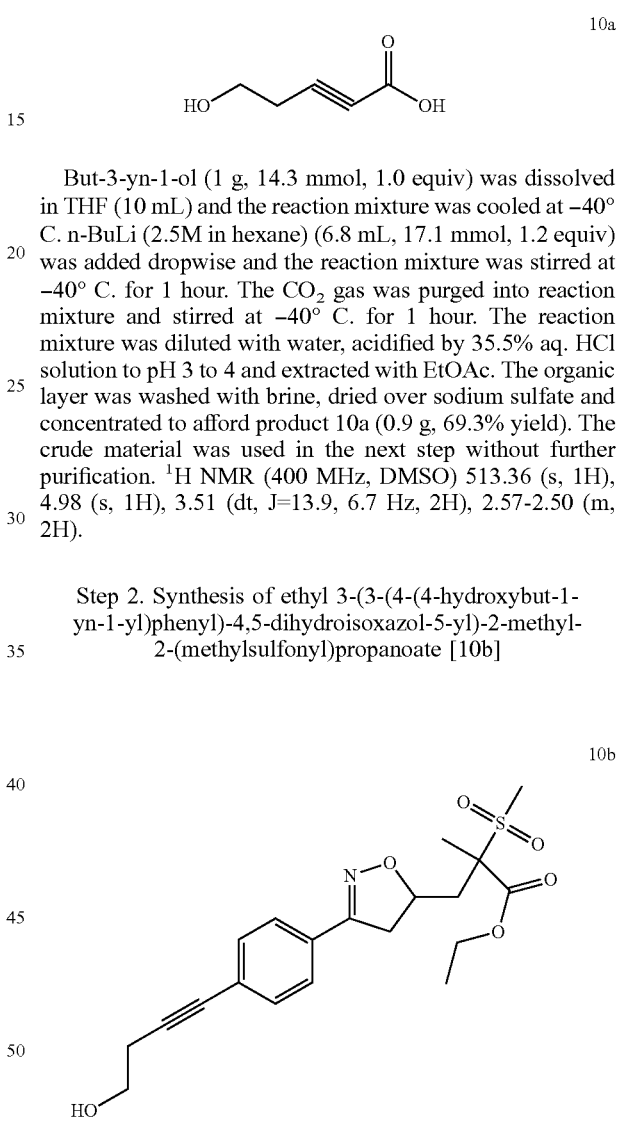

But-3-yn-1-ol (1 g, 14.3 mmol, 1.0 equiv) was dissolved in THF (10 mL) and the reaction mixture was cooled at −40° C. n-BuLi (2.5M in hexane) (6.8 mL, 17.1 mmol, 1.2 equiv) was added dropwise and the reaction mixture was stirred at −40° C. for 1 hour. The CO₂ gas was purged into reaction mixture and stirred at −40° C. for 1 hour. The reaction mixture was diluted with water, acidified by 35.5% aq. HCl solution to pH 3 to 4 and extracted with EtOAc. The organic layer was washed with brine, dried over sodium sulfate and concentrated to afford product 10a (0.9 g, 69.3% yield). The crude material was used in the next step without further purification. $^1$H NMR (400 MHz, DMSO) 513.36 (s, 1H), 4.98 (s, 1H), 3.51 (dt, J=13.9, 6.7 Hz, 2H), 2.57-2.50 (m, 2H).

Step 2. Synthesis of ethyl 3-(3-(4-(4-hydroxybut-1-yn-1-yl)phenyl)-4,5-dihydroisoxazol-5-yl)-2-methyl-2-(methylsulfonyl)propanoate [10b]

1d-A & 1d-B (0.77 g, 1.8 mmol, 1.0 equiv), 5-hydroxypent-2-ynoic acid (0.21 g, 1.8 mmol, 1.0 equiv), 1,4-bis(diphenylphosphino)butane (0.014 g, 0.04 mmol, 0.02 equiv) and DBU (0.56 g, 3.7 mmol, 2.0 equiv) were added in DMSO (10 mL) and the reaction mixture was degassed for 10 minutes. PdCl₂(PPh₃)₂ (0.013 g, 0.02 mmol, 0.01 equiv) was added and the reaction mixture was stirred at 100° C. for 3 hours. The reaction mixture was quenched with water and extracted with EtOAc. The organic layer was washed with brine, dried over sodium sulfate and concentrated. The residue was purified by silica gel column chromatography (30-50% EtOAc in Hexane) to afford product 10b (0.29 g, 74.5% yield). LCMS (m/z): 408.3 [M+H].

Step 3. Synthesis of 3-(3-(4-(4-hydroxybut-1-yn-1-yl)phenyl)-4,5-dihydroisoxazol-5-yl)-2-methyl-2-(methylsulfonyl)propanoic acid [10c]

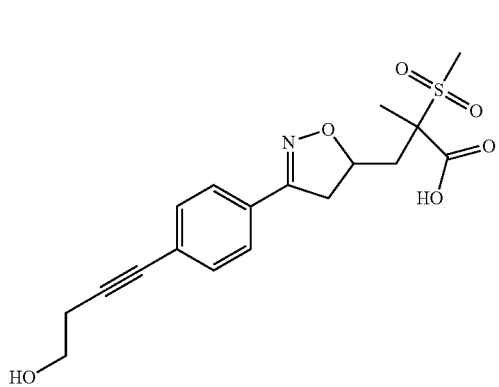

10b (0.290 g, 0.7 mmol, 1.0 equiv) was dissolved in THF (4 mL), MeOH (1 mL) and water (1 mL). LiOH.H$_2$O (0.086 g, 2.1 mmol, 3.0 equiv) was added and the reaction mixture was stirred at room temperature for 3 hours. The reaction mixture was diluted with water, acidified by 1.0 N HCl aqueous solution to the pH 3 to 4 and extracted with EtOAc. The organic layer was washed with brine, dried over sodium sulfate and concentrated to afford product 10c (0.23 g, 85.2% yield) which was used without purification in next step. LCMS (m/z): 380.3 [M+H].

Step 4. Synthesis of 3-(3-(4-(4-hydroxybut-1-yn-1-yl)phenyl)-4,5-dihydroisoxazol-5-yl)-2-methyl-2-(methylsulfonyl)-N-((tetrahydro-2H-pyran-2-yl)oxy)propanamide [10d]

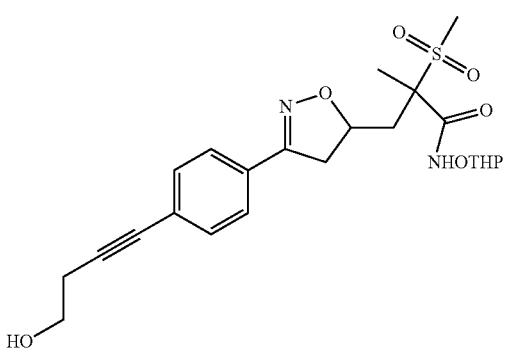

10c (0.18 g, 0.5 mmol, 1.0 equiv) was dissolved in THF (5 mL). N-methyl morpholine (0.24 g, 2.4 mmol, 5.0 equiv), EDC.HCl (0.14 g, 0.7 mmol, 1.5 equiv), HOBT (0.12 g, 0.8 mmol, 1.8 equiv), O-(tetrahydro-2H-pyran-2-yl) hydroxylamine (0.11 g, 0.9 mmol, 2.0 equiv) were added and the reaction mixture was stirred at room temperature for 24 hours. The reaction was then quenched with water and extracted with EtOAc. The organic layer was washed with brine, dried over sodium sulfate and concentrated. The residue was purified by silica gel column chromatography (1-2% MeOH in dichloromethane) to afford product 10d (0.19 g, 63.8% yield). LCMS (m/z): 395.2 [M-THP].

Step 5. Synthesis of N-hydroxy-3-(3-(4-(4-hydroxybut-1-yn-1-yl)phenyl)-4,5-dihydro isoxazol-5-yl)-2-methyl-2-(methylsulfonyl)propanamide [10-A, 10-B]

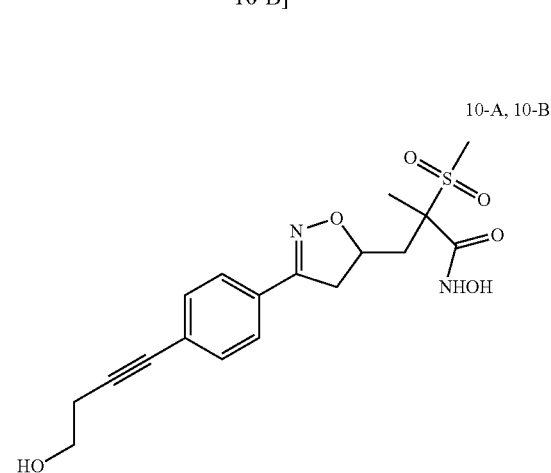

10 d (0.14 g, 0.3 mmol, 1.0 equiv) was dissolved in ethanol (5 mL). 35.5% aq. HCl (0.4 mL) was added and the reaction mixture was stirred at room temperature for 1 hour. The reaction mixture was diluted with water, neutralized by saturated aqueous sodium bicarbonate solution and extracted with EtOAc. The organic layer was washed with brine, dried over sodium sulfate and concentrated. The crude product was purified by preparative HPLC purification to afford 10 as two diastereomers. 10-A: 0.023 g, 15.1% yield. LCMS (m/z): 395.3 [M+H]. $^1$H NMR (400 MHz, DMSO) δ 10.81 (s, 1H), 9.16 (s, 1H), 7.62 (d, 2H), 7.47 (d, 2H), 4.96 (m, 1H), 4.77 (m, 1H), 3.59 (s, 3H), 3.12 (m, 1H), 3.05 (s, 3H), 2.73 (m, 1H), 2.58 (s, 2H), 2.07 (m, 1H), 1.55 (s, 3H). (10-B, 0.029 g, 19% yield), LCMS (m/z): 395.5 [M+H]. $^1$H NMR (400 MHz, DMSO) δ 11.21-10.87 (m, 1H), 9.55-9.21 (m, 1H), 7.62 (d, J=6.9 Hz, 2H), 7.47 (d, J=6.6 Hz, 2H), 4.94 (m, 1H), 4.64 (m, 1H), 3.60 (s, 3H), 3.15 (s, 1H), 3.06 (s, 3H), 2.65 (d, J=14.5 Hz, 1H), 2.58 (m, 2H), 2.04 (m, 1H), 1.58 (s, 3H).

Example 12

Synthesis of 3-(3-(3-fluoro-4-(prop-1-yn-1-yl)phenyl)-4,5-dihydroisoxazol-5-yl)-N-hydroxy-2-methyl-2-(methylsulfonyl)propanamide [12A, 12 B]

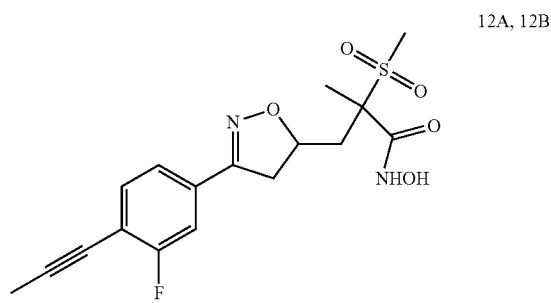

Synthetic scheme

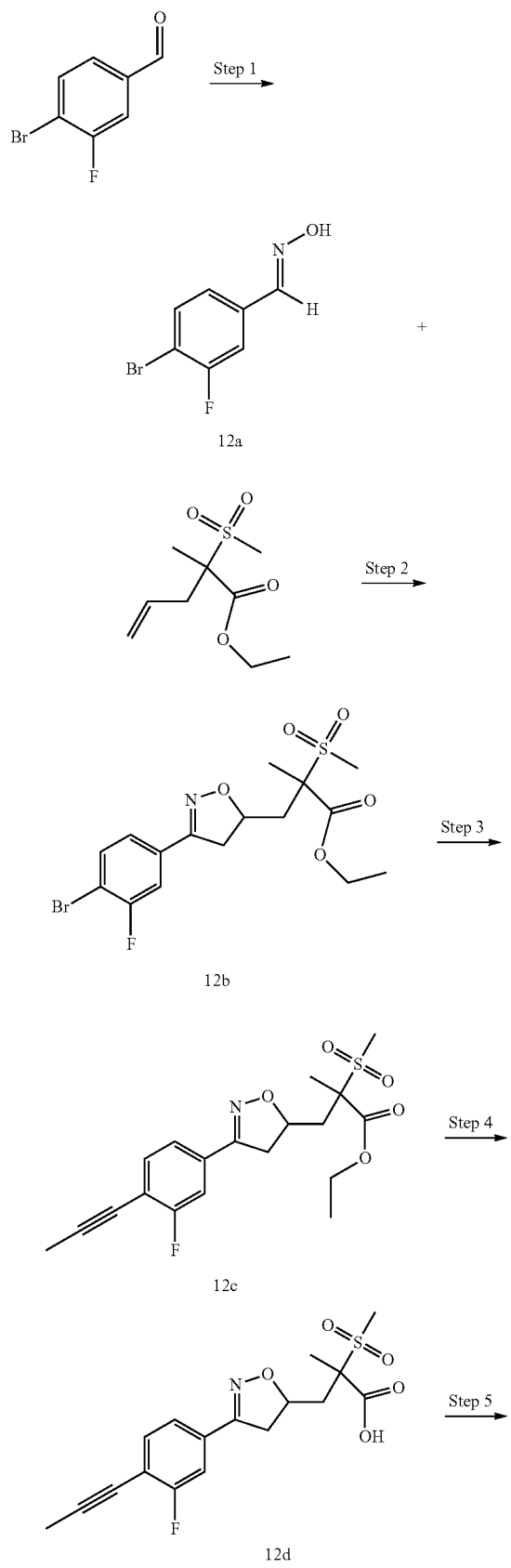

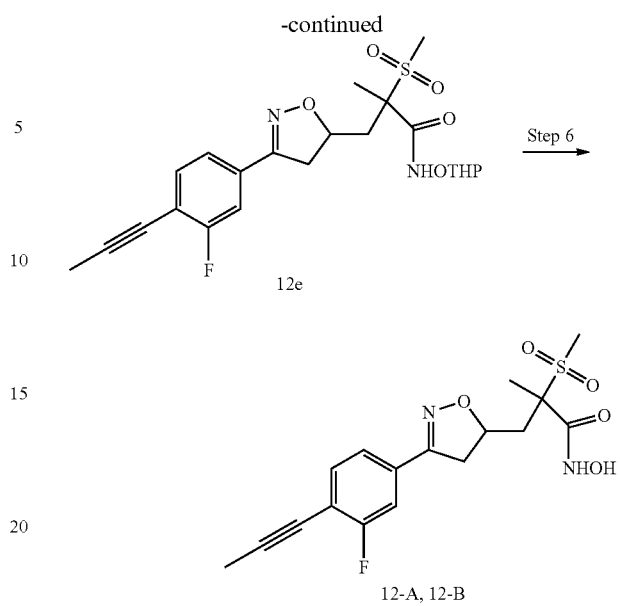

Reagents:

Step 1: NH$_2$OH.HCl, NaOH, water, 70° C. Step 2: Et$_2$Zn, (R,R)-DIPT, tBuOCl, chloroform, 1,4-dioxane, 0° C. to room temperature. Step 3: DBU, dppb, PdCl$_2$(PPh$_3$)$_2$, DMSO, 90° C. Step 4: LiOH.H$_2$O, THF, MeOH, water, room temperature to 40° C. Step 5: NH$_2$O-THP, EDC.HCl, HOBt, N-methyl morpholine, THF, room temperature. Step 6: 35.5% aq.HCl, EtOH, room temperature.

Step 1. Synthesis of 4-bromo-3-fluorobenzaldehyde oxime [12a]

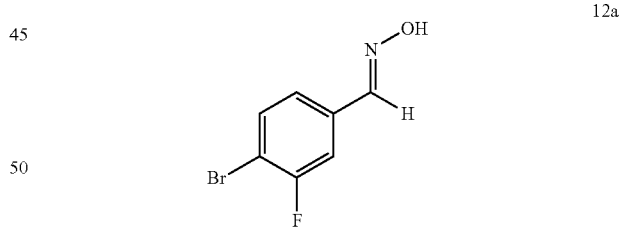

4-bromo-3-fluorobenzaldehyde (10 g, 49.2 mmol, 1.0 equiv) was added in water (150 mL) and the reaction mixture was stirred at 70° C. A solution of hydroxylamine hydrochloride (4.1 g, 59.1 mmol, 1.2 equiv) and sodium hydroxide (2.56 g, 64.0 mmol, 1.3 equiv) in water (50 mL) was added to the reaction mixture at same temperature and the reaction mixture was stirred for 4 hours. The reaction mixture was cooled to room temperature. The precipitate was collected by filtration and then washed with hexane to afford product 12a (7.5 g, 69.8% yield). LCMS (m/z): 218.0 [M+H].

Step 2. Synthesis of ethyl 3-(3-(4-bromo-3-fluoro-phenyl)-4,5-dihydroisoxazol-5-yl)-2-methyl-2-(methylsulfonyl)propanoate [12b]

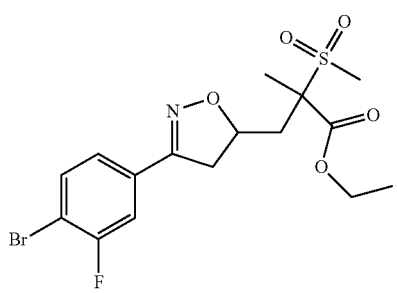

A solution of 1b (6.9 g, 31.3 mmol, 1.0 equiv) in chloroform (80 mL) was cooled in a ice-water bath. Diethyl zinc (1M in hexane) (4.3 g, 34.1 mmol, 1.1 equiv) was added and the reaction mixture was stirred at 0° C. for 20 minutes. (R,R)-DIPT (7.3 g, 31.3 mmol, 1.0 equiv) was added and the reaction mixture was stirred at 0° C. for 1 hour. Diethyl zinc (1M in hexane) (4.3 g, 34.1 mmol, 1.1 equiv), 1,4-dioxane (4.14 g, 47.0 mmol, 1.5 equiv) and 12a (6.8 g, 31.3 mmol, 1.0 equiv) in chloroform (20 mL) were added slowly. t-BuOCl (6.8 g, 62.7 mmol, 2.0 equiv) was added and the reaction mixture was stirred at room temperature for 24 hours. The reaction mixture was quenched with saturated aqueous ammonium chloride solution and extracted with EtOAc. The organic layer was washed with brine, dried over sodium sulfate and concentrated. The crude product was purified by silica gel column chromatography (0-40% EtOAc in Hexane) to afford product 12b (9.7 g, 70.9% yield). LCMS (m/z): 436.6 [M+H]. $^1$H NMR (400 MHz, DMSO) δ 7.82 (t, J=7.8 Hz, 1H), 7.63 (dt, J=9.8, 1.7 Hz, 1H), 7.53-7.43 (m, 1H), 4.93-4.76 (m, 1H), 4.24 (ddd, J=10.6, 10.0, 5.1 Hz, 2H), 3.66-3.54 (m, 1H), 3.23-3.17 (m, 1H), 3.11 (d, J=9.0 Hz, 3H), 2.72-2.55 (m, 1H), 2.24-2.03 (m, 1H), 1.65-1.57 (m, 3H), 1.22-1.17 (m, 3H).

Step 3. Synthesis of ethyl 3-(3-(3-fluoro-4-(prop-1-yn-1-yl)phenyl)-4,5-dihydroisoxazol-5-yl)-2-methyl-2-(methylsulfonyl)propanoate [12c]

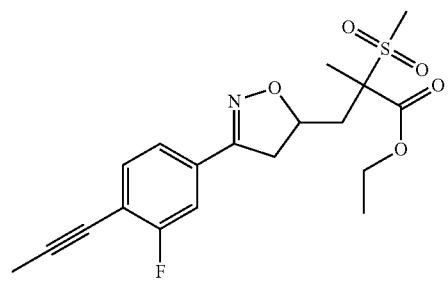

12b (0.25 g, 0.6 mmol, 1.0 equiv), but-2-ynoic acid (0.057 g, 0.7 mmol, 1.2 equiv), 1,4-bis(diphenylphosphino)butane (0.005 g, 0.013 mmol, 0.02 equiv) were added in DMSO (9 mL). DBU (0.17 g, 1.1 mmol, 2.0 equiv) was added and the reaction mixture was degassed for 10 minutes. PdCl$_2$(PPh$_3$)$_2$ (0.004 g, 0.006 mmol, 0.01 equiv) was added and the reaction mixture was stirred at 90° C. for 6 hours. The reaction mixture was quenched with water and extracted with EtOAc. The organic layer was washed with brine, dried over sodium sulfate and concentrated. The residue was purified by silica gel column chromatography (0-40% EtOAc in Hexane) to afford product 12c (0.18 g, 79.3% yield). LCMS (m/z): 396.1 [M+H]. $^1$H NMR (400 MHz, DMSO) δ 7.64-7.44 (m, 3H), 4.91-4.73 (m, 1H), 4.23 (dq, J=29.2, 7.1 Hz, 2H), 3.59 (ddd, J=20.1, 17.0, 10.3 Hz, 1H), 3.19 (dd, J=17.6, 6.3 Hz, 1H), 3.12 (d, J=20.0 Hz, 3H), 2.68-2.55 (m, 1H), 2.14-1.98 (m, 4H), 1.68-1.55 (m, 3H), 1.23-1.20 (m, 3H).

Step 4. Synthesis of 3-(3-(3-fluoro-4-(prop-1-yn-1-yl)phenyl)-4,5-dihydroisoxazol-5-yl)-2-methyl-2-(methylsulfonyl)propanoic acid [12d]

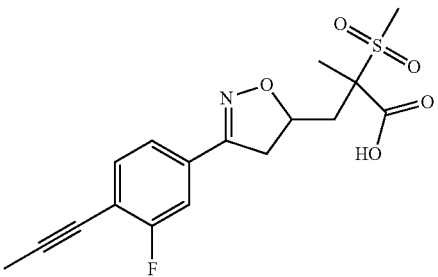

12c (0.18 g, 0.5 mmol, 1.0 equiv) was dissolved in THF (2 mL), MeOH (1 mL) and water (1 mL). LiOH.H$_2$O (0.038 g, 0.9 mmol, 2.0 equiv) was added and the reaction mixture was stirred at 40° C. for 2 hours. The reaction mixture was diluted with water and extracted with EtOAc. The aqueous layer was acidified by 1.0 N HCl aqueous solution to the pH 3 to 4 and extracted with EtOAc. The organic layer was washed with brine, dried over sodium sulfate and concentrated. To the residue was then added n-pentane. The solvent was decanted and the remaining material was dried to afford product 12d (0.16 g, 94.7% yield). LCMS (m/z): 368.4 [M+H]. $^1$H NMR (400 MHz, DMSO) δ 13.64 (s, 1H), 7.53 (ddd, J=27.3, 17.5, 8.6 Hz, 3H), 4.88 (d, J=56.3 Hz, 1H), 3.65-3.54 (m, 1H), 3.20 (dd, J=12.6, 5.0 Hz, 1H), 3.12 (t, J=11.9 Hz, 3H), 2.64 (d, J=13.9 Hz, 1H), 2.27-2.00 (m, 4H), 1.67-1.47 (m, 3H).

Step 5. Synthesis of 3-(3-(3-fluoro-4-(prop-1-yn-1-yl)phenyl)-4,5-dihydroisoxazol-5-yl)-2-methyl-2-(methylsulfonyl)-N-((tetrahydro-2H-pyran-2-yl)oxy)propanamide [12e]

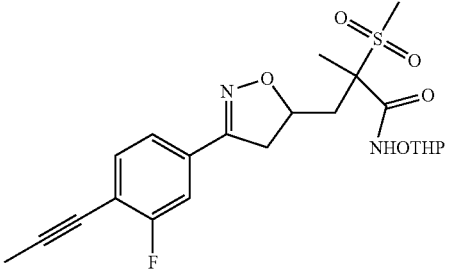

12d (0.16 g, 0.43 mmol, 1.0 equiv) was dissolved in THF (5 mL). N-methyl morpholine (0.22 g, 2.15 mmol, 5.0 equiv), EDC.HCl (0.12 g, 0.6 mmol, 1.5 equiv), HOBT (0.069 g, 0.5 mmol, 1.2 equiv), O-(tetrahydro-2H-pyran-2-yl) hydroxylamine (0.1 g, 0.8 mmol, 2.0 equiv) were added and the reaction mixture was stirred at room temperature for 15 hours. The reaction mixture was quenched with water and extracted with EtOAc. The organic layer was washed with brine, dried over sodium sulfate and concentrated. The residue was purified by silica gel column chromatography (0-5% MeOH in dichloromethane) to afford product 12e (0.16 g, 76.8% yield). LCMS (m/z): 467.4 [M+H]. $^1$H NMR (400 MHz, DMSO) δ 11.34 (s, 1H), 7.63-7.41 (m, 3H), 4.95 (s, 1H), 4.71 (s, 1H), 3.58 (s, 1H), 3.44 (dd, J=7.1, 3.6 Hz, 2H), 3.19-3.11 (m, 1H), 3.11-2.96 (m, 3H), 2.70 (d, J=14.0 Hz, 1H), 2.06 (d, J=9.9 Hz, 1H), 1.68 (d, J=13.8 Hz, 3H), 1.44 (ddd, J=13.0, 6.6, 3.2 Hz, 6H).

Step 6. Synthesis of 3-(3-(3-fluoro-4-(prop-1-yn-1-yl)phenyl)-4,5-dihydroisoxazol-5-yl)-N-hydroxy-2-methyl-2-(methylsulfonyl)propanamide [12-A, 12-B]

12-A, 12-B

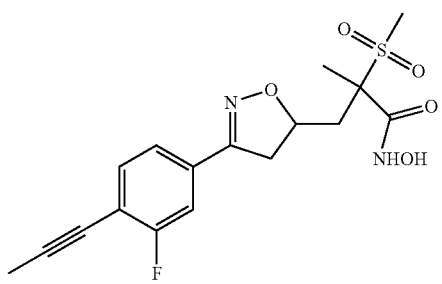

12e (0.16 g, 0.34 mmol, 1.0 equiv) was dissolved in ethanol (5 mL). 35.5% aq. HCl (0.3 mL) was added and the reaction mixture was stirred at room temperature for 1.5 hours. The reaction mixture was diluted with water, neutralized by saturated aqueous sodium bicarbonate solution and extracted with EtOAc. The organic layer was washed with brine, dried over sodium sulfate and concentrated. The crude product was purified by preparative HPLC purification to afford 12 as two diastereomers. 12-A: 0.023 g, 17.6% yield. LCMS (m/z): 383.4 [M+H]. $^1$H NMR (400 MHz, DMSO) δ 10.87 (s, 1H), 9.15 (s, 1H), 7.64-7.41 (m, 3H), 4.80 (s, 1H), 3.57 (dd, J=17.0, 10.4 Hz, 1H), 3.16 (dd, J=17.1, 7.8 Hz, 1H), 3.11-2.99 (m, 3H), 2.74 (dd, J=13.6, 8.4 Hz, 1H), 2.05 (dd, J=13.8, 4.5 Hz, 1H), 1.62-1.48 (m, 3H). 12-B: 0.020 g, 15.3% yield. LCMS (m/z): 383.4 [M+H]. $^1$H NMR (400 MHz, DMSO) δ 11.07 (s, 1H), 9.29 (s, 1H), 7.60-7.45 (m, 3H), 4.67 (d, J=6.8 Hz, 1H), 3.58 (dd, J=17.0, 10.3 Hz, 1H), 3.14 (dd, J=17.3, 8.1 Hz, 1H), 3.07 (s, 3H), 2.66 (d, J=14.2 Hz, 1H), 2.05 (dd, J=14.1, 8.5 Hz, 1H), 1.59 (s, 3H).

Example 13

Synthesis of 3-(3-(4-(cyclopropylethynyl)-3-fluorophenyl)-4,5-dihydroisoxazol-5-yl)-N-hydroxy-2-methyl-2-(methylsulfonyl)propanamide [13-A, 13-B]

13-A, 13-B

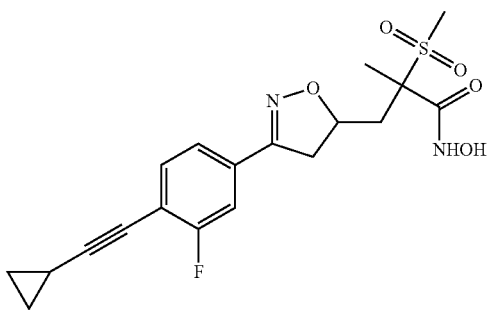

Synthetic scheme

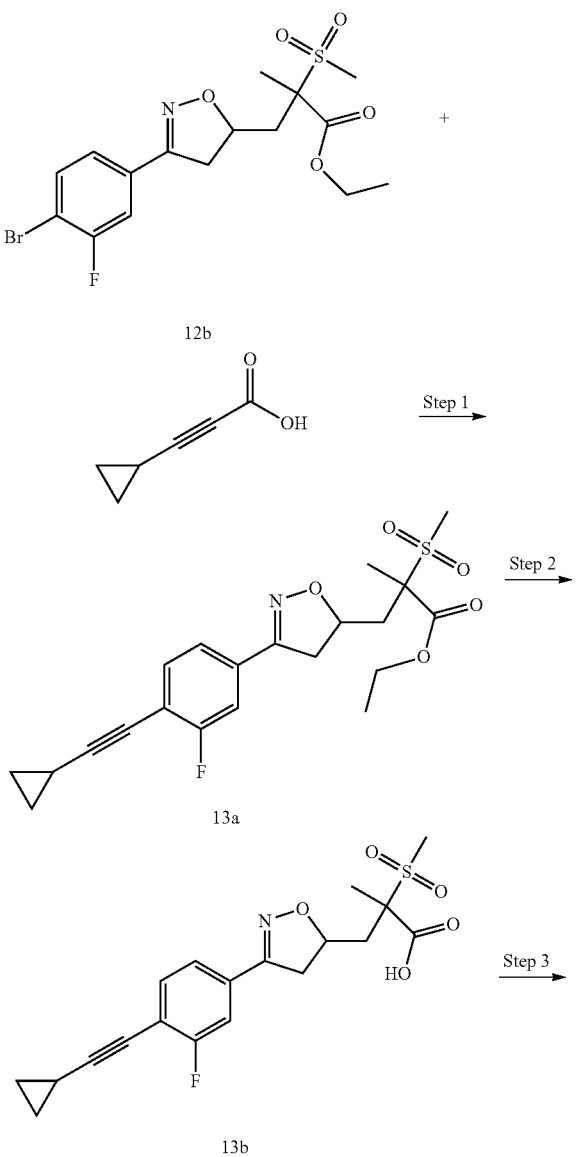

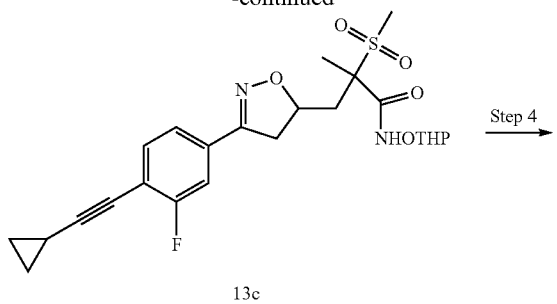

13c

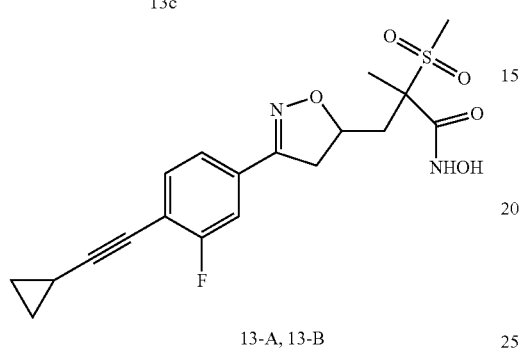

13-A, 13-B

Reagents:
Step 1: DBU, dppb, PdCl$_2$(PPh$_3$)$_2$, DMSO, 100° C. Step 2: NaOH, MeOH, room temperature. Step 3: NH$_2$O-THP, EDC.HCl, HOBT, N-methyl morpholine, THF, room temperature. Step 4: 35.5% aq.HCl, EtOH, room temperature.

Step 1. Synthesis of ethyl 3-(3-(4-(cyclopropylethynyl)-3-fluorophenyl)-4,5-dihydro isoxazol-5-yl)-2-methyl-2-(methylsulfonyl)propanoate [13a]

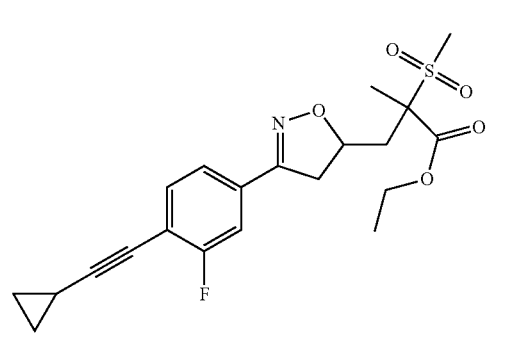

12b (0.3 g, 0.7 mmol, 1.0 equiv), 3-cyclopropylpropiolic acid (0.075 g, 0.7 mmol, 1.0 equiv), 1,4-bis(diphenylphosphino)butane (0.007 g, 0.015 mmol, 0.02 equiv) were added in DMSO (8 mL). DBU (0.21 g, 1.3 mmol, 2.0 equiv) was added and the reaction mixture was degassed for 10 minutes. PdCl$_2$(PPh$_3$)$_2$ (0.005 g, 0.007 mmol, 0.01 equiv) was added and the reaction mixture was stirred at 100° C. for 8 hours. The reaction mixture was quenched with water and extracted with EtOAc. The organic layer was washed with brine, dried over sodium sulfate and concentrated to afford a crude residue. The residue was purified by silica gel column chromatography (50-70% EtOAc in Hexane) to afford product 13a (0.21 g, 72% yield). LCMS (m/z): 422.5 [M+H]. $^1$H NMR (400 MHz, DMSO) δ 7.59-7.41 (m, 3H), 4.92-4.73 (m, 1H), 4.28-4.17 (m, 2H), 3.58 (ddd, J=20.0, 17.1, 10.3 Hz, 1H), 3.22-3.15 (m, 1H), 3.12 (d, J=20.0 Hz, 3H), 2.66-2.55 (m, 1H), 2.20-2.04 (m, 1H), 1.71-1.55 (m, 4H), 1.25-1.22 (m, 3H), 0.98-0.91 (m, 2H), 0.81-0.76 (m, 2H).

Step 2. Synthesis of 3-(3-(4-(cyclopropylethynyl)-3-fluorophenyl)-4,5-dihydroisoxazol-5-yl)-2-methyl-2-(methylsulfonyl)propanoic acid [13b]

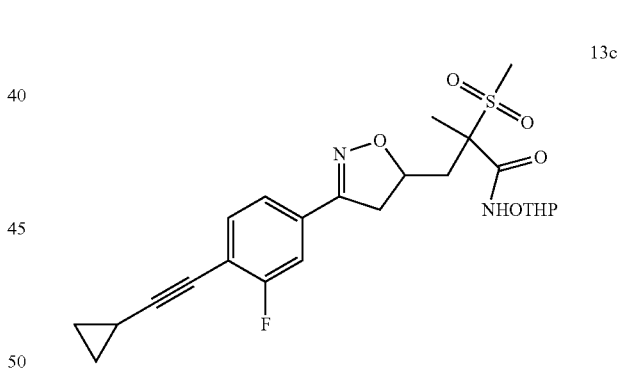

13a (0.21 g, 0.5 mmol, 1.0 equiv) was dissolved in MeOH (5 mL). NaOH (0.039 g, 0.9 mmol, 2.0 equiv) was added and the reaction mixture was stirred at room temperature for 2 hours. The reaction mixture was diluted with water and extracted with EtOAc. The aqueous layer was neutralized by 2.0 N HCl aqueous solution and extracted with EtOAc. The organic layer was washed with brine, dried over sodium sulfate and concentrated to afford product 13b (0.17 g, 87% yield) which was used without purification in next step. LCMS (m/z): 394.4 [M+H].

Step 3. Synthesis of 3-(3-(4-(cyclopropylethynyl)-3-fluorophenyl)-4,5-dihydroisoxazol-5-yl)-2-methyl-2-(methylsulfonyl)-N-((tetrahydro-2H-pyran-2-yl)oxy) propanamide [13c]

13b (0.17 g, 0.43 mmol, 1.0 equiv) was dissolved in THF (8 mL). N-methyl morpholine (0.22 g, 2.16 mmol, 5.0 equiv), EDC.HCl (0.12 g, 0.6 mmol, 1.5 equiv), HOBT (0.07 g, 0.5 mmol, 1.2 equiv), O-(tetrahydro-2H-pyran-2-yl) hydroxylamine (0.1 g, 0.9 mmol, 2.0 equiv) were added and the reaction mixture was stirred at room temperature for 24 hours. The reaction mixture was quenched with water and extracted with EtOAc. The organic layer was washed with brine, dried over sodium sulfate and concentrated to afford a crude residue. The residue was purified by silica gel column chromatography (50-70% EtOAc in Hexane) to afford product 13c (0.18 g, 89.5% yield). LCMS (m/z): 409.4 [M-THP]. $^1$H NMR (400 MHz, DMSO) δ 11.58-11.22 (m, 1H), 7.60-7.42 (m, 3H), 5.21-5.07 (m, 1H), 4.99-4.85 (m, 1H), 3.74 (qd, J=8.9, 4.6 Hz, 1H), 3.52 (ddd, J=12.6, 10.0, 4.1 Hz, 2H), 3.21-3.13 (m, 1H), 3.05 (dd, J=10.2, 4.7

Hz, 3H), 2.70 (ddd, J=21.8, 14.0, 8.1 Hz, 1H), 2.12-2.03 (m, 1H), 1.70-1.45 (m, 10H), 0.98-0.91 (m, 2H), 0.82-0.76 (m, 2H).

Step 4. Synthesis of 3-(3-(4-(cyclopropylethynyl)-3-fluorophenyl)-4,5-dihydroisoxazol-5-yl)-N-hydroxy-2-methyl-2-(methylsulfonyl)propanamide [13-A, 13-B]

13-A, 13-B 13c (0.18 g, 0.36 mmol, 1.0 equiv) was dissolved in ethanol (5 mL). 35.5% aq. HCl (0.2 mL) was added and the reaction mixture was stirred at room temperature for 2 hours. The reaction mixture was diluted with water, neutralized by saturated aqueous sodium bicarbonate solution and extracted with EtOAc. The organic layer was washed with brine, dried over sodium sulfate and concentrated to afford crude residue. The residue was purified by preparative HPLC purification to afford 13 as two diastereomers. 13-A: 0.028 g, 18.6% yield. LCMS (m/z): 409.3 [M+H]. $^1$H NMR (400 MHz, DMSO) δ 10.86 (s, 1H), 9.14 (s, 1H), 7.62-7.40 (m, 3H), 4.78 (d, J=4.5 Hz, 1H), 3.56 (dd, J=17.1, 10.4 Hz, 1H), 3.16 (dd, J=17.0, 7.9 Hz, 1H), 3.11-2.99 (m, 3H), 2.73 (dd, J=13.7, 8.4 Hz, 1H), 2.05 (dd, J=13.9, 4.7 Hz, 1H), 1.63 (ddd, J=13.2, 8.2, 5.0 Hz, 1H), 1.53 (d, J=20.1 Hz, 3H), 0.99-0.89 (m, 2H), 0.82-0.74 (m, 2H). 13-B: 0.020 g, 13.4% yield. LCMS (m/z): 409.3 [M+H]. $^1$H NMR (400 MHz, DMSO) δ 11.07 (s, 1H), 9.29 (s, 1H), 7.58-7.42 (m, 3H), 4.66 (d, J=7.9 Hz, 1H), 3.57 (dd, J=17.1, 10.5 Hz, 1H), 3.13 (dd, J=17.2, 8.0 Hz, 1H), 3.06 (s, 3H), 2.70-2.61 (m, 1H), 2.05 (dd, J=14.0, 8.5 Hz, 1H), 1.68-1.61 (m, 1H), 1.59 (s, 3H), 0.95 (td, J=6.7, 4.1 Hz, 2H), 0.84-0.76 (m, 2H).

Example 14

Synthesis of N-hydroxy-2-methyl-2-(methylsulfonyl)-3-(3-(5-(prop-1-yn-1-yl)pyridin-2-yl)-4,5-dihydroisoxazol-5-yl)propanamide [14-A, 14-B]

14-A, 14-B

Synthetic scheme

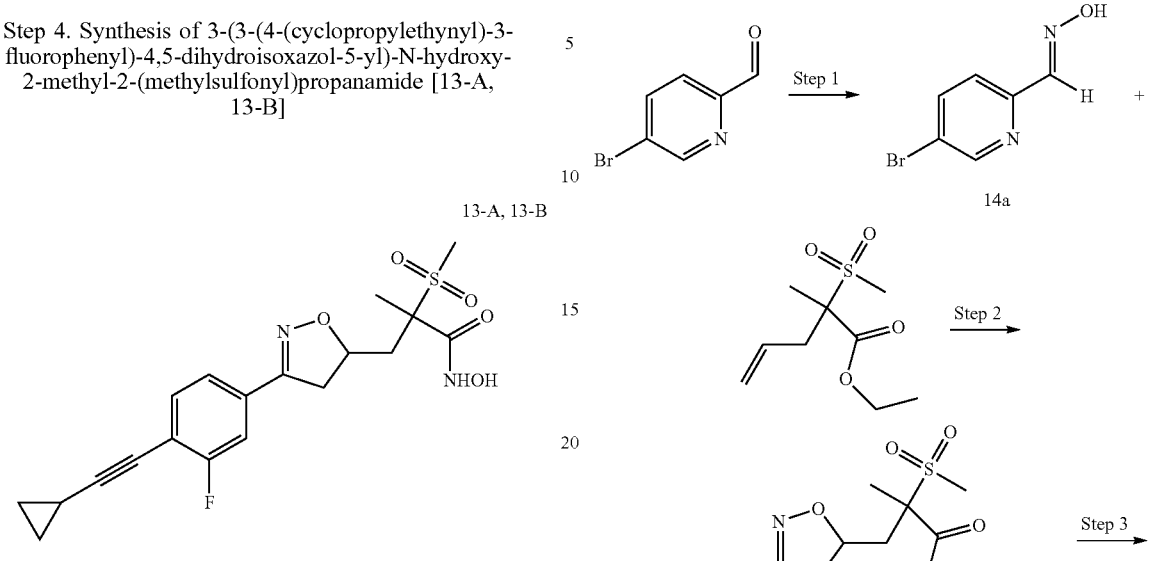

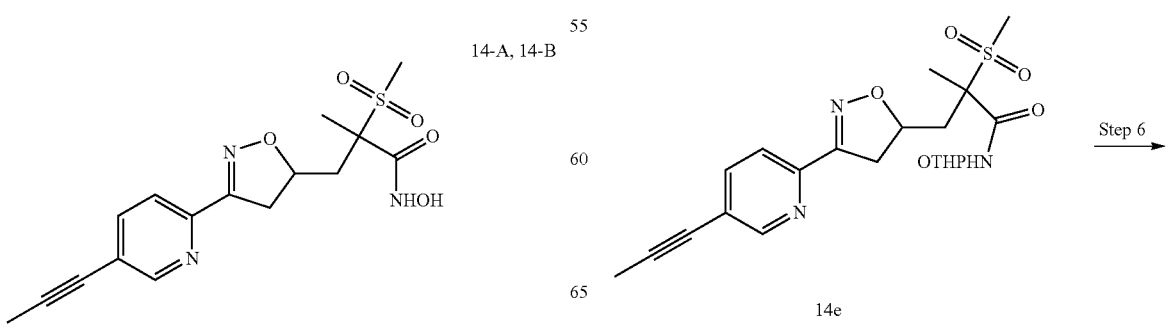

-continued

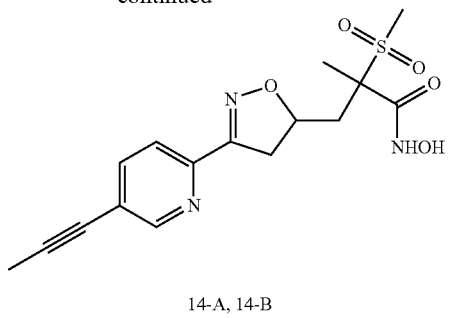

14-A, 14-B

Reagents:
Step 1: NH₂OH.HCl, Na₂CO₃, MeOH, water, room temperature. Step 2: NaOCl (14%), chloroform, 0° C. to room temperature. Step 3: DBU, dppb, PdCl₂(PPh₃)₂, DMSO, 120° C. Step 4: LiOH.H₂O, THF, MeOH, water, room temperature. Step 5: NH₂O-THP, EDC.HCl, HOBt, N-methyl morpholine, THF, room temperature. Step 6: 35.5% aq.HCl, EtOH, room temperature.

Step 1. Synthesis of 5-bromopicolinaldehyde oxime [14a]

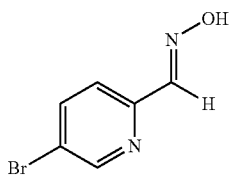

5-Bromopicolinaldehyde (1 g, 5.4 mmol, 1.0 equiv) was dissolved in MeOH (18 mL) and water (2 mL). Hydroxylamine hydrochloride (0.45 g, 6.4 mmol, 1.2 equiv), Sodium carbonate (0.57 g, 5.4 mmol, 1.0 equiv) in water (10 mL) was added and the reaction mixture was stirred at room temperature for 3 hours. The reaction mixture was quenched with water and extracted with EtOAc. The organic layer was washed with brine, dried over sodium sulfate and concentrated to afford product 14a (0.81 g, 75% yield) which was used without purification in next step. LCMS (m/z): 201.1 [M+H]. ¹H NMR (400 MHz, DMSO) δ 12.01-11.72 (m, 1H), 8.72 (d, J=2.2 Hz, 1H), 8.30-7.91 (m, 2H), 7.75 (d, J=8.5 Hz, 1H).

Step 2. Synthesis of ethyl 3-(3-(5-bromopyridin-2-yl)-4,5-dihydroisoxazol-5-yl)-2-methyl-2-(methylsulfonyl)propanoate [14b]

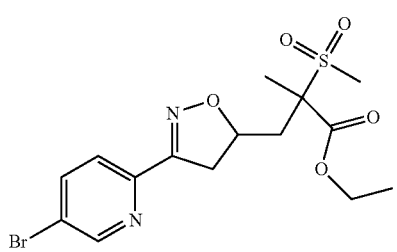

14a (0.6 g, 3.0 mmol, 1.0 equiv) and 1b (0.72 g, 3.3 mmol, 1.1 equiv) were dissolved in chloroform (20 mL) and cooled to 0° C. NaOCl (14%) (0.45 g, 6.0 mmol, 2.0 equiv) was added and the reaction mixture was stirred at room temperature for 24 hours. The reaction mixture was quenched with saturated aqueous ammonium chloride solution and extracted with EtOAc. The organic layer was washed with brine, dried over sodium sulfate and concentrated to afford a crude product. The crude product was purified by silica gel column chromatography (20-30% EtOAc in Hexane) to afford product 14b (0.49 g, 33.6% yield). LCMS (m/z): 419.3 [M+H]. ¹H NMR (400 MHz, DMSO) δ 8.81 (s, 1H), 8.18-8.09 (m, 1H), 7.87 (d, J=8.6 Hz, 1H), 4.75 (s, 1H), 4.26-4.14 (m, 2H), 3.58 (s, 1H), 3.13 (t, J=9.6 Hz, 3H), 2.96 (s, 1H), 2.67 (s, 1H), 2.09 (s, 1H), 1.61 (d, J=20.9 Hz, 3H), 1.27-1.24 (m, 4H).

Step 3. Synthesis of ethyl 2-methyl-2-(methylsulfonyl)-3-(3-(5-(prop-1-yn-1-yl)pyridin-2-yl)-4,5-dihydroisoxazol-5-yl)propanoate [14c]

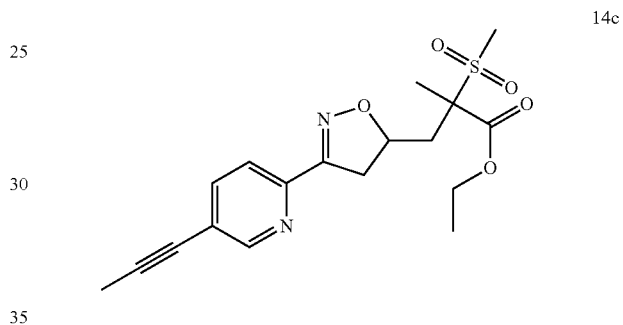

14b (0.25 g, 0.6 mmol, 1.0 equiv), but-2-ynoic acid (0.055 g, 0.7 mmol, 1.1 equiv), 1,4-bis(diphenylphosphino)butane (0.005 g, 0.012 mmol, 0.02 equiv) were added in DMSO (5 mL). DBU (0.18 g, 1.2 mmol, 2.0 equiv) was added and the reaction mixture was degassed for 10 minutes. PdCl₂(PPh₃)₂ (0.004 g, 0.006 mmol, 0.01 equiv) was added and the reaction mixture was stirred at 120° C. for 2 hours. The reaction mixture was quenched with water and extracted with EtOAc. The organic layer was washed with brine, dried over sodium sulfate and concentrated to afford a crude residue. The residue was purified by silica gel column chromatography (30-40% EtOAc in Hexane) to afford product 14c (0.17 g, 73.3% yield). LCMS (m/z): 379.4 [M+H].

Step 4. Synthesis of 2-methyl-2-(methylsulfonyl)-3-(3-(5-(prop-1-yn-1-yl)pyridin-2-yl)-4,5-dihydroisoxazol-5-yl)propanoic acid [14d]

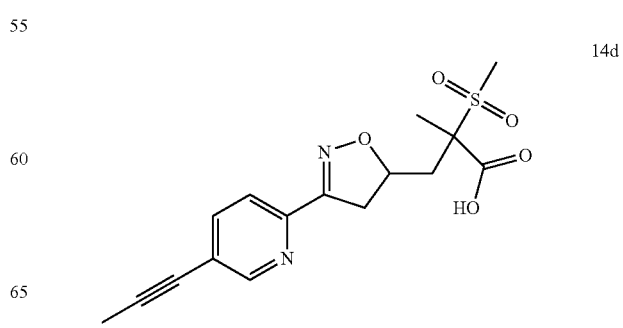

14c (0.17 g, 0.4 mmol, 1.0 equiv) was dissolved in THF (2 mL), MeOH (1 mL) and water (1 mL). LiOH.H₂O (0.055 g, 1.3 mmol, 3.0 equiv) was added and the reaction mixture was stirred at room temperature for 1 hour. The reaction mixture was diluted with water, acidified by 1.0 N HCl aqueous solution to the pH 5 to 6 and extracted with EtOAc. The organic layer was washed with brine, dried over sodium sulfate and concentrated to afford product 14d (0.095 g, 62.5% yield) which was used without purification in next step. LCMS (m/z): 351.3 [M+H]. ¹H NMR (400 MHz, DMSO) δ 14.24-13.67 (s, 1H), 8.63 (d, J=22.9 Hz, 1H), 7.97-7.82 (m, 2H), 4.89 (d, J=51.3 Hz, 1H), 3.65-3.59 (m, 1H), 3.23 (d, J=8.7 Hz, 1H), 3.13 (s, 3H), 2.59 (s, 1H), 2.14-2.03 (m, 4H), 1.57 (d, J=19.3 Hz, 3H).

Step 5. Synthesis of 2-methyl-2-(methylsulfonyl)-3-(3-(5-(prop-1-yn-1-yl)pyridin-2-yl)-4,5-dihydroisoxazol-5-yl)-N-((tetrahydro-2H-pyran-2-yl)oxy)propanamide [14e]

14e

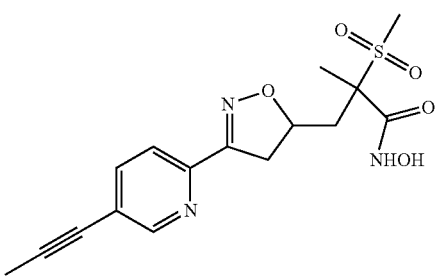

14d (0.095 g, 0.3 mmol, 1.0 equiv) was dissolved in THF (5 mL). N-methyl morpholine (0.14 g, 1.4 mmol, 5.0 equiv), EDC.HCl (0.078 g, 0.4 mmol, 1.5 equiv), HOBT (0.066 g, 0.5 mmol, 1.8 equiv), O-(tetrahydro-2H-pyran-2-yl) hydroxylamine (0.063 g, 0.5 mmol, 2.0 equiv) were added and the reaction mixture was stirred at room temperature for 24 hours. The reaction mixture was quenched with water and extracted with EtOAc. The organic layer was washed with brine, dried over sodium sulfate and concentrated. The residue was purified by silica gel column chromatography (2-3% MeOH in dichloromethane) to afford product 14e (0.09 g, 73.8% yield) which was used directly in next step. LCMS (m/z): 366.4 [M-THP].

Step 6. Synthesis of N-hydroxy-2-methyl-2-(methylsulfonyl)-3-(3-(5-(prop-1-yn-1-yl)pyridin-2-yl)-4,5-dihydroisoxazol-5-yl)propanamide [14-A, 14-B]

14-A, 14-B 14e (0.09 g, 0.2 mmol, 1.0 equiv) was dissolved in ethanol (5 mL). 35.5% aq. HCl (0.2 mL) was added and the reaction mixture was stirred at room temperature for 1 hour. The reaction mixture was diluted with water, neutralized by saturated aqueous sodium bicarbonate solution and extracted with EtOAc. The organic layer was washed with brine, dried over sodium sulfate and concentrated to afford crude residue. The crude residue was purified by preparative HPLC purification to afford 14 as two diastereomers. 14-A: 0.009 g, 12.9% yield. LCMS (m/z): 366.4 [M+H]. ¹H NMR (400 MHz, DMSO) δ 10.86 (s, 1H), 9.15 (s, 1H), 8.66 (s, 1H), 7.87 (s, 2H), 4.85 (s, 1H), 3.60 (d, J=7.1 Hz, 1H), 3.18 (dd, J=17.4, 8.2 Hz, 1H), 3.05 (s, 3H), 2.71 (d, J=8.9 Hz, 1H), 2.10 (d, J=13.3 Hz, 4H), 1.56 (s, 3H). 14-B: 0.014 g, 20% yield. LCMS (m/z): 366.4 [M+H]. ¹H NMR (400 MHz, DMSO) δ 11.06 (s, 1H), 9.31 (s, 1H), 8.66 (s, 1H), 7.88 (s, 2H), 4.69 (s, 1H), 3.59 (dd, J=17.5, 10.3 Hz, 1H), 3.19 (dd, J=17.9, 8.4 Hz, 1H), 3.07 (s, 3H), 2.69 (d, J=10.6 Hz, 1H), 2.14-2.03 (m, 4H), 1.59 (s, 3H).

Example 15

Synthesis of 3-(3-(5-(cyclopropylethynyl)pyridin-2-yl)-4,5-dihydroisoxazol-5-yl)-N-hydroxy-2-methyl-2-(methylsulfonyl)propanamide [15-A, 15-B]

15-A, 15-B

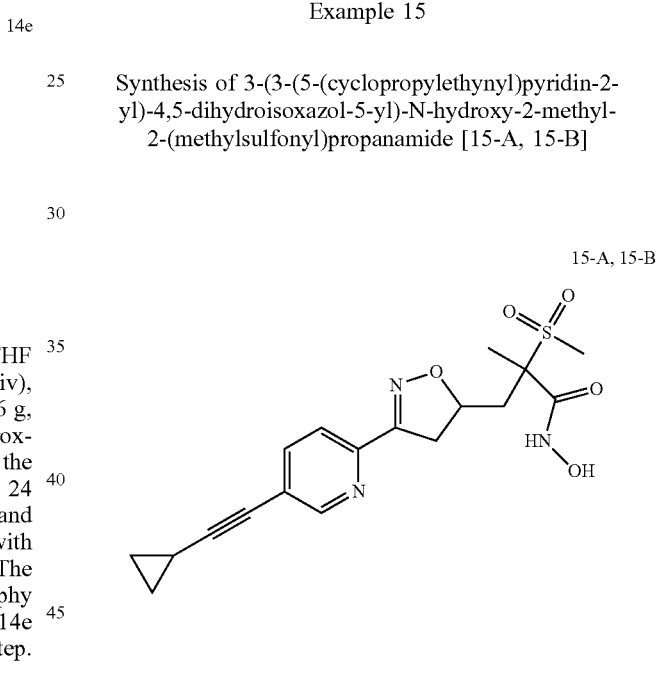

Synthetic scheme

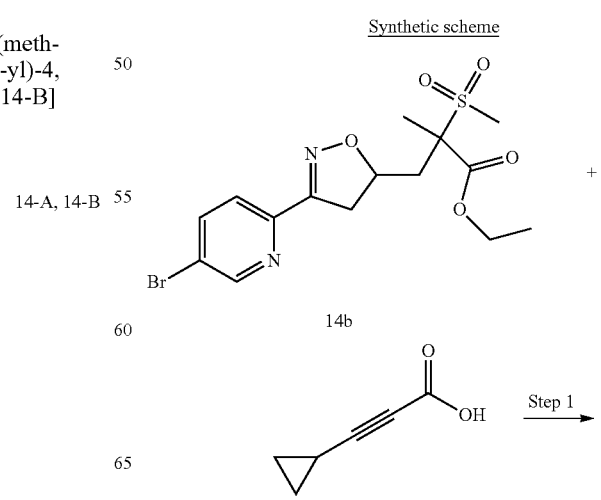

-continued

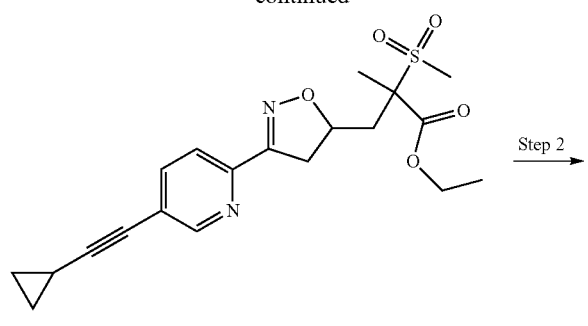

15a

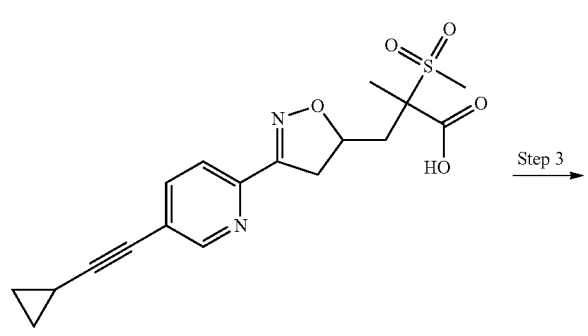

15b

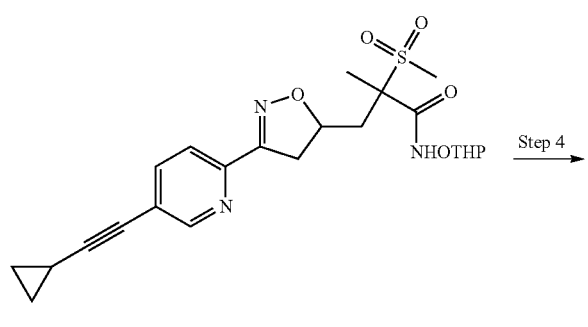

15c

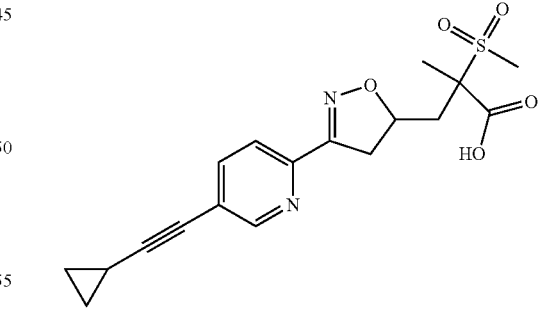

15-A, 15-B

Reagents:
Step 1: DBU, dppb, PdCl₂(PPh₃)₂, DMSO, 120° C. Step 2: LiOH.H₂O, THF, MeOH, water, room temperature. Step 3: NH₂O-THP, EDC.HCl, HOBT, N-methyl morpholine, THF, room temperature. Step 4: 35.5% aq.HCl, EtOH, room temperature.

Step 1. Synthesis of ethyl 3-(3-(5-(cyclopropylethynyl)pyridin-2-yl)-4,5-dihydroisoxazol-5-yl)-2-methyl-2-(methylsulfonyl)propanoate [15a]

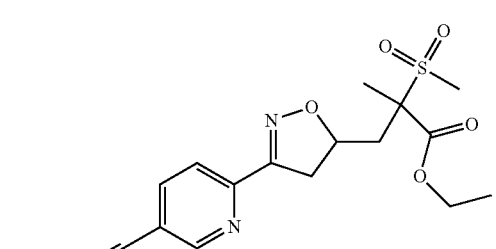

14b (0.24 g, 0.6 mmol, 1.0 equiv), 3-cyclopropylpropiolic acid (0.069 g, 0.7 mmol, 1.1 equiv), 1,4-bis(diphenylphosphino)butane (0.005 g, 0.012 mmol, 0.02 equiv) were added in DMSO (5 mL). DBU (0.17 g, 1.1 mmol, 2.0 equiv) was added and the reaction mixture was degassed for 10 minutes. PdCl₂(PPh₃)₂ (0.004 g, 0.006 mmol, 0.01 equiv) was added and the reaction mixture was stirred at 120° C. for 2 hours. The reaction mixture was quenched with water and extracted with EtOAc. The organic layer was washed with brine, dried over sodium sulfate and concentrated. The residue was purified by silica gel column chromatography (30-40% EtOAc in Hexane) to afford product 15a (0.17 g, 73.6% yield).

Step 2. Synthesis of 3-(3-(5-(cyclopropylethynyl) pyridin-2-yl)-4,5-dihydroisoxazol-5-yl)-2-methyl-2-(methylsulfonyl)propanoic acid [15b]

15a (0.17 g, 0.4 mmol, 1.0 equiv) was dissolved in THF (2 mL), MeOH (1 mL) and water (1 mL). LiOH.H₂O (0.053 g, 1.3 mmol, 3.0 equiv) was added and the reaction mixture was stirred at room temperature for 1 hour. The reaction mixture was diluted with water, acidified by 1.0 N HCl aqueous solution to the pH 5 to 6 and extracted with EtOAc. The organic layer was washed with brine, dried over sodium sulfate and concentrated to afford product 15b (0.1 g, 63.3% yield) which was used in next step without purification.

LCMS (m/z): 377.3 [M+H]. $^1$H NMR (400 MHz, DMSO) δ 12.09 (s, 1H), 8.63 (s, 1H), 7.91 (d, J=44.3 Hz, 2H), 4.83 (s, 1H), 3.66 (s, 1H), 3.19-3.05 (m, 3H), 2.95 (s, 1H), 2.19 (s, 1H), 1.81-1.45 (m, 4H), 0.88 (d, J=55.2 Hz, 4H).

Step 3. Synthesis of 3-(3-(5-(cyclopropylethynyl) pyridin-2-yl)-4,5-dihydroisoxazol-5-yl)-2-methyl-2-(methylsulfonyl)-N-((tetrahydro-2H-pyran-2-yl)oxy) propanamide [15c]

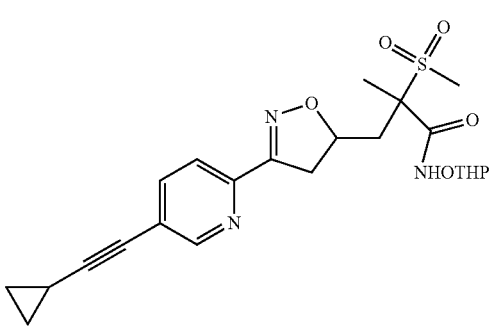

15c 15b (0.1 g, 0.3 mmol, 1.0 equiv) was dissolved in THF (5 mL). N-methyl morpholine (0.13 g, 1.3 mmol, 5.0 equiv), EDC.HCl (0.076 g, 0.4 mmol, 1.5 equiv), HOBT (0.065 g, 0.5 mmol, 1.8 equiv), O-(tetrahydro-2H-pyran-2-yl) hydroxylamine (0.062 g, 0.5 mmol, 2.0 equiv) were added and the reaction mixture was stirred at room temperature for 24 hours. The reaction mixture was quenched with water and extracted with EtOAc. The organic layer was washed with brine, dried over sodium sulfate and concentrated. The residue was purified by silica gel column chromatography (2-3% MeOH in dichloromethane) to afford product 15c (0.09 g, 71.4% yield). LCMS (m/z): 392.4 [M−THP].

Step 4. Synthesis of 3-(3-(5-(cyclopropylethynyl) pyridin-2-yl)-4,5-dihydroisoxazol-5-yl)-N-hydroxy-2-methyl-2-(methylsulfonyl)propanamide [15-A, 15-B]

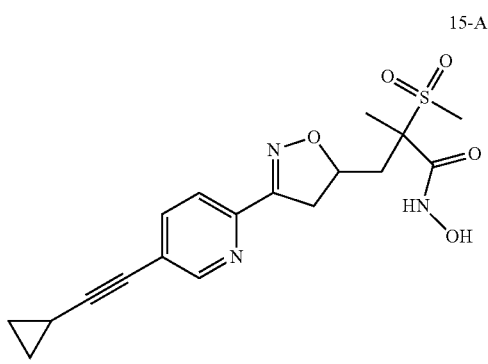

15-A, 15-B 15c (0.09 g, 0.2 mmol, 1.0 equiv) was dissolved in ethanol (5 mL). 35.5% aq. HCl (0.2 mL) was added and the reaction mixture was stirred at room temperature for 1 hour. The reaction mixture was diluted with water, neutralized by saturated aqueous sodium bicarbonate solution and extracted with EtOAc. The organic layer was washed with brine, dried over sodium sulfate and concentrated. The crude residue was purified by preparative HPLC purification to afford 15 as two diastereomers. 15-A: 0.007 g, 9.5% yield. LCMS (m/z): 392.3 [M+H]. $^1$H NMR (400 MHz, DMSO) δ 10.86 (s, 1H), 9.15 (s, 1H), 8.62 (s, 1H), 7.85 (s, 2H), 4.84 (s, 1H), 3.59 (s, 1H), 3.21-3.15 (m, 1H), 3.05 (s, 3H), 2.68 (s, 1H), 2.08 (s, 1H), 1.56 (s, 4H), 0.89 (dd, J=41.2, 13.1 Hz, 4H). 15-B: 0.010 g, 13.5% yield. LCMS (m/z): 392.3 [M+H]. $^1$H NMR (400 MHz, DMSO) δ 11.06 (s, 1H), 9.31 (s, 1H), 8.62 (s, 1H), 7.85 (s, 2H), 4.70 (s, 1H), 3.58 (dd, J=17.6, 10.4 Hz, 1H), 3.18 (dd, J=17.8, 8.1 Hz, 1H), 3.12-3.02 (m, 3H), 2.68 (d, J=10.8 Hz, 1H), 2.06 (dd, J=13.8, 8.3 Hz, 1H), 1.66-1.54 (m, 4H), 0.94 (dd, J=8.2, 2.7 Hz, 2H), 0.80 (dd, J=4.8, 2.5 Hz, 2H).

Example 16

Synthesis of 3-(3-(2-fluoro-4-(prop-1-yn-1-yl)phenyl)-4,5-dihydroisoxazol-5-yl)-N-hydroxy-2-methyl-2-(methylsulfonyl)propanamide [16-A, 16-B]

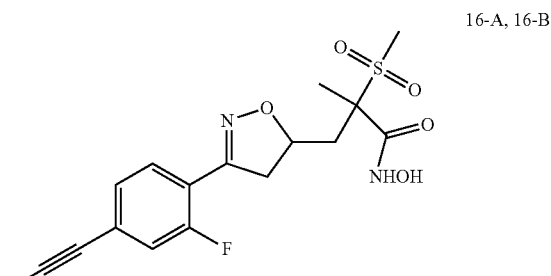

16-A, 16-B

Synthetic scheme

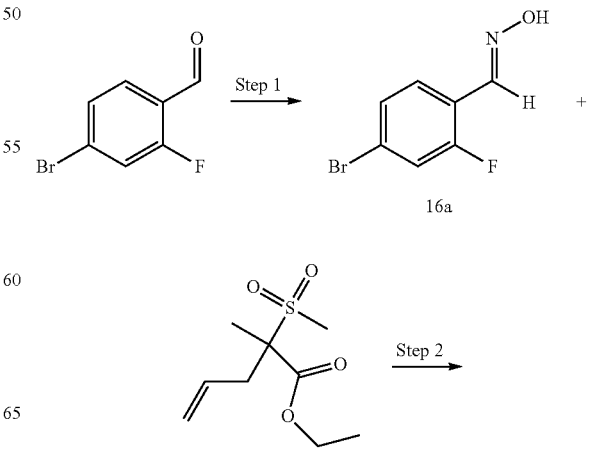

-continued

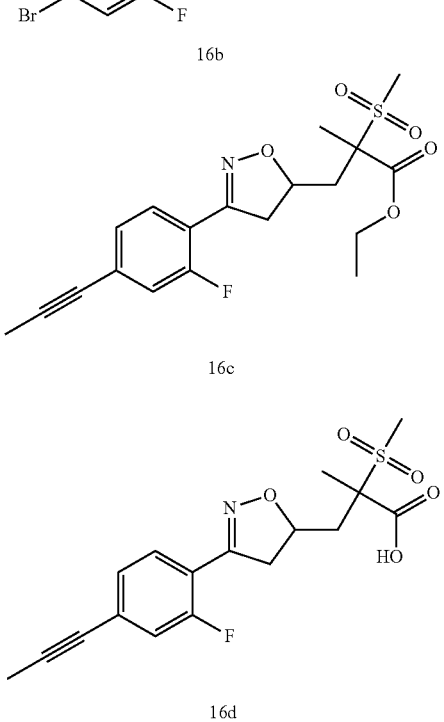

16b

16c

16d

16e

16-A, 16-B

Reagents:
Step 1: NH₂OH.HCl, NaOH, water, 80° C. Step 2: NaOCl, THF, room temperature. Step 3: DBU, dppb, PdCl₂ (PPh₃)₂, DMSO, 120° C. Step 4: LiOH.H₂O, THF, MeOH, water, room temperature. Step 5: NH₂O-THP, EDC.HCl, HOBT, N-methyl morpholine, THF, room temperature. Step 6: 35.5% aq.HCl, EtOH, room temperature.

Step 1. Synthesis of 4-bromo-2-fluorobenzaldehyde oxime [16a]

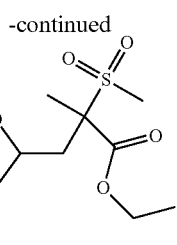

16a 4-bromo-2-fluorobenzaldehyde (10 g, 49.2 mmol, 1.0 equiv) was dissolved in water (80 mL) and the reaction mixture was stirred at 70° C. A solution of hydroxylamine hydrochloride (6.6 g, 98 mmol, 2.0 equiv) and sodium hydroxide (3.94 g, 98 mmol, 2.0 equiv) in water (20 mL) was added to the reaction mixture at same temperature. The reaction mixture was stirred at 70° C. for 6 hours. The reaction mixture was cooled to room temperature and filtered. The collected solid was triturated with hexane, the solvent was decanted and dried to afford product 16a (9.12 g, 84% yield) which was used in next step without purification. ¹H NMR (400 MHz, DMSO) δ 11.71 (d, J=19.9 Hz, 1H), 8.16 (d, J=20.1 Hz, 1H), 7.78-7.58 (m, 2H), 7.52-7.41 (m, 1H).

Step 2. Synthesis of ethyl 3-(3-(4-bromo-2-fluorophenyl)-4,5-dihydroisoxazol-5-yl)-2-methyl-2-(methylsulfonyl)propanoate [16b]

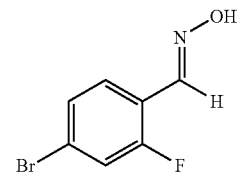

16b 16a (6 g, 25 mmol, 1.0 equiv) was dissolved in THF (50 mL). 1b (5.6 g, 25 mmol, 1.0 equiv) and sodium hypochlorite (7.6 g, 50 mmol, 2.0 equiv) were added and the reaction mixture was stirred at room temperature for 6 hours. The reaction mixture was quenched with water and extracted with EtOAc. The organic layer was washed with brine, dried over sodium sulfate and concentrated. The crude residue was purified by silica gel column chromatography (10-15% EtOAc in Hexane) to afford product 16b (8 g, 68% yield). LCMS (m/z): 436.4 [M+H]. ¹H NMR (400 MHz, DMSO) δ 7.78-7.65 (m, 2H), 7.54 (dd, J=8.4, 2.0 Hz, 1H), 4.84 (dd, J=68.4, 8.4 Hz, 1H), 4.29-4.16 (m, 2H), 3.63 (dd, J=16.7, 8.5 Hz, 1H), 3.21 (d, J=17.3 Hz, 1H), 3.17-3.09 (m, 3H), 2.68-2.57 (m, 1H), 2.25-2.10 (m, 1H), 1.63 (t, J=20.8 Hz, 3H).

Step 3. Synthesis of ethyl 3-(3-(2-fluoro-4-(prop-1-yn-1-yl)phenyl)-4,5-dihydroisoxazol-5-yl)-2-methyl-2-(methylsulfonyl)propanoate [16c]

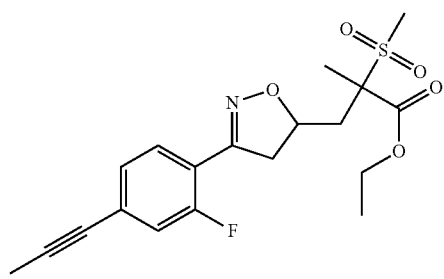

16b (0.6 g, 1.37 mmol, 1.0 equiv), but-2-ynoic acid (0.25 g, 2.75 mmol, 2.0 equiv), 1,4-bis(diphenylphosphino)butane (0.009 g, 0.027 mmol, 0.02 equiv) were added in DMSO (10 mL). DBU (0.41 g, 2.7 mmol, 2.0 equiv) was added and the reaction mixture was degassed for 10 minutes. PdCl$_2$(PPh$_3$)$_2$ (0.012 g, 0.014 mmol, 0.01 equiv) was added and the reaction mixture was stirred at 120° C. for 12 hours. The reaction mixture was quenched with water and extracted with EtOAc. The organic layer was washed with brine, dried over sodium sulfate and concentrated. The residue was purified by silica gel column chromatography (20-25% EtOAc in Hexane) to afford product 16c (0.42 g, 77% yield). LCMS (m/z): 396.4 [M+H]. $^1$H NMR (400 MHz, DMSO) δ 7.69 (t, J=7.4 Hz, 1H), 7.34 (dd, J=29.6, 9.5 Hz, 2H), 4.83 (d, J=67.9 Hz, 1H), 4.23 (dq, J=24.8, 7.1 Hz, 2H), 3.22 (s, 1H), 3.16-3.07 (m, 3H), 2.65-2.58 (m, 1H), 2.20 (dd, J=14.5, 8.5 Hz, 1H), 1.60 (d, J=21.6 Hz, 3H), 1.24 (dt, J=9.2, 7.1 Hz, 3H).

Step 4. Synthesis of 3-(3-(2-fluoro-4-(prop-1-yn-1-yl)phenyl)-4,5-dihydroisoxazol-5-yl)-2-methyl-2-(methylsulfonyl)propanoic acid [16d]

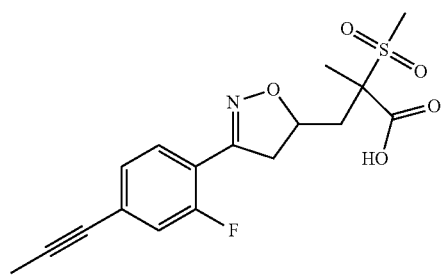

16c (0.42 g, 1.0 mmol, 1.0 equiv) was dissolved in THF (6 mL), MeOH (2 mL) and water (2 mL). LiOH.H$_2$O (0.069 g, 1.6 mmol, 1.5 equiv) was added and the reaction mixture was stirred at room temperature for 3 hours. The reaction mixture was acidified by 1.0 N HCl aqueous solution to the pH 3 to 4 and extracted with EtOAc. The organic layer was washed with brine, dried over sodium sulfate and concentrated to afford product 16d (0.35 g, 92% yield) which was used in next step without purification. LCMS (m/z): 368.3 [M+H]. $^1$H NMR (400 MHz, DMSO) δ 12.09 (s, 1H), 7.68 (td, J=8.0, 3.3 Hz, 1H), 7.33 (dd, J=28.9, 10.1 Hz, 2H), 4.83 (dd, J=55.1, 8.4 Hz, 1H), 3.67-3.55 (m, 1H), 3.20 (dd, J=17.1, 7.3 Hz, 1H), 3.11 (d, J=15.3 Hz, 3H), 2.62 (dd, J=13.9, 10.1 Hz, 1H), 2.20-2.04 (m, 4H), 1.54 (t, J=18.6 Hz, 3H).

Step 5. Synthesis of 3-(3-(2-fluoro-4-(prop-1-yn-1-yl)phenyl)-4,5-dihydroisoxazol-5-yl)-2-methyl-2-(methylsulfonyl)-N-((tetrahydro-2H-pyran-2-yl)oxy)propanamide [16e]

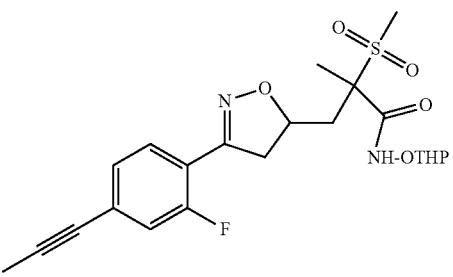

16d (0.35 g, 0.95 mmol, 1.0 equiv) was dissolved in THF (10 mL). N-methyl morpholine (0.48 g, 4.76 mmol, 5.0 equiv), EDC.HCl (0.33 g, 1.7 mmol, 1.8 equiv), HOBT (0.19 g, 1.43 mmol, 1.5 equiv), O-(tetrahydro-2H-pyran-2-yl) hydroxylamine (0.22 g, 1.9 mmol, 2.0 equiv) were added and the reaction mixture was stirred at room temperature for 24 hours. The reaction mixture was quenched with water and extracted with EtOAc. The organic layer was washed with brine, dried over sodium sulfate and concentrated. The residue was purified by silica gel column chromatography (30-40% EtOAc in Hexane) to afford product 16e (0.3 g, 68% yield). LCMS (m/z): 383.6 [M-THP]. $^1$H NMR (400 MHz, DMSO) δ 11.34 (s, 1H), 7.68 (d, J=6.0 Hz, 1H), 7.33 (dd, J=28.6, 9.9 Hz, 2H), 5.13 (d, J=34.3 Hz, 1H), 4.84 (d, J=26.2 Hz, 1H), 3.58 (s, 1H), 3.47 (d, J=10.2 Hz, 2H), 3.17 (d, J=18.0 Hz, 1H), 3.09-3.02 (m, 3H), 2.70 (d, J=14.0 Hz, 1H), 2.06 (d, J=20.6 Hz, 4H), 1.69 (s, 3H), 1.49 (d, J=33.0 Hz, 6H).

Step 6. Synthesis of 3-(3-(2-fluoro-4-(prop-1-yn-1-yl)phenyl)-4,5-dihydroisoxazol-5-yl)-N-hydroxy-2-methyl-2-(methylsulfonyl)propanamide [16-A, 16-B]

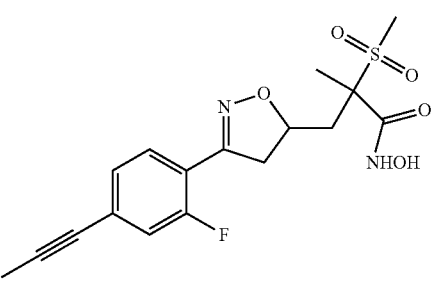

16e (0.3 g, 0.64 mmol, 1.0 equiv) was dissolved in ethanol (10 mL). 35.5% aq. HCl (0.2 mL) was added and the reaction mixture was stirred at room temperature for 4 hours. The reaction mixture was diluted with water, neutralized by saturated aqueous sodium bicarbonate solution and extracted with EtOAc. The organic layer was washed with brine, dried over sodium sulfate and concentrated. The crude residue was purified by preparative HPLC purification to afford 16 as two diastereomers. 16-A: 0.030 g, 12.5% yield. LCMS (m/z): 383.4 [M+18]. $^1$H NMR (400 MHz, DMSO) δ 10.84 (s, 1H), 9.15 (s, 1H), 7.68 (t, J=7.9 Hz, 1H), 7.33 (dd, J=28.0, 9.9 Hz, 2H), 4.77 (s, 1H), 3.60 (dd, J=16.6, 10.7 Hz, 1H), 3.18 (dd, J=16.7, 7.6 Hz, 1H), 3.14-2.89 (m, 3H), 2.72 (d, J=15.4 Hz, 1H), 2.15 (d, J=55.6 Hz, 4H), 1.55 (s, 3H). 16-B: 0.028 g, 11.7% yield), LCMS (m/z): 383.4 [M+18]. $^1$H NMR (400 MHz, DMSO) δ 11.04 (s, 1H), 9.28 (s, 1H), 7.68 (t, J=8.0 Hz, 1H), 7.33 (dd, J=28.4, 10.0 Hz, 2H), 4.63 (d, J=7.8 Hz, 1H), 3.69-3.58 (m, 1H), 3.18 (dd, J=16.9, 7.6 Hz, 1H), 3.12-2.99 (m, 3H), 2.75-2.64 (m, 1H), 2.17-1.91 (m, 4H), 1.75-1.49 (m, 3H).

Example 17

Synthesis of 3-(3-(4-(cyclopropylethynyl)-2-fluorophenyl)-4,5-dihydroisoxazol-5-yl)-N-hydroxy-2-methyl-2-(methylsulfonyl)propanamide [17-A, 17-B]

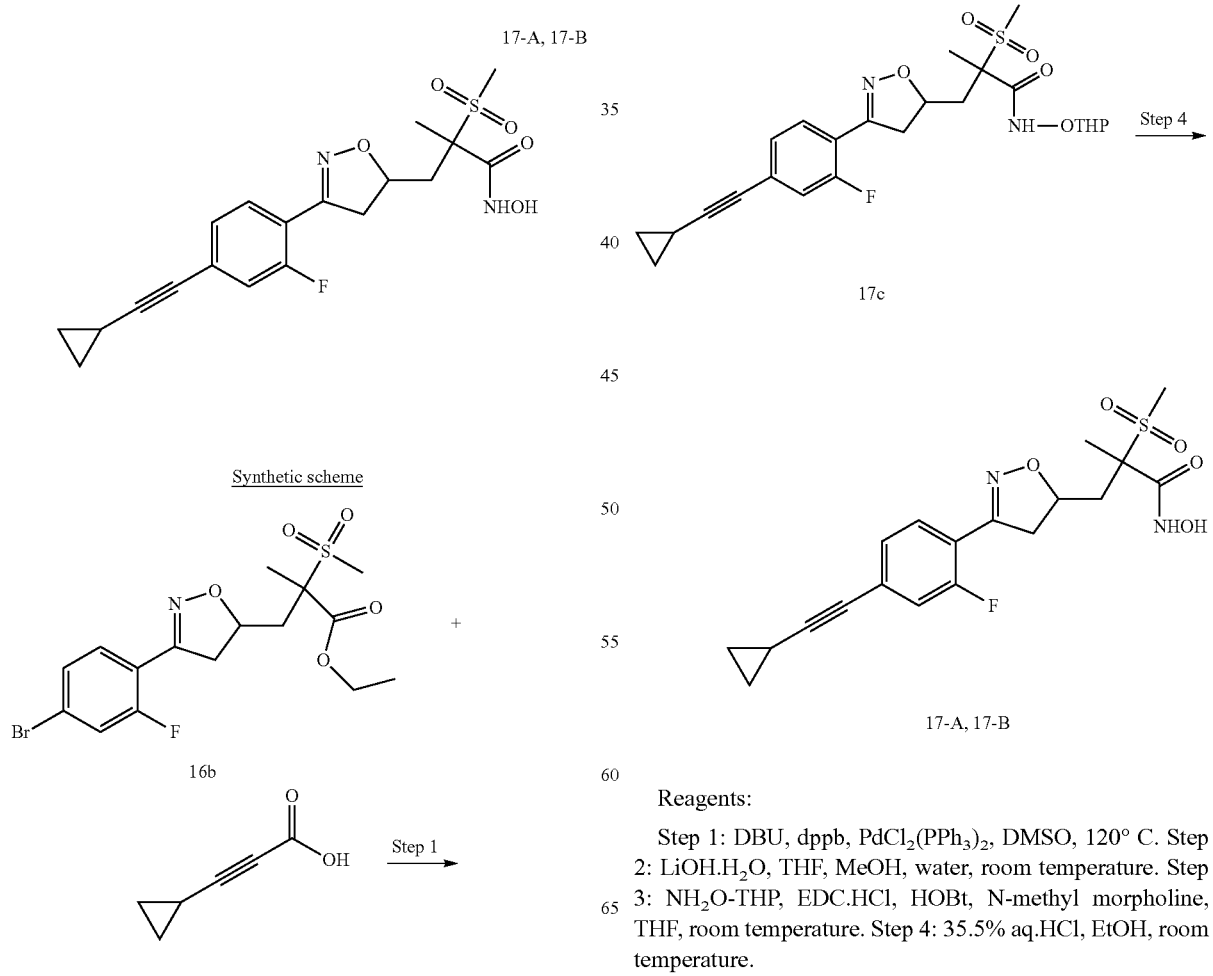

Reagents:

Step 1: DBU, dppb, PdCl$_2$(PPh$_3$)$_2$, DMSO, 120° C. Step 2: LiOH.H$_2$O, THF, MeOH, water, room temperature. Step 3: NH$_2$O-THP, EDC.HCl, HOBt, N-methyl morpholine, THF, room temperature. Step 4: 35.5% aq.HCl, EtOH, room temperature.

Step 1. Synthesis of ethyl 3-(3-(4-(cyclopropylethynyl)-2-fluorophenyl)-4,5-dihydro isoxazol-5-yl)-2-methyl-2-(methylsulfonyl)propanoate [17a]

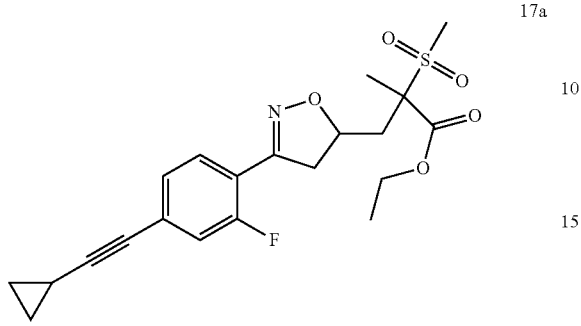

17a 16b (0.6 g, 1.3 mmol, 1.0 equiv), 3-cyclopropylpropiolic acid (0.3 g, 2.7 mmol, 2.0 equiv), 1,4-bis(diphenylphosphino)butane (0.011 g, 0.027 mmol, 0.02 equiv) were added in DMSO (10 mL). DBU (0.41 g, 2.7 mmol, 2.0 equiv) was added and the reaction mixture was degassed for 10 minutes. $PdCl_2(PPh_3)_2$ (0.009 g, 0.014 mmol, 0.01 equiv) was added and the reaction mixture was stirred at 120° C. for 15 hours. The reaction mixture was quenched with water and extracted with EtOAc. The organic layer was washed with brine, dried over sodium sulfate and concentrated. The residue was purified by silica gel column chromatography (20-22% EtOAc in Hexane) to afford product 17a (0.54 g, 93% yield). LCMS (m/z): 422.4 [M+H]. $^1$H NMR (400 MHz, DMSO) δ 7.68 (t, J=7.5 Hz, 1H), 7.46-7.21 (m, 2H), 4.99-4.70 (m, 1H), 4.30-4.16 (m, 2H), 3.67-3.54 (m, 1H), 3.21 (d, J=9.5 Hz, 1H), 3.15-3.07 (m, 3H), 2.61 (ddd, J=18.2, 12.9, 9.6 Hz, 1H), 2.13 (ddd, J=17.2, 14.2, 5.8 Hz, 1H), 1.71-1.50 (m, 4H), 1.24 (dt, J=9.7, 7.1 Hz, 3H), 0.98-0.86 (m, 2H), 0.83-0.73 (m, 2H).

Step 2. Synthesis of 3-(3-(4-(cyclopropylethynyl)-2-fluorophenyl)-4,5-dihydroisoxazol-5-yl)-2-methyl-2-(methylsulfonyl)propanoic acid [17b]

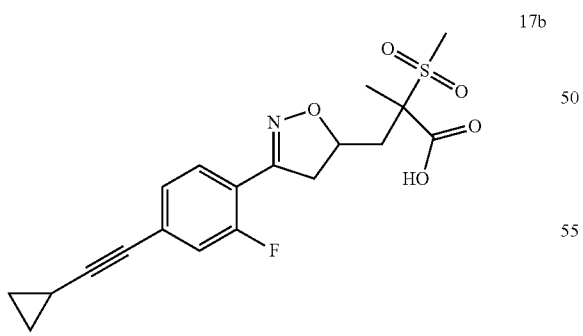

17b 17a (0.54 g, 1.2 mmol, 1.0 equiv) was dissolved in THF (6 mL), MeOH (2 mL) and water (2 mL). $LiOH \cdot H_2O$ (0.08 g, 1.9 mmol, 1.5 equiv) was added and the reaction mixture was stirred at room temperature for 4 hours. The reaction mixture was acidified by 1.0 N HCl aqueous solution to the pH 3 to 4 and extracted with EtOAc. The organic layer was washed with brine, dried over sodium sulfate and concentrated to afford product 17b (0.45 g, 83% yield) which was used in next step without purification. LCMS (m/z): 394.4 [M+H].

Step 3. Synthesis of 3-(3-(4-(cyclopropylethynyl)-2-fluorophenyl)-4,5-dihydroisoxazol-5-yl)-2-methyl-2-(methylsulfonyl)-N-((tetrahydro-2H-pyran-2-yl)oxy)propanamide [17c]

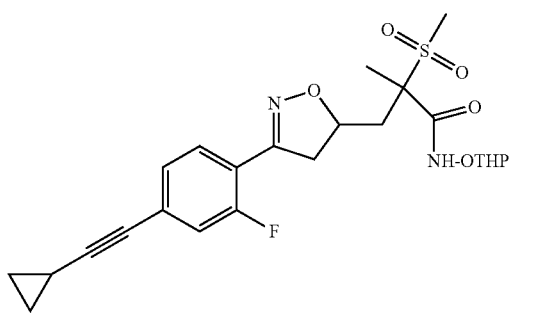

17c 17b (0.45 g, 1.14 mmol, 1.0 equiv) was dissolved in THF (10 mL). N-methyl morpholine (0.58 g, 5.71 mmol, 5.0 equiv), EDC.HCl (0.39 g, 2.05 mmol, 1.8 equiv), HOBT (0.23 g, 1.72 mmol, 1.5 equiv), O-(tetrahydro-2H-pyran-2-yl) hydroxylamine (0.27 g, 2.28 mmol, 2.0 equiv) were added and the reaction mixture was stirred at room temperature for 24 hours. The reaction mixture was quenched with water and extracted with EtOAc. The organic layer was washed with brine, dried over sodium sulfate and concentrated. The residue was purified by silica gel column chromatography (30-50% EtOAc in Hexane) to afford product 17c (0.42 g, 75% yield). LCMS (m/z): 491.5 [M+H]. $^1$H NMR (400 MHz, DMSO) δ 11.46 (s, 1H), 7.67 (d, J=6.9 Hz, 1H), 7.30 (dd, J=29.9, 10.0 Hz, 2H), 5.12 (d, J=29.4 Hz, 1H), 4.84 (d, J=25.4 Hz, 1H), 3.75 (d, J=11.1 Hz, 1H), 3.53 (d, J=36.4 Hz, 2H), 3.21-3.13 (m, 1H), 3.05 (dd, J=8.7, 4.5 Hz, 3H), 2.68 (s, 1H), 2.06 (s, 1H), 1.79-1.64 (m, 4H), 1.56 (dd, J=15.3, 8.9 Hz, 6H), 0.93 (dt, J=6.3, 4.0 Hz, 2H), 0.81-0.75 (m, 2H).

Step 4. Synthesis of 3-(3-(4-(cyclopropylethynyl)-2-fluorophenyl)-4,5-dihydroisoxazol-5-yl)-N-hydroxy-2-methyl-2-(methylsulfonyl)propanamide [17-A, 17-B]

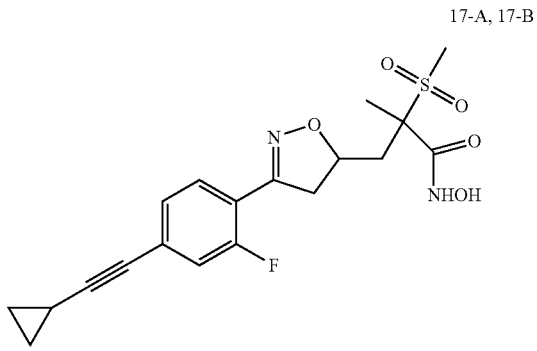

17-A, 17-B 17c (0.42 g, 0.87 mmol, 1.0 equiv) was dissolved in ethanol (10 mL). 35.5% aq. HCl (0.2 mL) was added and the reaction mixture was stirred at room temperature for 4 hours. The reaction mixture was diluted with water, neutralized by saturated aqueous sodium bicarbonate solution and extracted with EtOAc. The organic layer was washed with brine, dried over sodium sulfate and concentrated to afford crude residue. The crude residue was purified by preparative HPLC purification to afford 17 as two diastereomers. 17-A: 0.080 g, 25.6% yield), LCMS (m/z): 409.4 [M+H]. $^1$H NMR (400 MHz, DMSO) δ 10.86 (s, 1H), 9.14 (s, 1H), 7.67 (t, J=7.6 Hz, 1H), 7.30 (dd, J=27.7, 9.8 Hz, 2H), 4.77 (s, 1H), 3.59 (dd, J=16.8, 10.7 Hz, 1H), 3.17 (dd, J=16.5, 7.5 Hz, 1H), 3.03 (d, J=19.7 Hz, 3H), 2.85-2.61 (m, 1H), 2.08 (d, J=10.4 Hz, 1H), 1.90-1.22 (m, 4H), 1.19-0.48 (m, 4H). 17-B: 0.070 g, 22.4% yield. LCMS (m/z): 409.4 [M+H]. $^1$H NMR (400 MHz, DMSO) δ 11.01 (s, 1H), 9.28 (s, 1H), 7.67 (t, J=8.0 Hz, 1H), 7.49-7.20 (m, 2H), 4.63 (dd, J=15.5, 8.1 Hz, 1H), 3.59 (dd, J=16.8, 10.1 Hz, 1H), 3.26-3.14 (m, 1H), 3.11-2.88 (m, 3H), 2.67 (dd, J=14.0, 3.1 Hz, 1H), 2.13-1.94 (m, 1H), 1.77-1.33 (m, 4H), 1.05-0.64 (m, 4H).

Example 22

Synthesis of (R)-3-((R)-3-(4-(4-fluorobut-1-yn-1-yl)phenyl)-4,5-dihydroisoxazol-5-yl)-N-hydroxy-2-methyl-2-(methylsulfonyl)propanamide 22

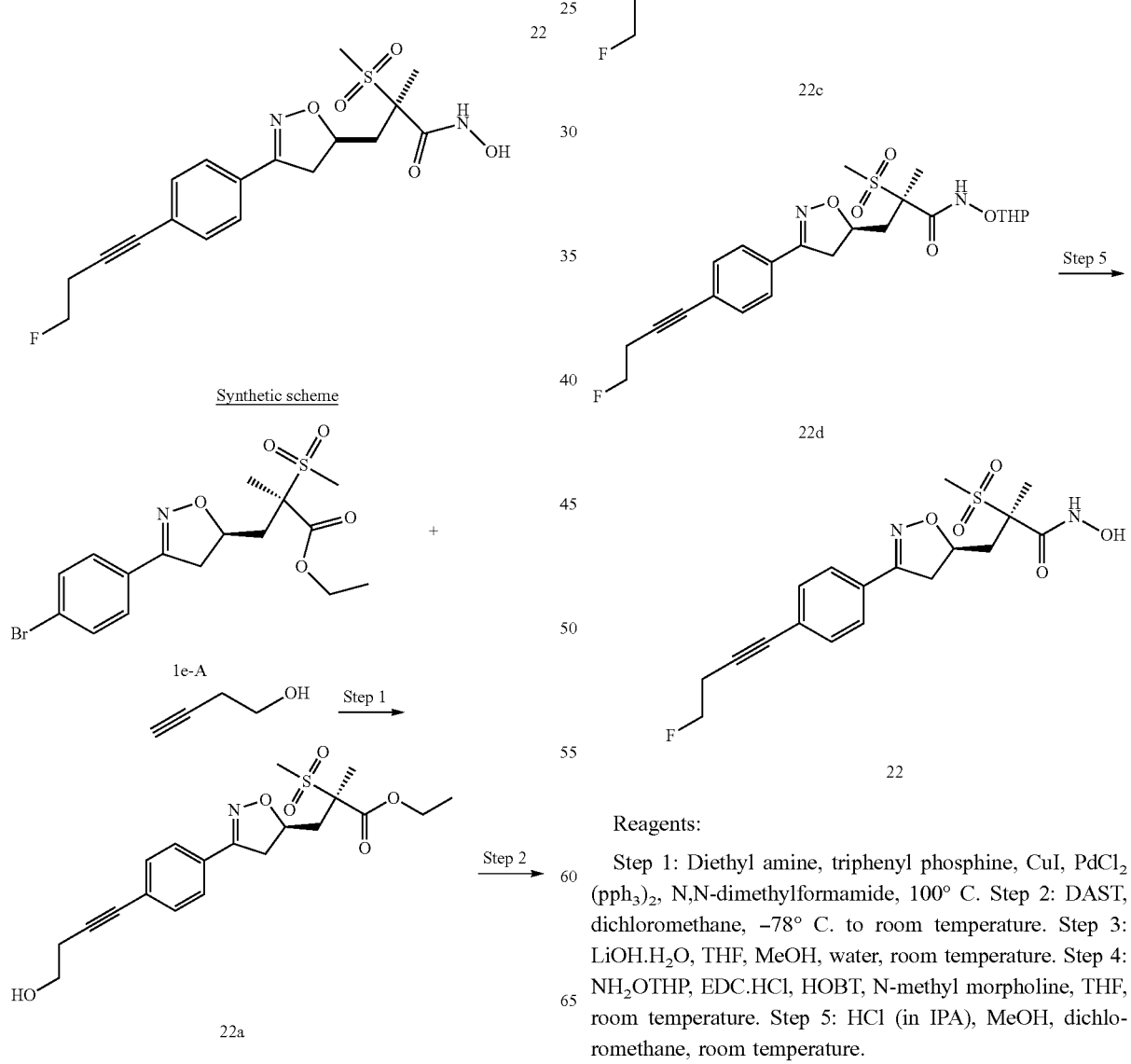

Reagents:

Step 1: Diethyl amine, triphenyl phosphine, CuI, PdCl$_2$(pph$_3$)$_2$, N,N-dimethylformamide, 100° C. Step 2: DAST, dichloromethane, −78° C. to room temperature. Step 3: LiOH.H$_2$O, THF, MeOH, water, room temperature. Step 4: NH$_2$OTHP, EDC.HCl, HOBT, N-methyl morpholine, THF, room temperature. Step 5: HCl (in IPA), MeOH, dichloromethane, room temperature.

Step 1. Synthesis of (R)-ethyl 3-((R)-3-(4-(4-hydroxybut-1-yn-1-yl)phenyl)-4,5-dihydroisoxazol-5-yl)-2-methyl-2-(methylsulfonyl)propanoate [22a]

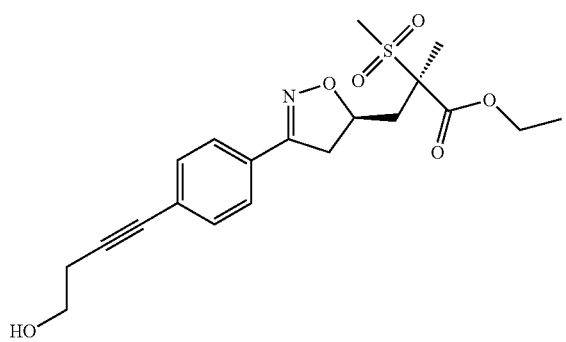

22a (R)-1d-A (0.25 g, 0.59 mmol, 1.0 equiv) was added with diethyl amine (10 mL) and N,N-dimethylformamide (2 mL). CuI (0.011 g, 0.059 mmol, 0.1 equiv), triphenyl phosphine (0.031 g, 0.12 mmol, 0.2 equiv) were added and the reaction mixture was degassed for 10 minutes. PdCl$_2$(pph$_3$)$_2$ (0.02 g, 0.03 mmol, 0.05 equiv), but-3-yn-1-ol (0.083 g, 1.19 mmol, 2.0 equiv) were added and the reaction mixture was stirred at 100° C. for 2 hours. The reaction mixture was quenched with water and extracted with EtOAc. The organic layer was washed with brine, dried over sodium sulfate and concentrated. The residue was purified by silica gel column chromatography (50-55% EtOAc/Hexane) to afford product 22a (0.2 g, 82% yield). LCMS (m/z): 408.2 [M+H]. $^1$H NMR (400 MHz, DMSO) δ 7.63 (dd, J=8.1, 4.3 Hz, 2H), 7.47 (d, J=8.4 Hz, 2H), 4.94 (t, J=5.6 Hz, 1H), 4.76 (td, J=11.3, 3.3 Hz, 1H), 4.26 (q, J=7.1 Hz, 2H), 3.65-3.53 (m, 3H), 3.22-3.06 (m, 4H), 2.59 (dd, J=12.9, 6.1 Hz, 3H), 2.21-2.14 (m, 1H), 1.61 (d, J=22.3 Hz, 3H), 1.26 (t, J=7.1 Hz, 3H).

Step 2. Synthesis of (R)-ethyl 3-((R)-3-(4-(4-fluorobut-1-yn-1-yl)phenyl)-4,5-dihydroisoxazol-5-yl)-2-methyl-2-(methylsulfonyl)propanoate [22b]

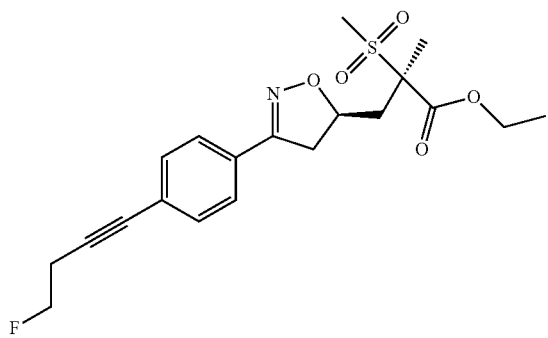

22b 22a (0.18 g, 0.44 mmol, 1.0 equiv) was dissolved in dichloromethane (10 mL) and cooled to −78° C. DAST (0.14 g, 0.88 mmol, 2.0 equiv) was added dropwisely and the reaction mixture was stirred at room temperature for 12 hours. The reaction mixture was poured to water, neutralized with saturated aqueous sodium bicarbonate solution and extracted with EtOAc. The organic layer was washed with brine, dried over sodium sulfate and concentrated. The residue was purified by silica gel column chromatography (25-30% EtOAc/Hexane) to afford product 22b (0.08 g, 45% yield). LCMS (m/z): 410.1 [M+H]. $^1$H NMR (400 MHz, DMSO) δ 7.64 (d, J=8.4 Hz, 2H), 7.51 (t, J=10.8 Hz, 2H), 4.76 (ddd, J=18.8, 8.4, 3.3 Hz, 1H), 4.65 (t, J=6.0 Hz, 1H), 4.54 (t, J=6.0 Hz, 1H), 4.33-4.18 (m, 2H), 3.61 (dd, J=17.0, 10.4 Hz, 1H), 3.24-3.04 (m, 4H), 2.93 (t, J=6.0 Hz, 1H), 2.87 (t, J=6.0 Hz, 1H), 2.59 (dd, J=14.5, 3.2 Hz, 1H), 2.18 (dd, J=9.3, 5.2 Hz, 1H), 1.61 (d, J=22.2 Hz, 3H), 1.26 (t, J=7.1 Hz, 3H).

Step 3. Synthesis of (R)-3-((R)-3-(4-(4-fluorobut-1-yn-1-yl)phenyl)-4,5-dihydroisoxazol-5-yl)-2-methyl-2-(methylsulfonyl)propanoic acid [22c]

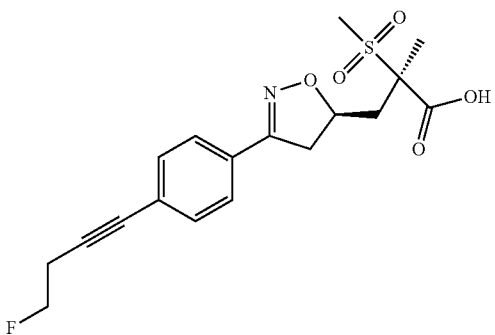

22c 22b (0.08 g, 0.19 mmol, 1.0 equiv) was dissolved in THF (4 mL), MeOH (1 mL) and water (1 mL). LiOH.H$_2$O (0.024 g, 0.58 mmol, 3.0 equiv) was added and the reaction mixture was stirred at room temperature for 2 hours. The reaction mixture was poured to water, acidified by 1.0 N HCl aqueous solution up to pH 4 to 5 and extracted with EtOAc. The organic layer was washed with brine, dried over sodium sulfate and concentrated to afford product 22c (0.065 g, 87% yield). The product was directly used in the next step with no further purification. LCMS (m/z): 382.1 [M+H]. $^1$H NMR (400 MHz, DMSO) δ 14.03 (s, 1H), 7.67-7.60 (m, 2H), 7.52 (dd, J=22.8, 8.4 Hz, 2H), 4.77 (d, J=7.4 Hz, 1H), 4.65 (t, J=6.0 Hz, 1H), 4.54 (t, J=6.0 Hz, 1H), 3.63 (dd, J=17.0, 10.4 Hz, 1H), 3.23-3.16 (m, 1H), 3.14 (d, J=7.7 Hz, 3H), 2.93 (t, J=6.0 Hz, 1H), 2.87 (t, J=6.1 Hz, 1H), 2.56 (s, 1H), 2.20-2.14 (m, 1H), 1.60 (s, 3H).

Step 4. Synthesis of (2R)-3-((R)-3-(4-(4-fluorobut-1-yn-1-yl)phenyl)-4,5-dihydroisoxazol-5-yl)-2-methyl-2-(methylsulfonyl)-N-((tetrahydro-2H-pyran-2-yl)oxy)propanamide [22d]

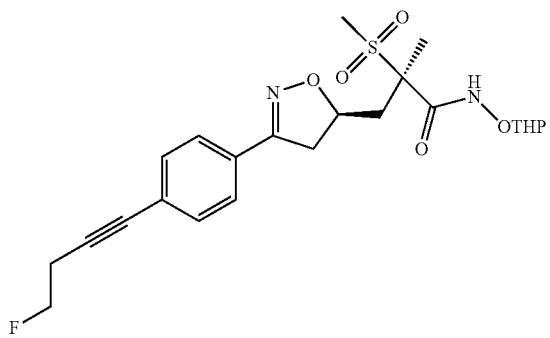

22d 22c (0.065 g, 0.17 mmol, 1.0 equiv) was dissolved in THF (5 mL). N-methyl morpholine (0.086 g, 0.852 mmol, 5.0 equiv), HOBT (0.027 g, 0.2 mmol, 1.2 equiv), O-(tetrahydro-2H-pyran-2-yl) hydroxylamine (0.04 g, 0.34 mmol, 2.0 equiv), EDC.HCl (0.048 g, 0.26 mmol, 1.5 equiv) were added and the reaction mixture was stirred at room temperature for 24 hours. The reaction mixture was quenched with water and extracted with EtOAc. The organic layer was washed with brine, dried over sodium sulfate and concentrated. The residue was purified by silica gel column chromatography (30-40% EtOAc/Hexane) to afford product 22d (0.065 g, 79% yield). LCMS (m/z): 498.3 [M+18]. $^1$H NMR (400 MHz, DMSO) δ 11.47 (s, 1H), 7.71-7.59 (m, 2H), 7.52 (dd, J=23.0, 8.4 Hz, 2H), 4.97 (d, J=8.3 Hz, 1H), 4.65 (t, J=6.0 Hz, 2H), 4.53 (t, J=6.0 Hz, 1H), 4.05 (dt, J=14.3, 9.8 Hz, 2H), 3.64-3.49 (m, 2H), 3.15 (dd, J=17.3, 7.7 Hz, 1H), 3.06 (d, J=8.7 Hz, 3H), 2.90 (dt, J=24.2, 6.1 Hz, 2H), 2.68 (d, J=12.3 Hz, 1H), 2.07 (dd, J=13.0, 8.4 Hz, 1H), 1.70 (s, 3H), 1.61 (d, J=4.3 Hz, 3H), 1.54 (s, 3H).

Step 5. Synthesis of (R)-3-((R)-3-(4-(4-fluorobut-1-yn-1-yl)phenyl)-4,5-dihydroisoxazol-5-yl)-N-hydroxy-2-methyl-2-(methylsulfonyl)propanamide [22]

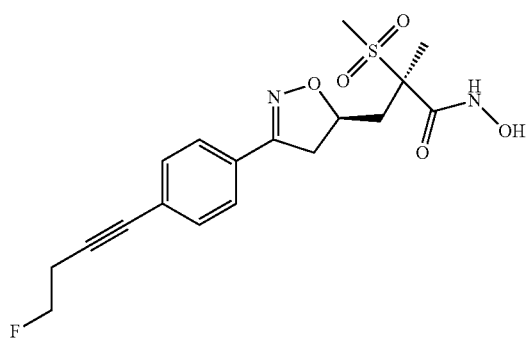

22

22d (0.065 g, 0.14 mmol, 1.0 equiv) was dissolved in methanol (2 mL) and dichloromethane (2 mL). 10% HCl (in IPA) (0.02 mL) was added and the reaction mixture was stirred at room temperature for 2 hours. The reaction mixture was quenched with water, neutralized by saturated aqueous sodium bicarbonate solution and extracted with EtOAc. The organic layer was washed with brine, dried over sodium sulfate and concentrated. The residue was triturated with n-pentane/diethyl ether. The solvent was decanted and the remaining material was dried to afford product 22 (0.02 g, 38% yield). LCMS (m/z): 397.2 [M+H]. $^1$H NMR (400 MHz, DMSO) δ 11.07 (s, 1H), 9.29 (s, 1H), 7.64 (d, J=8.4 Hz, 2H), 7.50 (d, J=8.4 Hz, 2H), 4.65 (t, J=6.0 Hz, 2H), 4.54 (t, J=6.0 Hz, 1H), 3.58 (dd, J=17.0, 10.5 Hz, 1H), 3.14 (dd, J=17.0, 8.1 Hz, 1H), 3.07 (s, 3H), 2.93 (t, J=6.0 Hz, 1H), 2.87 (t, J=6.0 Hz, 1H), 2.70-2.62 (m, 1H), 2.04 (dd, J=14.0, 8.4 Hz, 1H), 1.59 (s, 3H).

Example 23

Synthesis of (R)-N-hydroxy-2-methyl-2-(methylsulfonyl)-3-((R)-3-(4-propylphenyl)-4,5-dihydroisoxazol-5-yl)propanamide [23]

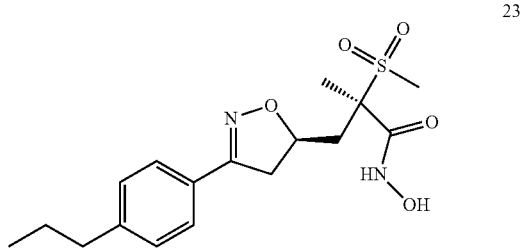 [SMILES: CCCc1ccc(C2=NO[C@@H](C[C@](C)(C(=O)NO)S(C)(=O)=O)C2)cc1]

23

Synthetic scheme

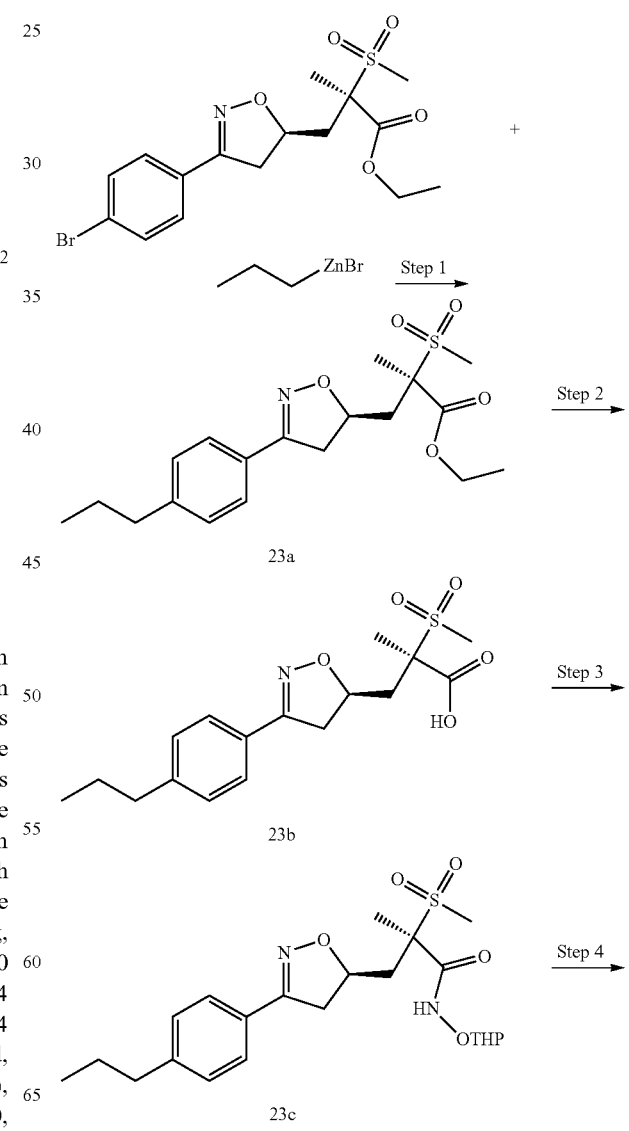

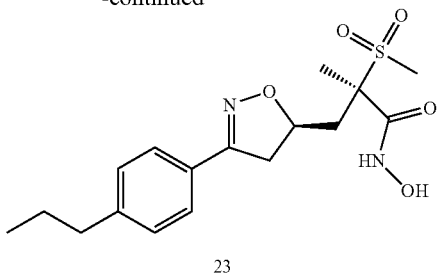

Reagents:

Step 1: CuI, PdCl$_2$(dppf), THF, 160° C. (MW). Step 2: LiOH.H$_2$O, THF, MeOH, water, room temperature. Step 3: NH$_2$OTHP, EDC.HCl, HOBT, N-methyl morpholine, THF, room temperature. Step 4: HCl (in IPA), MeOH, dichloromethane, 10° C. to room temperature.

Step 1. Synthesis of (R)-ethyl 2-methyl-2-(methylsulfonyl)-3-((R)-3-(4-propylphenyl)-4,5-dihydroisoxazol-5-yl)propanoate [23a]

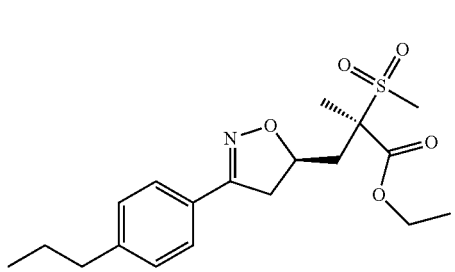

(R)-1d-A (0.2 g, 0.47 mmol, 1.0 equiv) was dissolved in THF (1 mL). CuI (0.005 g, 0.024 mmol, 0.05 equiv), PdCl$_2$(dppf) (0.017 g, 0.024 mmol, 0.05 equiv), propylzinc (II) bromide (5.0M in THF) (1.9 mL, 9.56 mmol, 20.0 equiv) were added and the reaction mixture was stirred at 160° C. for 10 minutes under microwave irradiation. The reaction mixture was filtered through Celite, washed with EtOAc. Te filtrate was diluted with water and extracted with EtOAc. The organic layer was washed with brine, dried over sodium sulfate and concentrated. The residue was purified by silica gel column chromatography (15% EtOAc/Hexane) to afford product 23a (0.1 g, 55% yield). LCMS (m/z): 382.2 [M+H]. $^1$H NMR (400 MHz, DMSO) δ 7.57 (d, J=8.2 Hz, 2H), 7.28 (d, J=8.3 Hz, 2H), 4.72 (dt, J=11.3, 5.5 Hz, 1H), 4.27 (q, J=7.1 Hz, 2H), 3.60 (dd, J=16.9, 10.3 Hz, 1H), 3.22-3.08 (m, 4H), 2.59 (dd, J=9.3, 5.5 Hz, 3H), 2.17 (dd, J=14.4, 8.5 Hz, 1H), 1.71-1.53 (m, 5H), 1.26 (t, J=7.1 Hz, 3H), 0.89 (t, J=7.3 Hz, 3H).

Step 2. Synthesis of (R)-2-methyl-2-(methylsulfonyl)-3-((R)-3-(4-propylphenyl)-4,5-dihydroisoxazol-5-yl)propanoic acid [23b]

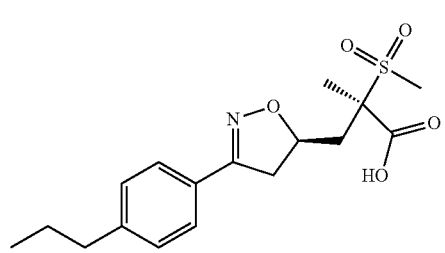

23a (0.1 g, 0.26 mmol, 1.0 equiv) was dissolved in THF (5 mL), MeOH (1 mL) and water (1 mL). LiOH.H$_2$O (0.022 g, 0.52 mmol, 2.0 equiv) was added and the reaction mixture was stirred at room temperature for 2 hours. The reaction mixture was acidified by 1.0 N HCl aqueous solution to pH 3 to 4 and extracted with EtOAc. The organic layer was washed with brine, dried over sodium sulfate and concentrated to afford product 23b (0.09 g, 97.8% yield). LCMS (m/z): 354.2 [M+H]. The product was directly used in the next step with no further purification. $^1$H NMR (400 MHz, DMSO) δ 7.55 (d, J=8.2 Hz, 2H), 7.27 (d, J=8.2 Hz, 2H), 4.77-4.68 (m, 1H), 3.58 (dd, J=17.0, 10.3 Hz, 1H), 3.19-3.12 (m, 1H), 3.10 (d, J=4.6 Hz, 3H), 2.57 (t, J=7.5 Hz, 3H), 2.11 (dd, J=14.3, 8.5 Hz, 1H), 1.63-1.46 (m, 5H), 0.86 (t, J=7.3 Hz, 3H).

Step 3. Synthesis of (2R)-2-methyl-2-(methylsulfonyl)-3-((R)-3-(4-propylphenyl)-4,5-dihydroisoxazol-5-yl)-N-((tetrahydro-2H-pyran-2-yl)oxy)propanamide [23c]

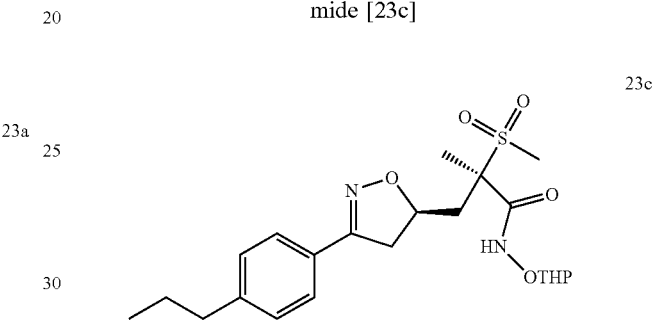

23b (0.09 g, 0.25 mmol, 1.0 equiv) was dissolved in THF (5 mL). N-methyl morpholine (0.13 g, 1.3 mmol, 5.0 equiv), HOBT (0.041 g, 0.31 mmol, 1.2 equiv), O-(tetrahydro-2H-pyran-2-yl) hydroxylamine (0.06 g, 0.5 mmol, 2.0 equiv), EDC.HCl (0.073 g, 0.38 mmol, 1.5 equiv) were added and the reaction mixture was stirred at room temperature for 24 hours. The reaction mixture was quenched with water and extracted with EtOAc. The organic layer was washed with brine, dried over sodium sulfate and concentrated. The residue was purified by silica gel column chromatography (30% EtOAc/Hexane) to afford product 23c (0.09 g, 78.3% yield). LCMS (m/z): 369.3 [M-THP]. $^1$H NMR (400 MHz, DMSO) δ 11.46 (s, 1H), 7.56 (d, J=7.5 Hz, 2H), 7.28 (d, J=8.1 Hz, 2H), 4.98 (d, J=9.3 Hz, 1H), 4.64 (d, J=6.9 Hz, 1H), 4.07 (dd, J=28.7, 6.2 Hz, 1H), 3.63-3.46 (m, 2H), 3.14 (dd, J=16.9, 8.0 Hz, 1H), 3.06 (d, J=8.5 Hz, 3H), 2.67 (d, J=14.3 Hz, 1H), 2.59 (t, J=7.5 Hz, 2H), 2.06 (dd, J=14.3, 8.8 Hz, 1H), 1.70 (s, 3H), 1.64-1.51 (m, 8H), 0.89 (t, J=7.3 Hz, 3H).

Step 4. Synthesis of (R)-N-hydroxy-2-methyl-2-(methylsulfonyl)-3-((R)-3-(4-propylphenyl)-4,5-dihydroisoxazol-5-yl)propanamide [23]

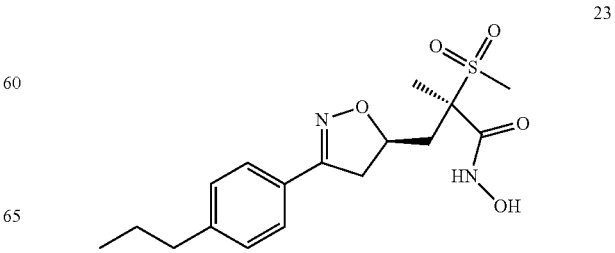

23c (0.09 g, 0.19 mmol, 1.0 equiv) was dissolved in dichloromethane (2 mL), methanol (0.5 mL) and the reaction mixture was cooled to 10° C. 10% HCl (in IPA) (0.2 mL) was added and the reaction mixture was stirred at room temperature for 1 hour. The reaction mixture was neutralized by saturated aqueous sodium bicarbonate solution and extracted with EtOAc. The organic layer was washed with brine, dried over sodium sulfate and concentrated to afford crude residue. The residue was triturated with n-pentane and diethyl ether. The solvent was decanted and the remaining solid was dried under vacuum to afford product 23 (0.043 g, 56.6% yield). LCMS (m/z): 369.2 [M+H]. ¹H NMR (400 MHz, DMSO) δ 11.11 (s, 1H), 9.11 (s, 1H), 7.56 (d, J=8.0 Hz, 2H), 7.28 (d, J=8.0 Hz, 2H), 4.63 (s, 1H), 3.53 (dd, J=16.6, 10.0 Hz, 1H), 3.13 (dd, J=16.7, 7.7 Hz, 1H), 3.06 (s, 3H), 2.70-2.55 (m, 3H), 2.02 (dd, J=13.8, 8.1 Hz, 1H), 1.60 (dd, J=16.0, 8.4 Hz, 5H), 0.89 (t, J=7.3 Hz, 3H).

Example 24

Synthesis of (R)-N-hydroxy-2-methyl-2-(methylsulfonyl)-3-((R)-3-(4-((E)-prop-1-en-1-yl)phenyl)-4,5-dihydroisoxazol-5-yl)propanamide [24]

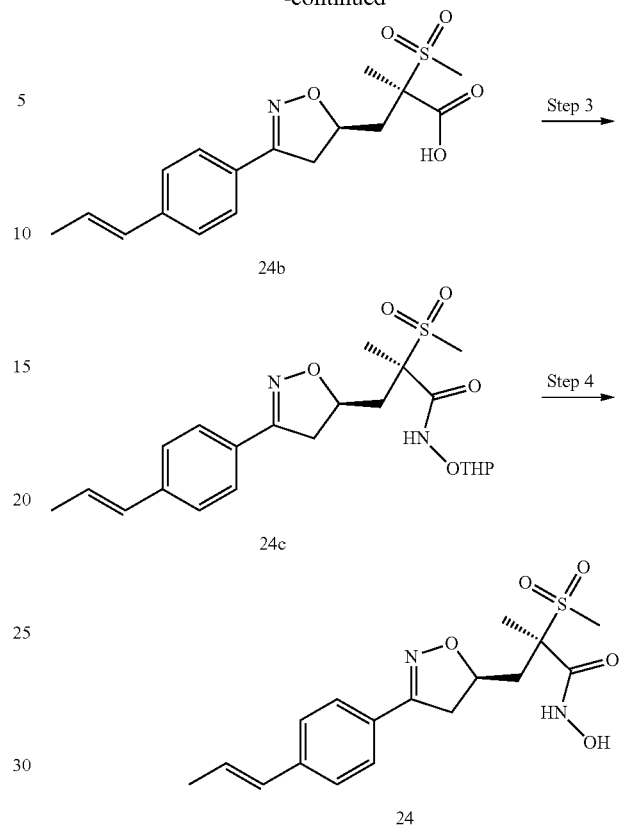

Reagents:
Step 1: Cs₂CO₃, PdCl₂(dppf), 1,4-dioxane, 100° C. Step 2: LiOH.H₂O, THF, MeOH, water, room temperature. Step 3: NH₂OTHP, EDC.HCl, HOBT, N-methyl morpholine, THF, room temperature. Step 4: HCl (in IPA), MeOH, dichloromethane, room temperature.

Step a. Synthesis of (R)-ethyl 2-methyl-2-(methylsulfonyl)-3-((R)-3-(4-((E)-prop-1-en-1-yl)phenyl)-4,5-dihydroisoxazol-5-yl)propanoate [24a]

Synthetic scheme

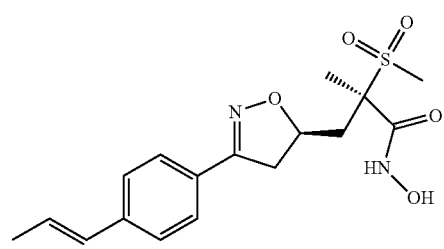

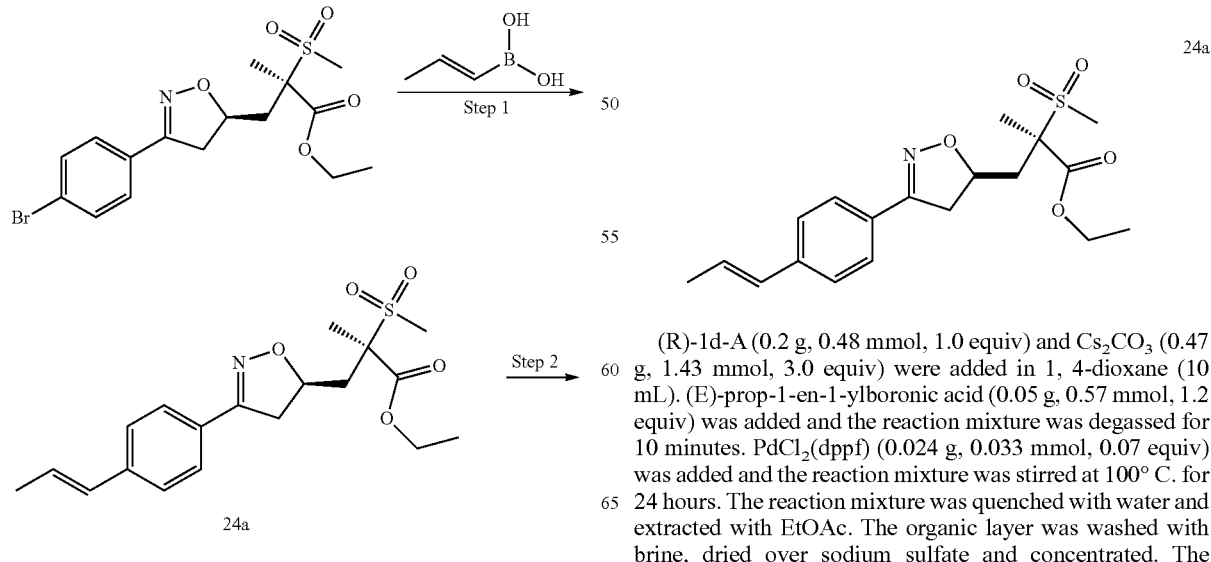

(R)-1d-A (0.2 g, 0.48 mmol, 1.0 equiv) and Cs₂CO₃ (0.47 g, 1.43 mmol, 3.0 equiv) were added in 1, 4-dioxane (10 mL). (E)-prop-1-en-1-ylboronic acid (0.05 g, 0.57 mmol, 1.2 equiv) was added and the reaction mixture was degassed for 10 minutes. PdCl₂(dppf) (0.024 g, 0.033 mmol, 0.07 equiv) was added and the reaction mixture was stirred at 100° C. for 24 hours. The reaction mixture was quenched with water and extracted with EtOAc. The organic layer was washed with brine, dried over sodium sulfate and concentrated. The residue was purified by silica gel column chromatography (25-35% EtOAc/Hexane) to afford product 24a (0.15 g, 80% yield). LCMS (m/z): 380.3 [M+H]. $^1$H NMR (400 MHz, DMSO) δ 7.67 (s, 1H), 7.59 (d, J=8.1 Hz, 1H), 7.47 (s, 2H), 6.47 (d, J=16.0 Hz, 1H), 4.74 (s, 1H), 4.35-4.19 (m, 2H), 3.61 (dt, J=20.7, 10.3 Hz, 1H), 3.24-3.00 (m, 4H), 2.60 (d, J=14.5 Hz, 1H), 2.19 (s, 1H), 1.87 (d, J=4.9 Hz, 1H), 1.64 (s, 3H), 1.26 (t, J=7.1 Hz, 3H).

Step 2. Synthesis of (R)-2-methyl-2-(methylsulfonyl)-3-((R)-3-(4-((E)-prop-1-en-1-yl)phenyl)-4,5-dihydroisoxazol-5-yl)propanoic acid [24b]

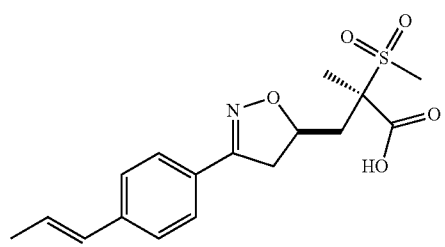

24b 24a (0.15 g, 0.38 mmol, 1.0 equiv) was dissolved in THF (4 mL), MeOH (1 mL) and water (1 mL). LiOH.H$_2$O (0.024 g, 0.57 mmol, 1.5 equiv) was added and the reaction mixture was stirred at room temperature for 2 hours. The reaction mixture was poured to water, acidified by 1.0 N HCl aqueous solution up to pH 4 to 5 and extracted with EtOAc. The organic layer was washed with brine, dried over sodium sulfate and concentrated to afford product 24b (0.11 g, 78% yield). LCMS (m/z): 352.2 [M+H]. $^1$H NMR (400 MHz, DMSO) δ 14.04 (s, 1H), 7.67 (s, 1H), 7.62-7.54 (m, 1H), 7.47 (s, 2H), 6.51-6.34 (m, 1H), 4.76 (s, 1H), 3.62 (dt, J=16.9, 10.3 Hz, 1H), 3.19 (dd, J=17.4, 9.7 Hz, 1H), 3.13 (s, 3H), 2.56 (s, 1H), 2.16 (dd, J=11.8, 6.9 Hz, 1H), 1.88 (dd, J=48.3, 43.2 Hz, 3H), 1.60 (s, 3H).

Step 3. Synthesis of (2R)-2-methyl-2-(methylsulfonyl)-3-((R)-3-(4-((E)-prop-1-en-1-yl)phenyl)-4,5-dihydroisoxazol-5-yl)-N-((tetrahydro-2H-pyran-2-yl)oxy)propanamide [24c]

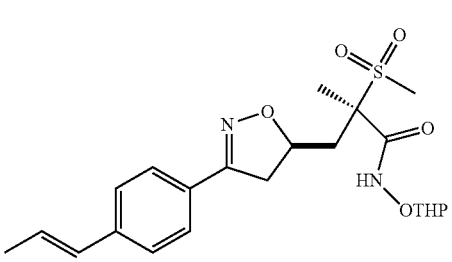

24c 24b (0.11 g, 0.3 mmol, 1.0 equiv) was dissolved in THF (10 mL). N-methyl morpholine (0.15 g, 1.5 mmol, 5.0 equiv), HOBT (0.048 g, 0.36 mmol, 1.2 equiv), O-(tetrahydro-2H-pyran-2-yl) hydroxylamine (0.071 g, 0.6 mmol, 2.0 equiv), EDC.HCl (0.086 g, 0.45 mmol, 1.5 equiv) were added and the reaction mixture was stirred at room temperature for 24 hours. The reaction mixture was quenched with water and extracted with EtOAc. The organic layer was washed with brine, dried over sodium sulfate and concentrated to afford product 24c (0.11 g, 78% yield). LCMS (m/z): 450.4 [M+H]. $^1$H NMR (400 MHz, DMSO) δ 11.44 (s, 1H), 7.67-7.61 (m, 1H), 7.59-7.52 (m, 1H), 7.49-7.39 (m, 2H), 6.48-6.31 (m, 1H), 4.96 (d, J=8.9 Hz, 1H), 4.63 (s, 1H), 4.16-4.02 (m, 1H), 3.65-3.42 (m, 2H), 3.14 (dd, J=17.2, 8.5 Hz, 1H), 3.02 (t, J=12.6 Hz, 3H), 2.72-2.60 (m, 1H), 2.10-2.00 (m, 1H), 1.82 (dd, J=24.6, 5.3 Hz, 3H), 1.68 (s, 3H), 1.60 (d, J=2.4 Hz, 3H), 1.53 (s, 3H).

Step 4. Synthesis of (R)-N-hydroxy-2-methyl-2-(methylsulfonyl)-3-((R)-3-(4-((E)-prop-1-en-1-yl)phenyl)-4,5-dihydroisoxazol-5-yl)propanamide [24]

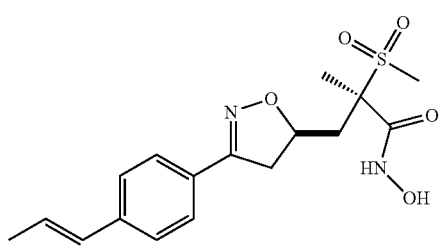

24

24c (0.11 g, 0.23 mmol, 1.0 equiv) was dissolved in methanol (2 mL) and dichloromethane (2 mL). 10% HCl (in IPA) (0.05 mL) was added and the reaction mixture was stirred at room temperature for 2 hours. The reaction mixture was quenched with saturated aqueous sodium bicarbonate solution and extracted with EtOAc. The organic layer was washed with brine, dried over sodium sulfate and concentrated. The crude residue was purified by preparative HPLC to afford product 24 (0.02 g, 23% yield). LCMS (m/z): 367.1 [M+H]. $^1$H NMR (400 MHz, DMSO) δ 11.05 (s, 1H), 9.28 (s, 1H), 7.58 (d, J=8.4 Hz, 2H), 7.46 (d, J=8.4 Hz, 2H), 6.52-6.35 (m, 2H), 4.62 (d, J=7.3 Hz, 1H), 3.56 (dd, J=17.0, 10.2 Hz, 1H), 3.13 (dd, J=17.0, 8.1 Hz, 1H), 3.07 (s, 3H), 2.66 (d, J=13.8 Hz, 1H), 2.04 (dd, J=14.0, 8.4 Hz, 1H), 1.87 (d, J=5.2 Hz, 3H), 1.59 (s, 3H).

Example 29

Synthesis of (R)-3-((R)-3-(4-((Z)-1-fluoroprop-1-en-1-yl)phenyl)-4,5-dihydroisoxazol-5-yl)-N-hydroxy-2-methyl-2-(methylsulfonyl)propanamide [29]

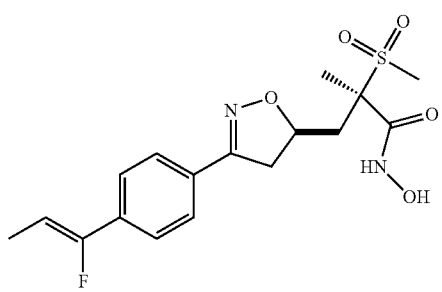

29

Synthetic scheme

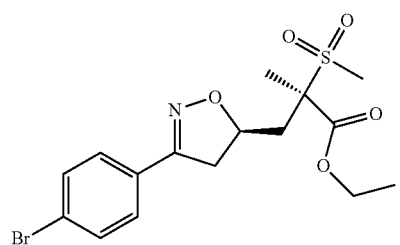

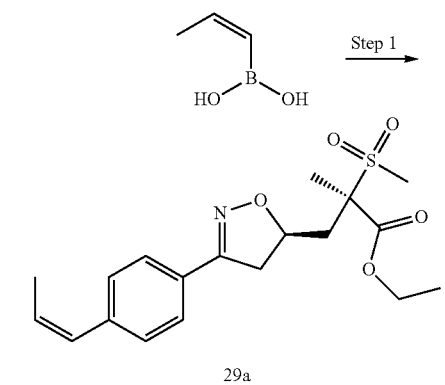

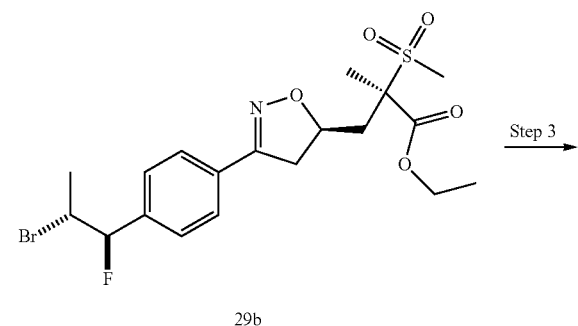

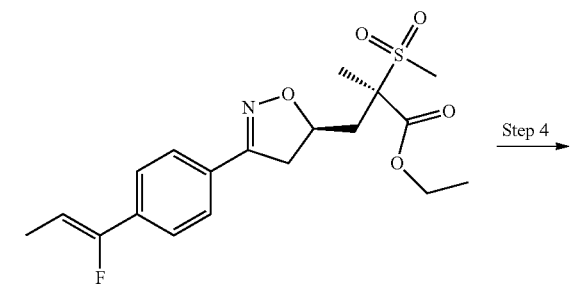

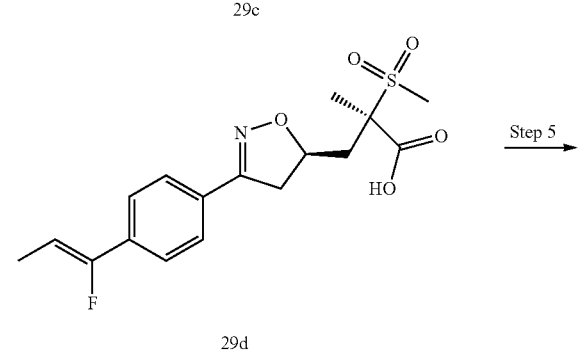

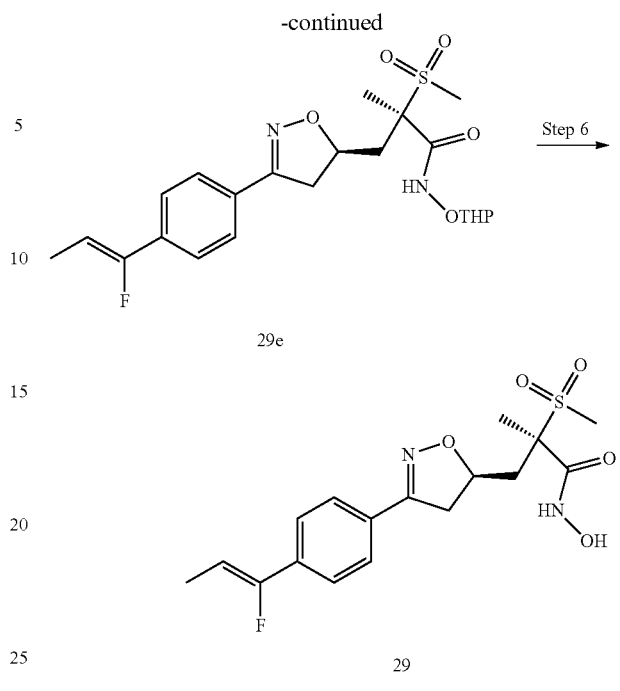

Reagents:
Step 1: PdCl$_2$(dppf), Cs$_2$CO$_3$, 1, 4-dioxane, 110° C. Step 2: NEt$_3$.3HF, NBS, dichloromethane, 0° C. to room temperature. Step 3: DBU, 85° C. Step 4: LiOH.H$_2$O, THF, MeOH, water, room temperature. Step 5: NH$_2$OTHP, EDC.HCl, HOBT, N-Methyl morpholine, THF, room temperature. Step 6: HCl (in IPA), MeOH, dichloromethane, room temperature.

Step 1. Synthesis of (R)-ethyl 2-methyl-2-(methylsulfonyl)-3-((R)-3-(4-((Z)-prop-1-en-1-yl)phenyl)-4,5-dihydroisoxazol-5-yl)propanoate [29a]

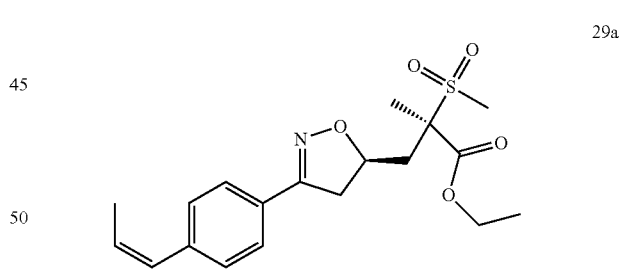

(R)-1d-A (0.2 g, 0.47 mmol, 1.0 equiv), (Z)-prop-1-en-1-ylboronic acid (0.053 g, 0.62 mmol, 1.3 equiv) were added in 1, 4-dioxane (4 mL) in sealed tube. Cs$_2$CO$_3$ (0.47 g, 1.43 mmol, 3.0 equiv) was added and the reaction mixture was degassed for 15 minutes. PdCl$_2$(dppf) (0.017 g, 0.023 mmol, 0.05 equiv) was added and the reaction mixture was stirred at 110° C. for 24 hours. The reaction mixture was filtered through Celite, washed with EtOAc and the filtrate was concentrated. The crude residue was purified by silica gel column chromatography (5% MeOH/dichloromethane) to afford product 29a (0.17 g, 93.7% yield). LCMS (m/z): 380.6 [M+H]. $^1$H NMR (400 MHz, DMSO) δ 7.65 (d, J=8.4 Hz, 2H), 7.40 (d, J=8.3 Hz, 2H), 6.47 (d, J=13.8 Hz, 1H), 5.92-5.82 (m, 1H), 4.80-4.70 (m, 1H), 4.27 (q, J=7.1 Hz, 2H), 3.66-3.57 (m, 1H), 3.23-3.06 (m, 4H), 2.60 (dd, J=14.4, 3.2 Hz, 1H), 2.19 (dd, J=14.4, 8.5 Hz, 1H), 1.89 (dt, J=7.3, 3.6 Hz, 3H), 1.64 (s, 3H), 1.26 (t, J=7.1 Hz, 3H).

Step 2. Synthesis of (2R)-ethyl 3-((5R)-3-(4-(2-bromo-1-fluoropropyl)phenyl)-4,5-dihydroisoxazol-5-yl)-2-methyl-2-(methylsulfonyl)propanoate [29b]

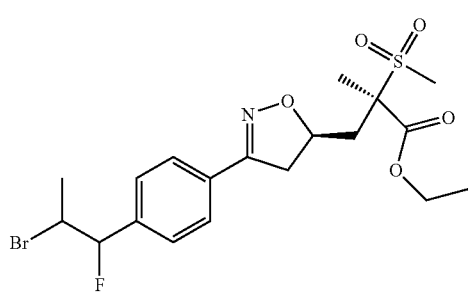

29a (0.17 g, 0.44 mmol, 1.0 equiv) was added in dichloromethane (6 mL) and cooled to 0° C. NEt$_3$.3HF (0.11 g, 0.66 mmol, 1.5 equiv) and NBS (0.086 g, 0.48 mmol, 1.1 equiv) were added. The reaction mixture was stirred at room temperature for 24 hours. The reaction mixture was quenched with water and the mixture was neutralize by NH$_4$OH. The mixture was then extracted with dichloromethane. The organic layer was washed with 1.0 N HCl and saturate aqueous sodium bicarbonate solution, dried over sodium sulfate and concentrated. The crude residue was purified by silica gel column chromatography (30-50% EtOAc/Hexane) to afford product 29b (0.045 g, 20.9% yield). LCMS (m/z): 480.3 [M+H]. $^1$H NMR (400 MHz, DMSO) δ 7.77-7.58 (m, 2H), 7.56-7.20 (m, 2H), 5.64 (ddd, J=44.4, 22.9, 6.1 Hz, 1H), 4.75 (dd, J=17.0, 6.5 Hz, 1H), 4.27 (q, J=7.1 Hz, 2H), 3.68-3.57 (m, 1H), 3.24-3.04 (m, 4H), 2.64-2.53 (m, 1H), 2.19 (dd, J=14.3, 8.5 Hz, 1H), 2.05-1.77 (m, 1H), 1.63 (q, J=6.7 Hz, 3H), 1.25 (d, J=7.1 Hz, 3H).

Step 3. Synthesis of (R)-ethyl 3-((R)-3-(4-((Z)-1-fluoroprop-1-en-1-yl)phenyl)-4,5-dihydroisoxazol-5-yl)-2-methyl-2-(methylsulfonyl)propanoate [29c]

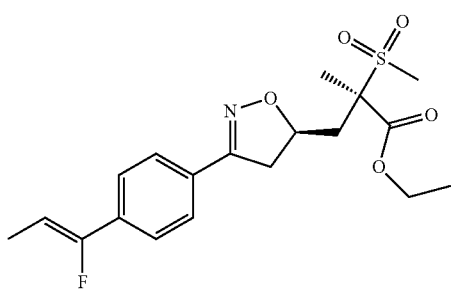

29b (0.19 g, 0.39 mmol, 1.0 equiv) was added in DBU (0.06 g, 0.39 mmol, 1.0 equiv) and the reaction mixture was stirred at 85° C. for 1 hour. The reaction mixture was quenched with water and extracted with dichloromethane. The organic layer was washed with brine, dried over sodium sulfate and concentrated. The residue was purified by silica gel column chromatography (30% EtOAc/Hexane) to afford product 29c (0.09 g, 57.3% yield). LCMS (m/z): 398.3 [M+H]. $^1$H NMR (400 MHz, DMSO) δ 7.80-7.35 (m, 4H), 5.88 (dt, J=46.1, 6.9 Hz, 1H), 4.76 (d, J=7.5 Hz, 1H), 4.27 (q, J=7.1 Hz, 2H), 3.63 (dd, J=17.0, 10.4 Hz, 1H), 3.26-3.09 (m, 4H), 2.60 (dd, J=14.4, 3.3 Hz, 1H), 2.19 (dd, J=14.4, 8.5 Hz, 1H), 2.04-1.68 (m, 3H), 1.69-1.57 (m, 3H), 1.26 (t, J=7.1 Hz, 3H).

Step 4. Synthesis of (R)-3-((R)-3-(4-((Z)-1-fluoroprop-1-en-1-yl)phenyl)-4,5-dihydroisoxazol-5-yl)-2-methyl-2-(methylsulfonyl)propanoic acid [29d]

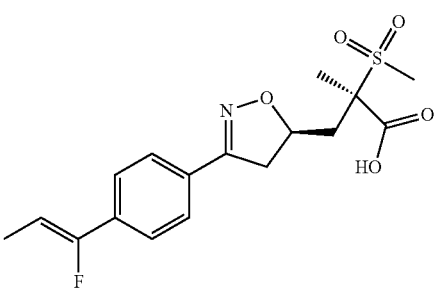

29c (0.09 g, 0.23 mmol, 1.0 equiv) was dissolved in THF (4 mL), MeOH (1 mL) and water (1 mL). LiOH.H$_2$O (0.01 g, 0.23 mmol, 1.0 equiv) was added and the reaction mixture was stirred at room temperature for 3 hours. The reaction mixture was concentrated under reduced pressure. The residue was diluted with water and extracted with EtOAc. The aqueous layer was acidified by 1.0 N HCl aqueous solution to the pH 4 to 5 and extracted with EtOAc. The organic layer was washed with brine, dried over sodium sulfate and concentrated to afford product 29d (0.075 g, 90.4% yield) which was used without purification in next step. LCMS (m/z): 370.3 [M+H].

Step 5. Synthesis of (2R)-3-((R)-3-(4-((Z)-1-fluoroprop-1-en-1-yl)phenyl)-4,5-dihydroisoxazol-5-yl)-2-methyl-2-(methylsulfonyl)-N-((tetrahydro-2H-pyran-2-yl)oxy)propanamide [29e]

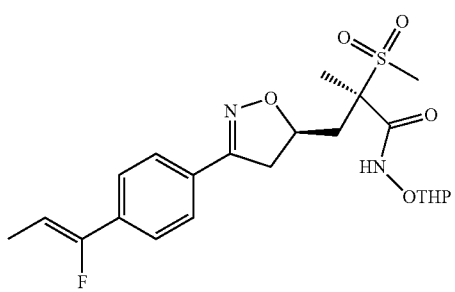

29d (0.075 g, 0.2 mmol, 1.0 equiv) was added in THF (5 mL). N-methyl morpholine (0.1 g, 1.01 mmol, 5.0 equiv), HOBT (0.033 g, 0.24 mmol, 1.2 equiv), O-(tetrahydro-2H-pyran-2-yl) hydroxylamine (0.047 g, 0.41 mmol, 2.0 equiv) were added and the reaction mixture was stirred at room temperature for 5 minutes. EDC.HCl (0.058 g, 0.3 mmol, 1.5 equiv) was added and the reaction mixture was stirred at room temperature for 6 hours. The reaction mixture was quenched with water and extracted with EtOAc. The organic layer was washed with brine, dried over sodium sulfate and concentrated to afford crude residue. The crude residue was purified by silica gel column chromatography (40% EtOAc/Hexane) to afford product 29e (0.09 g, 94.7% yield). LCMS (m/z): 385.3 [M-THP]. $^1$H NMR (400 MHz, DMSO) δ 11.47 (s, 1H), 7.87-7.53 (m, 4H), 5.88 (dd, J=39.2, 7.1 Hz, 1H), 4.98 (d, J=9.1 Hz, 1H), 4.68 (s, 1H), 4.09-3.97 (m, 1H), 3.58 (ddd, J=28.7, 16.3, 11.2 Hz, 2H), 3.21-3.12 (m, 3H), 2.68 (dd, J=8.3, 6.4 Hz, 1H), 2.09 (t, J=6.0 Hz, 1H), 1.74-1.65 (m, 3H), 1.62 (d, J=4.3 Hz, 3H), 1.55 (s, 3H), 1.27-1.20 (m, 3H).

Step 6. Synthesis of (R)-3-((R)-3-(4-((Z)-1-fluoroprop-1-en-1-yl)phenyl)-4,5-dihydroisoxazol-5-yl)-N-hydroxy-2-methyl-2-(methylsulfonyl)propanamide [29]

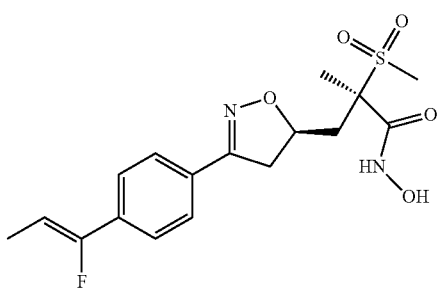

29

29e (0.09 g, 0.19 mmol, 1.0 equiv) was dissolved in dichloromethane (4 mL) and methanol (1 mL). 10% HCl (in IPA) (0.1 mL) was added and the reaction mixture was stirred at room temperature for 2 hours. The reaction mixture was concentrated under reduced pressure, triturated with diethyl ether and n-pentane, the solvent was decanted to afford crude residue. The crude residue was purified by preparative HPLC purification to afford product 29 as Z-isomer (0.022 g, 30% yield). LCMS (m/z): 385.3 [M+H]. $^1$H NMR (400 MHz, DMSO) δ 11.27-10.76 (m, 1H), 9.85-9.32 (m, 1H), 7.68 (d, J=8.4 Hz, 2H), 7.65-7.56 (m, 2H), 5.88 (dq, J=39.3, 7.0 Hz, 1H), 4.70-4.59 (m, 1H), 3.58 (dd, J=16.9, 10.4 Hz, 1H), 3.16 (dd, J=17.1, 8.0 Hz, 1H), 3.05 (d, J=14.1 Hz, 3H), 2.65 (dd, J=13.9, 3.4 Hz, 1H), 2.04 (dd, J=14.0, 8.3 Hz, 1H), 1.78 (dd, J=7.1, 2.2 Hz, 3H), 1.58 (s, 3H).

31

Synthesis of (R)-3-((R)-3-(4-ethylphenyl)-4,5-dihydroisoxazol-5-yl)-N-hydroxy-2-methyl-2-(methylsulfonyl)propanamide [31]

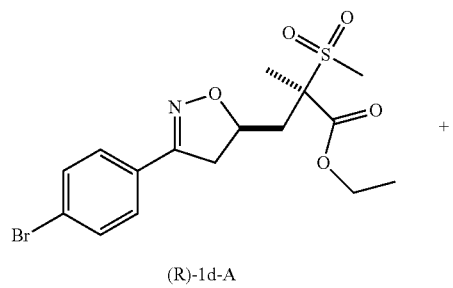

(R)-1d-A

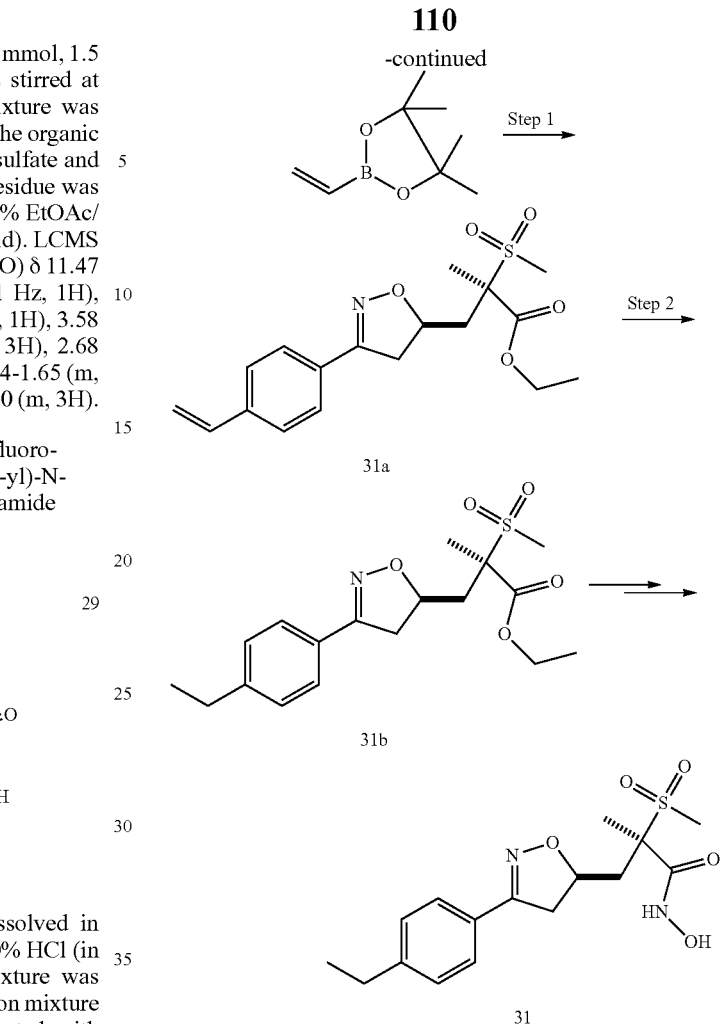

Step 1. Synthesis of ethyl (R)-2-methyl-2-(methylsulfonyl)-3-((R)-3-(4-vinylphenyl)-4, 5-dihydroisoxazol-5-yl) propanoate [31a]

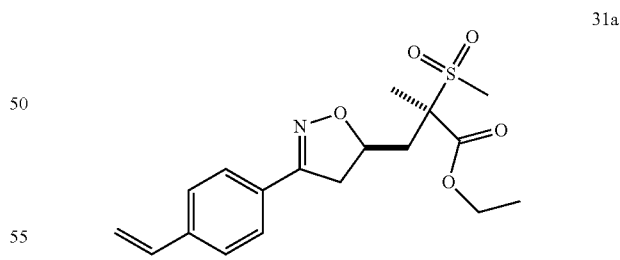

31a (R)-1d-A (0.2 g, 0.48 mmol, 1.0 equiv) was dissolved in 1, 4-dioxane (5 mL). 4, 4, 5, 5-Tetramethyl-2-vinyl-1, 3, 2-dioxaborolane (0.1 g, 0.62 mmol, 1.3 equiv), Cs$_2$CO$_3$ (0.47 g, 1.43 mmol, 3.0 equiv) were added and the reaction mixture was degassed for 15 minutes. PdCl$_2$(dppf) (0.025 g, 0.033 mmol, 0.07 equiv) was added and the reaction mixture was stirred at 100° C. for 24 hours. The reaction mixture was quenched with water and extracted with EtOAc. The organic layer was washed with brine, dried over sodium sulfate and concentrated to afford the desired product 31 (0.16 g, 94% yield). LCMS (m/z): 366.3 [M+H]+. ¹H NMR (400 MHz, DMSO) δ 7.60 (dd, J=28.7, 8.3 Hz, 4H), 6.78 (dd, J=17.8, 10.9 Hz, 1H), 5.94 (d, J=17.7 Hz, 1H), 5.35 (d, J=11.0 Hz, 1H), 4.75 (d, J=8.1 Hz, 1H), 4.33-4.16 (m, 2H), 3.67-3.55 (m, 1H), 3.31-2.98 (m, 4H), 2.60 (d, J=11.2 Hz, 1H), 2.19 (dd, J=14.4, 8.5 Hz, 1H), 1.64 (s, 3H), 1.26 (t, J=7.1 Hz, 3H).

Step 2. Synthesis of ethyl (R)-3-((R)-3-(4-ethylphenyl)-4, 5-dihydroisoxazol-5-yl)-2-methyl-2-(methylsulfonyl) propanoate [31b]

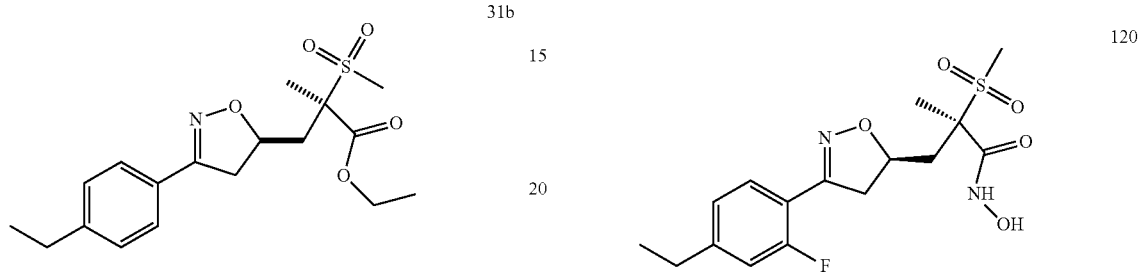

31a (0.16 g, 0.45 mmol, 1.0 equiv) was dissolved in methanol (5 mL). Pd/C (0.02 g) was added to the solution and the H₂ (gas) was purged into the reaction mixture at room temperature for 50 minutes. The reaction mixture was filtered through celite bed and the filtrate was concentrated to afford a crude residue. The crude residue was purified by silica gel column chromatography (20% EtOAc/Hexane) to afford the desired product 31b (0.13 g, 78% yield). LCMS (m/z): 368.4 [M+H]+. ¹H NMR (400 MHz, DMSO) δ 7.58 (d, J=8.2 Hz, 2H), 7.31 (d, J=8.2 Hz, 2H), 4.72 (d, J=7.7 Hz, 1H), 4.27 (q, J=7.1 Hz, 2H), 3.60 (dd, J=16.9, 10.2 Hz, 1H), 3.21-3.11 (m, 4H), 2.64 (dd, J=15.3, 7.8 Hz, 3H), 2.17 (dd, J=14.3, 8.4 Hz, 1H), 1.64 (s, 3H), 1.26 (d, J=1.9 Hz, 3H), 1.19 (t, J=7.6 Hz, 3H).

Step 3. Synthesis of (R)-3-((R)-3-(4-ethylphenyl)-4, 5-dihydroisoxazol-5-yl)-N-hydroxy-2-methyl-2-(methylsulfonyl)propanamide [31]

Ethyl ester 31b was converted to compound 31 by the procedures described for the synthesis of 2-A. LCMS (m/z): 355.2 [M+H]+. ¹H NMR (400 MHz, DMSO) δ 11.06 (s, 1H), 9.29 (s, 1H), 7.57 (d, J=7.8 Hz, 2H), 7.31 (d, J=8.0 Hz, 2H), 4.60 (s, 1H), 3.56 (dd, J=17.1, 10.3 Hz, 1H), 3.20-3.10 (m, 1H), 3.07 (s, 3H), 2.64 (dd, J=14.8, 7.7 Hz, 3H), 2.03 (dd, J=13.4, 8.8 Hz, 1H), 1.59 (s, 3H), 1.20 (dd, J=17.7, 10.2 Hz, 3H).

101. Synthesis of (R)-3-((R)-3-(4-ethyl-3-fluorophenyl)-4,5-dihydroisoxazol-5-yl)-N-hydroxy-2-methyl-2-(methylsulfonyl)propanamide [101]

Compound 101 was synthesized by the process of example 31. LCMS (m/z): 373.1 [M+H]+. ¹H NMR (400 MHz, CD3CN) 1.23 (t, J=7.56 Hz, 3H) 1.69 (s, 3H) 2.22 (dd, J=14.18, 8.66 Hz, 1H) 2.55-2.81 (m, 3H) 3.01 (s, 3H) 3.11 (dd, J=16.92, 8.36 Hz, 1H) 3.54 (dd, J=16.92, 10.37 Hz, 1H) 4.56-4.87 (m, 1H) 7.19-7.47 (m, 3H)

120. (R)-3-((R)-3-(4-ethyl-2-fluorophenyl)-4,5-dihydroisoxazol-5-yl)-N-hydroxy-2-methyl-2-(methylsulfonyl)propanamide [120]

Compound 120 was synthesized by the process of example 31. LCMS (m/z): 373.0 [M+H]+. ¹H NMR (400 MHz, CD₃CN) 1.24 (t, J=7.63 Hz, 3H) 1.96 (dt, J=4.69, 2.35 Hz, 4H) 2.17 (dd, J=13.89, 3.72 Hz, 1H) 2.63-2.82 (m, 4H) 3.01 (s, 3H) 3.19 (ddd, J=17.22, 7.43, 1.96 Hz, 1H) 3.61 (ddd, J=17.22, 10.17, 1.96 Hz, 1H) 4.86 (dt, J=7.14, 3.28 Hz, 1H) 6.94-7.23 (m, 2H) 7.68 (t, J=8.02 Hz, 1H) 9.35-9.67 (m, 1H)

32

Synthesis of (R)-3-((R)-3-(4-(ethylthio)phenyl)-4,5-dihydroisoxazol-5-yl)-N-hydroxy-2-methyl-2-(methylsulfonyl)propanamide [32]

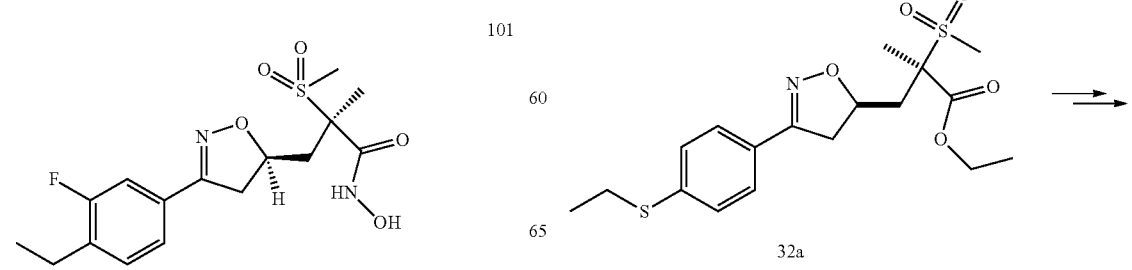

113

-continued

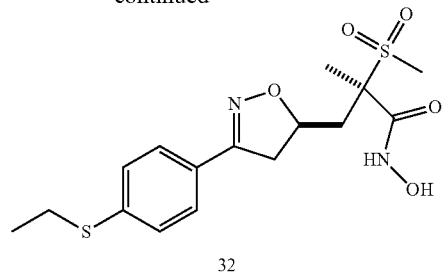

32

Step 1. Synthesis of ethyl (R)-3-((R)-3-(4-(ethylthio) phenyl)-4, 5-dihydroisoxazol-5-yl)-2-methyl-2-(methyl sulfonyl) propanoate [32a]

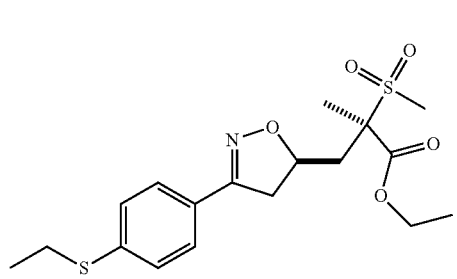

32a

K$_2$CO$_3$ (0.07 g, 0.48 mmol, 1.0 equiv) was dissolved in xylene (4 mL) and cooled to 0° C. Ethanethiol (0.15 g, 2.39 mmol, 5.0 equiv) was added drop wise and the reaction mixture was stirred at room temperature for 1 hour. (R)-1d-A (0.2 g, 0.48 mmol, 1.0 equiv), Pd$_2$(dba)$_3$ (0.022 g, 0.024 mmol, 0.05 equiv), xantphos (0.028 g, 0.048 mmol, 0.1 equiv) were added in xylene (8 mL). The reaction mixture was stirred at room temperature for 20 minutes. This solution was added to above potassium thiolate and the reaction mixture was stirred at reflux temperature for 24 hours. The reaction mixture was quenched with water and extracted with EtOAc. The organic layer was washed with brine, dried over sodium sulfate and concentrated to afford a crude residue. The crude residue was purified by silica gel column chromatography (60% EtOAc/Hexane) to afford the desired product 32a (0.17 g, 86.2% yield). LCMS (m/z): 400.4 [M+H]$^+$. $^1$H NMR (400 MHz, DMSO) δ 7.60 (t, J=8.6 Hz, 2H), 7.37 (d, J=8.6 Hz, 2H), 4.73 (dd, J=15.3, 8.0 Hz, 1H), 4.27 (q, J=7.1 Hz, 2H), 3.59 (dd, J=16.9, 10.3 Hz, 1H), 3.20-3.11 (m, 4H), 3.07-3.00 (m, 2H), 2.59 (dd, J=14.4, 3.2 Hz, 1H), 2.21 (dd, J=10.1, 5.4 Hz, 1H), 1.63 (s, 3H), 1.27 (dd, J=7.2, 1.1 Hz, 3H).

Step 2. Synthesis of (R)-3-((R)-3-(4-(ethylthio)phenyl)-4,5-dihydroisoxazol-5-yl)-N-hydroxy-2-methyl-2-(methylsulfonyl)propanamide [32]

32

Ethyl ester 32a was converted to compound 31 by the procedures described for the synthesis of 2-A. LCMS (m/z): 387.4 [M+H]. $^1$H NMR (400 MHz, DMSO) δ 11.00 (s, 1H), 9.28 (s, 1H), 7.58 (d, J=8.4 Hz, 2H), 7.37 (d, J=8.5 Hz, 2H), 4.62 (d, J=7.2 Hz, 1H), 3.55 (dd, J=17.0, 10.3 Hz, 1H), 3.12 (dd, J=17.0, 8.0 Hz, 1H), 3.04 (dd, J=13.9, 6.6 Hz, 5H), 2.65 (dd, J=14.0, 3.1 Hz, 1H), 2.08-1.99 (m, 1H), 1.59 (s, 3H), 1.26 (t, J=7.3 Hz, 3H).

33

Synthesis of (R)-3-((R)-3-(4-(3-fluoropropyl) phenyl)-4, 5-dihydroisoxazol-5-yl)-N-hydroxy-2-methyl-2-(methyl sulfonyl) propanamide [33]

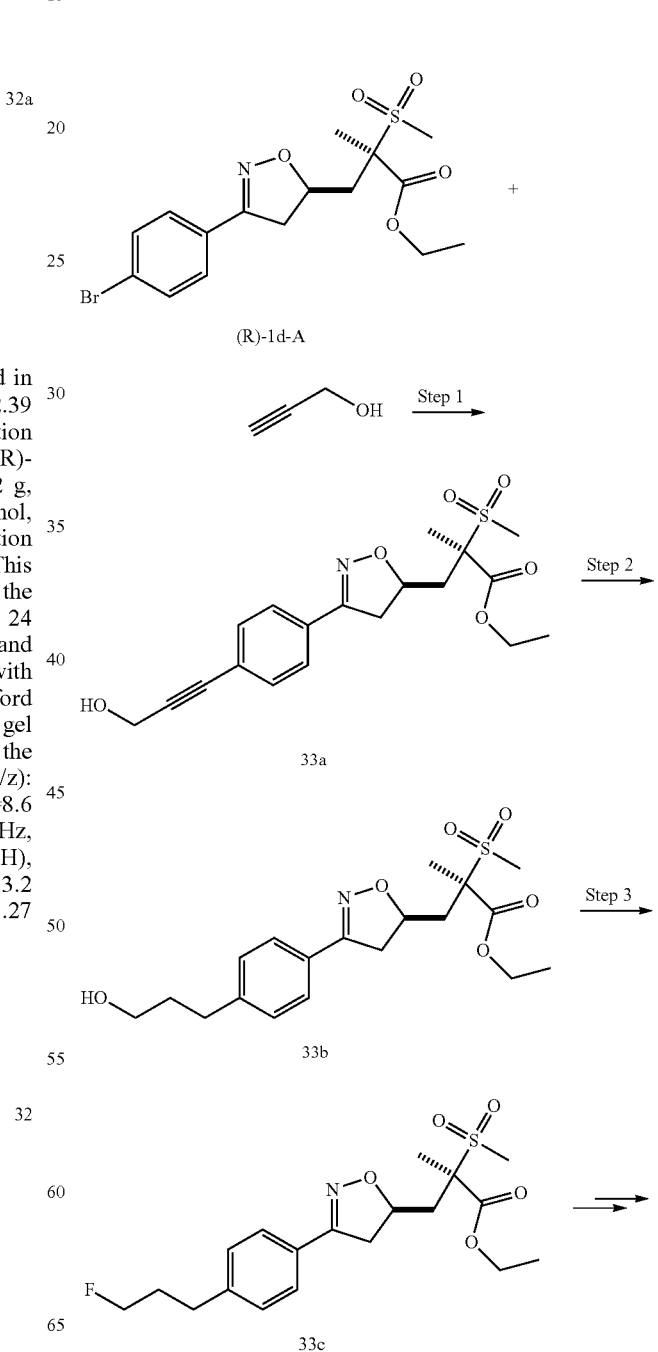

-continued

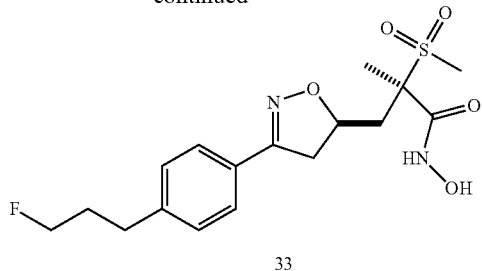

33

Step 1. Synthesis of ethyl (R)-3-((R)-3-(4-(3-hydroxyprop-1-yn-1-yl) phenyl)-4, 5-dihydroisoxazol-5-yl)-2-methyl-2-(methyl sulfonyl) propanoate [33a]

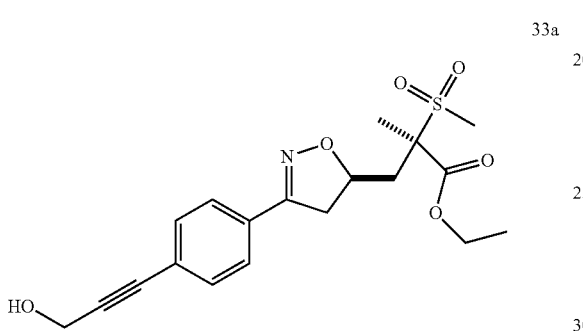

33a (R)-1d-A (0.3 g, 0.72 mmol, 1.0 equiv) was dissolved in diethyl amine: N, N-dimethylformamide (5:1) (20 mL). CuI (0.013 g, 0.071 mmol, 0.1 equiv), triphenylphosphine (0.037 g, 0.14 mmol, 0.2 equiv) were added and the reaction mixture was degassed for 15 minutes. PdCl$_2$(pph$_3$)$_2$ (0.024 g, 0.035 mmol, 0.05 equiv), prop-2-yn-1-ol (0.06 g, 1.07 mmol, 1.5 equiv) were added and the reaction mixture was stirred at 120° C. for 24 hours. The reaction mixture was quenched with water and extracted with EtOAc. The organic layer was washed with brine, dried over sodium sulfate and concentrated to afford a crude residue. The crude residue was purified by silica gel column chromatography (65-70% EtOAc/Hexane) to afford product 33a (0.27 g, 87.1% yield). LCMS (m/z): 394.4 [M+H]$^+$. $^1$H NMR (400 MHz, DMSO) δ 7.66 (d, J=8.2 Hz, 2H), 7.51 (d, J=8.2 Hz, 2H), 5.39 (t, J=6.0 Hz, 1H), 4.78 (s, 1H), 4.33 (d, J=6.0 Hz, 1H), 4.27 (d, J=7.1 Hz, 1H), 3.61 (s, 1H), 3.27-3.07 (m, 4H), 2.61 (s, 1H), 2.19 (dd, J=14.5, 8.5 Hz, 1H), 1.64 (s, 3H), 1.26 (t, J=7.1 Hz, 3H).

Step 2. Synthesis of ethyl (R)-3-((R)-3-(4-(3-hydroxypropyl) phenyl)-4, 5-dihydroisoxazol-5-yl)-2-methyl-2-(methyl sulfonyl) propanoate [33b]

33b

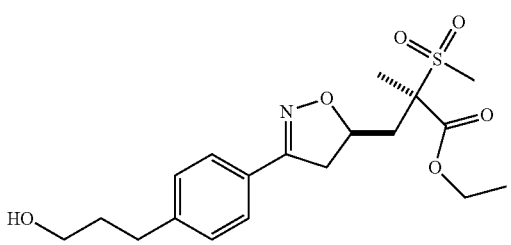

33a (0.27 g, 0.68 mmol, 1.0 equiv) was dissolved in methanol (10 mL). Pd/C (10%) (0.027 g) was added to the solution and the H$_2$ (gas) was purged into the reaction mixture at room temperature for 1 hour. The reaction mixture was filtered through celite bed, washed with methanol and the filtrate was concentrated to afford the desired product 33b (0.2 g, 73.5% yield). LCMS (m/z): 398.5 [M+H]$^+$. $^1$H NMR (400 MHz, DMSO) δ 7.58 (s, 2H), 7.29 (d, J=8.2 Hz, 2H), 4.79-4.69 (m, 1H), 4.51 (s, 1H), 4.27 (q, J=7.1 Hz, 2H), 3.60 (dd, J=16.9, 10.3 Hz, 1H), 3.41 (dd, J=10.4, 6.1 Hz, 2H), 3.18-3.16 (m, 1H), 3.14 (s, 3H), 2.68-2.62 (m, 2H), 2.59 (dd, J=14.6, 3.4 Hz, 1H), 2.17 (dd, J=14.4, 8.5 Hz, 1H), 1.77-1.67 (m, 2H), 1.64 (s, 3H), 1.26 (t, J=7.1 Hz, 3H).

Step 3. Synthesis of ethyl (R)-3-((R)-3-(4-(3-fluoropropyl) phenyl)-4, 5-dihydroisoxazol-5-yl)-2-methyl-2-(methyl sulfonyl) propanoate [33c]

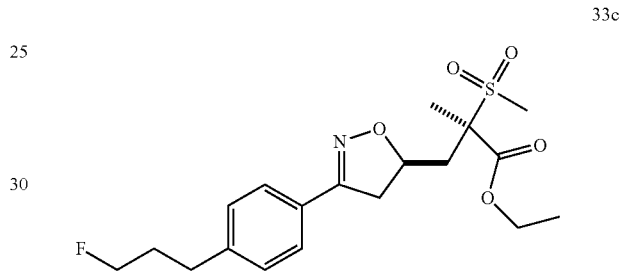

33c 33b (0.15 g, 0.38 mmol, 1.0 equiv) was dissolved in dichloromethane (18 mL) and cooled to −78° C. DAST (0.12 g, 0.75 mmol, 2.0 equiv) was added drop wise and the reaction mixture was stirred at room temperature for 3 hours. The reaction mixture was quenched with saturated aqueous sodium bicarbonate solution and extracted with EtOAc. The organic layer was washed with brine, dried over sodium sulfate and concentrated to afford a crude residue. The crude residue was purified by silica gel column chromatography (30-35% EtOAc/Hexane) to afford the desired product 33c (0.1 g, 49.8% yield). LCMS (m/z): 400.4 [M+H]. $^1$H NMR (400 MHz, DMSO) δ 7.59 (d, J=8.3 Hz, 2H), 7.32 (d, J=8.3 Hz, 2H), 4.73 (d, J=7.5 Hz, 1H), 4.51 (t, J=6.0 Hz, 1H), 4.39 (t, J=6.0 Hz, 1H), 4.27 (q, J=7.1 Hz, 2H), 3.65-3.55 (m, 1H), 3.21-3.09 (m, 4H), 2.74-2.69 (m, 1H), 2.59 (d, J=14.7 Hz, 2H), 2.18 (dt, J=15.8, 6.5 Hz, 2H), 2.00 (d, J=5.8 Hz, 1H), 1.64 (s, 3H), 1.26 (dd, J=8.7, 5.5 Hz, 3H).

Step 4. Synthesis of (R)-3-((R)-3-(4-(3-fluoropropyl) phenyl)-4, 5-dihydroisoxazol-5-yl)-N-hydroxy-2-methyl-2-(methyl sulfonyl) propanamide [33]

Ethyl ester 33ca was converted to compound 33 by the procedures described for the synthesis of 2-A. LCMS (m/z): 387.5 [M+H]. $^1$H NMR (400 MHz, DMSO) δ 11.15-10.72 (m, 1H), 9.51-9.09 (m, 1H), 7.58 (d, J=7.8 Hz, 2H), 7.32 (d, J=7.7 Hz, 2H), 4.63 (s, 1H), 4.51 (t, J=5.7 Hz, 1H), 4.40 (t, J=6.0 Hz, 1H), 3.55 (dd, J=17.1, 10.0 Hz, 1H), 3.20-3.11 (m, 1H), 3.07 (s, 3H), 2.76-2.69 (m, 2H), 2.65 (d, J=14.9 Hz, 1H), 2.00 (dd, J=29.9, 21.4 Hz, 3H), 1.58 (s, 3H).

34

Synthesis of (R)-3-((R)-3-(4-(4-fluorobutyl) phenyl)-4, 5-dihydroisoxazol-5-yl)-N-hydroxy-2-methyl-2-(methyl sulfonyl) propanamide [34]

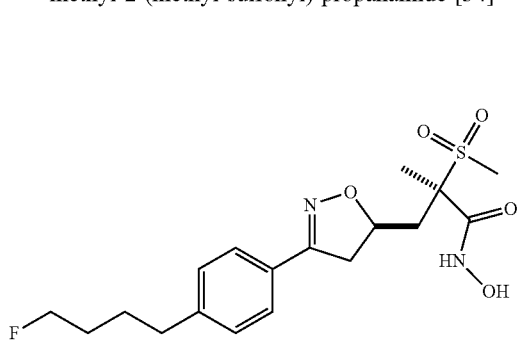

Compound 34 was synthesized by the process of example 33. LCMS (m/z): 401.4 [M+H]$^+$. $^1$H NMR (400 MHz, DMSO) δ 11.06 (s, 1H), 9.29 (s, 1H), 7.57 (d, J=7.8 Hz, 2H), 7.30 (d, J=8.0 Hz, 2H), 4.60 (s, 1H), 4.52 (s, 1H), 4.40 (s, 1H), 3.55 (s, 1H), 3.19-3.00 (m, 4H), 2.65 (d, J=6.6 Hz, 3H), 2.08-1.98 (m, 1H), 1.63 (d, J=31.6 Hz, 7H).

39

Synthesis of Synthesis of (R)-N-hydroxy-3-((R)-3-(4-((3-(2-hydroxypropan-2-yl) cyclobutyl) ethynyl) phenyl)-4, 5-dihydroisoxazol-5-yl)-2-methyl-2-(methyl sulfonyl) propanamide [39A & 39B]

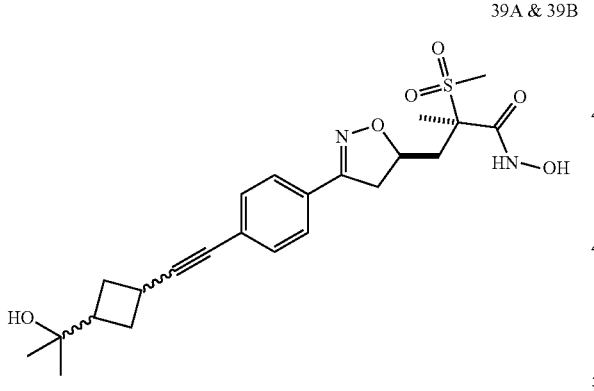

39A (0.065 g, 21.9% yield). LCMS (m/z): 463.6 [M+H]$^+$. $^1$H NMR (400 MHz, DMSO) δ 11.07 (s, 1H), 9.29 (s, 1H), 7.62 (d, J=8.4 Hz, 2H), 7.47 (d, J=8.4 Hz, 2H), 4.64 (d, J=6.7 Hz, 1H), 4.25 (s, 1H), 3.62-3.51 (m, 1H), 3.19-3.09 (m, 2H), 3.07 (s, 3H), 2.66 (d, J=13.5 Hz, 1H), 2.46 (d, J=8.0 Hz, 1H), 2.37 (dd, J=18.1, 8.3 Hz, 2H), 2.08-1.95 (m, 3H), 1.59 (s, 3H), 1.01 (s, 6H). 39B (0.055 g, 18.6% yield). LCMS (m/z): 463.6 [M+H]$^+$. $^1$H NMR (400 MHz, DMSO) δ 11.21-10.94 (m, 1H), 9.45-9.16 (m, 1H), 7.61 (d, J=8.4 Hz, 2H), 7.44 (d, J=8.3 Hz, 2H), 4.63 (s, 1H), 4.23 (s, 1H), 3.56 (dd, J=17.1, 10.5 Hz, 1H), 3.14 (dd, J=17.2, 7.8 Hz, 1H), 3.06 (s, 3H), 3.02 (d, J=8.2 Hz, 1H), 2.65 (d, J=14.6 Hz, 1H), 2.16 (s, 1H), 2.15 (d, J=5.9 Hz, 3H), 2.11-2.00 (m, 3H), 1.58 (s, 3H), 0.97 (s, 6H).

Compounds 40-122 was synthesized by one of the following methods.

Method A

Synthesis of (R)-N-hydroxy-2-methyl-2-(methylsulfonyl)-3-((R)-3-(4-(thiophen-3-yl)phenyl)-4,5-dihydroisoxazol-5-yl)propanamide [91]

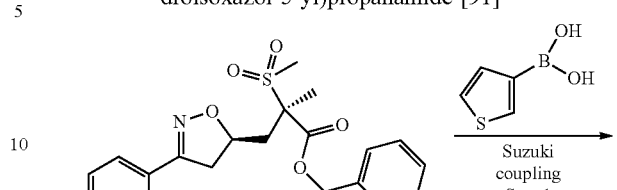

91a

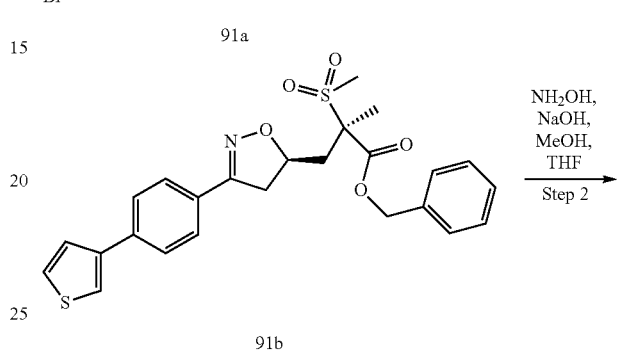

91b

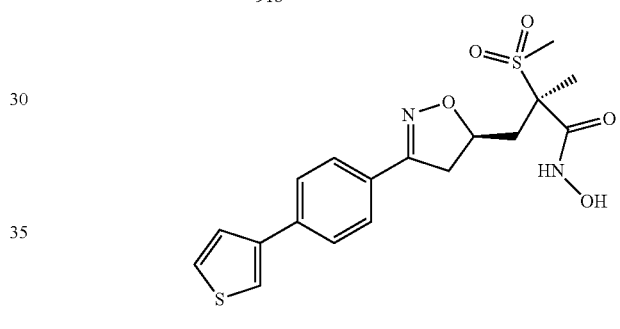

91

Step 1. Synthesis of (R)-benzyl 2-methyl-2-(methylsulfonyl)-3-((R)-3-(4-(thiophen-3-yl)phenyl)-4,5-dihydroisoxazol-5-yl)propanoate [91b]

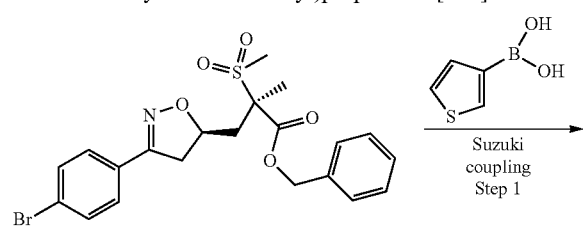

91a

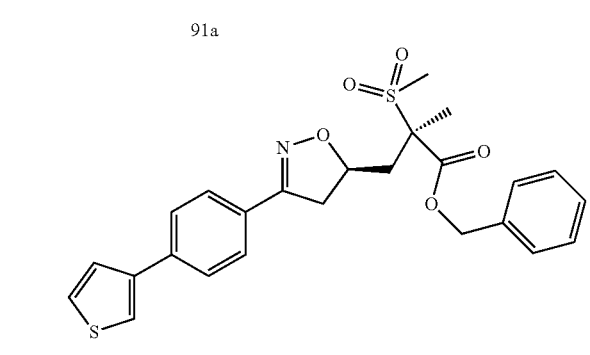

91b

To a mixture of (R)-benzyl 3-((R)-3-(4-bromophenyl)-4,5-dihydroisoxazol-5-yl)-2-methyl-2-(methylsulfonyl)propanoate (91a, 70 mg, 0.146 mmol) and thiophen-3-ylboronic acid (37.3 mg, 0.291 mmol) in DME (2 mL) was added PdCl$_2$(dppf).CH$_2$Cl$_2$ adduct (11.90 mg, 0.015 mmol), followed by Na$_2$CO$_3$ (46.3 mg, 0.437 mmol) and water (0.5 mL). The resultant mixture was sealed and was stirred at 110° C. for 10 min using microwave reactor. The reaction mixture was diluted with EtOAc. The organic layer was separated, dried over Na$_2$SO$_4$, and concentrated. The crude residue was purified by silica gel column chromatography (EtOAc/heptane, 10 to 80%) to give product 91b (29 mg, 41.2% yield). LCMS: m/e: 484.3 [M+H].

Step 2: Synthesis of (R)-N-hydroxy-2-methyl-2-(methylsulfonyl)-3-((R)-3-(4-(thiophen-3-yl)phenyl)-4,5-dihydroisoxazol-5-yl)propanamide [91]

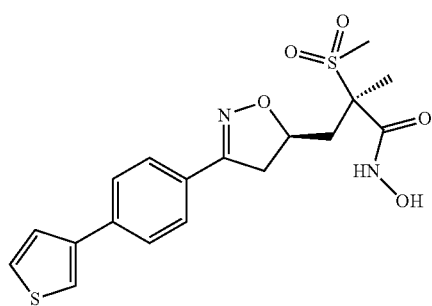

91

Compound 91 could be synthesized from 91a by the procedure of 2-A or by the following one step procedure.

To a mixture of 91a and NH$_2$OH (0.091 mL, 50% in water, 2.89 mmol) in THF (0.15 mL) and MeOH (0.30 mL) was added NaOH (23.16 mg, 0.579 mmol). The resultant mixture was stirred at rt for 1 hour. The mixture was purified on reverse phase HPLC to afford product 91 (9 mg, 0.021 mmol, 36.5% yield). LCMS: m/e: 409.3 [M+H]$^+$, $^1$H NMR (400 MHz, DMSO) 1.58 (s, 4H) 1.93-2.14 (m, 2H) 2.59-2.74 (m, 2H) 3.05 (s, 3H) 3.09-3.23 (m, 2H) 3.49-3.67 (m, 1H) 4.50-4.80 (m, 2H) 7.66 (d, J=7.68 Hz, 4H) 7.80 (s, 2H) 7.88-8.08 (m, 1H) 9.14-9.39 (m, 1H) 10.84-11.19 (m, 1H)

Method B

Synthesis of (R)-N-hydroxy-3-((R)-3-(4-(2-(2-hydroxypropan-2-yl)pyridin-4-yl)phenyl)-4,5-dihydroisoxazol-5-yl)-2-methyl-2-(methylsulfonyl)propanamide [81]

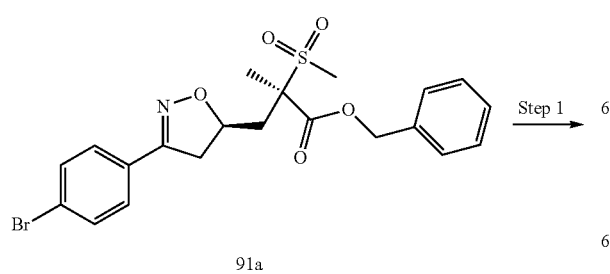

91a

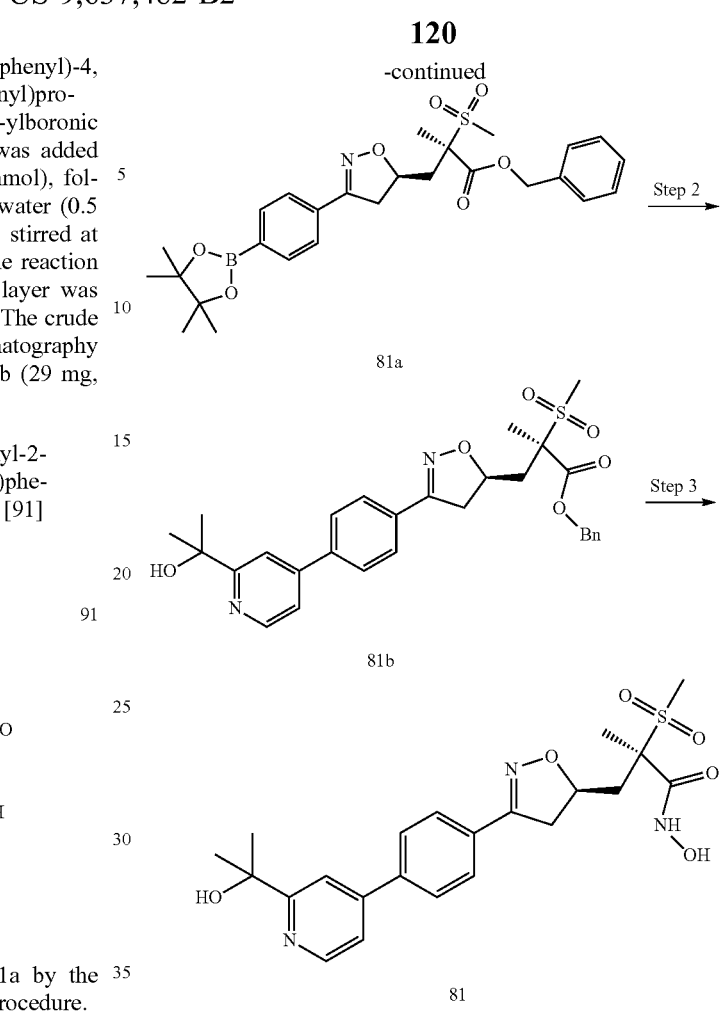

Step 1. Synthesis of (R)-benzyl 2-methyl-2-(methylsulfonyl)-3-((R)-3-(4-(4,4,5,5-tetramethyl-1,3,2-dioxaborolan-2-yl)phenyl)-4,5-dihydroisoxazol-5-yl)propanoate [81a]

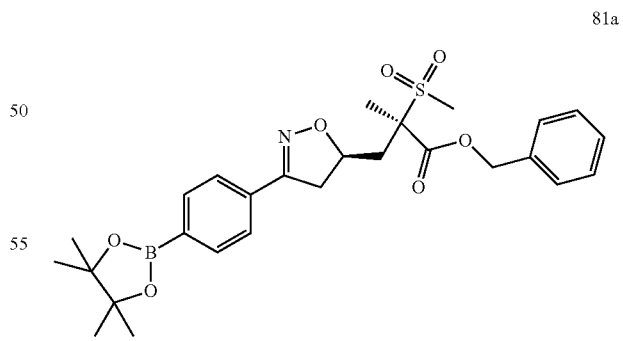

81a

A solution of 91a (140 mg, 0.29 mmol, 1.0 equiv), pinacol diboron (81 mg, 0.32 mmol, 1.1 equiv) and potassium acetate (86 mg, 0.87 mmol, 3.0 equiv) in 1,4-dioxane (1.5 mL) was degassed for 5 minutes. PdCl$_2$(dppf).CH$_2$Cl$_2$ (12 mg, 0.015 mmol, 0.05 equiv) was added to the reaction mixture. The resulting reaction mixture was stirred at 100° C. for 2 hours. The reaction mixture was quenched with water and extracted with EtOAc. The organic layer was washed with brine, dried over sodium sulfate and concentrated. The residue was purified by silica gel column chromatography (20-75% EtOAc in Hexane) to afford 81a (145 mg, 94% yield). LCMS (m/z): 528.3 [M+H]+. 1H NMR (400 MHz, Chloroform-d) 7.82 (d, J=8.2 Hz, 2H), 7.57 (d, J=8.2 Hz, 2H), 7.42-7.34 (m, 5H), 5.32 (d, J=12.1 Hz, 1H), 5.27 (d, J=12.1 Hz, 1H), 4.79 (qd, J=8.3, 3.5 Hz, 1H), 3.39 (dd, J=16.7, 10.3 Hz, 1H), 3.01-2.95 (m, 1H), 2.97 (s, 3H), 2.61 (dd, J=14.2, 3.4 Hz, 1H), 2.41 (dd, J=14.2, 8.4 Hz, 1H), 1.55 (s, 3H), 1.35 (s, 12H).

Step 2: Synthesis of (R)-benzyl 3-((R)-3-(4-(2-(2-hydroxypropan-2-yl)pyridin-4-yl)phenyl)-4,5-dihydroisoxazol-5-yl)-2-methyl-2-(methylsulfonyl)propanoate [81 b]

81a (60 mg, 0.114 mmol, 1.0 equiv), 2-(4-bromopyridin-2-yl)propan-2-ol (0.32 mmol, 1.2 equiv) and potassium acetate (60 mg, 0.284 mmol, 2.5 equiv) were dissolved in THF (0.6 mL)/H2O (0.3 mL) and degassed for 5 minutes. PdCl2(dppf).CH2Cl2 (10 mg, 0.012 mmol, 0.1 equiv) was added to the reaction mixture. The resulting reaction mixture was stirred at 65° C. overnight. The reaction mixture was quenched with water and extracted with EtOAc. The organic layer was washed with brine, dried over sodium sulfate and concentrated. The residue was purified by silica gel column chromatography (25-100% EtOAc in Hexane) to give product (32 mg, 52% yield). LCMS (m/z): 537.3 [M+H].

Step 3. Synthesis of (R)-N-hydroxy-3-((R)-3-(4-(2-(2-hydroxypropan-2-yl)pyridin-4-yl)phenyl)-4,5-dihydroisoxazol-5-yl)-2-methyl-2-(methylsulfonyl)propanamide [81]

Compound 81 was synthesized from 81b by the procedure described for the synthesis of 91 step 2. LCMS (m/z): 462.2 [M+H]+. 1H NMR (400 MHz, DMSO-d6) 11.04 (s, 1H), 8.63 (d, J=5.4 Hz, 1H), 8.20-8.12 (m, 1H), 7.99 (d, J=7.7 Hz, 2H), 7.82 (d, J=8.4 Hz, 2H), 4.76-4.61 (m, 1H), 3.63 (dd, J=17.0, 10.4 Hz, 1H), 3.20 (dd, J=17.1, 8.1 Hz, 1H), 3.05 (s, 3H), 2.72-2.63 (m, 1H), 2.06 (dd, J=13.8, 8.6 Hz, 1H), 1.59 (s, 3H), 1.55 (s, 6H).

Method C

Synthesis of (R)-N-hydroxy-2-methyl-3-((R)-3-(4-(6-methylpyridin-3-yl)phenyl)-4,5-dihydroisoxazol-5-yl)-2-(methylsulfonyl)propanamide [67]

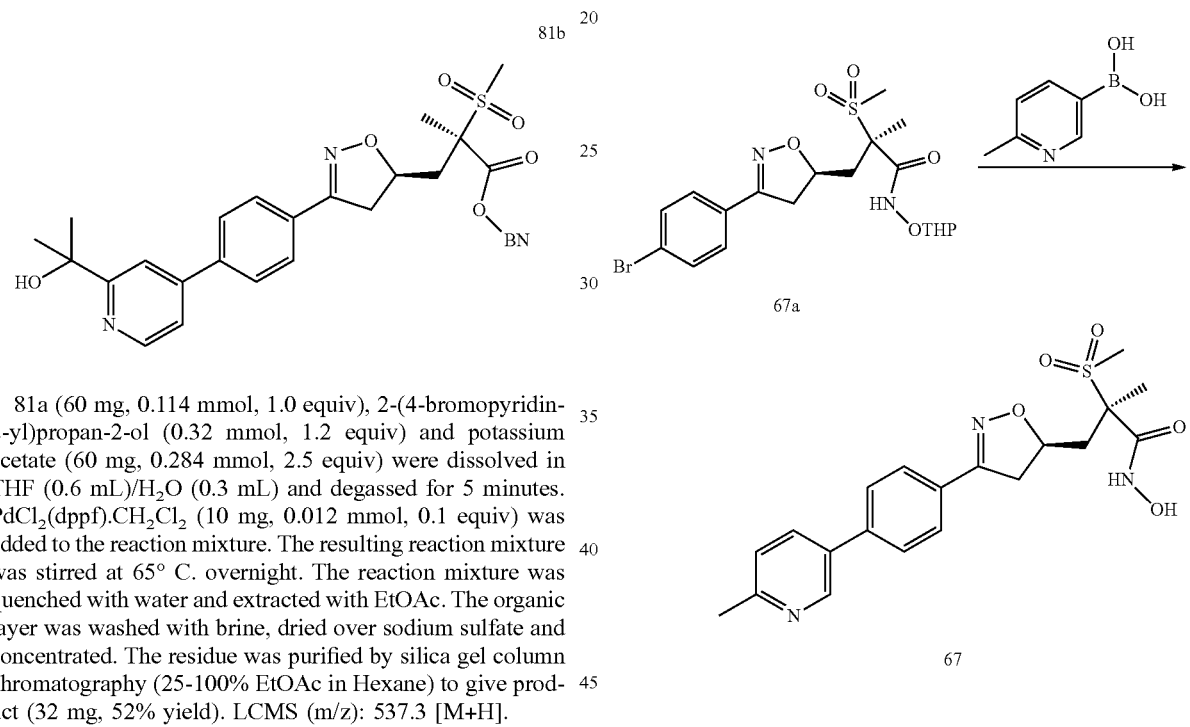

Compound 67a was synthesized from 91a by the procedures described in the synthesis of 2-A. A mixture 67a (40 mg, 0.082 mmol), (6-methylpyridin-3-yl)boronic acid (22.39 mg, 0.163 mmol), PdCl2(dppf).CH2Cl2 adduct (6.67 mg, 8.17 μmol) and Na2CO3 (26.0 mg, 0.245 mmol) in DME (3 mL) was stirred at 110° C. for 15 min using microwave reactor. The reaction mixture was diluted water (10 ml) and extracted with EtOAc. The organic layer was washed with water, dried on Na2SO4, filtered, and concentrated. The crude material was dissolved in MeOH (5.0 mL) followed by 4.0 N HCl in dioxane (1.0 mL). The resultant mixture was stirred for 25 min and then was concentrated. The residue was purified by reverse phase HPLC to give product 67 (22 mg, 61.2% yield). LCMS (m/z): 418.1 [M+H]+. 1H NMR (400 MHz, DMSO-d6) ppm 1.50-1.67 (m, 3H) 2.05 (dd, J=13.99, 8.41 Hz, 1H) 2.59-2.74 (m, 4H) 2.99-3.10 (m, 3H) 3.18 (dd, J=17.07, 8.12 Hz, 2H) 3.61 (dd, J=16.99, 10.39 Hz, 3H) 4.66 (d, J=7.09 Hz, 2H) 7.64-7.97 (m, 5H) 8.43 (d, J=7.63 Hz, 1H) 8.99 (d, J=1.61 Hz, 1H) 11.04 (br. s., 1H)

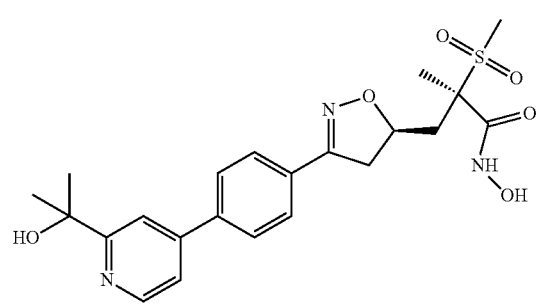

40

Synthesis of (R)-N-hydroxy-3-((R)-3-(4'-(2-hydroxyethyl)-[1,1-biphenyl]-4-yl)-4,5-dihydroisoxazol-5-yl)-2-methyl-2-(methylsulfonyl)propanamide [40]

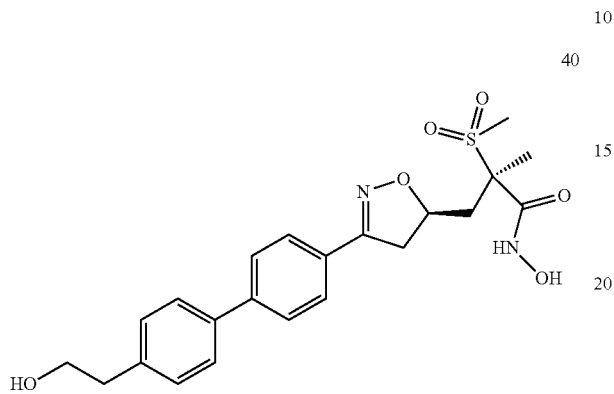

Compound 40 was synthesized by method A. LCMS (m/z): 447.4 [M+H]+. $^1$H NMR (400 MHz, DMSO-d6) ppm 1.59 (s, 3H) 1.89-2.14 (m, 1H) 2.59-2.71 (m, 1H) 2.75 (t, J=6.94 Hz, 2H) 3.05 (s, 3H) 3.18 (d, J=8.17 Hz, 1H) 3.47-3.73 (m, 3H) 4.64 (br. s., 2H) 7.31 (d, J=8.12 Hz, 2H) 7.61 (d, J=8.12 Hz, 2H) 7.65-7.80 (m, 4H) 9.25 (s, 1H) 11.03 (s, 1H)

41

Synthesis of (R)-N-hydroxy-3-((R)-3-(4'-(hydroxymethyl)-[1,1'-biphenyl]-4-yl)-4,5-dihydroisoxazol-5-yl)-2-methyl-2-(methylsulfonyl)propanamide

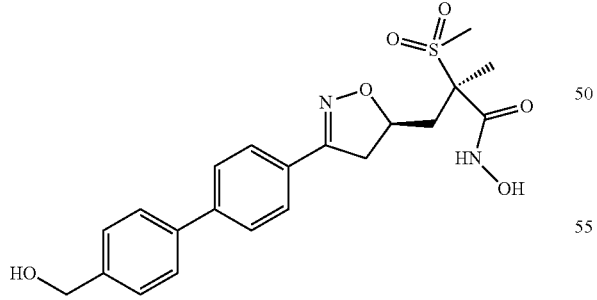

Compound 41 was synthesized by method A. LCMS (m/z): 433.4 [M+H]+. $^1$H NMR (400 MHz, DMSO-d6) ppm 1.59 (s, 3H) 2.05 (dd, J=14.06, 8.34 Hz, 1H) 2.66 (dd, J=14.06, 3.35 Hz, 1H) 3.05 (s, 3H) 3.16 (dd, J=17.04, 8.09 Hz, 1H) 3.59 (dd, J=16.95, 10.29 Hz, 1H) 4.53 (s, 2H) 4.63 (dd, J=10.27, 3.13 Hz, 1H) 5.07-5.42 (m, 1H) 7.41 (d, J=8.12 Hz, 2H) 7.61-7.84 (m, 6H) 9.26 (s, 1H) 11.04 (s, 1H)

42

Synthesis of (R)-3-((R)-3-(4-(3-fluoropyridin-4-yl)phenyl)-4,5-dihydroisoxazol-5-yl)-N-hydroxy-2-methyl-2-(methylsulfonyl)propanamide [42]

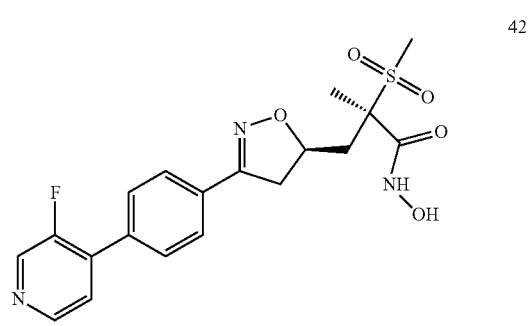

Compound 42 was synthesized by method A. LCMS (m/z): 422.2 [M+H]+. $^1$H NMR (400 MHz, DMSO-d$_6$) 11.05 (s, 1H), 8.69 (d, J=2.6 Hz, 1H), 8.54 (d, J=5.6 Hz, 1H), 7.84-7.76 (m, 4H), 7.69 (dd, J=7.0, 5.0 Hz, 1H), 4.68 (ddt, J=11.8, 8.6, 3.7 Hz, 1H), 3.63 (dd, J=17.0, 10.4 Hz, 1H), 3.20 (dd, J=17.1, 8.2 Hz, 1H), 3.06 (s, 3H), 2.76-2.66 (m, 1H), 2.13-2.04 (m, 1H), 1.61 (s, 3H).

43

(R)-3-((R)-3-(4-(2H-1,2,3-triazol-2-yl)phenyl)-4,5-dihydroisoxazol-5-yl)-N-hydroxy-2-methyl-2-(methylsulfonyl)propanamide [43]

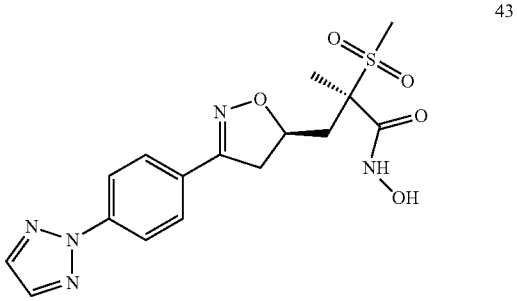 [SMILES: C[C@@](C[C@H]1CC(c2ccc(-n3nccn3)cc2)=NO1)(C(=O)NO)S(C)(=O)=O]

LCMS (m/z): 394.3 [M+H]+. $^1$H NMR (400 MHz, DMSO-d$_6$) 11.04 (s, 1H), 9.26 (s, 1H), 8.16 (s, 2H), 8.10 (d, J=8.7 Hz, 2H), 7.83 (d, J=8.7 Hz, 2H), 4.64 (dd, J=13.4, 5.3 Hz, 1H), 3.61 (dd, J=17.0, 10.4 Hz, 1H), 3.20 (dd, J=17.1, 8.2 Hz, 1H), 3.05 (s, 3H), 2.71-2.64 (m, 1H), 2.05 (dd, J=14.0, 8.5 Hz, 1H), 1.59 (s, 3H).

45

Synthesis of (R)-N-hydroxy-3-((R)-3-(4'-((R)-2-hydroxypropyl)-[1,1-biphenyl]-4-yl)-4,5-dihydroisoxazol-5-yl)-2-methyl-2-(methylsulfonyl)propanamide

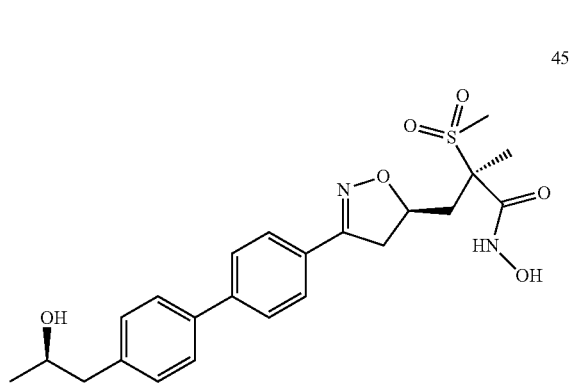 [SMILES: C[C@@H](O)Cc1ccc(-c2ccc(C3=NO[C@@H](C[C@](C)(C(=O)NO)S(C)(=O)=O)C3)cc2)cc1]

Compound 45 was synthesized by method A. LCMS (m/z): 461.3 [M+H]+. 1H NMR (400 MHz, DMSO-d6) ppm 1.04 (d, J=6.11 Hz, 3H) 1.59 (s, 3H) 1.95-2.16 (m, 1H) 2.68 (s, 3H) 3.05 (s, 3H) 3.12-3.22 (m, 2H) 3.51-3.69 (m, 2H) 3.73-3.93 (m, 1H) 4.48-4.71 (m, 1H) 7.29 (d, J=8.17 Hz, 2H) 7.53-7.82 (m, 6H) 11.03 (s, 1H)

46

Synthesis of (R)-N-hydroxy-3-((R)-3-(4'-((S)-2-hydroxypropyl)-[1,1-biphenyl]-4-yl)-4,5-dihydroisoxazol-5-yl)-2-methyl-2-(methylsulfonyl)propanamide

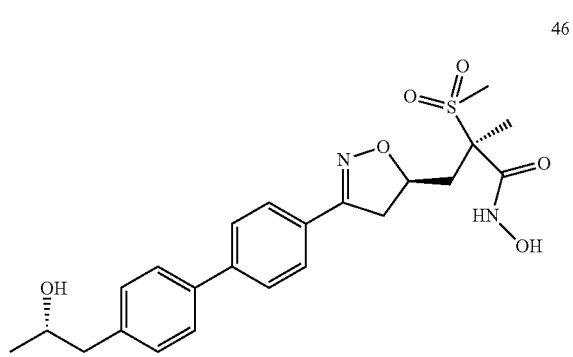 [SMILES: C[C@H](O)Cc1ccc(-c2ccc(C3=NO[C@@H](C[C@](C)(C(=O)NO)S(C)(=O)=O)C3)cc2)cc1]

Compound 46 was synthesized by method A. LCMS (m/z): 461.3 [M+H]+. 1H NMR (400 MHz, DMSO-d6) ppm 1.04 (d, J=6.11 Hz, 3H) 1.59 (s, 3H) 2.05 (dd, J=14.18, 8.22 Hz, 1H) 2.54-2.76 (m, 3H) 2.97-3.08 (m, 3H) 3.16 (dd, J=17.02, 8.12 Hz, 1H) 3.59 (dd, J=16.92, 10.27 Hz, 7H) 3.77-3.93 (m, 2H) 4.51-4.74 (m, 1H) 7.29 (d, J=8.12 Hz, 2H) 7.54-7.82 (m, 6H) 11.04 (br. s., 1H)

47

Synthesis of (R)-N-hydroxy-2-methyl-2-(methylsulfonyl)-3-((R)-3-(4'-(morpholinomethyl)-[1,1-biphenyl]-4-yl)-4,5-dihydroisoxazol-5-yl)propanamide

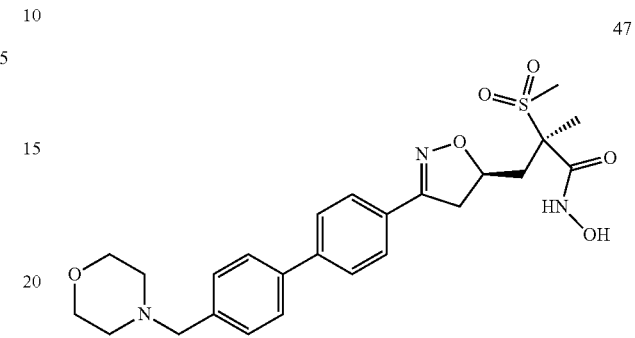

Compound 47 was synthesized by method C. LCMS (m/z): 502.5 [M+H]+. 1H NMR (400 MHz, DMSO-d6) ppm 1.59 (s, 3H) 1.93-2.16 (m, 1H) 2.60-2.74 (m, 1H) 3.05 (s, 3H) 3.08-3.22 (m, 4H) 3.54-3.70 (m, 3H) 3.84-4.05 (m, 2H) 4.39 (br. s., 2H) 4.56-4.78 (m, 1H) 7.43-7.97 (m, 8H) 9.06-9.38 (m, 1H) 9.69-10.06 (m, 1H) 11.04 (s, 1H)

48

Synthesis of (R)-N-hydroxy-3-((R)-3-(4'-(2-methoxyethoxy)-[1,1-biphenyl]-4-yl)-4,5-dihydroisoxazol-5-yl)-2-methyl-2-(methylsulfonyl)propanamide

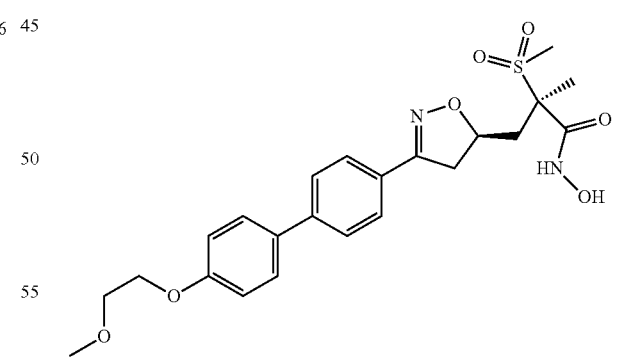

Compound 48 was synthesized by method C. LCMS (m/z): 477.4 [M+H]+. 1H NMR (400 MHz, DMSO-d6) ppm 1.59 (s, 3H) 2.06 (d, J=8.41 Hz, 1H) 2.65 (br. s., 1H) 3.05 (s, 3H) 3.15 (dd, J=17.04, 8.09 Hz, 1H) 3.52-3.63 (m, 1H) 3.63-3.72 (m, 2H) 4.05-4.24 (m, 2H) 4.49-4.76 (m, 1H) 7.03 (d, J=8.75 Hz, 2H) 7.47-7.81 (m, 6H) 9.08-9.41 (m, 1H) 11.03 (s, 1H)

49

Synthesis of (R)-N-hydroxy-3-((R)-3-(4'-((R)-1-hydroxyethyl)-[1,1-biphenyl]-4-yl)-4,5-dihydroisoxazol-5-yl)-2-methyl-2-(methylsulfonyl)propanamide

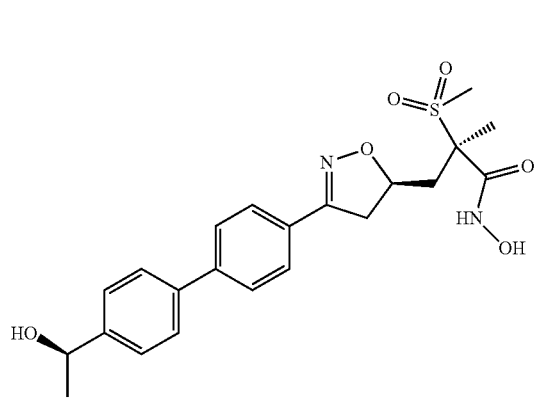

Compound 49 was synthesized by method C. LCMS (m/z): 447.3 [M+H]. $^1$H NMR (400 MHz, DMSO-d6) ppm 1.19-1.40 (m, 3H) 1.50-1.66 (m, 3H) 1.93-2.13 (m, 1H) 2.57-2.77 (m, 2H) 3.05 (s, 3H) 3.10-3.24 (m, 2H) 3.50-3.74 (m, 1H) 4.52-4.68 (m, 1H) 4.69-4.85 (m, 1H) 4.99-5.38 (m, 1H) 7.30-7.54 (m, 2H) 7.58-7.90 (m, 5H) 9.02-9.48 (m, 1H) 10.92-11.17 (m, 1H)

50

Synthesis of (R)-N-hydroxy-3-((R)-3-(4'-(2-hydroxyethoxy)-[1,1-biphenyl]-4-yl)-4,5-dihydroisoxazol-5-yl)-2-methyl-2-(methylsulfonyl)propanamide

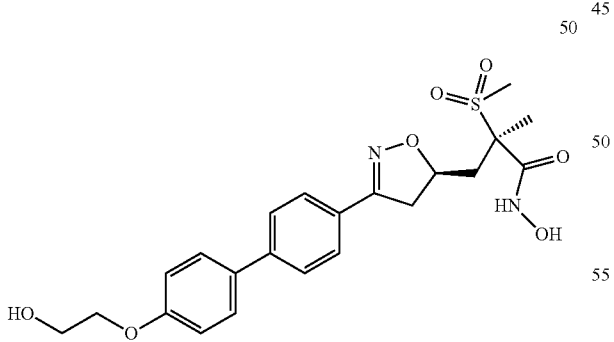

Compound 50 was synthesized by method C. LCMS (m/z): 463.4 [M+H]$^+$. $^1$H NMR (400 MHz, DMSO-d6) ppm 1.59 (s, 3H) 2.04 (dd, J=14.04, 8.36 Hz, 1H) 2.66 (dd, J=13.96, 3.35 Hz, 1H) 3.05 (s, 3H) 3.15 (dd, J=16.99, 8.14 Hz, 2H) 3.58 (dd, J=16.97, 10.32 Hz, 2H) 3.72 (t, J=4.96 Hz, 2H) 4.02 (t, J=4.99 Hz, 2H) 4.46-4.72 (m, 1H) 7.03 (d, J=8.80 Hz, 2H) 7.59-7.79 (m, 6H) 11.03 (s, 1H)

51

(2R)-N-hydroxy-3-((5R)-3-(4'-(2-hydroxy-1-methoxypropan-2-yl)-[,1-biphenyl]-4-yl)-4,5-dihydroisoxazol-5-yl)-2-methyl-2-(methylsulfonyl)propanamide [51]

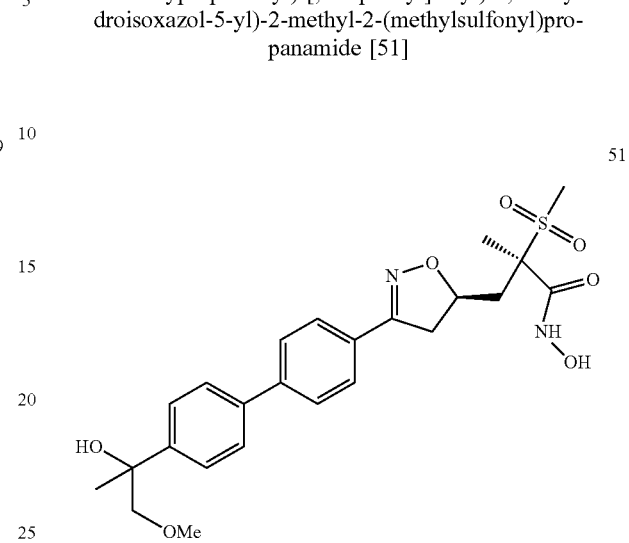

Compound 51 was synthesized by method A. LCMS (m/z): 491.2 [M+H]$^+$. $^1$H NMR (400 MHz, DMSO-d$_6$) 11.06 (s, 1H), 7.76 (d, J=8.5 Hz, 2H), 7.72 (d, J=8.5 Hz, 2H), 7.65 (d, J=8.4 Hz, 2H), 7.55 (d, J=8.5 Hz, 2H), 4.68-4.62 (m, 1H), 3.61 (dd, J=16.9, 10.3 Hz, 1H), 3.45-3.35 (m, 2H), 3.24 (s, 3H), 3.18 (dd, J=17.0, 8.1 Hz, 1H), 3.07 (s, 3H), 2.68 (dd, J=14.2, 3.6 Hz, 1H), 2.10-2.04 (m, 1H), 1.61 (s, 3H), 1.43 (s, 3H).

56

Synthesis of (R)-N-hydroxy-3-((R)-3-(4'-((S)-1-hydroxyethyl)-[1,1-biphenyl]-4-yl)-4,5-dihydroisoxazol-5-yl)-2-methyl-2-(methylsulfonyl)propanamide

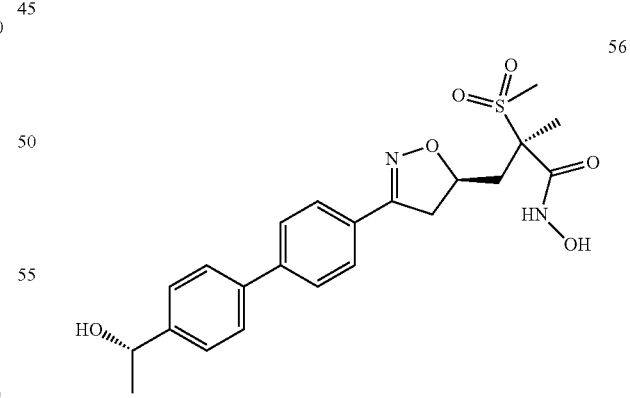

Compound 56 was synthesized by method C. LCMS (m/z): 447.3 [M+H]$^+$. $^1$H NMR (400 MHz, DMSO-d6) ppm 1.27-1.38 (m, 3H) 1.97-2.14 (m, 1H) 2.62-2.73 (m, 1H) 2.98-3.08 (m, 3H) 3.10-3.22 (m, 2H) 3.51-3.67 (m, 2H) 4.54-4.69 (m, 1H) 4.70-4.82 (m, 1H) 5.08-5.29 (m, 1H) 7.32-7.49 (m, 2H) 7.60-7.67 (m, 2H) 7.68-7.82 (m, 3H)

57

Synthesis of (R)-N-hydroxy-3-((R)-3-(3'-(hydroxymethyl)-[1,1-biphenyl]-4-yl)-4,5-dihydroisoxazol-5-yl)-2-methyl-2-(methylsulfonyl)propanamide

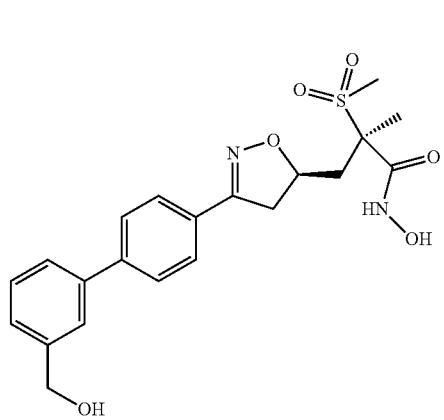

Compound 57 was synthesized by method C. LCMS (m/z): 433.4 [M+H]+. 1H NMR (400 MHz, DMSO-d6) ppm 1.59 (s, 3H) 1.92-2.16 (m, 1H) 2.58-2.73 (m, 1H) 3.05 (s, 3H) 3.11-3.22 (m, 2H) 3.48-3.59 (m, 1H) 4.56 (s, 2H) 4.59-4.72 (m, 1H) 7.24-7.37 (m, 1H) 7.37-7.49 (m, 1H) 7.73 (d, J=4.11 Hz, 6H) 10.88-11.18 (m, 1H)

58

Synthesis of (R)-N-hydroxy-2-methyl-2-(methylsulfonyl)-3-((R)-3-(4'-(methylsulfonyl)-[1,1-biphenyl]-4-yl)-4,5-dihydroisoxazol-5-yl)propanamide

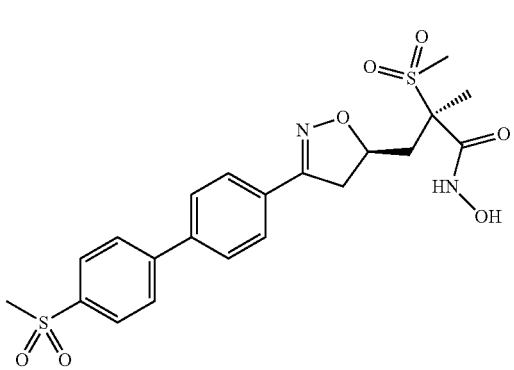

Compound 58 was synthesized by method C. LCMS (m/z): 481.4 [M+H]+. 1H NMR (400 MHz, DMSO-d6) ppm 1.51-1.68 (m, 3H) 1.90-2.18 (m, 2H) 2.59-2.78 (m, 2H) 3.05 (s, 3H) 3.10-3.20 (m, 1H) 3.25 (s, 4H) 3.53-3.74 (m, 1H) 4.54-4.79 (m, 1H) 7.70-7.82 (m, 2H) 7.82-7.90 (m, 2H) 7.92-8.12 (m, 4H) 9.12-9.37 (m, 1H) 10.93-11.13 (m, 1H)

59

Synthesis of (R)-3-((R)-3-(2-fluoro-4-methoxy-[1,1'-biphenyl]-4-yl)-4,5-dihydroisoxazol-5-yl)-N-hydroxy-2-methyl-2-(methylsulfonyl)propanamide

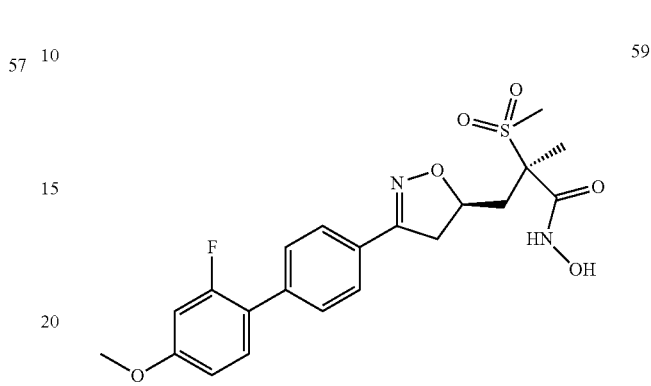

Compound 59 was synthesized by method C. LCMS (m/z): 451.4 [M+H]+. 1H NMR (400 MHz, DMSO-d6) ppm 1.44-1.66 (m, 3H) 2.05 (dd, J=14.06, 8.34 Hz, 1H) 2.40-2.53 (m, 4H) 2.66 (dd, J=14.04, 3.33 Hz, 27H) 2.99-3.07 (m, 2H) 3.16 (dd, J=17.02, 8.12 Hz, 1H) 3.59 (dd, J=16.97, 10.27 Hz, 1H) 3.74-3.87 (m, 2H) 4.63 (dd, J=10.17, 3.28 Hz, 1H) 6.80-7.05 (m, 2H) 7.42-7.77 (m, 6H) 9.01-9.09 (m, 1H) 11.04 (s, 1H)

60

Synthesis of (R)-N-hydroxy-3-((R)-3-(4'-((R)-2-hydroxy-3-methoxypropyl)-[1,1-biphenyl]-4-yl)-4,5-dihydroisoxazol-5-yl)-2-methyl-2-(methylsulfonyl)propanamide [60]

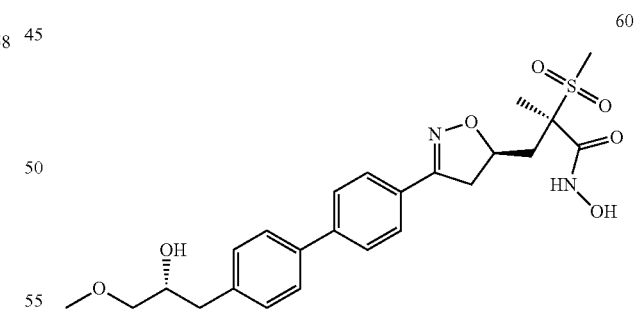

Compound 60 was synthesized by method A. LCMS (m/z): 491.3 [M+H]. 1H NMR (400 MHz, DMSO-d6) 11.06 (s, 1H), 9.29 (s, 1H), 7.75 (d, J=8.5 Hz, 2H), 7.72 (d, J=8.5 Hz, 2H), 7.62 (d, J=8.2 Hz, 2H), 7.32 (d, J=8.2 Hz, 2H), 4.69-4.62 (m, 1H), 3.81 (dd, J=7.7, 5.0 Hz, 1H), 3.60 (dd, J=17.0, 10.4 Hz, 1H), 3.27 (s, 3H), 3.26-3.23 (m, 2H), 3.18 (dd, J=17.0, 8.1 Hz, 1H), 3.07 (s, 3H), 2.78 (dd, J=13.6, 4.7 Hz, 1H), 2.68 (d, J=14.1 Hz, 1H), 2.61 (dd, J=13.6, 7.7 Hz, 1H), 2.09-2.03 (m, 2H), 1.60 (s, 3H).

61

Synthesis of (R)-N-hydroxy-3-((R)-3-(4'-((R)-2-hydroxypropoxy)-[1,1-biphenyl]-4-yl)-4,5-dihydroisoxazol-5-yl)-2-methyl-2-(methylsulfonyl)propanamide

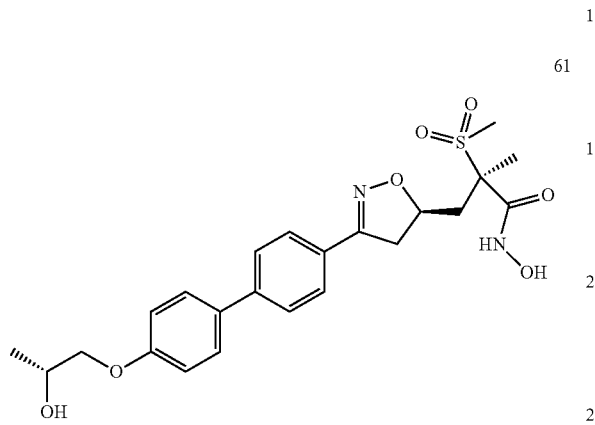

Compound 61 was synthesized by method C. LCMS (m/z): 477.1 [M+H]+. $^1$H NMR (400 MHz, DMSO-d6) ppm 1.15 (d, J=6.26 Hz, 3H) 1.59 (s, 3H) 1.93-2.14 (m, 1H) 2.54-2.74 (m, 1H) 3.05 (s, 3H) 3.09-3.24 (m, 2H) 3.49-3.67 (m, 1H) 3.75-3.89 (m, 2H) 3.89-4.03 (m, 1H) 4.52-4.76 (m, 1H) 7.02 (d, J=8.75 Hz, 2H) 7.49-7.81 (m, 6H) 9.02-9.42 (m, 1H) 10.85-11.19 (m, 1H)

62

Synthesis of (R)-3-((R)-3-(4-(but-1-yn-1-yl)phenyl)-4,5-dihydroisoxazol-5-yl)-N-hydroxy-2-methyl-2-(methylsulfonyl)propanamide [62]

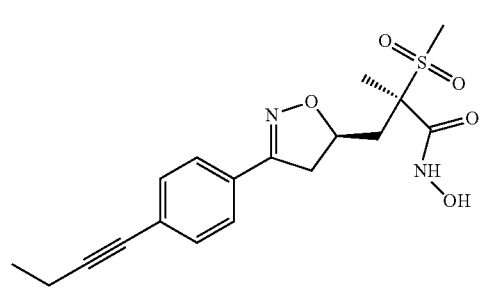

Compound 62 was synthesized by method C. LCMS (m/z): 379.3 [M+H]+. $^1$H NMR (400 MHz, DMSO-d$_6$) 11.04 (s, 1H), 9.28-9.22 (m, 1H), 7.61 (d, J=8.4 Hz, 2H), 7.45 (d, J=8.4 Hz, 2H), 4.68-4.59 (m, 1H), 3.56 (dd, J=17.0, 10.4 Hz, 1H), 3.17-3.09 (m, 1H), 3.06 (s, 3H), 2.67-2.61 (m, 1H), 2.47-2.42 (m, 2H), 2.04 (dd, J=14.1, 8.4 Hz, 1H), 1.59 (s, 3H), 1.17 (t, J=7.5 Hz, 3H).

64

Synthesis of (R)-N-hydroxy-2-methyl-2-(methylsulfonyl)-3-((R)-3-(4-(6-(trifluoromethyl)pyridin-3-yl)phenyl)-4,5-dihydroisoxazol-5-yl)propanamide [64]

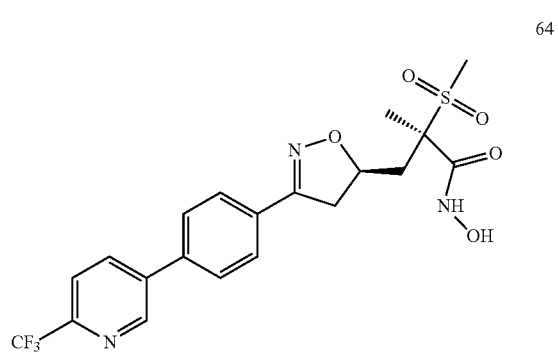 [SMILES: C[C@@](C[C@H]1CC(c2ccc(-c3ccc(C(F)(F)F)nc3)cc2)=NO1)(C(=O)NO)S(C)(=O)=O]

Compound 64 was synthesized by method A. LCMS (m/z): 472.2 [M+H]+. $^1$H NMR (400 MHz, DMSO-d$_6$) 11.06 (s, 1H), 9.28 (s, 1H), 9.16 (s, 1H), 8.44 (d, J=8.2 Hz, 1H), 8.02 (d, J=8.3 Hz, 1H), 7.95 (d, J=8.5 Hz, 2H), 7.82 (d, J=8.4 Hz, 2H), 4.68 (qd, J=8.4, 3.4 Hz, 1H), 3.64 (dd, J=17.0, 10.4 Hz, 1H), 3.21 (dd, J=17.2, 8.2 Hz, 1H), 3.07 (s, 3H), 2.75-2.66 (m, 1H), 2.08 (dd, J=14.1, 8.4 Hz, 1H), 1.61 (s, 3H).

65

Synthesis of (R)-N-hydroxy-3-((R)-3-(4-(6-(hydroxymethyl)pyridin-3-yl)phenyl)-4,5-dihydroisoxazol-5-yl)-2-methyl-2-(methylsulfonyl)propanamide

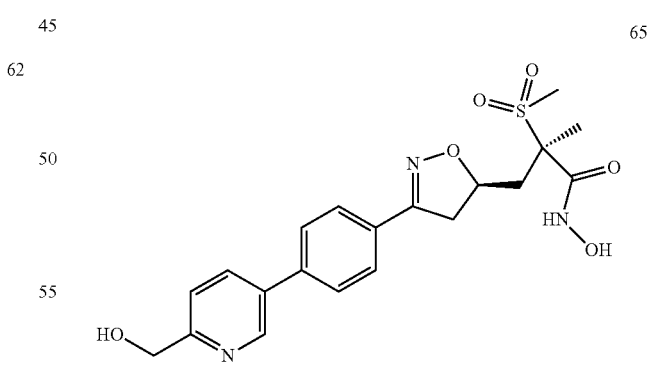

Compound 65 was synthesized by method C. LCMS (m/z): 434.1 [M+H]+. $^1$H NMR (400 MHz, DMSO-d6) ppm 1.59 (s, 3H) 2.05 (dd, J=14.01, 8.39 Hz, 1H) 2.56-2.75 (m, 1H) 2.99-3.10 (m, 3H) 3.18 (dd, J=17.07, 8.22 Hz, 2H) 3.61 (dd, J=17.02, 10.42 Hz, 5H) 4.67 (s, 3H) 7.68 (d, J=8.17 Hz, 1H) 7.76 (d, J=8.36 Hz, 2H) 7.80-7.97 (m, 2H) 8.31 (d, J=8.12 Hz, 1H) 8.90 (d, J=2.01 Hz, 1H) 11.04 (s, 1H)

66

Synthesis of (R)-N-hydroxy-3-((R)-3-(4-(6-methoxypyridin-3-yl)phenyl)-4,5-dihydroisoxazol-5-yl)-2-methyl-2-(methylsulfonyl)propanamide

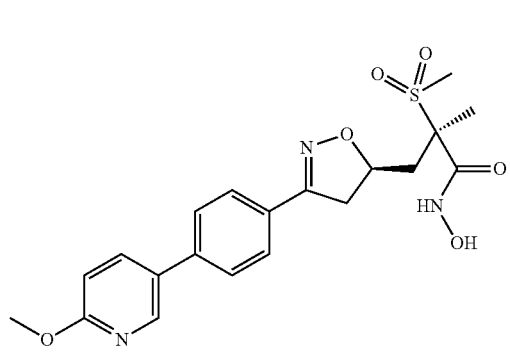

Compound 66 was synthesized by method C. LCMS (m/z): 434.0 [M+H]$^+$. $^1$H NMR (400 MHz, DMSO-d6) ppm 1.59 (s, 3H) 2.05 (dd, J=14.04, 8.41 Hz, 1H) 2.66 (dd, J=14.01, 3.45 Hz, 1H) 3.05 (s, 3H) 3.16 (dd, J=17.04, 8.14 Hz, 2H) 3.89 (s, 4H) 4.63 (d, J=7.14 Hz, 1H) 6.92 (d, J=8.71 Hz, 1H) 7.59-7.85 (m, 4H) 8.06 (dd, J=8.66, 2.59 Hz, 1H) 8.54 (d, J=2.45 Hz, 1H) 11.04 (br. s., 1H)

69

Synthesis of (R)-3-((R)-3-(4'-(2-cyanopropan-2-yl)-[1,1-biphenyl]-4-yl)-4,5-dihydroisoxazol-5-yl)-N-hydroxy-2-methyl-2-(methylsulfonyl)propanamide

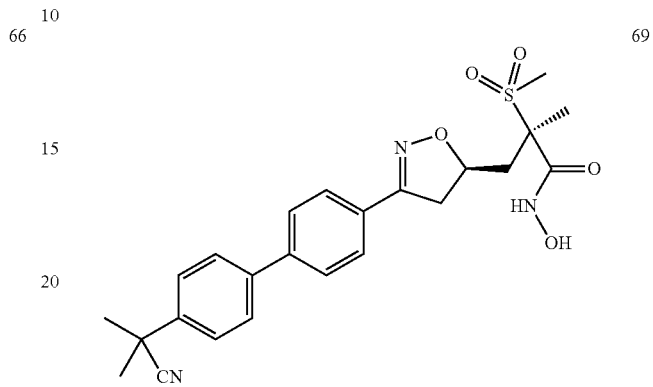

Compound 69 was synthesized by method C. LCMS (m/z): 470.1 [M+H]$^+$. $^1$H NMR (400 MHz, DMSO-d6) ppm 1.45-1.78 (m, 9H) 2.07 (d, J=8.36 Hz, 1H) 2.65 (d, J=2.64 Hz, 1H) 3.05 (s, 3H) 3.10-3.25 (m, 2H) 3.50-3.69 (m, 1H) 4.51-4.78 (m, 1H) 7.61 (d, J=8.46 Hz, 2H) 7.67-7.84 (m, 5H) 11.04 (s, 1H)

68

Synthesis of (R)-N-hydroxy-2-methyl-3-((R)-3-(4-(1-methyl-6-oxo-1,6-dihydropyridin-3-yl)phenyl)-4,5-dihydroisoxazol-5-yl)-2-(methylsulfonyl)propanamide

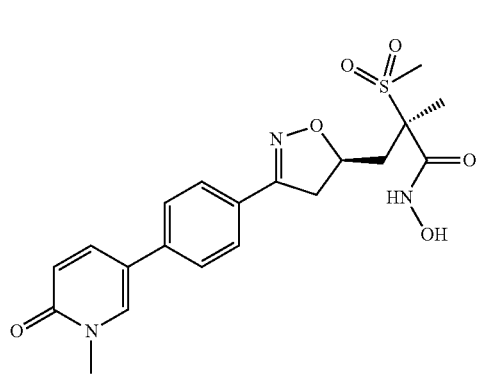

Compound 68 was synthesized by method C. LCMS (m/z): 434.1 [M+H]$^+$. $^1$H NMR (400 MHz, DMSO-d6) ppm 1.58 (s, 3H) 1.92-2.15 (m, 1H) 2.58-2.73 (m, 1H) 3.05 (s, 3H) 3.15 (dd, J=17.02, 8.12 Hz, 2H) 4.45-4.76 (m, 1H) 6.48 (d, J=9.44 Hz, 1H) 7.67 (s, 3H) 7.87 (dd, J=9.44, 2.64 Hz, 1H) 8.22 (d, J=2.54 Hz, 1H) 11.03 (s, 1H)

70

Synthesis of (R)-N-hydroxy-2-methyl-2-(methylsulfonyl)-3-((R)-3-(4-(2-(trifluoromethyl)pyridin-4-yl)phenyl)-4,5-dihydroisoxazol-5-yl)propanamide

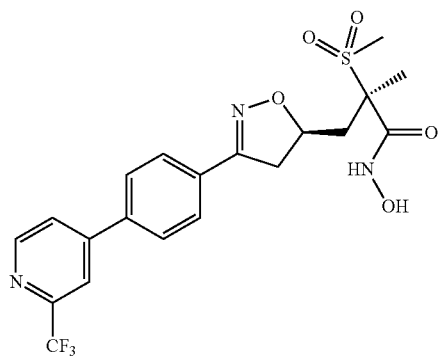

Compound 70 was synthesized by method C. LCMS (m/z): 472.0 [M+H]$^+$. $^1$H NMR (400 MHz, DMSO-d6) ppm 1.59 (s, 3H) 2.06 (dd, J=14.01, 8.39 Hz, 1H) 2.67 (dd, J=14.11, 3.30 Hz, 1H) 3.05 (s, 3H) 3.19 (dd, J=17.12, 8.17 Hz, 2H) 3.56-3.70 (m, 3H) 4.67 (d, J=7.09 Hz, 1H) 7.80 (d, J=8.41 Hz, 2H) 8.03 (d, J=8.41 Hz, 2H) 8.09 (d, J=4.30 Hz, 1H) 8.23 (s, 1H) 8.83 (d, J=5.14 Hz, 1H) 11.04 (s, 1H)

71

Synthesis of (R)-3-((R)-3-(4-(2-ethylpyridin-4-yl)phenyl)-4,5-dihydroisoxazol-5-yl)-N-hydroxy-2-methyl-2-(methylsulfonyl)propanamide

73

Synthesis of (R)-N-hydroxy-3-((R)-3-(4'-(1-(hydroxymethyl)cyclopropyl)-[1,1-biphenyl]-4-yl)-4,5-dihydroisoxazol-5-yl)-2-methyl-2-(methylsulfonyl)propanamide

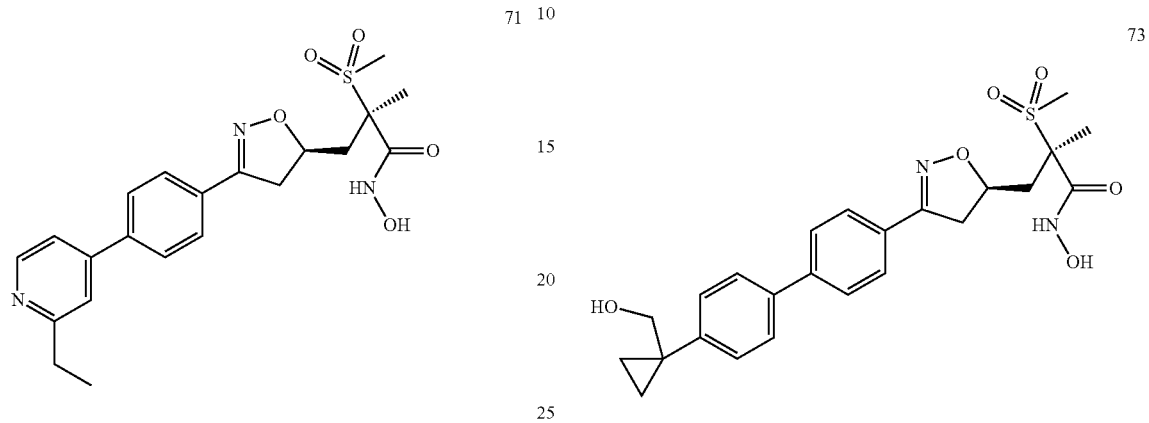

Compound 71 was synthesized by method C. LCMS (m/z): 432.1 [M+H]$^+$. $^1$H NMR (400 MHz, DMSO-d6) ppm 1.16-1.39 (m, 2H) 1.49-1.66 (m, 2H) 2.09 (s, 1H) 2.65 (br. s., 1H) 2.85-2.99 (m, 2H) 3.00-3.10 (m, 2H) 3.20 (dd, J=17.22, 8.17 Hz, 2H) 3.63 (dd, J=16.99, 10.39 Hz, 2H) 4.51-4.81 (m, 2H) 7.74-8.13 (m, 4H) 8.71 (d, J=5.58 Hz, 1H) 11.05 (s, 1H)

Compound 73 was synthesized by method C. LCMS (m/z): 473.1 [M+H]$^+$. $^1$H NMR (400 MHz, DMSO-d6) ppm 0.64-0.91 (m, 4H) 1.59 (s, 3H) 1.92-2.15 (m, 1H) 2.57-2.74 (m, 2H) 3.05 (s, 3H) 3.10-3.23 (m, 2H) 3.55 (s, 3H) 4.46-4.78 (m, 2H) 7.38 (d, J=8.31 Hz, 2H) 7.51-7.82 (m, 6H) 9.05-9.42 (m, 1H) 11.03 (s, 1H)

72

Synthesis of (2R)-3-((5R)-3-(4'-(1,2-dihydroxyethyl)-[1,1-biphenyl]-4-yl)-4,5-dihydroisoxazol-5-yl)-N-hydroxy-2-methyl-2-(methylsulfonyl)propanamide

74

Synthesis of (2R)-N-hydroxy-2-methyl-3-((5R)-3-(4'-(methylsulfinyl)-[1,1-biphenyl]-4-yl)-4,5-dihydroisoxazol-5-yl)-2-(methylsulfonyl)propanamide [74]

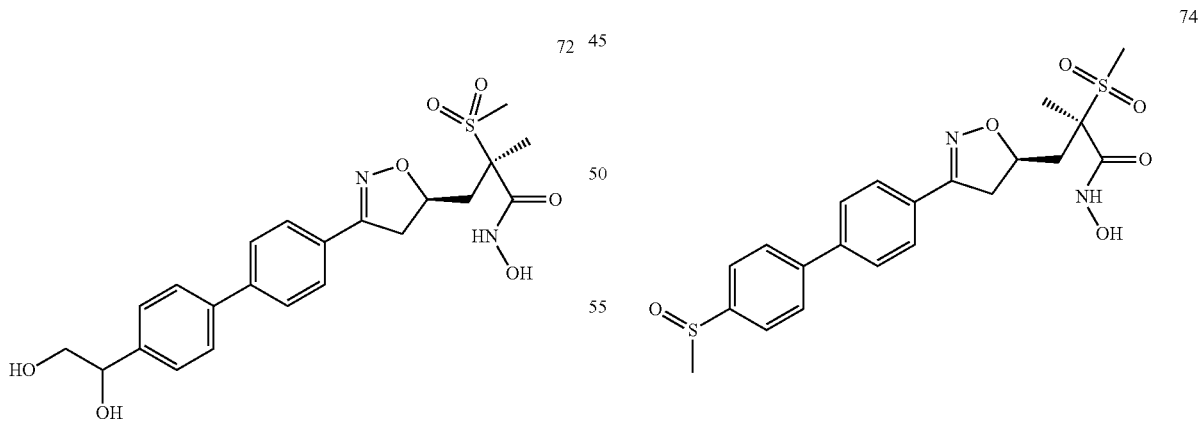

Compound 72 was synthesized by method A. LCMS (m/z): 463.1 [M+H]$^+$. $^1$H NMR (400 MHz, DMSO-d6) ppm 1.59 (s, 3H) 1.94-2.14 (m, 1H) 2.60-2.74 (m, 1H) 3.05 (s, 3H) 3.10-3.22 (m, 2H) 3.41-3.51 (m, 2H) 3.53-3.70 (m, 1H) 4.42-4.77 (m, 3H) 7.27-7.50 (m, 2H) 7.72 (d, J=7.68 Hz, 6H) 9.11-9.35 (m, 1H) 10.89-11.15 (m, 1H)

Compound 74 was synthesized by method A. LCMS (m/z): 465.2 [M+H]. $^1$H NMR (400 MHz, DMSO-d$_6$) 11.07 (s, 1H), 7.94 (d, J=8.5 Hz, 2H), 7.85 (d, J=8.6 Hz, 2H), 7.80 (d, J=8.4 Hz, 2H), 7.77 (d, J=8.4 Hz, 2H), 4.67 (qd, J=8.4, 3.8 Hz, 1H), 3.63 (dd, J=16.9, 10.3 Hz, 1H), 3.20 (dd, J=17.0, 8.1 Hz, 1H), 3.08 (s, 3H), 2.80 (s, 3H), 2.69 (dd, J=14.0, 3.5 Hz, 1H), 2.08 (dd, J=14.0, 8.4 Hz, 1H), 1.62 (s, 3H).

75

Synthesis of (2R)-N-hydroxy-3-((5R)-3-(4'-(2-hydroxy-1-methoxyethyl)-[1,1'-biphenyl]-4-yl)-4,5-dihydroisoxazol-5-yl)-2-methyl-2-(methylsulfonyl)propanamidepropanamide [75]

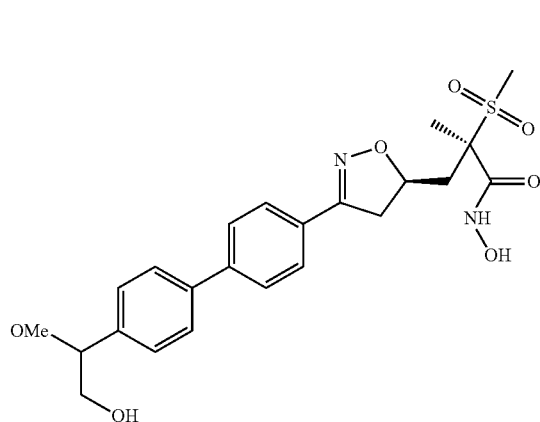

Compound 75 was synthesized by method A. LCMS (m/z): 477.3 [M+H]$^+$. $^1$H NMR (400 MHz, DMSO-d$_6$)$^1$H NMR (500 MHz, DMSO-d$_6$) 11.06 (s, 1H), 9.29 (s, 1H), 7.77 (d, J=8.6 Hz, 2H), 7.73 (d, J=8.6 Hz, 2H), 7.71 (d, J=8.3 Hz, 2H), 7.40 (d, J=8.3 Hz, 2H), 4.65 (qd, J=8.3, 3.5 Hz, 1H), 4.27-4.22 (m, 1H), 3.65-3.53 (m, 2H), 3.44 (dd, J=11.4, 4.5 Hz, 1H), 3.21 (s, 3H), 3.22-3.14 (m, 1H), 3.07 (s, 3H), 2.68 (dd, J=14.1, 3.4 Hz, 1H), 2.06 (dd, J=13.9, 8.3 Hz, 1H), 1.60 (s, 3H).

76

Synthesis of (2R)-N-hydroxy-2-methyl-3-((5R)-3-(4'-(S-methylsulfonimidoyl)-[1,1-biphenyl]-4-yl)-4,5-dihydroisoxazol-5-yl)-2-(methylsulfonyl)propanamide [76]

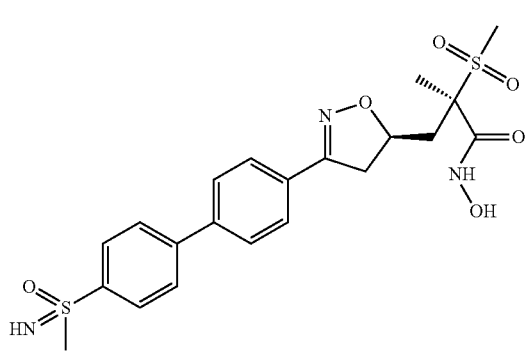

Compound 76 was synthesized by method A. LCMS (m/z): 480.2 [M+H]$^+$. $^1$H NMR (500 MHz, DMSO-d$_6$) 11.08 (s, 1H), 8.15 (d, J=8.7 Hz, 2H), 8.10 (d, J=8.8 Hz, 2H), 7.91 (d, J=8.6 Hz, 2H), 7.81 (d, J=8.5 Hz, 2H), 4.72-4.65 (m, 1H), 3.73-3.59 (m, 1H), 3.64 (s, 3H), 3.21 (dd, J=17.0, 8.1 Hz, 1H), 3.08 (s, 3H), 2.73-2.67 (m, 1H), 2.13-2.05 (m, 1H), 1.62 (s, 3H).

77

Synthesis of (R)-3-((R)-3-(4'-(2H-1,2,3-triazol-2-yl)-[1,1-biphenyl]-4-yl)-4,5-dihydroisoxazol-5-yl)-N-hydroxy-2-methyl-2-(methylsulfonyl)propanamide [77]

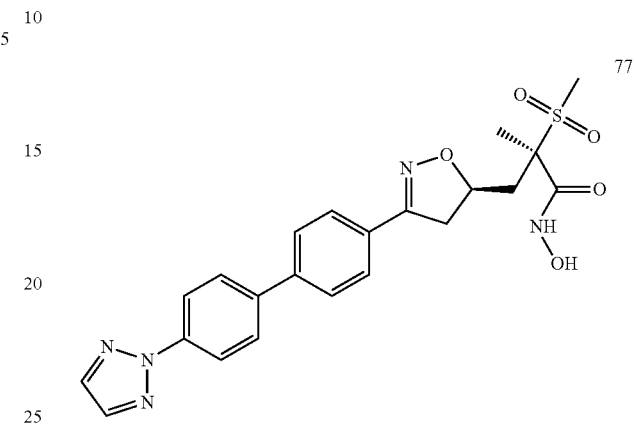

Compound 77 was synthesized by method A. LCMS (m/z): 470.2 [M+H]$^+$. $^1$H NMR (400 MHz, DMSO-d$_6$) 11.04 (s, 1H), 9.26 (s, 1H), 8.15 (s, 2H), 8.12 (d, J=8.8 Hz, 2H), 7.93 (d, J=8.8 Hz, 2H), 7.84 (d, J=8.5 Hz, 2H), 7.75 (d, J=8.5 Hz, 2H), 4.70-4.58 (m, 1H), 3.61 (dd, J=17.0, 10.3 Hz, 1H), 3.18 (dd, J=17.0, 8.2 Hz, 1H), 3.06 (s, 3H), 2.67 (dd, J=14.6, 4.3 Hz, 1H), 2.06 (dd, J=14.2, 8.4 Hz, 1H), 1.59 (s, 3H).

78

Synthesis of (R)-3-((R)-3-(4-(pyridin-4-yl)phenyl)-4,5-dihydroisoxazol-5-yl)-N-hydroxy-2-methyl-2-(methylsulfonyl)propanamide [78]

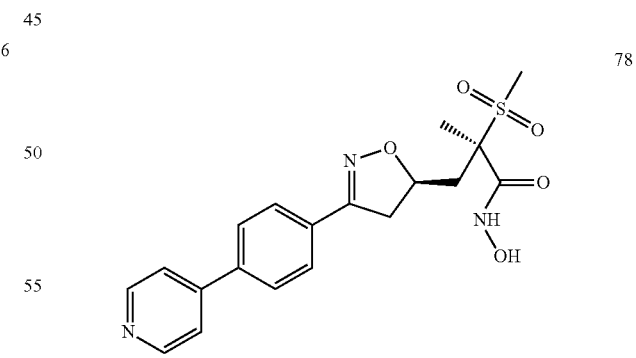

Compound 78 was synthesized by method A. LCMS (m/z): 404.3 [M+H]$^+$. $^1$H NMR (400 MHz, DMSO-d$_6$) 11.05 (s, 1H), 8.88-8.79 (m, 2H), 8.19-8.08 (m, 2H), 8.03 (d, J=7.9 Hz, 2H), 7.82 (d, J=8.2 Hz, 2H), 4.68 (ddt, J=12.1, 8.7, 3.9 Hz, 1H), 3.63 (dd, J=17.0, 10.4 Hz, 1H), 3.19 (dd, J=17.1, 8.1 Hz, 1H), 3.05 (s, 3H), 2.68 (dd, J=14.9, 3.6 Hz, 1H), 2.11-2.02 (m, 1H), 1.59 (s, 3H).

79

Synthesis of (R)-3-((R)-3-(2',6'-difluoro-4'-methoxy-[1,1-biphenyl]-4-yl)-4,5-dihydroisoxazol-5-yl)-N-hydroxy-2-methyl-2-(methylsulfonyl)propanamide [79]

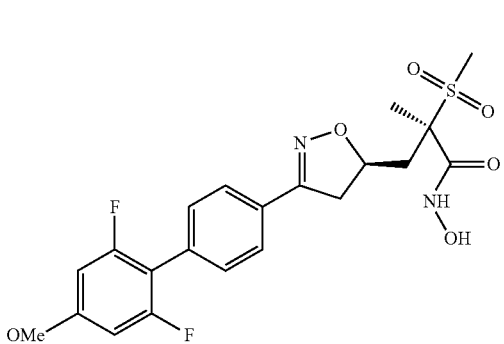

Compound 79 was synthesized by method A. LCMS (m/z): 469.2 [M+H]+. $^1$H NMR (400 MHz, DMSO-d$_6$)$^1$H NMR (400 MHz, DMSO-d$_6$) 11.05 (s, 1H), 9.29 (s, 1H), 7.74 (d, J=8.4 Hz, 2H), 7.50 (d, J=8.2 Hz, 2H), 6.89 (d, J=10.1 Hz, 2H), 4.72-4.60 (m, 1H), 3.84 (s, 3H), 3.61 (dd, J=17.0, 10.3 Hz, 1H), 3.18 (dd, J=17.1, 8.1 Hz, 1H), 3.07 (s, 3H), 2.72-2.66 (m, 1H), 2.07 (dd, J=13.7, 8.7 Hz, 1H), 1.60 (s, 3H).

80

Synthesis of (R)-3-((R)-3-(4-(5-fluoro-2-methoxy-pyridin-4-yl)phenyl)-4,5-dihydroisoxazol-5-yl)-N-hydroxy-2-methyl-2-(methylsulfonyl)propanamide [80]

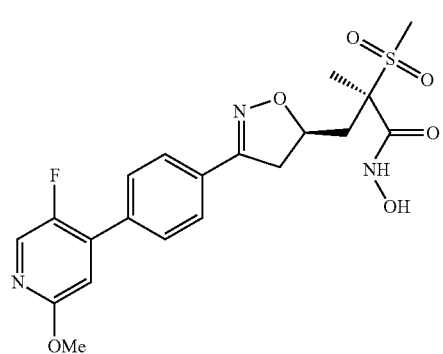

Compound 80 was synthesized by method A. LCMS (m/z): 452.2 [M+H]+. $^1$H NMR (400 MHz, DMSO-d$_6$) 11.04 (s, 1H), 8.25 (d, J=2.4 Hz, 1H), 7.77 (d, J=8.6 Hz, 2H), 7.73 (d, J=7.4 Hz, 2H), 7.04 (d, J=5.4 Hz, 1H), 4.72-4.58 (m, 1H), 3.87 (s, 3H), 3.61 (dd, J=17.0, 10.4 Hz, 1H), 3.17 (dd, J=17.1, 8.1 Hz, 1H), 3.05 (s, 3H), 2.67 (dd, J=13.8, 2.8 Hz, 1H), 2.05 (dd, J=14.1, 8.5 Hz, 1H), 1.59 (s, 3H).

82

Synthesis of (R)-3-((R)-3-(4-(3-chloropyridin-4-yl)phenyl)-4,5-dihydroisoxazol-5-yl)-N-hydroxy-2-methyl-2-(methylsulfonyl)propanamide [82]

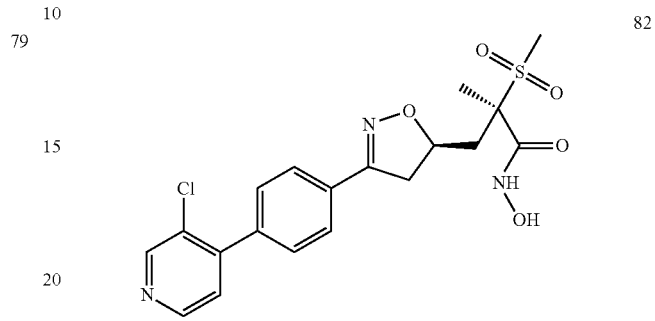

Compound 82 was synthesized by method A. LCMS (m/z): 438.2 [M+H]+. $^1$H NMR (400 MHz, DMSO-d$_6$) 11.04 (s, 1H), 8.75 (s, 1H), 8.60 (d, J=5.0 Hz, 1H), 7.78 (d, J=8.4 Hz, 2H), 7.61 (d, J=8.4 Hz, 2H), 7.51 (d, J=4.8 Hz, 1H), 4.70-4.61 (m, 1H), 3.62 (dd, J=17.0, 10.3 Hz, 1H), 3.18 (dd, J=17.1, 8.1 Hz, 1H), 3.05 (s, 3H), 2.73-2.64 (m, 1H), 2.06 (dd, J=14.2, 8.4 Hz, 1H), 1.59 (s, 3H).

83

Synthesis of (R)-3-((R)-3-(4-(4-fluoropyridin-3-yl)phenyl)-4,5-dihydroisoxazol-5-yl)-N-hydroxy-2-methyl-2-(methylsulfonyl)propanamide [83]

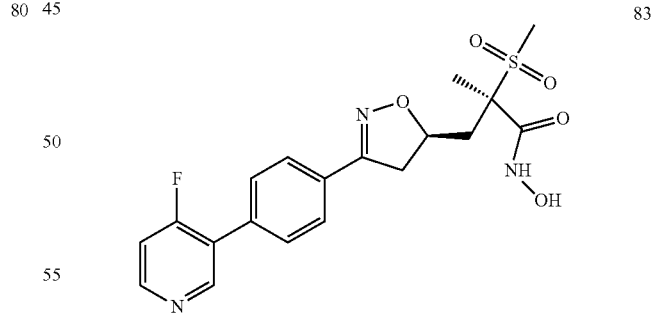

Compound 83 was synthesized by method B. LCMS (m/z): 422.2 [M+H]+. $^1$H NMR (400 MHz, DMSO-d$_6$) 11.05 (s, 1H), 8.69 (d, J=2.9 Hz, 1H), 8.15 (d, J=8.6 Hz, 2H), 8.15-8.10 (m, 1H), 7.86 (td, J=8.8, 3.0 Hz, 1H), 7.77 (d, J=8.5 Hz, 2H), 4.67 (ddt, J=11.8, 8.6, 4.0 Hz, 1H), 3.62 (dd, J=17.0, 10.4 Hz, 1H), 3.19 (dd, J=17.0, 8.1 Hz, 1H), 3.07 (s, 3H), 2.76-2.64 (m, 1H), 2.07 (dd, J=14.0, 8.4 Hz, 1H), 1.61 (s, 3H).

84

Synthesis of (R)-N-hydroxy-3-((R)-3-(4-(6-(2-hydroxypropan-2-yl)pyridin-3-yl)phenyl)-4,5-dihydroisoxazol-5-yl)-2-methyl-2-(methylsulfonyl)propanamide [84]

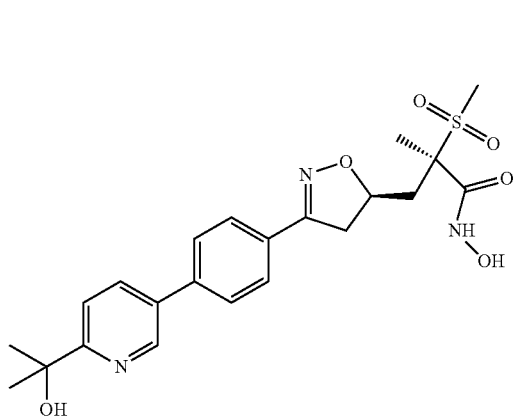

Compound 84 was synthesized by method B. LCMS (m/z): 462.3 [M+H]$^+$. $^1$H NMR (400 MHz, DMSO-d$_6$) 11.05 (s, 1H), 8.85 (s, 1H), 8.28-8.13 (m, 1H), 7.84 (d, J=8.0 Hz, 2H), 7.83-7.77 (m, 1H), 7.76 (d, J=8.3 Hz, 2H), 4.71-4.58 (m, 1H), 3.62 (dd, J=17.0, 10.3 Hz, 1H), 3.18 (dd, J=17.0, 8.1 Hz, 1H), 3.06 (s, 3H), 2.68 (dd, J=13.6, 2.8 Hz, 1H), 2.06 (dd, J=14.0, 8.5 Hz, 1H), 1.60 (s, 3H), 1.49 (s, 6H).

85

Synthesis of (R)-3-((R)-3-(4-(3-methylpyridin-4-yl)phenyl)-4,5-dihydroisoxazol-5-yl)-N-hydroxy-2-methyl-2-(methylsulfonyl)propanamide [85]

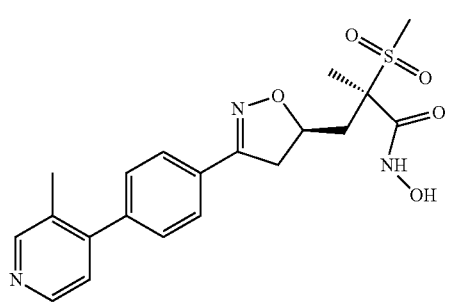

Compound 85 was synthesized by method B. LCMS (m/z): 418.2 [M+H]$^+$. $^1$H NMR (400 MHz, DMSO-d$_6$) 11.06 (s, 1H), 8.84-8.58 (m, 3H), 7.80 (d, J=8.2 Hz, 2H), 7.58 (d, J=8.3 Hz, 2H), 4.76-4.62 (m, 1H), 3.64 (dd, J=17.0, 10.4 Hz, 1H), 3.26-3.14 (m, 1H), 3.07 (s, 3H), 2.72-2.65 (m, 1H), 2.34 (s, 3H), 2.07 (dd, J=14.1, 8.4 Hz, 1H), 1.61 (s, 3H).

86

Synthesis of (R)-N-hydroxy-3-((R)-3-(4'-((R)-3-hydroxy-2-methoxypropyl)-[1,1'-biphenyl]-4-yl)-4,5-dihydroisoxazol-5-yl)-2-methyl-2-(methylsulfonyl)propanamide [86]

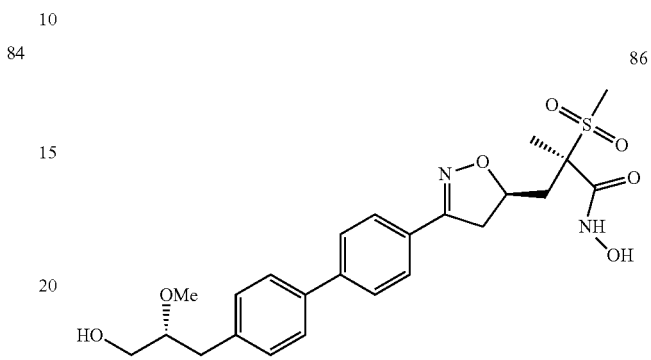

Compound 86 was synthesized by method B. LCMS (m/z): 491.3 [M+H]$^+$. $^1$H NMR (400 MHz, DMSO-d$_6$) 11.03 (s, 1H), 9.25 (s, 1H), 7.75 (d, J=8.5 Hz, 2H), 7.70 (d, J=8.5 Hz, 2H), 7.62 (d, J=8.2 Hz, 2H), 7.32 (d, J=8.2 Hz, 2H), 4.63 (ddt, J=11.6, 8.4, 3.6 Hz, 1H), 3.59 (dd, J=16.9, 10.3 Hz, 1H), 3.40-3.23 (m, 2H), 3.26 (s, 3H), 3.16 (dd, J=17.0, 8.1 Hz, 1H), 3.05 (s, 3H), 2.85-2.62 (m, 3H), 2.05 (dd, J=14.6, 7.8 Hz, 1H), 1.59 (s, 3H).

87

Synthesis of (R)-N-hydroxy-3-((R)-3-(4'-(hydroxymethyl)-2-methyl-[1,1'-biphenyl]-4-yl)-4,5-dihydroisoxazol-5-yl)-2-methyl-2-(methylsulfonyl)propanamide

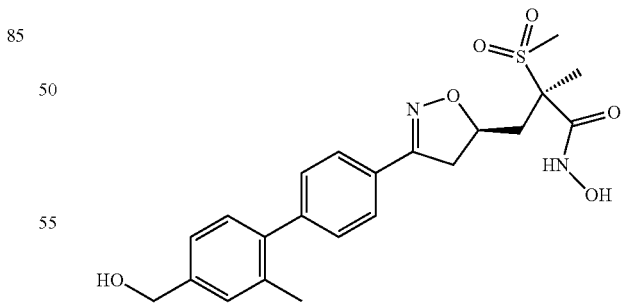

Compound 87 was synthesized by method C. LCMS (m/z): 447.3 [M+H]$^+$. $^1$H NMR (400 MHz, DMSO-d6) ppm 1.15 (s, 2H) 1.59 (s, 3H) 1.99-2.12 (m, 1H) 2.22 (s, 3H) 2.60-2.73 (m, 1H) 3.05 (s, 3H) 3.12-3.23 (m, 2H) 3.51-3.66 (m, 2H) 3.93-4.11 (m, 1H) 4.49 (s, 2H) 4.56-4.75 (m, 1H) 5.73 (s, 3H) 7.09-7.28 (m, 3H) 7.40 (d, J=8.12 Hz, 2H) 7.69 (d, J=8.07 Hz, 2H) 11.04 (s, 1H)

88

Synthesis of (R)-3-((R)-3-(2',6'-difluoro-4'-((R)-2-hydroxypropyl)-[1,1-biphenyl]-4-yl)-4,5-dihydroisoxazol-5-yl)-N-hydroxy-2-methyl-2-(methylsulfonyl)propanamide [88]

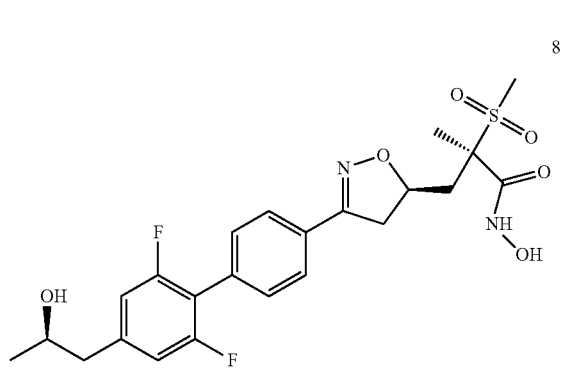

Compound 88 was synthesized by method B. LCMS (m/z): 497.2 [M+H]+. ¹H NMR (400 MHz, DMSO-d₆) 11.04 (s, 1H), 9.25 (s, 1H), 7.83 (d, J=8.5 Hz, 2H), 7.71 (d, J=8.4 Hz, 2H), 7.47 (d, J=8.6 Hz, 2H), 4.71-4.57 (m, 1H), 3.85 (q, J=6.5 Hz, 1H), 3.60 (dd, J=17.0, 10.4 Hz, 1H), 3.16 (dd, J=17.0, 8.1 Hz, 1H), 3.05 (s, 3H), 2.75 (dd, J=13.1, 6.8 Hz, 1H), 2.65 (m, 2H), 2.05 (dd, J=14.0, 8.4 Hz, 1H), 1.58 (s, 3H), 1.07 (d, J=6.1 Hz, 3H).

89

Synthesis of (R)-3-((R)-3-(2'-fluoro-4'-((R)-2-hydroxypropyl)-[1,1-biphenyl]-4-yl)-4,5-dihydroisoxazol-5-yl)-N-hydroxy-2-methyl-2-(methylsulfonyl)propanamide [89]

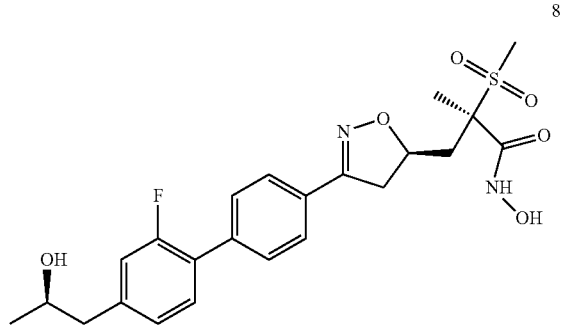

Compound 89 was synthesized by method A. LCMS (m/z): 479.2 [M+H]+. ¹H NMR (400 MHz, DMSO-d₆) 11.06 (s, 1H), 9.28 (s, 1H), 7.74 (d, J=8.3 Hz, 2H), 7.62 (d, J=7.2 Hz, 2H), 7.38 (m, 1H), 7.34 (m, 1H), 7.22 (t, J=7.6 Hz, 1H), 4.73-4.53 (m, 1H), 3.89 (q, J=6.1 Hz, 1H), 3.62 (dd, J=16.9, 10.2 Hz, 1H), 3.24-3.13 (m, 1H), 3.07 (s, 3H), 2.77 (dd, J=13.7, 6.8 Hz, 1H), 2.73-2.64 (m, 2H), 2.07 (dd, J=14.1, 8.4 Hz, 1H), 1.61 (s, 3H), 1.09 (d, J=6.1 Hz, 3H).

90

Synthesis of (R)-3-((R)-3-(7-methyl-4'-((R)-2-hydroxypropyl)-[1,1-biphenyl]-4-yl)-4,5-dihydroisoxazol-5-yl)-N-hydroxy-2-methyl-2-(methylsulfonyl)propanamide [90]

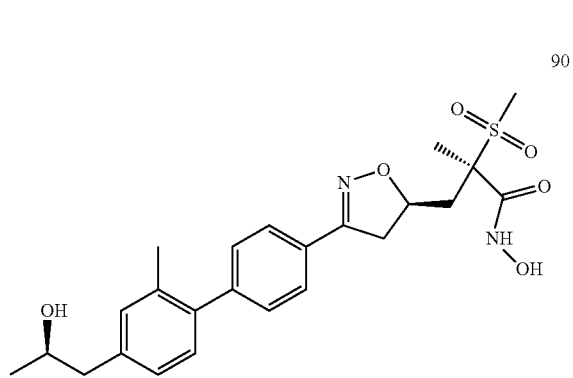 [SMILES: Cc1cc(C[C@@H](C)O)ccc1-c1ccc(C2=NO[C@@H](C[C@](C)(C(=O)NO)S(C)(=O)=O)C2)cc1]

Compound 90 was synthesized by method A. LCMS (m/z): 475.4 [M+H]+. ¹H NMR (400 MHz, DMSO-d₆) 11.05 (s, 1H), 9.27 (s, 1H), 7.70 (d, J=8.3 Hz, 2H), 7.42 (d, J=8.3 Hz, 2H), 7.14-7.07 (m, 3H), 4.72-4.60 (m, 1H), 3.88-3.80 (m, 1H), 3.61 (dd, J=16.9, 10.5 Hz, 1H), 3.24-3.16 (m, 1H), 3.07 (s, 3H), 2.74-2.66 (m, 1H), 2.62-2.53 (m, 2H), 2.22 (s, 3H), 2.06 (dd, J=15.1, 7.5 Hz, 1H), 1.61 (s, 3H), 1.07 (d, J=6.1 Hz, 3H).

92

Synthesis of (R)-N-hydroxy-3-((R)-3-(4-(isothiazol-4-yl)phenyl)-4,5-dihydroisoxazol-5-yl)-2-methyl-2-(methylsulfonyl)propanamide [92]

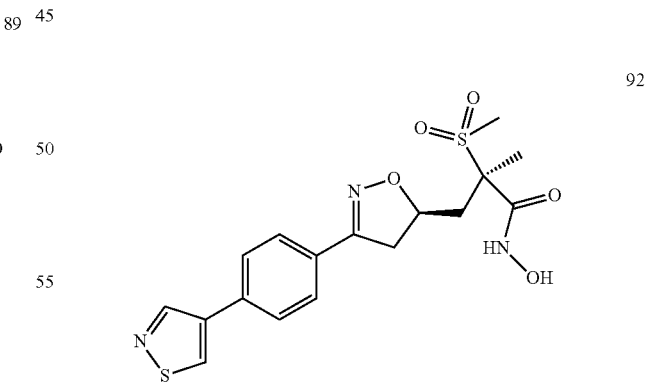

Compound 92 was synthesized by method A. LCMS (m/z): 410.3 [M+H]+. ¹H NMR (400 MHz, DMSO-d6) ppm 1.59 (s, 3H) 1.96-2.19 (m, 1H) 2.58-2.76 (m, 1H) 3.05 (s, 3H) 3.12-3.25 (m, 1H) 3.49-3.74 (m, 1H) 4.52-4.78 (m, 1H) 7.71 (d, J=8.02 Hz, 2H) 7.90 (d, J=8.02 Hz, 2H) 9.10 (s, 1H) 9.19-9.34 (m, 1H) 9.45 (s, 1H) 10.88-11.25 (m, 1H)

93

Synthesis of (R)-3-((R)-3-(4'-((2S,3R)-2,3-dihydroxybutyl)-[1,1-biphenyl]-4-yl)-4,5-dihydroisoxazol-5-yl)-N-hydroxy-2-methyl-2-(methylsulfonyl)propanamide [93]

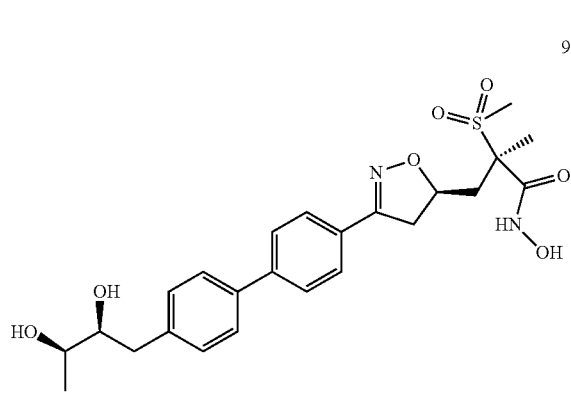

Compound 93 was synthesized by method A. LCMS (m/z): 491.4 [M+H]$^+$. $^1$H NMR (400 MHz, CD3CN) ppm 1.18 (d, J=5.48 Hz, 3H) 1.71 (s, 3H) 1.96 (br. s., 4H) 2.55-2.79 (m, 3H) 2.83-2.99 (m, 2H) 3.11-3.33 (m, 1H) 3.50-3.80 (m, 3H) 4.75 (d, J=7.48 Hz, 1H) 7.22-7.47 (m, 2H) 7.51-7.90 (m, 6H)

94

Synthesis of (R)-3-((R)-3-(4'-((S)-1,2-dihydroxyethyl)-[1,1-biphenyl]-4-yl)-4,5-dihydroisoxazol-5-yl)-N-hydroxy-2-methyl-2-(methylsulfonyl)propanamide [94]

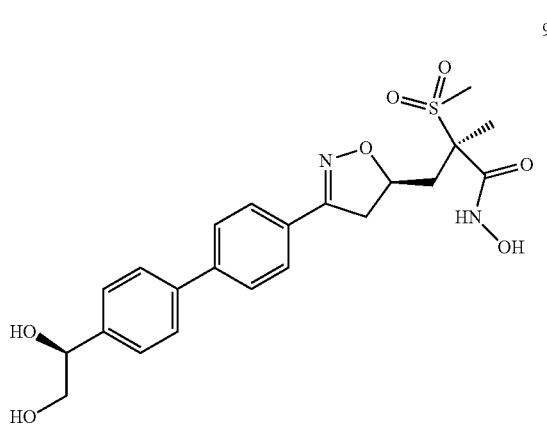

Compound 94 was synthesized by method A. LCMS (m/z): 463.1 [M+H]$^+$. $^1$H NMR (400 MHz, DMSO-d6) ppm 1.59 (s, 3H) 1.89-2.13 (m, 1H) 2.66 (dd, J=14.01, 3.30 Hz, 1H) 3.05 (s, 3H) 3.16 (dd, J=17.02, 8.12 Hz, 2H) 3.41-3.48 (m, 4H) 3.59 (dd, J=16.97, 10.27 Hz, 2H) 4.47-4.76 (m, 2H) 7.28-7.87 (m, 8H)

95

Synthesis of (R)-3-((R)-3-(4-((R)-1,2-dihydroxyethyl)-[1,1'-biphenyl]-4-yl)-4,5-dihydroisoxazol-5-yl)-N-hydroxy-2-methyl-2-(methylsulfonyl)propanamide [95]

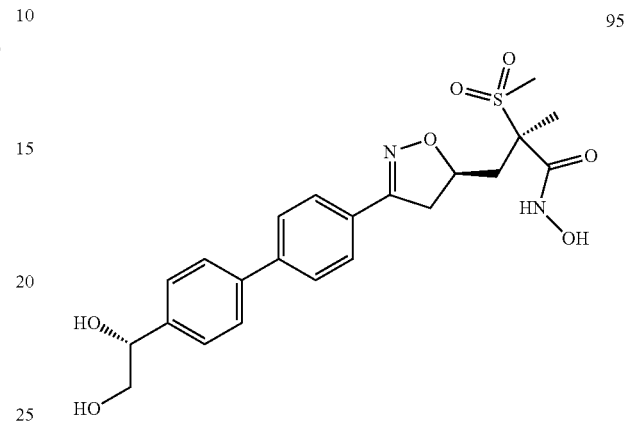

Compound 95 was synthesized by method A. LCMS (m/z): 463.1 [M+H]$^+$. $^1$H NMR (400 MHz, DMSO-d6) ppm 1.59 (s, 3H) 1.92-2.17 (m, 1H) 2.54-2.80 (m, 1H) 3.05 (s, 3H) 3.11-3.23 (m, 1H) 3.45 (d, J=5.87 Hz, 2H) 3.51-3.71 (m, 1H) 4.57 (s, 3H) 5.13-5.35 (m, 1H) 7.43 (d, J=8.27 Hz, 2H) 7.57-7.86 (m, 6H) 9.24 (s, 1H)

96

Synthesis of (2R)-3-((5R)-3-(4'-(1,3-dihydroxypropyl)-[,1-biphenyl]-4-yl)-4,5-dihydroisoxazol-5-yl)-N-hydroxy-2-methyl-2-(methylsulfonyl)propanamide [96]

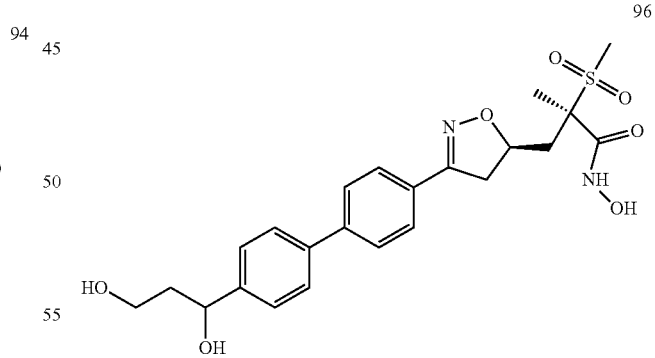

Compound 96 was synthesized by method B. LCMS (m/z): 477.2 [M+H]$^+$. $^1$H NMR (500 MHz, DMSO-d$_6$) 11.06 (s, 1H), 9.29 (s, 1H), 7.83-7.70 (m, 4H), 7.68 (d, J=8.3 Hz, 2H), 7.43 (d, J=8.3 Hz, 2H), 5.24-5.09 (m, 1H), 4.72 (dd, J=7.8, 4.9 Hz, 1H), 4.66 (dd, J=10.2, 3.5 Hz, 1H), 3.66-3.58 (m, 1H), 3.58-3.50 (m, 1H), 3.46 (dt, J=10.4, 6.1 Hz, 1H), 3.19 (dd, J=17.0, 8.1 Hz, 1H), 3.08 (s, 3H), 2.69 (dd, J=14.1, 3.4 Hz, 1H), 2.11-2.03 (m, 1H), 1.87-1.68 (m, 2H), 1.61 (s, 3H).

97

Synthesis of (R)-3-((R)-3-(4-((4-((R)-1,2-dihydroxyethyl)phenyl)ethynyl)phenyl)-4,5-dihydroisoxazol-5-yl)-N-hydroxy-2-methyl-2-(methylsulfonyl)propanamide [97]

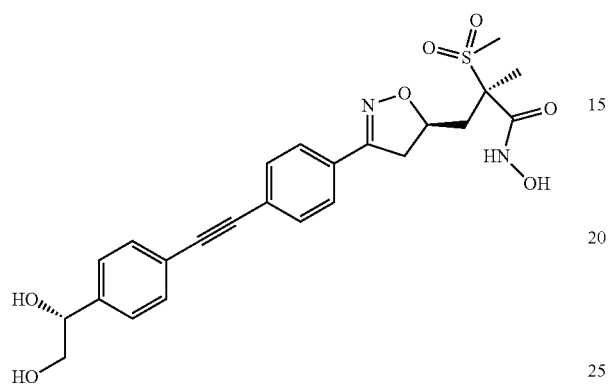

Compound 97 was synthesized by the process of example 22. LCMS (m/z): 487.3 [M+H]$^+$. $^1$H NMR (400 MHz, DMSO-d6) ppm 1.58 (s, 3H) 1.89-2.18 (m, 3H) 2.56-2.80 (m, 2H) 3.05 (s, 3H) 3.09-3.23 (m, 2H) 3.36-3.48 (m, 3H) 3.48-3.69 (m, 1H) 4.45-4.58 (m, 1H) 4.58-4.98 (m, 2H) 5.19-5.47 (m, 1H) 7.25-7.87 (m, 8H)

98

Synthesis of (R)-N-hydroxy-2-methyl-2-(methylsulfonyl)-3-((R)-3-(4-((tetrahydro-2H-pyran-4-yl)ethynyl)phenyl)-4,5-dihydroisoxazol-5-yl)propanamide [98]

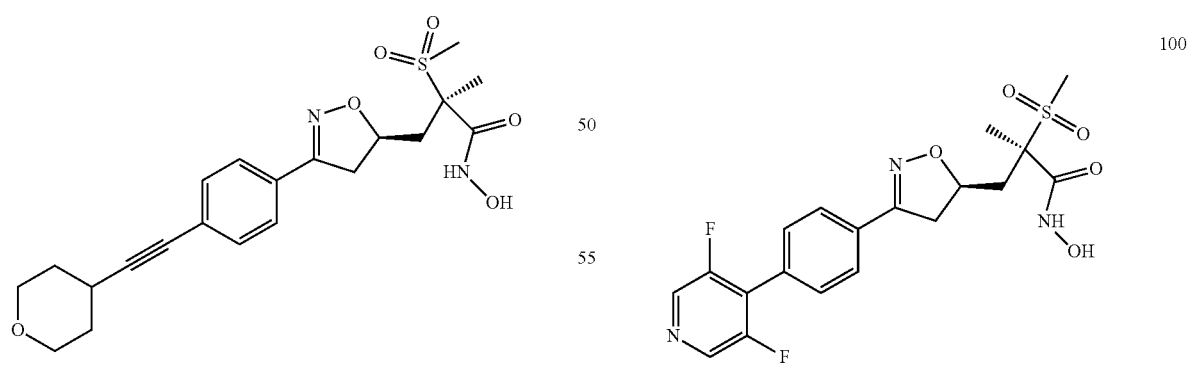

Compound 98 was synthesized by the process of example 22. LCMS (m/z): 487.3 [M+H]$^+$. $^1$H NMR (400 MHz, DMSO-d6) ppm 1.49-1.67 (m, 5H) 1.75-1.89 (m, 2H) 2.03 (dd, J=13.62, 7.95 Hz, 1H) 2.63 (dd, J=14.04, 3.28 Hz, 1H) 2.78-3.05 (m, 4H) 3.12 (dd, J=17.04, 8.05 Hz, 2H) 3.54 (dd, J=17.02, 10.42 Hz, 2H) 3.79 (dt, J=11.51, 4.18 Hz, 2H) 4.63 (dd, J=10.25, 3.06 Hz, 1H) 7.35-7.74 (m, 4H) 11.01 (s, 1H)

99

Synthesis of (R)-3-((R)-3-(4-((4-((S)-1,2-dihydroxyethyl)phenyl)ethynyl)phenyl)-4,5-dihydroisoxazol-5-yl)-N-hydroxy-2-methyl-2-(methylsulfonyl)propanamide [99]

Compound 99 was synthesized by the process of example 22. LCMS (m/z): 487.3 [M+H]$^+$. $^1$H NMR (400 MHz, DMSO-d6) ppm 1.58 (s, 3H) 1.89-2.18 (m, 3H) 2.56-2.80 (m, 2H) 3.05 (s, 3H) 3.09-3.23 (m, 2H) 3.36-3.48 (m, 3H) 3.48-3.69 (m, 1H) 4.45-4.58 (m, 1H) 4.58-4.98 (m, 2H) 5.19-5.47 (m, 1H) 7.25-7.87 (m, 8H)

100

Synthesis of (R)-N-hydroxy-2-methyl-2-(methylsulfonyl)-3-((R)-3-(4-(3-(trifluoromethyl)pyridin-4-yl)phenyl)-4,5-dihydroisoxazol-5-yl)propanamide [100]

Compound 100 was synthesized by method A. LCMS (m/z): 440.2 [M+H]$^+$. $^1$H NMR (400 MHz, DMSO-d$_6$) 11.05 (s, 1H), 8.67 (s, 2H), 7.90-7.74 (m, 2H), 7.74-7.58 (m, 2H), 4.69 (dtd, J=11.7, 8.4, 3.6 Hz, 1H), 3.69-3.57 (m, 1H), 3.20 (dd, J=17.1, 8.1 Hz, 1H), 3.07 (s, 3H), 2.78-2.62 (m, 1H), 2.08 (dd, J=14.1, 8.4 Hz, 1H), 1.61 (s, 3H).

102

Synthesis of (R)-3-((R)-3-(2-fluoro-4-(2-hydroxyethyl)-[1,1'-biphenyl]-4-yl)-4,5-dihydroisoxazol-5-yl)-N-hydroxy-2-methyl-2-(methylsulfonyl)propanamide [102]

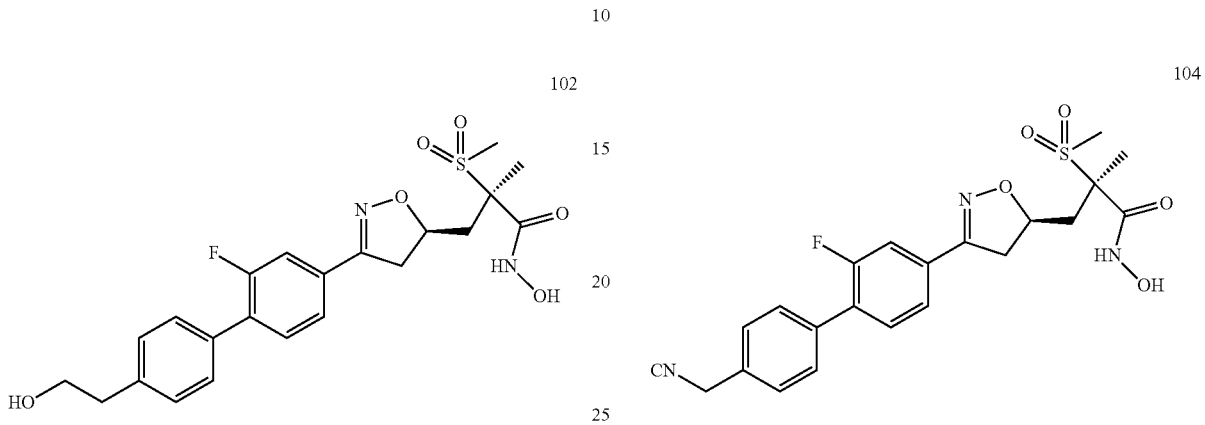

Compound 102 was synthesized by method A. LCMS (m/z): 465.4 [M+H]$^+$. $^1$H NMR (400 MHz, CD3CN) ppm 1.50-1.78 (m, 3H) 1.87-2.07 (m, 10H) 2.75-3.07 (m, 4H) 3.17 (dd, J=16.99, 8.49 Hz, 1H) 3.60 (dd, J=16.92, 10.32 Hz, 1H) 3.77 (t, J=6.77 Hz, 2H) 4.70-4.98 (m, 2H) 7.38 (d, J=8.12 Hz, 2H) 7.44-7.73 (m, 4H).

103

Synthesis of (R)-3-((R)-3-(2-fluoro-4'-(hydroxymethyl)-[1,1-biphenyl]-4-yl)-4,5-dihydroisoxazol-5-yl)-N-hydroxy-2-methyl-2-(methylsulfonyl)propanamide [103]

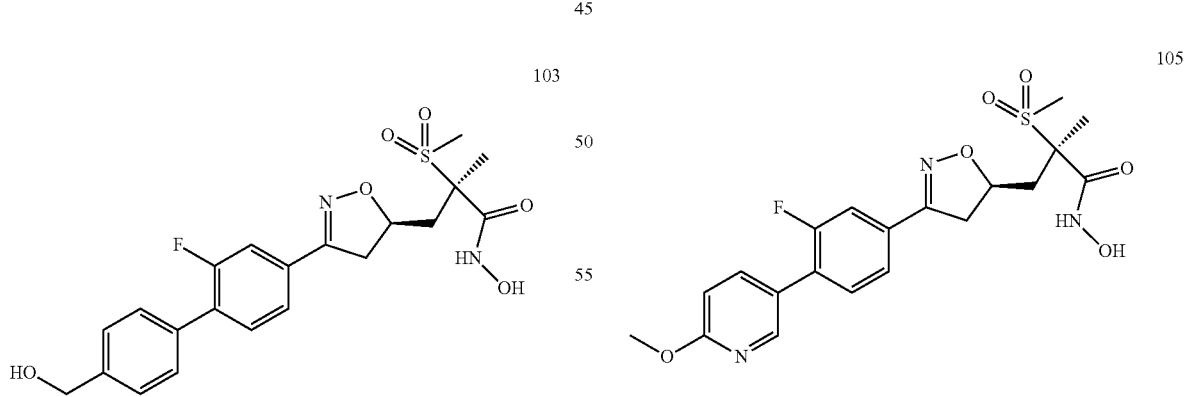

Compound 103 was synthesized by method C. LCMS (m/z): 451.0 [M+H]$^+$. $^1$H NMR (400 MHz, CD3CN) ppm 1.63-1.75 (m, 4H) 1.76-1.85 (m, 2H) 2.61-2.79 (m, 3H) 3.02 (s, 3H) 3.09-3.27 (m, 2H) 3.50-3.71 (m, 2H) 4.59-4.70 (m, 2H) 4.71-4.87 (m, 1H) 7.42-7.51 (m, 2H) 7.51-7.67 (m, 5H)

104

Synthesis of (R)-3-((R)-3-(4'-(cyanomethyl)-2-fluoro-[1,1-biphenyl]-4-yl)-4,5-dihydroisoxazol-5-yl)-N-hydroxy-2-methyl-2-(methylsulfonyl)propanamide [104]

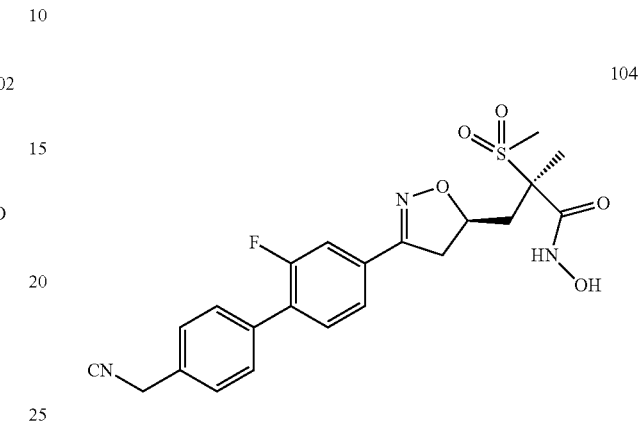

Compound 104 was synthesized by method A. LCMS (m/z): 460.4 [M+H]$^+$. $^1$H NMR (400 MHz, DMSO-d6) ppm 1.59 (s, 4H) 1.94-2.18 (m, 1H) 2.58-2.72 (m, 1H) 3.05 (s, 3H) 3.09-3.24 (m, 2H) 3.48-3.68 (m, 1H), 4.10 (s, 3H) 4.55-4.78 (m, 1H) 6.51 (s, 1H) 7.47 (d, J=8.17 Hz, 3H) 7.52-7.72 (m, 6H) 9.25 (s, 1H) 11.04 (s, 1H)

105

Synthesis of (R)-3-((R)-3-(3-fluoro-4-(6-methoxypyridin-3-yl)phenyl)-4,5-dihydroisoxazol-5-yl)-N-hydroxy-2-methyl-2-(methylsulfonyl)propanamide [105]

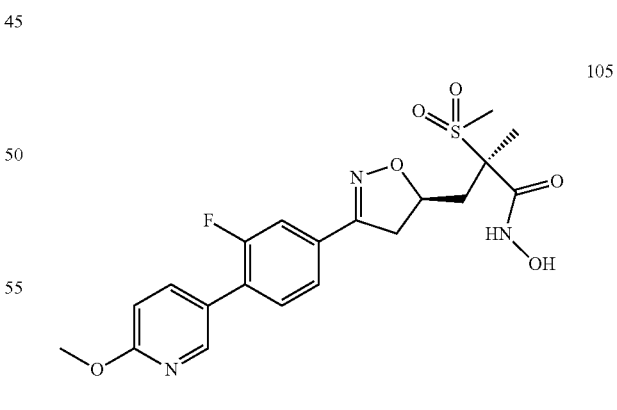

Compound 105 was synthesized by method C, LCMS (m/z): 452.4 [M+H]$^+$. $^1$H NMR (400 MHz, DMSO-d6) ppm 1.58 (s, 3H) 1.97-2.18 (m, 2H) 2.61-2.75 (m, 2H) 3.05 (s, 4H) 3.10-3.24 (m, 3H) 3.50-3.72 (m, 3H) 3.89 (s, 3H) 4.50-4.81 (m, 2H) 6.83-7.07 (m, 2H) 7.50-7.60 (m, 2H) 7.60-7.74 (m, 1H) 7.87-8.06 (m, 1H) 8.26-8.52 (m, 1H)

107

Synthesis of (R)-3-((R)-3-(2-fluoro-4'-((R)-2-hydroxypropyl)-[1,1-biphenyl]-4-yl)-4,5-dihydroisoxazol-5-yl)-N-hydroxy-2-methyl-2-(methylsulfonyl)propanamide [107]

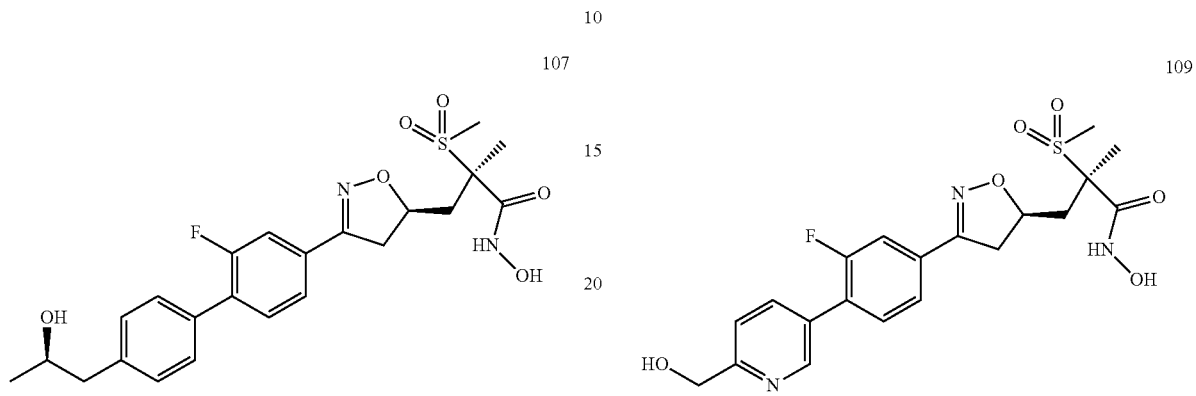

Compound 107 was synthesized by method C. LCMS (m/z): 479.4 [M+H]⁺. ¹H NMR (400 MHz, DMSO-d6) ppm 1.04 (d, J=6.11 Hz, 3H) 1.59 (s, 3H) 1.95-2.16 (m, 1H) 2.68 (s, 3H) 3.05 (s, 3H) 3.12-3.22 (m, 2H) 3.51-3.69 (m, 2H) 3.73-3.93 (m, 1H) 4.48-4.71 (m, 1H) 7.29 (d, J=8.17 Hz, 2H) 7.53-7.82 (m, 5H), 9.30 (s, 1H), 11.03 (s, 1H)

108

Synthesis of (R)-3-((R)-3-(3-fluoro-4-(1-methyl-2-oxo-1,2-dihydropyridin-4-yl)phenyl)-4,5-dihydroisoxazol-5-yl)-N-hydroxy-2-methyl-2-(methylsulfonyl)propanamide [108]

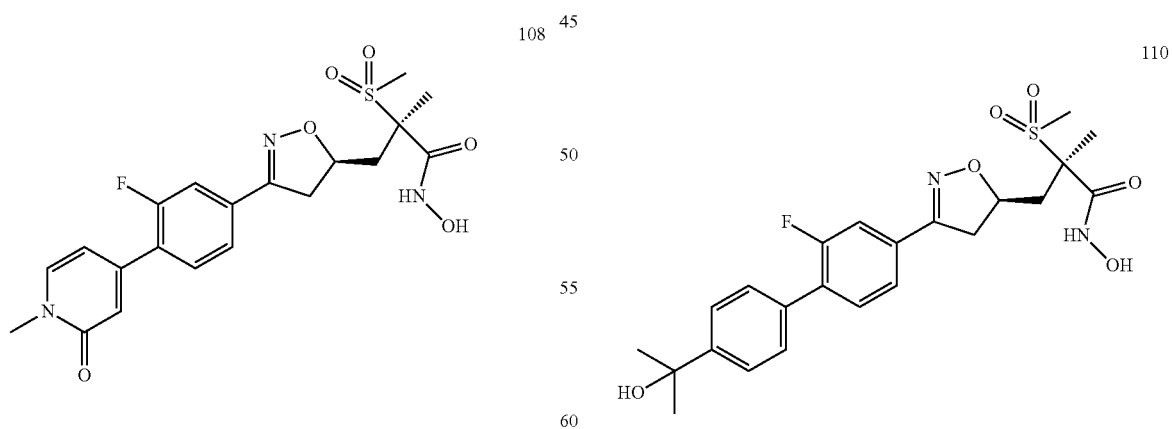

Compound 108 was synthesized by method C. LCMS (m/z): 452.4 [M+H]⁺. ¹H NMR (400 MHz, DMSO-d6) ppm 1.58 (s, 3H) 1.98-2.16 (m, 1H) 2.56-2.78 (m, 1H) 3.05 (s, 3H) 3.09-3.24 (m, 2H) 3.57 (d, J=10.37 Hz, 2H) 4.58-4.79 (m, 1H) 6.42 (d, J=7.04 Hz, 1H) 6.57 (s, 1H) 7.47-7.61 (m, 2H) 7.66 (s, 1H) 7.78 (d, J=7.09 Hz, 1H) 11.04 (s, 1H)

109

Synthesis of (R)-3-((R)-3-(3-fluoro-4-(6-(hydroxymethyl)pyridin-3-yl)phenyl)-4,5-dihydroisoxazol-5-yl)-N-hydroxy-2-methyl-2-(methylsulfonyl)propanamide [109]

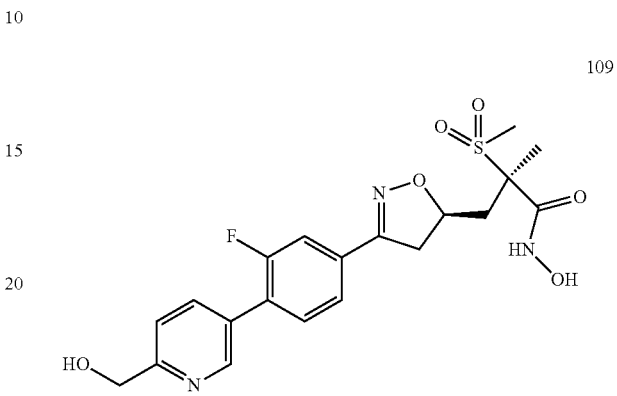

Compound 109 was synthesized by method C. LCMS (m/z): 452.4 [M+H]⁺. ¹H NMR (400 MHz, DMSO-d6) ppm 1.59 (s, 3H) 1.96-2.17 (m, 2H) 2.58-2.74 (m, 2H) 3.05 (s, 3H) 3.12-3.23 (m, 3H) 3.54-3.68 (m, 3H) 4.62 (s, 3H) 7.61 (s, 3H) 7.66-7.76 (m, 1H) 7.94-8.13 (m, 1H) 8.58-8.81 (m, 1H) 10.88-11.12 (m, 1H)

110

Synthesis of (R)-3-((R)-3-(2-fluoro-4'-(2-hydroxypropan-2-yl)-[1,1-biphenyl]-4-yl)-4,5-dihydroisoxazol-5-yl)-N-hydroxy-2-methyl-2-(methylsulfonyl)propanamide [110]

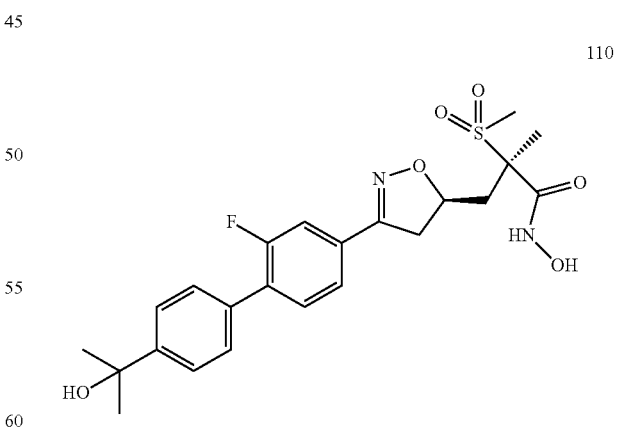

Compound 110 was synthesized by method C. LCMS (m/z): 479.4 [M+H]⁺. ¹H NMR (400 MHz, DMSO-d6) ppm 1.31-1.67 (m, 8H) 1.95-2.11 (m, 2H) 2.60-2.78 (m, 2H) 3.05 (s, 3H) 3.11-3.22 (m, 2H) 3.47-3.70 (m, 2H) 4.51-4.80 (m, 2H) 7.56 (s, 7H) 9.11-9.42 (m, 1H) 10.84-11.15 (m, 1H)

111

Synthesis of (R)-N-hydroxy-2-methyl-2-(methylsulfonyl)-3-((R)-3-(4-(3-(trifluoromethyl)pyridin-4-yl)phenyl)-4,5-dihydroisoxazol-5-yl)propanamide [111]

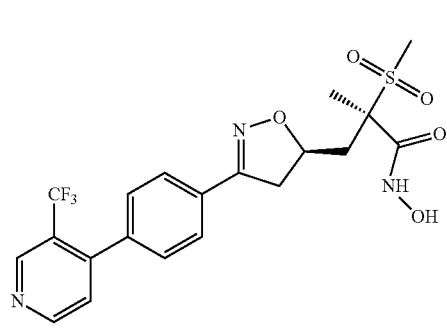

Compound 111 was synthesized by method B. LCMS (m/z): 472.2 [M+H]⁺. ¹H NMR (400 MHz, DMSO-d$_6$) 11.05 (s, 1H), 9.05 (s, 1H), 8.93 (d, J=5.0 Hz, 1H), 7.78 (d, J=8.4 Hz, 2H), 7.53 (d, J=5.1 Hz, 1H), 7.48 (d, J=8.2 Hz, 2H), 4.75-4.59 (m, 1H), 3.64 (dd, J=17.0, 10.3 Hz, 1H), 3.20 (dd, J=17.1, 8.0 Hz, 1H), 3.07 (s, 3H), 2.73-2.66 (m, 1H), 2.08 (dd, J=14.1, 8.4 Hz, 1H), 1.61 (s, 3H).

112

Synthesis of (R)-3-((R)-3-(3-fluoro-4-(2-isopropylpyridin-4-yl)phenyl)-4,5-dihydroisoxazol-5-yl)-N-hydroxy-2-methyl-2-(methylsulfonyl)propanamide [112]

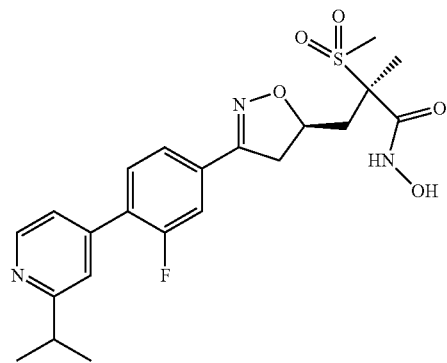

Compound 112 was synthesized by method C. LCMS (m/z): 464.1 [M+H]⁺. ¹H NMR (400 MHz, DMSO-d6) ppm 1.02-1.35 (m, 10H) 2.01-2.17 (m, 2H) 2.55-2.75 (m, 2H) 2.91-3.27 (m, 8H) 4.01 (d, J=7.09 Hz, 2H) 4.57-4.80 (m, 1H) 7.51 (s, 1H) 7.59 (d, J=9.83 Hz, 2H) 7.71 (s, 1H) 7.92-8.11 (m, 1H) 8.74 (s, 1H) 11.04 (s, 1H)

113

Synthesis of (R)-3-((R)-3-(2-fluoro-4-methoxy-2-methyl-[1,1'-biphenyl]-4-yl)-4,5-dihydroisoxazol-5-yl)-N-hydroxy-2-methyl-2-(methylsulfonyl)propanamide [113]

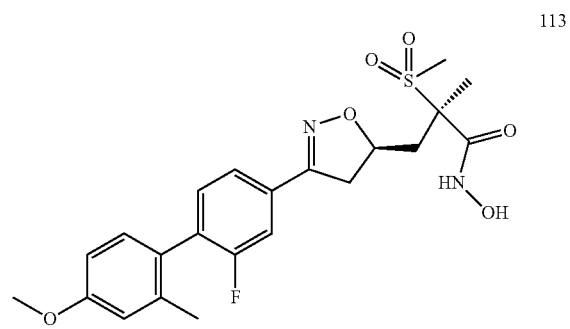 [SMILES: COc1ccc(-c2ccc(C3=NO[C@@H](C[C@](C)(C(=O)NO)S(C)(=O)=O)C3)cc2F)c(C)c1]

Compound 113 was synthesized by method C. LCMS (m/z): 465.1 [M+H]⁺. ¹H NMR (400 MHz, DMSO-d6) ppm 1.58 (s, 3H) 2.11 (s, 5H) 2.55-2.73 (m, 2H) 3.05 (s, 3H) 3.10-3.22 (m, 2H) 3.77 (s, 5H) 4.54-4.79 (m, 1H) 6.72-6.96 (m, 2H) 7.04-7.18 (m, 1H) 7.31-7.41 (m, 1H) 7.44-7.57 (m, 2H) 9.12-9.37 (m, 1H) 10.89-11.11 (m, 1H)

114

Synthesis of (R)-3-((R)-3-(2-fluoro-4'-(2H-tetrazol-5-yl)-[1,1-biphenyl]-4-yl)-4,5-dihydroisoxazol-5-yl)-N-hydroxy-2-methyl-2-(methylsulfonyl)propanamide [114]

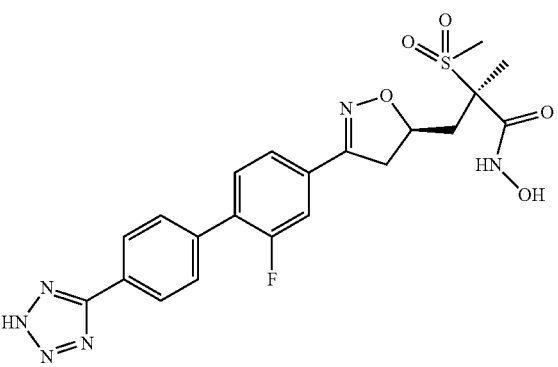

Compound 114 was synthesized by method C. LCMS (m/z): 489.1 [M+H]⁺. ¹H NMR (400 MHz, DMSO-d6) ppm 1.94-2.18 (m, 2H) 2.57-2.75 (m, 2H) 3.05 (s, 3H) 3.10-3.23 (m, 3H) 3.53-3.69 (m, 1H) 4.58-4.80 (m, 2H) 7.54-7.89 (m, 6H) 8.06-8.23 (m, 2H) 9.11-9.33 (m, 1H) 10.93-11.13 (m, 1H)

115

Synthesis of (R)-3-((R)-3-(2,2'-difluoro-4'-((R)-2-hydroxypropyl)-[1,1-biphenyl]-4-yl)-4,5-dihydroisoxazol-5-yl)-N-hydroxy-2-methyl-2-(methylsulfonyl)propanamide [115]

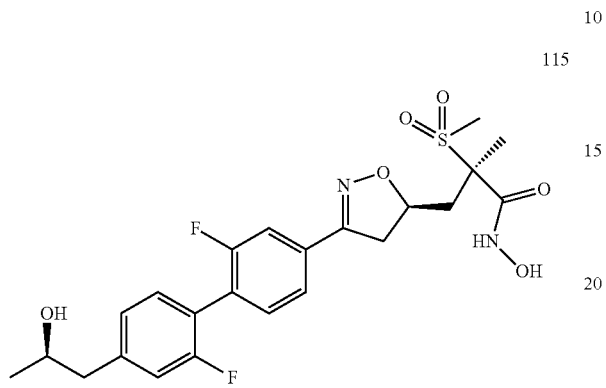

Compound 115 was synthesized by method C. LCMS (m/z): 497.3 [M+H]+. $^1$H NMR (400 MHz, DMSO-d6) ppm 1.06 (d, J=6.06 Hz, 3H) 1.97-2.15 (m, 1H) 2.67 (d, J=12.08 Hz, 4H) 3.05 (s, 3H) 3.20 (s, 2H) 3.52-3.69 (m, 2H) 3.76-3.95 (m, 1H) 4.53-4.78 (m, 2H) 7.23 (d, J=7.53 Hz, 2H) 7.37 (s, 1H) 7.45-7.65 (m, 3H) 11.04 (s, 1H)

116

Synthesis of (R)-N-hydroxy-2-methyl-2-(methylsulfonyl)-3-((R)-3-(2,2',6'-trifluoro-4'-((R)-2-hydroxypropyl)-[1,1'-biphenyl]-4-yl)-4,5-dihydroisoxazol-5-yl)propanamide

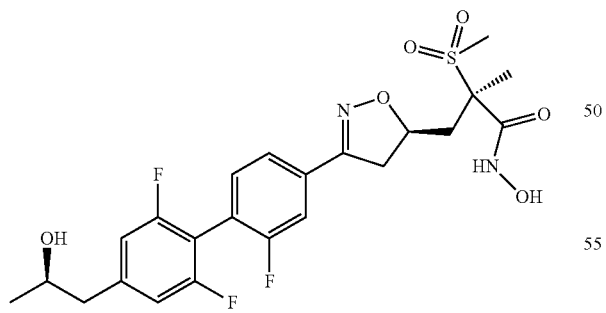

Compound 116 was synthesized by method C. LCMS (m/z): 515.3 [M+H]+. $^1$H NMR (400 MHz, DMSO-d6) ppm 0.98-1.15 (m, 3H) 1.18-1.31 (m, 1H) 1.99-2.17 (m, 2H) 2.59-2.70 (m, 2H) 2.70-2.81 (m, 1H) 3.05 (s, 3H) 3.10-3.22 (m, 2H) 3.52-3.66 (m, 1H) 3.76-3.95 (m, 1H) 4.58-4.74 (m, 1H) 4.75-4.86 (m, 1H) 7.23-7.37 (m, 2H) 7.48-7.62 (m, 2H) 7.64-7.79 (m, 1H)

117

Synthesis of (R)-3-((R)-3-(3-fluoro-4-(3-fluoropyridin-4-yl)phenyl)-4,5-dihydroisoxazol-5-yl)-N-hydroxy-2-methyl-2-(methylsulfonyl)propanamide [117]

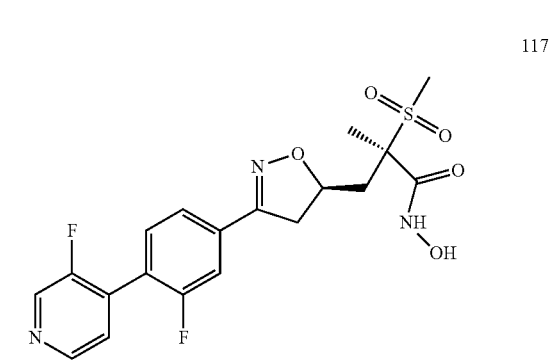 [SMILES: C[C@@](C[C@H]1CC(c2ccc(-c3ccncc3F)c(F)c2)=NO1)(C(=O)NO)S(C)(=O)=O]

Compound 117 was synthesized by method A. LCMS (m/z): 440.2 [M+H]+. $^1$H NMR (400 MHz, DMSO-d$_6$) 11.04 (s, 1H), 8.72 (d, J=1.7 Hz, 1H), 8.60-8.53 (m, 1H), 7.70-7.57 (m, 5H), 4.70 (ddd, J=19.0, 8.5, 3.9 Hz, 1H), 3.63 (dd, J=17.1, 10.4 Hz, 1H), 3.19 (dd, J=17.2, 8.2 Hz, 1H), 3.06 (s, 3H), 2.71-2.63 (m, 1H), 2.14-2.04 (m, 1H), 1.60 (s, 3H).

118

Synthesis of (R)-3-((R)-3-(4-(2,6-dimethylpyridin-4-yl)-3-fluorophenyl)-4,5-dihydroisoxazol-5-yl)-N-hydroxy-2-methyl-2-(methylsulfonyl)propanamide [118]

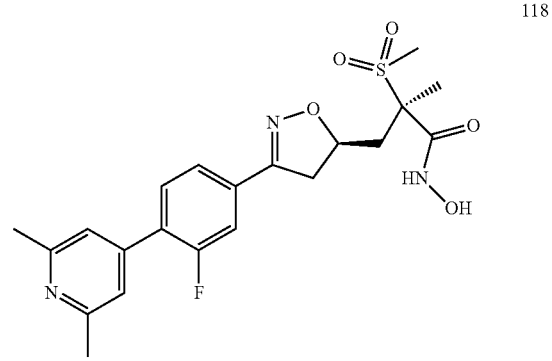 [SMILES: Cc1cc(-c2ccc(C3=NO[C@@H](C[C@](C)(C(=O)NO)S(C)(=O)=O)C3)cc2F)cc(C)n1]

Compound 118 was synthesized by method C. LCMS (m/z): 450.1 [M+H]+. $^1$H NMR (400 MHz, DMSO-d6) ppm 1.59 (s, 2H) 1.90-2.19 (m, 1H) 2.57-2.69 (m, 3H) 2.98-3.10 (m, 2H) 3.12-3.27 (m, 1H) 3.57-3.70 (m, 2H) 4.49-4.90 (m, 2H) 7.44-7.88 (m, 3H) 9.11-9.45 (m, 1H) 11.05 (s, 1H)

119

Synthesis of (R)-3-((R)-3-(2-fluoro-4-(3-fluoropyridin-4-yl)phenyl)-4,5-dihydroisoxazol-5-yl)-N-hydroxy-2-methyl-2-(methylsulfonyl)propanamide [119]

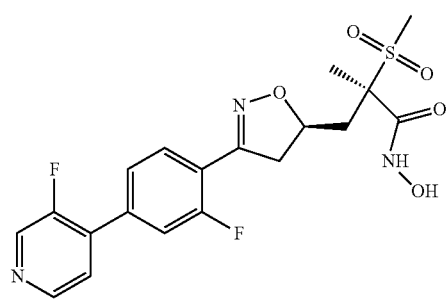

Compound 119 was synthesized by method A. LCMS (m/z): 440.2 [M+H]$^+$. $^1$H NMR (400 MHz, DMSO-d$_6$) 11.04 (s, 1H), 8.72 (d, J=2.6 Hz, 1H), 8.55 (dd, J=5.0, 1.0 Hz, 1H), 7.88 (t, J=8.0 Hz, 1H), 7.77-7.67 (m, 2H), 7.62 (dt, J=8.2, 1.6 Hz, 1H), 4.67 (dtd, J=10.4, 8.4, 3.5 Hz, 1H), 3.65 (ddd, J=17.4, 10.5, 1.7 Hz, 1H), 3.24 (ddd, J=17.4, 8.4, 1.7 Hz, 1H), 3.07 (s, 3H), 2.71 (dd, J=14.2, 3.5 Hz, 1H), 2.12-2.05 (m, 1H), 1.61 (s, 3H).

121

Synthesis of (R)-N-hydroxy-3-((R)-3-(4'-((R)-2-hydroxypropyl)-2-methyl-[1,1'-biphenyl]-4-yl)-4,5-dihydroisoxazol-5-yl)-2-methyl-2-(methylsulfonyl)propanamide

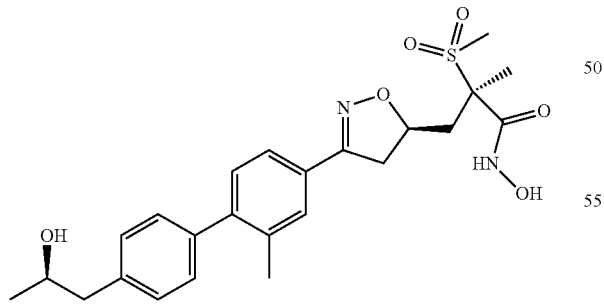

Compound 121 was synthesized by method A. LCMS (m/z): 475.3 [M+H]$^+$. $^1$H NMR (400 MHz, DMSO-d6) ppm 1.06 (d, J=6.06 Hz, 4H) 1.88-2.11 (m, 2H) 2.26 (s, 4H) 2.55-2.77 (m, 4H) 3.05 (s, 3H) 3.09-3.20 (m, 2H) 3.47-3.65 (m, 2H) 3.74-3.97 (m, 1H) 4.51-4.75 (m, 1H) 7.25 (d, J=2.35 Hz, 5H) 7.41-7.64 (m, 2H) 10.86-11.13 (m, 1H)

122

Synthesis of (R)-3-((R)-3-(2,6-difluoro-4'-((R)-2-hydroxypropyl)-[1,1-biphenyl]-4-yl)-4,5-dihydroisoxazol-5-yl)-N-hydroxy-2-methyl-2-(methylsulfonyl)propanamide [122]

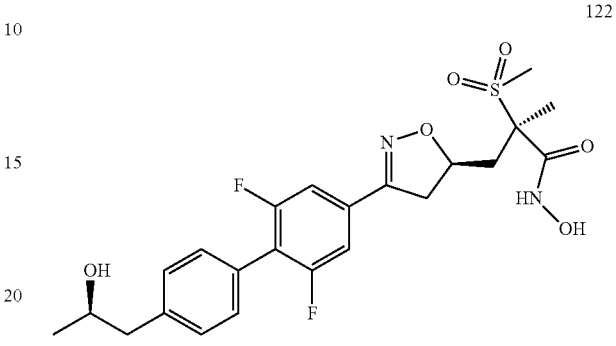

Compound 122 was synthesized by method A. LCMS (m/z): 497.3 [M+H]$^+$. $^1$H NMR (400 MHz, DMSO-d6) ppm 1.06 (d, J=6.11 Hz, 3H) 1.96-2.20 (m, 2H) 2.55-2.76 (m, 3H) 3.05 (s, 3H) 3.08-3.22 (m, 2H) 3.51-3.67 (m, 2H) 3.76-3.96 (m, 1H) 4.57-4.81 (m, 1H) 7.34 (q, J=8.15 Hz, 4H) 7.46 (d, J=8.12 Hz, 2H) 11.05 (s, 1H)

123

Synthesis of (R)-3-((R)-3-(2-fluoro-4-(prop-1-yn-1-yl)phenyl)-4,5-dihydroisoxazol-5-yl)-N-hydroxy-2-methyl-2-(methylsulfonyl)propanamide [123]

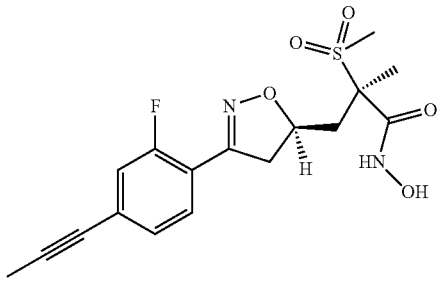

Step 1: Synthesis of (R)-benzyl 3-((S)-3-(4-bromo-2-fluorophenyl)-4,5-dihydroisoxazol-5-yl)-2-methyl-2-(methylsulfonyl)propanoate [123a]

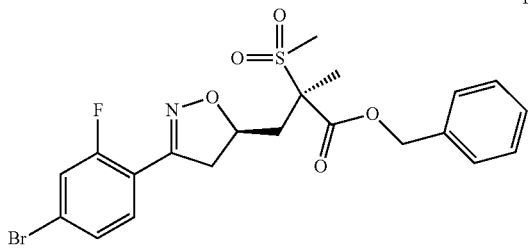

To a mixture of (R)-benzyl 2-methyl-2-(methylsulfonyl)pent-4-enoate (11 g, 39.0 mmol) and (Z)-4-bromo-2-fluoro-N-hydroxybenzimidoyl chloride (11.02 g, 43.6 mmol) in Et₂O (150 mL) at RT was added triethylamine (10.86 mL, 78 mmol). White suspension was formed right after the addition of the TEA. The reaction mixture was stirred at RT for 3 hours. The reaction mixture was diluted with EtOAc, then filtered. The solution was concentrated and the remaining material was purified by silica gel column chromatography (EtOAc/heptane, 5 to 20%). The less polar fraction is the desired diastereomer (3.2 g, 6.42 mmol, 16.48% yield). LCMS: (m/z): 500.1 [M+H]⁺.

Step 2: Synthesis of (R)-benzyl 3-((R)-3-(2-fluoro-4-(prop-1-yn-1-yl)phenyl)-4,5-dihydroisoxazol-5-yl)-2-methyl-2-(methylsulfonyl)propanoate [123b]

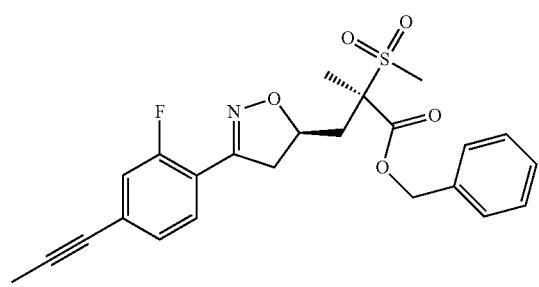

123b

To a mixture of (R)-benzyl 3-((R)-3-(4-bromo-2-fluorophenyl)-4,5-dihydroisoxazol-5-yl)-2-methyl-2-(methylsulfonyl)propanoate (1.4 g, 2.81 mmol), but-2-ynoic acid (0.354 g, 4.21 mmol), DBU (0.847 mL, 5.62 mmol), 1,4-bis(diphenylphosphino)-butane (0.024 g, 0.056 mmol) and bis(triphenylphosphine)palladium dichloride (0.020 g, 0.028 mmol) was added DMSO (14 mL). The resultant mixture was flushed with argon for 5 min. The mixture was stirred at 95° C. for 3 h after which, 200 mg of but-2-ynoic acid, 15 mg of 1,4-bis(diphenylphosphino)-butane, 10 mg of palladium catalyst and 0.3 ml of DBU was added. The flask was flushed again with argon, and the mixture was stirred at 95° C. for another 2 hours. After cooled to RT, the mixture was quenched with water and extracted with EtOAc. The organic layer was washed with brine, dried over sodium sulfate and concentrated. The crude material was purified by silica gel column chromatography, (EtOAc/heptane, 10 to 40%) to give product 123b (570 mg, 44.3% yield). LCMS: (m/z) 458.4 [M+H]⁺.

Step 3. Synthesis of (R)-3-((R)-3-(2-fluoro-4-(prop-1-yn-1-yl)phenyl)-4,5-dihydroisoxazol-5-yl)-2-methyl-2-(methylsulfonyl)propanoic acid [123c]

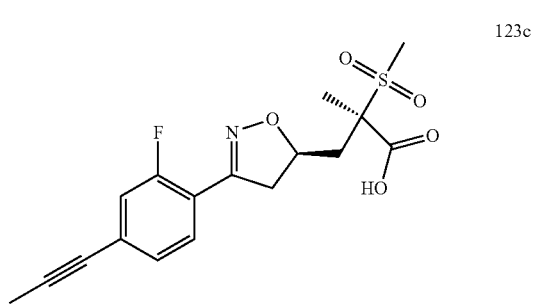 [SMILES: CC#Cc1ccc(C2=NO[C@@H](C[C@](C)(C(=O)O)S(C)(=O)=O)C2)c(F)c1]

123c

To a mixture of (R)-benzyl 3-((R)-3-(2-fluoro-4-(prop-1-yn-1-yl)phenyl)-4,5-dihydroisoxazol-5-yl)-2-methyl-2-(methylsulfonyl)propanoate (470 mg, 1.027 mmol) in MeOH (3 ml), THF (3 mL) and Water (3 mL) was added LiOH (123 mg, 5.14 mmol). The resultant mixture was stirred at 25° C. for 2 h. The reaction mixture was concentrated, diluted with 5 ml of water, and was then acidified with 3.0 N aq HCl solution. The resultant mixture was extracted with EtOAc. The organic layer was washed with water, dried over sodium sulfate and concentrated. The crude material was continued to the next step with no further purification. LCMS: (m/z) 368.2 [M+H]⁺.

Step 4. Synthesis of (2R)-3-((R)-3-(2-fluoro-4-(prop-1-yn-1-yl)phenyl)-4,5-dihydroisoxazol-5-yl)-2-methyl-2-(methylsulfonyl)-N-((tetrahydro-2H-pyran-2-yl)oxy)propanamide [123d]

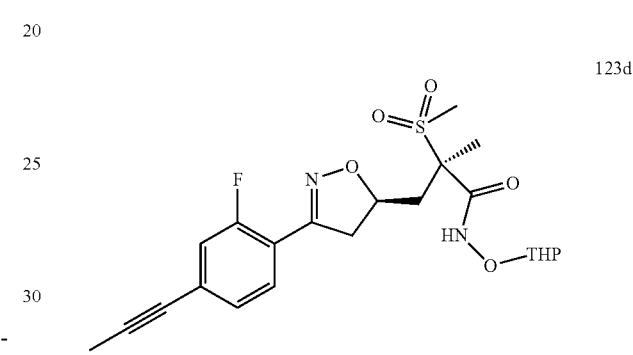

123d

To (R)-3-((R)-3-(2-fluoro-4-(prop-1-yn-1-yl)phenyl)-4,5-dihydroisoxazol-5-yl)-2-methyl-2-(methylsulfonyl)propanoic acid (377 mg, 1.027 mmol) in DCM (4 mL) was added EDC.HCl (354 mg, 1.849 mmol) and HOAT (280 mg, 2.054 mmol) and the resultant mixture was stirred for 10-20 min. Triethylamine (0.358 mL, 2.57 mmol) was then added, followed by O-(Tetrahydro-2H-pyran-2-yl)hydroxylamine (241 mg, 2.054 mmol). The mixture was stirred at room temperature for 18 hours. The reaction mixture was filtered and the filtrate was purified by silica gel column chromatography, (EtOAc/heptane, 20 to 75%) to give product 123d (397 mg, 83% yield).

Step 5. Synthesis of (R)-3-((R)-3-(2-fluoro-4-(prop-1-yn-1-yl)phenyl)-4,5-dihydroisoxazol-5-yl)-N-hydroxy-2-methyl-2-(methylsulfonyl)propanamide [123]

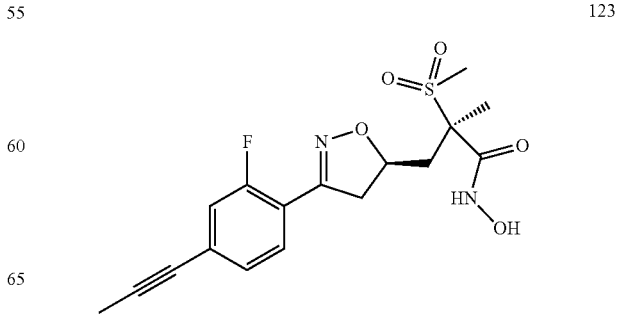

123

To a solution of 123d (397 mg, 0.851 mmol) in MeOH (20 mL) was added a solution of HCl in dioxane (4.0 M, 3.19 mL, 12.76 mmol). The resultant mixture was stirred at 25° C. for 25 min. The reaction solution was then concentrated, and the crude material was purified by silica gel column chromatography, (MeOH/DCM, 0% to 2.5%) to give product 123 (235 mg, 71.5% yield). LC-MS: (m/z) 383.3 $[M+H]^+$. $^1$H NMR (400 MHz, $CD_3CN$) 1.69 (s, 3H) 1.90-2.02 (m, 1H) 2.02-2.11 (m, 3H) 2.13-2.29 (m, 6H) 2.66 (dd, J=14.18, 3.33 Hz, 1H) 3.01 (s, 3H) 3.18 (ddd, J=17.31, 8.51, 2.01 Hz, 1H) 3.60 (ddd, J=17.30, 10.36, 2.03 Hz, 1H) 4.65-4.82 (m, 1H) 7.08-7.31 (m, 2H) 7.58-7.79 (m, 1H)

Pharmaceutical Activity Examples

P. aeruginosa LpxC Inhibition Assay

The P. aeruginosa LpxC protein is produced according to the general method of Hyland et al (Journal of Bacteriology 1997 179, 2029-2037: Cloning, expression and purification of UDP-3-O-acyl-GlcNAc deacetylase from Pseudomonas aeruginosa: a metalloamidase of the lipid A biosynthesis pathway). The LC-MS/MS method for quantitation of LpxC product was developed using an Agilent 1200 Capillary HPLC system coupled to an Applied Biosystems MDS Sciex 4000QTRAP mass spectrometer. Both instruments are controlled using the Applied Biosystems MDS Sciex Analyst software. LpxC reaction product (UDP-3-O—(R-3-hydroxyacyl)-glucosamine) was produced by hydrolysis of LpxC substrate catalyzed by P.a. LpxC and purified using reversed phase chromatography on a Phenomenex Luna C18(2) 4.6×50 mm column. An LpxC product calibration curve was generated to evaluate the sensitivity and dynamic range of the LC-MS/MS method. Briefly, compounds are pre-incubated with 1 nM P. aeruginosa LpxC for 30 min. at room temperature. Reactions are initiated by the addition of 2 µM UDP-3-O—(R-3-hydroxydecanoyl)-GlcNAc. Reactions are conducted in a 384-well plate with a total volume of 50 µL in each well containing 50 mM Sodium phosphate pH 7.5, 0.005% Trition X-100 for 20 min at room temperature. After quenching with 1.8% HOAc (5 µL of a 20% HOAc added to each well), reaction mixtures are analyzed using the LC-MS/MS method and peak areas are transformed into product concentration using a LpxC product calibration curve. Total activity (0% inhibition control) is obtained from reactions with no inhibitors and 100% inhibition control is the background using quenched samples before reaction starts. For $IC_{50}$ determinations, peak areas are converted to percent inhibition in Microsoft Excel. Percent inhibition values are plotted vs. log compound concentration using XLfit. Data is fit to the four-parameter logistic equation using the non-linear regression algorithm in XLfit to return the $IC_{50}$ and hill slope values.

Bacterial Screens and Cultures

Bacterial isolates were cultivated from –70° C. frozen stocks by two consecutive overnight passages at 35° C. in ambient air on 5% blood agar (Remel, Lenexa, Kans.). Quality control and P. aeruginosa ATCC 27853) is from the American Type Culture Collection (ATCC; Rockville, Md.) and PAO1 was received from Dr. K. Poole.

Susceptibility Testing

Minimal Inhibitory Concentrations (MICs) were determined by the broth microdilution method in accordance with Clinical and Laboratories Institute (CLSI) guidelines. In brief, fresh bacterial overnight cultures were resuspended in sterile saline, adjusted to a 0.5 McFarland turbidity standard and then diluted 20010-fold in cation adjusted Mueller-Hinton Broth II (MHB; Remel BBL) to yield a final inoculum of approximately $5 \times 10^5$ colony-forming units (CFU)/mL. Two-fold serial dilutions of compounds were prepared in 100% dimethyl sulfoxide (DMSO) at 100-fold the highest final assay concentration; the resulting dilution series of compounds were diluted 1:10 with sterile water. Ten µl of the drug dilution series in 10% DMSO was transferred to microtiter wells and 90 µl of bacterial suspension was inoculated into the wells. All inoculated microdilution trays were incubated in ambient air at 37 35° C. for 20 hours. Following incubation, assay plates were read in a microtiter plate reader at 600 nm and visually inspected to confirm the MIC endpoint well with the OD value. The lowest concentration of the compound that prevented visible growth was recorded as the MIC. Performance of the assay was monitored by testing ciprofloxacin against laboratory quality control strains in accordance with guidelines of the CLSI.

The P. aeruginosa LpxC inhibitory activity for selected compounds and MIC data for inhibition of growth of P. aeruginosa measured by the methods described above are reported in Table A.

TABLE A

| Cmpd No. | Compound structure | LCMS [M + H]+ | PA LpxC IC50 (nM) | PAO1 MIC (ug/mL) |
|---|---|---|---|---|
| 1-B | 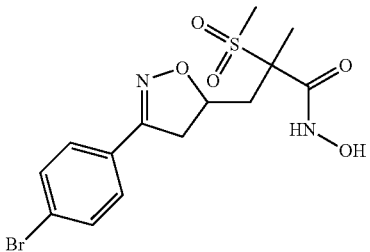 | 424.1 [M + 18] | <0.0005 | 1.0 |

TABLE A-continued

| Cmpd No. | Compound structure | LCMS [M + H]+ | PA LpxC IC50 (nM) | PAO1 MIC (ug/mL) |
|---|---|---|---|---|
| 2-A | 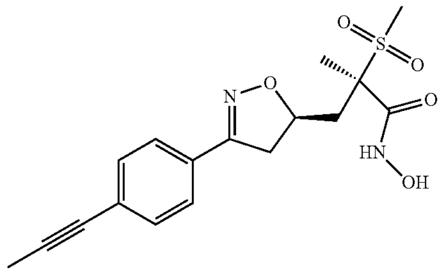 [SMILES: CC#Cc1ccc(C2=NO[C@@H](C[C@](C)(C(=O)NO)S(C)(=O)=O)C2)cc1] | 365.3 | 0.0008 | 0.25 |
| 3-B | 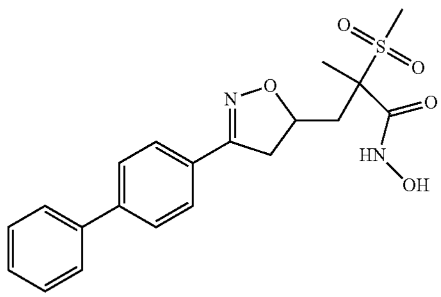 [SMILES: CC(CC1CC(c2ccc(-c3ccccc3)cc2)=NO1)(C(=O)NO)S(C)(=O)=O] | 403.2 | 0.001 | 0.25 |
| 4-B | 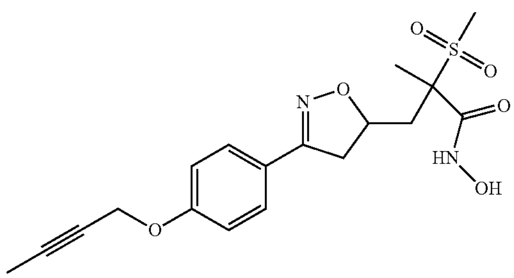 [SMILES: CC#CCOc1ccc(C2=NOC(CC(C)(C(=O)NO)S(C)(=O)=O)C2)cc1] | 395.3 | 0.024 | 8 |
| 5-A | 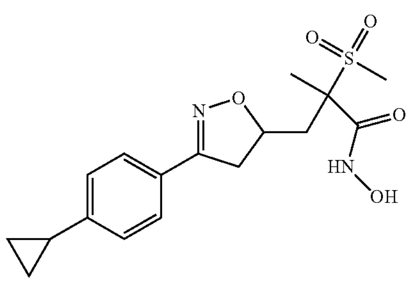 [SMILES: CC(CC1CC(c2ccc(C3CC3)cc2)=NO1)(C(=O)NO)S(C)(=O)=O] | 367.2 | 0.007 | 2 |
| 6-A | 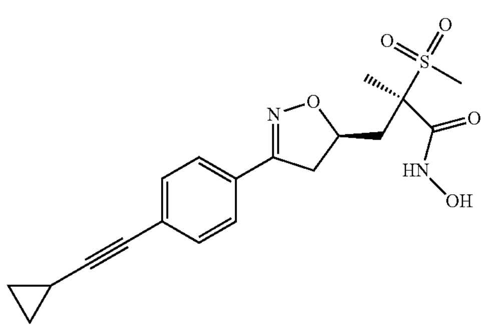 [SMILES: C[C@@](C[C@H]1CC(c2ccc(C#CC3CC3)cc2)=NO1)(C(=O)NO)S(C)(=O)=O] | 391.3 | 0.0007 | 0.25 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 8-B | 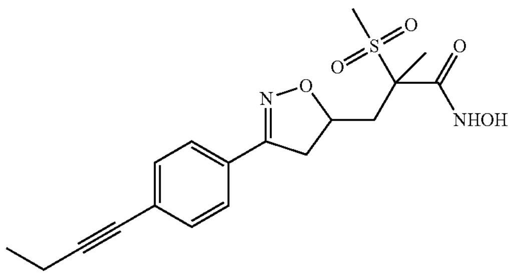 | 379.2 | 0.0005 | 1 |
| 10-B | 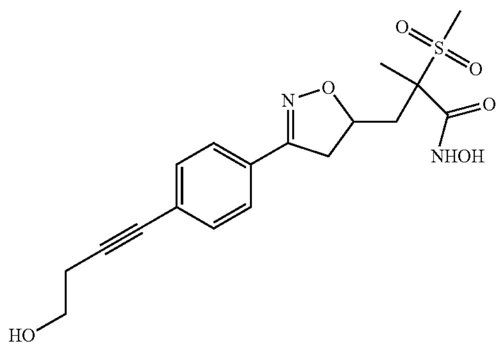 | 395.3 | <0.0005 | 1 |
| 12-B | 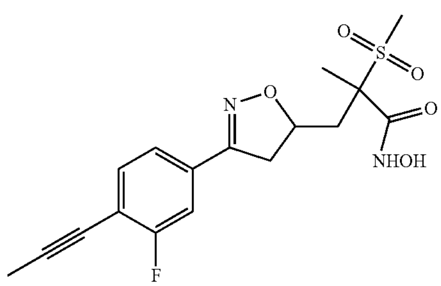 | 383.4 | 0.002 | 2 |
| 13-B | 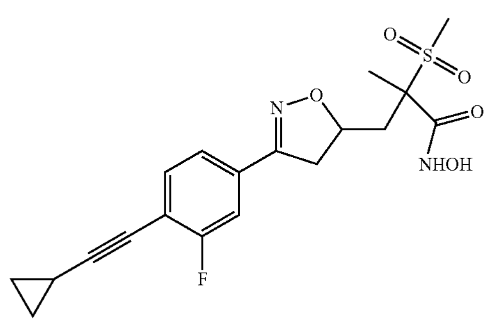 | 409.3 | 0.001 | 1 |
| 14-B | 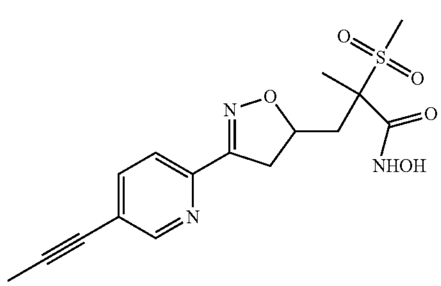 | 366.4 | 0.017 | 8 |

TABLE A-continued

| Cmpd No. | Compound structure | LCMS [M + H]⁺ | PA LpxC IC$_{50}$ (nM) | PAO1 MIC (ug/mL) |
|---|---|---|---|---|
| 15-B | 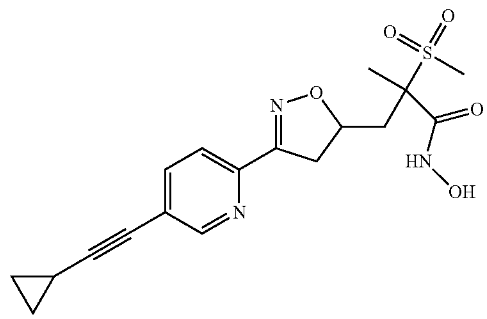 [SMILES: CC(CC1CC(c2ccc(C#CC3CC3)cn2)=NO1)(C(=O)NO)S(C)(=O)=O] | 392.3 | 0.004 | 8 |
| 16-B | 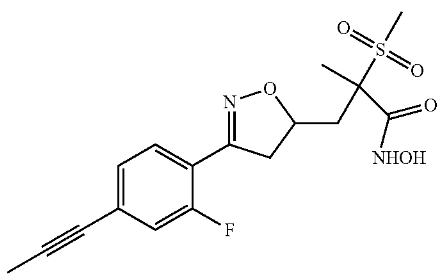 | 383.4 [M + 18] | 0.0006 | 1 |
| 17-B | 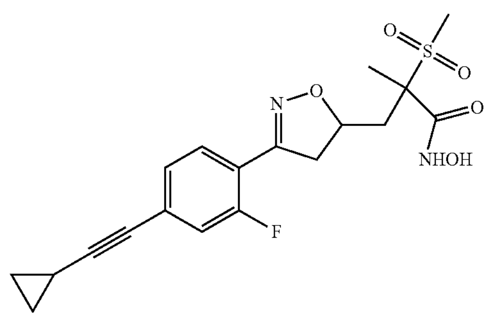 | 409.4 | <0.0005 | 0.5 |
| 22 | 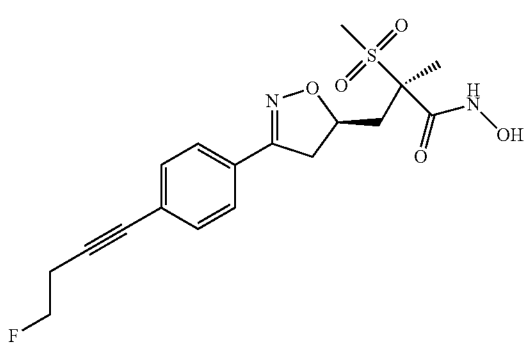 [SMILES: C[C@@](C[C@H]1CC(c2ccc(C#CCCF)cc2)=NO1)(C(=O)NO)S(C)(=O)=O] | 397.2 | <0.0005 | 0.5 |
| 23 | 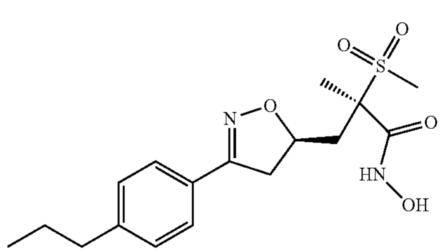 [SMILES: CCCc1ccc(C2=NO[C@@H](C[C@](C)(C(=O)NO)S(C)(=O)=O)C2)cc1] | 369.2 | <0.0005 | 0.5 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 24 | 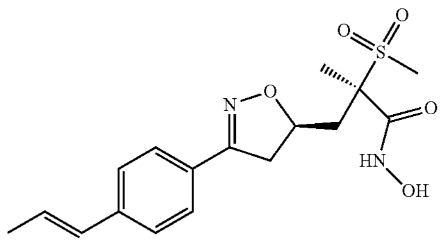 [SMILES: C/C=C/c1ccc(C2=NO[C@@H](C[C@](C)(C(=O)NO)S(C)(=O)=O)C2)cc1] | 367.1 | 0.0008 | 0.5 |
| 29 | 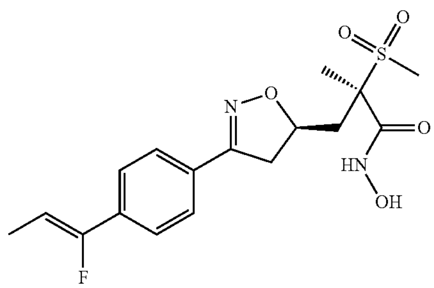 [SMILES: C/C=C(\F)c1ccc(C2=NO[C@@H](C[C@](C)(C(=O)NO)S(C)(=O)=O)C2)cc1] | 385.3 | 0.0006 | 0.125 |
| 30 | 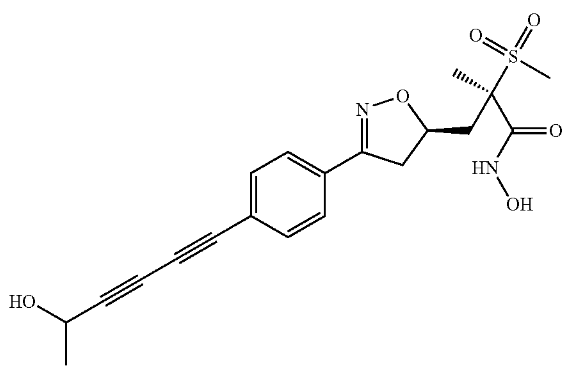 [SMILES: CC(O)C#CC#Cc1ccc(C2=NO[C@@H](C[C@](C)(C(=O)NO)S(C)(=O)=O)C2)cc1] | 419.4 | 0.0005 | 0.06 |
| 31 | 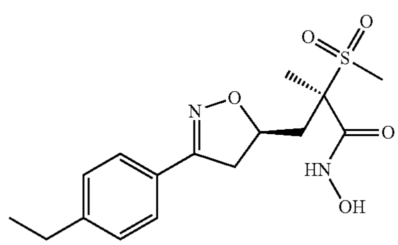 [SMILES: CCc1ccc(C2=NO[C@@H](C[C@](C)(C(=O)NO)S(C)(=O)=O)C2)cc1] | 355.2 | 0.001 | 0.22 |
| 32 | 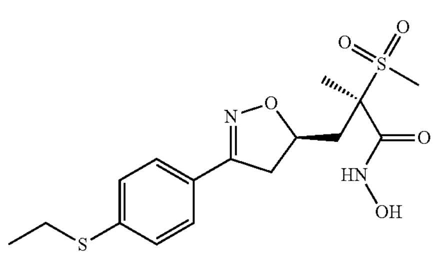 [SMILES: CCSc1ccc(C2=NO[C@@H](C[C@](C)(C(=O)NO)S(C)(=O)=O)C2)cc1] | 387.4 | 0.0009 | 0.4 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 33 | 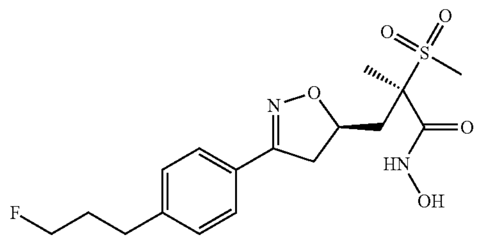 [SMILES: C[C@@](C[C@H]1CC(c2ccc(CCCF)cc2)=NO1)(C(=O)NO)S(C)(=O)=O] | 387.5 | 0.002 | 0.5 |
| 34 | 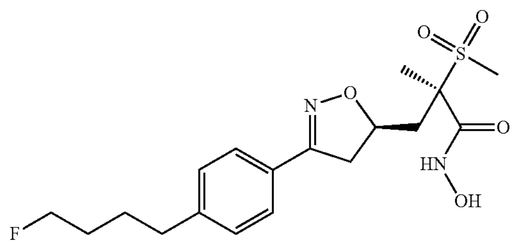 [SMILES: C[C@@](C[C@H]1CC(c2ccc(CCCCF)cc2)=NO1)(C(=O)NO)S(C)(=O)=O] | 401.4 | 0.002 | 0.5 |
| 39A | 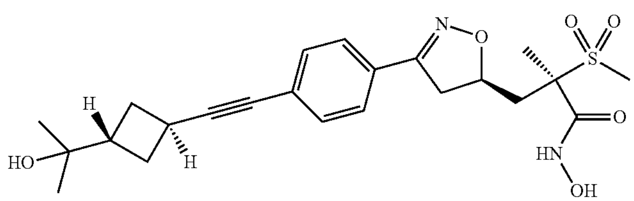 [SMILES: CC(C)(O)[C@H]1C[C@H](C#Cc2ccc(C3=NO[C@@H](C[C@](C)(C(=O)NO)S(C)(=O)=O)C3)cc2)C1] | 463.6 | 0.0005 | 0.5 |
| 39B | 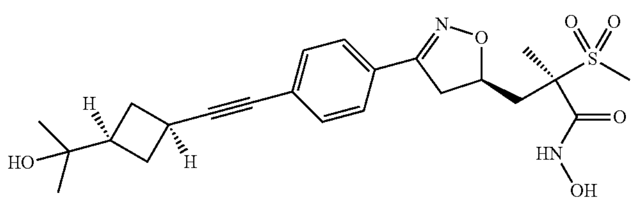 [SMILES: CC(C)(O)[C@H]1C[C@@H](C#Cc2ccc(C3=NO[C@@H](C[C@](C)(C(=O)NO)S(C)(=O)=O)C3)cc2)C1] | 463.6 | 0.002 | 1 |
| 40 | 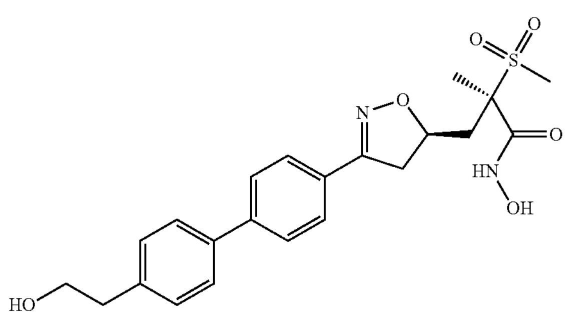 [SMILES: C[C@@](C[C@H]1CC(c2ccc(-c3ccc(CCO)cc3)cc2)=NO1)(C(=O)NO)S(C)(=O)=O] | 447.4 | 0.0005 | 0.16 |
| 41 | 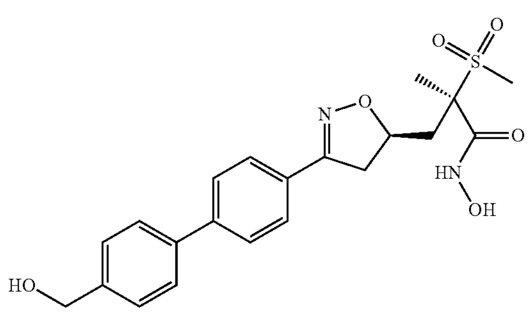 [SMILES: C[C@@](C[C@H]1CC(c2ccc(-c3ccc(CO)cc3)cc2)=NO1)(C(=O)NO)S(C)(=O)=O] | 433.4 | 0.0005 | 0.125 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 42 | 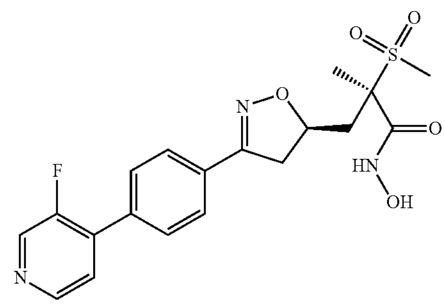 [SMILES: C[C@@](C[C@H]1CC(c2ccc(-c3ccncc3F)cc2)=NO1)(C(=O)NO)S(C)(=O)=O] | 422.2 | 0.0005 | 0.25 |
| 43 | 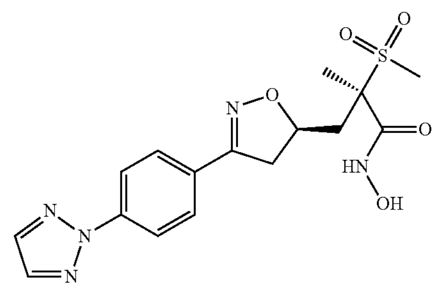 [SMILES: C[C@@](C[C@H]1CC(c2ccc(-n3nccn3)cc2)=NO1)(C(=O)NO)S(C)(=O)=O] | 394.3 | 0.005 | 1.4 |
| 44 | 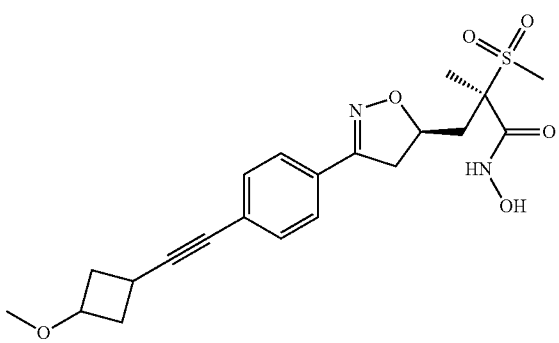 [SMILES: COC1CC(C#Cc2ccc(C3=NO[C@@H](C[C@](C)(C(=O)NO)S(C)(=O)=O)C3)cc2)C1] | 435.4 | 0.0008 | 0.5 |
| 45 | 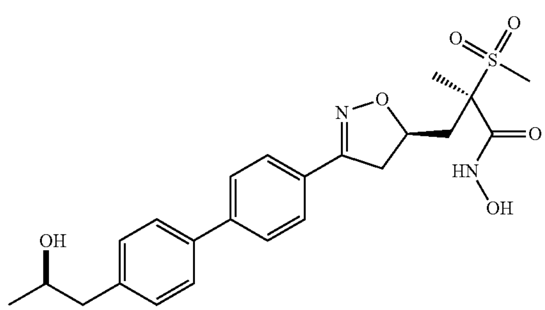 [SMILES: C[C@@H](O)Cc1ccc(-c2ccc(C3=NO[C@@H](C[C@](C)(C(=O)NO)S(C)(=O)=O)C3)cc2)cc1] | 461.3 | 0.0006 | 0.16 |
| 46 | 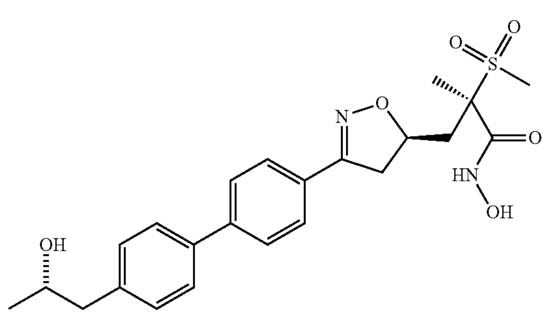 [SMILES: C[C@H](O)Cc1ccc(-c2ccc(C3=NO[C@@H](C[C@](C)(C(=O)NO)S(C)(=O)=O)C3)cc2)cc1] | 461.3 | 0.001 | 0.125 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 47 | 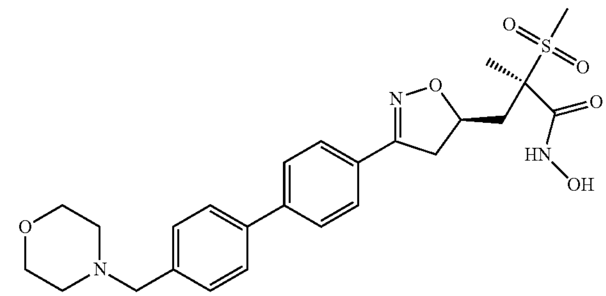 [SMILES: C[C@@](C[C@H]1CC(c2ccc(-c3ccc(CN4CCOCC4)cc3)cc2)=NO1)(C(=O)NO)S(C)(=O)=O] | 502.5 | 0.0006 | 0.35 |
| 48 | 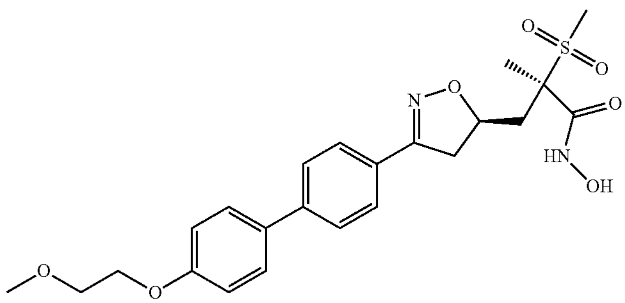 [SMILES: COCCOc1ccc(-c2ccc(C3=NO[C@@H](C[C@](C)(C(=O)NO)S(C)(=O)=O)C3)cc2)cc1] | 477.4 | 0.001 | 0.25 |
| 49 | 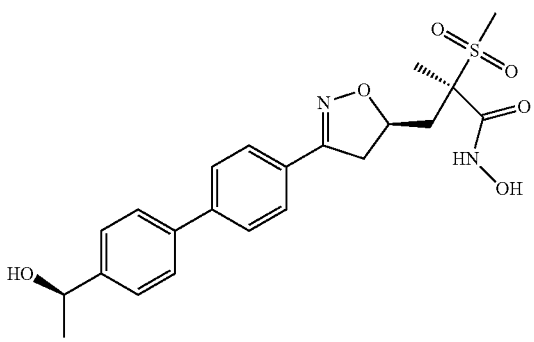 [SMILES: C[C@@H](O)c1ccc(-c2ccc(C3=NO[C@@H](C[C@](C)(C(=O)NO)S(C)(=O)=O)C3)cc2)cc1] | 447.3 | 0.001 | 0.25 |
| 50 | 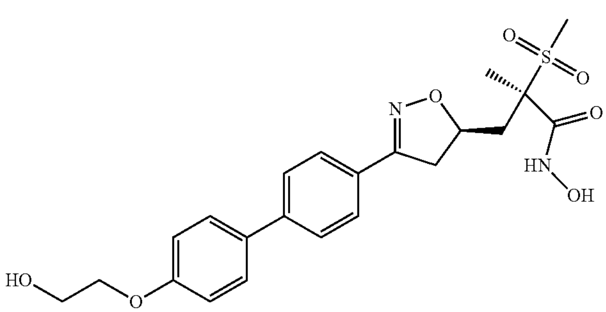 [SMILES: C[C@@](C[C@H]1CC(c2ccc(-c3ccc(OCCO)cc3)cc2)=NO1)(C(=O)NO)S(C)(=O)=O] | 463.4 | 0.0007 | 0.18 |

TABLE A-continued

| Cmpd No. | Compound structure | LCMS [M + H]+ | PA LpxC IC50 (nM) | PAO1 MIC (ug/mL) |
|---|---|---|---|---|
| 51 | 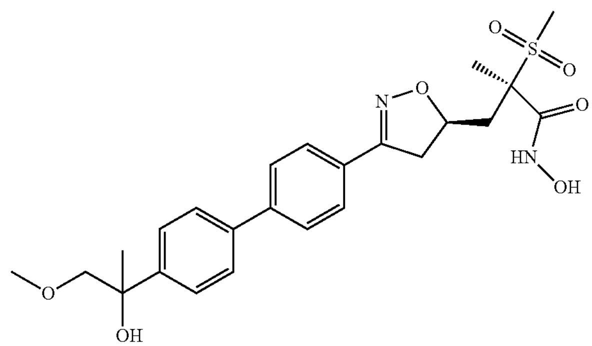 [SMILES: COCC(C)(O)c1ccc(-c2ccc(C3=NO[C@@H](C[C@](C)(C(=O)NO)S(C)(=O)=O)C3)cc2)cc1] | 491.2 | 0.0008 | 1.4 |
| 52 | 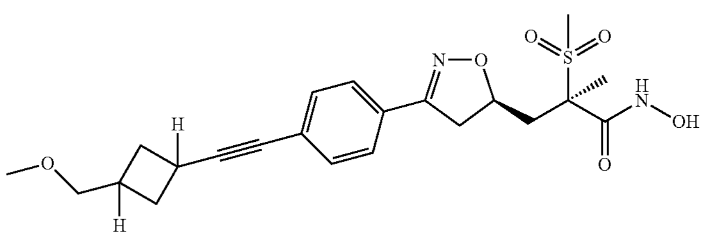 [SMILES: COCC1CC(C#Cc2ccc(C3=NO[C@@H](C[C@](C)(C(=O)NO)S(C)(=O)=O)C3)cc2)C1] | 449.9 | 0.0008 | 1 |
| 53 | 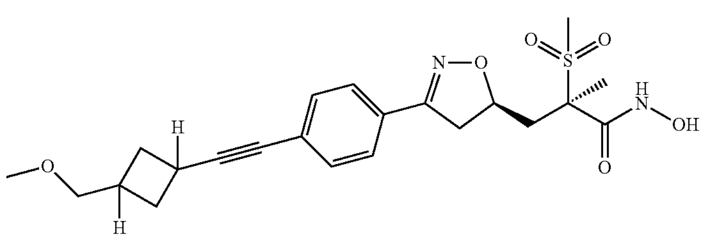 [SMILES: COCC1CC(C#Cc2ccc(C3=NO[C@@H](C[C@](C)(C(=O)NO)S(C)(=O)=O)C3)cc2)C1] | 449.9 | 0.0005 | 0.5 |
| 54 | 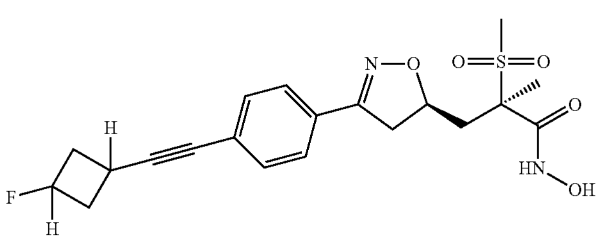 [SMILES: C[C@@](C[C@H]1CC(c2ccc(C#CC3CC(F)C3)cc2)=NO1)(C(=O)NO)S(C)(=O)=O] | 423.5 | 0.0007 | 1 |
| 55 | 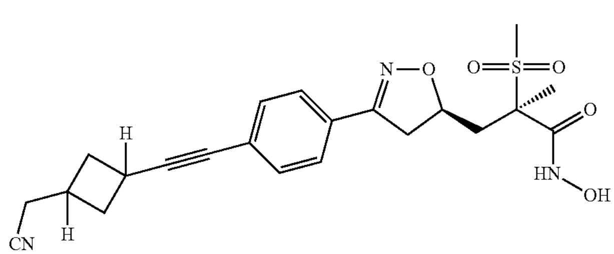 [SMILES: C[C@@](C[C@H]1CC(c2ccc(C#CC3CC(CC#N)C3)cc2)=NO1)(C(=O)NO)S(C)(=O)=O] | 444.7 | <0.0005 | 0.5 |

TABLE A-continued

| Cmpd No. | Compound structure | LCMS [M + H]+ | PA LpxC IC50 (nM) | PAO1 MIC (ug/mL) |
|---|---|---|---|---|
| 56 | 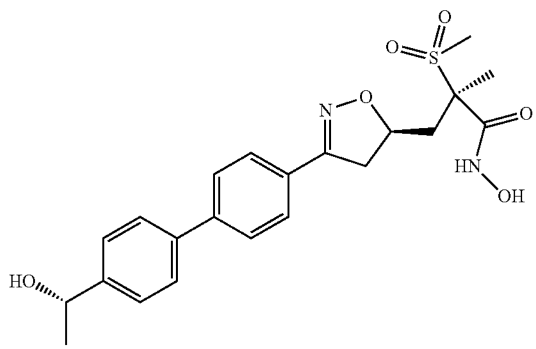 [SMILES: C[C@H](O)c1ccc(-c2ccc(C3=NO[C@@H](C[C@](C)(C(=O)NO)S(C)(=O)=O)C3)cc2)cc1] | 447.3 | 0.001 | 0.25 |
| 57 | 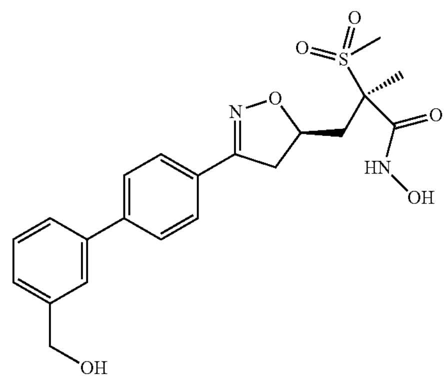 [SMILES: C[C@@](C[C@H]1CC(c2ccc(-c3cccc(CO)c3)cc2)=NO1)(C(=O)NO)S(C)(=O)=O] | 433.4 | <0.0005 | 1 |
| 58 | 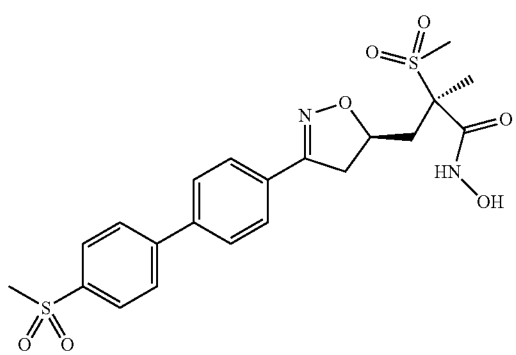 [SMILES: C[C@@](C[C@H]1CC(c2ccc(-c3ccc(S(C)(=O)=O)cc3)cc2)=NO1)(C(=O)NO)S(C)(=O)=O] | 481.4 | <0.0005 | 0.5 |
| 59 | 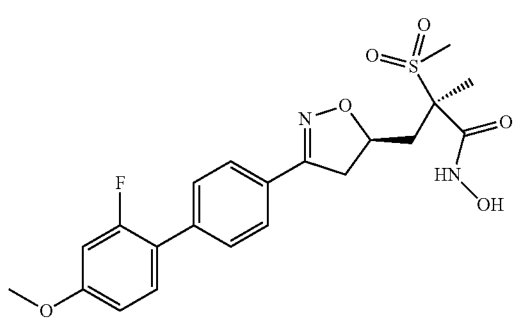 [SMILES: COc1ccc(-c2ccc(C3=NO[C@@H](C[C@](C)(C(=O)NO)S(C)(=O)=O)C3)cc2)c(F)c1] | 451.4 | <0.0005 | 0.35 |

TABLE A-continued

| Cmpd No. | Compound structure | LCMS [M + H]+ | PA LpxC IC50 (nM) | PAO1 MIC (ug/mL) |
|---|---|---|---|---|
| 60 | 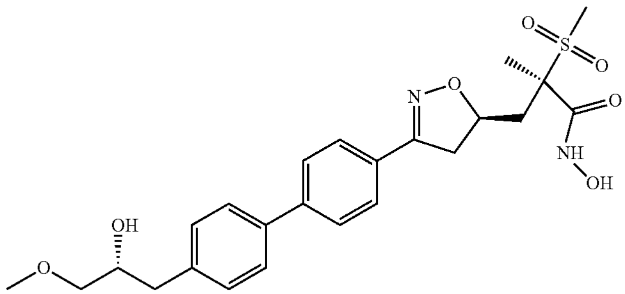 [SMILES: COC[C@H](O)Cc1ccc(-c2ccc(C3=NO[C@@H](C[C@](C)(C(=O)NO)S(C)(=O)=O)C3)cc2)cc1] | 491.3 | <0.0005 | 0.25 |
| 61 | 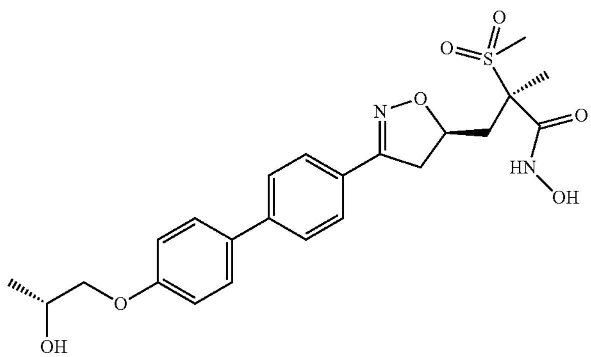 [SMILES: C[C@@H](O)COc1ccc(-c2ccc(C3=NO[C@@H](C[C@](C)(C(=O)NO)S(C)(=O)=O)C3)cc2)cc1] | 477.1 | | 0.25 |
| 62 | 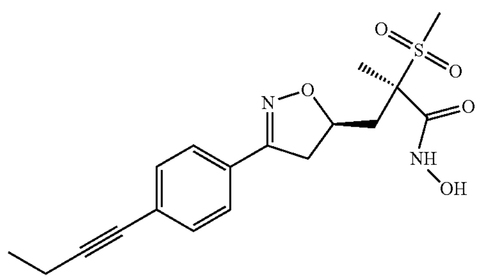 [SMILES: CCC#Cc1ccc(C2=NO[C@@H](C[C@](C)(C(=O)NO)S(C)(=O)=O)C2)cc1] | 379.3 | <0.0005 | 0.33 |
| 64 | 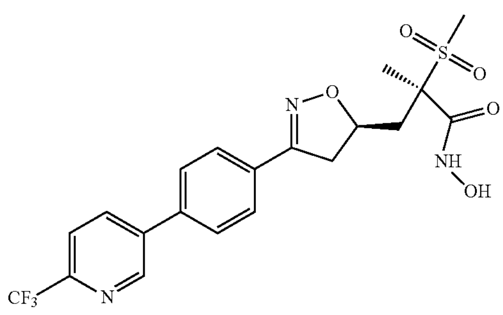 [SMILES: C[C@@](C[C@H]1CC(c2ccc(-c3ccc(C(F)(F)F)nc3)cc2)=NO1)(C(=O)NO)S(C)(=O)=O] | 472.2 [ | <0.0005 | 0.25 |
| 65 | 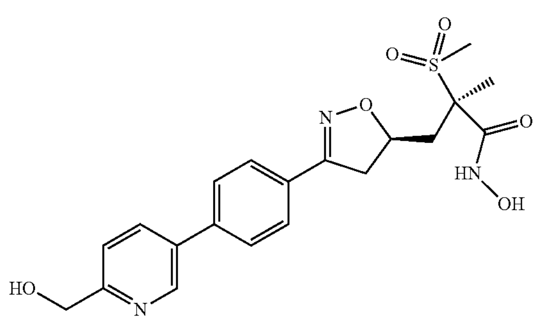 [SMILES: C[C@@](C[C@H]1CC(c2ccc(-c3ccc(CO)nc3)cc2)=NO1)(C(=O)NO)S(C)(=O)=O] | 434.1 | <0.0005 | 1 |

TABLE A-continued

| Cmpd No. | Compound structure | LCMS [M + H]+ | PA LpxC IC50 (nM) | PAO1 MIC (ug/mL) |
| --- | --- | --- | --- | --- |
| 66 | 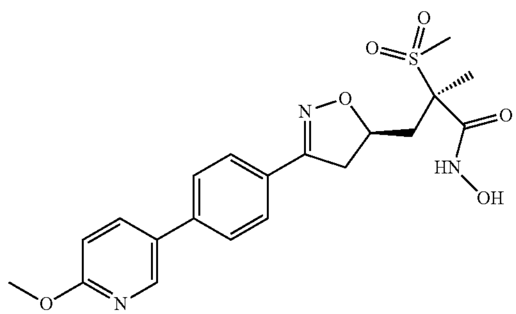 [SMILES: COc1ccc(-c2ccc(C3=NO[C@@H](C[C@](C)(C(=O)NO)S(C)(=O)=O)C3)cc2)cn1] | 434.0 | <0.0005 | 0.25 |
| 67 | 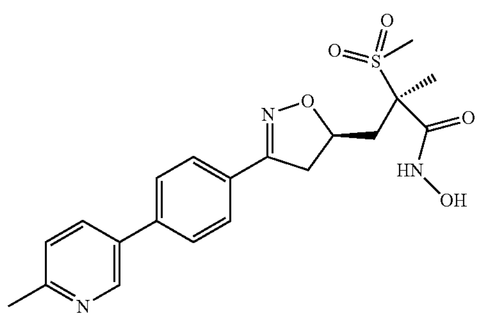 [SMILES: Cc1ccc(-c2ccc(C3=NO[C@@H](C[C@](C)(C(=O)NO)S(C)(=O)=O)C3)cc2)cn1] | 418.1 | <0.0005 | 0.35 |
| 68 | 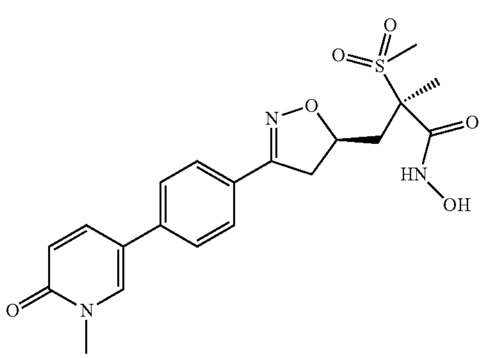 [SMILES: Cn1cc(-c2ccc(C3=NO[C@@H](C[C@](C)(C(=O)NO)S(C)(=O)=O)C3)cc2)ccc1=O] | 434.1 | 0.002 | 16 |
| 69 | 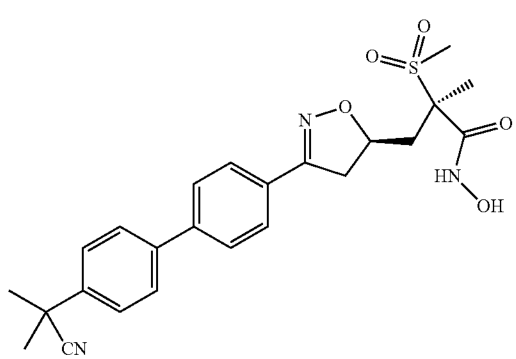 [SMILES: CC(C)(C#N)c1ccc(-c2ccc(C3=NO[C@@H](C[C@](C)(C(=O)NO)S(C)(=O)=O)C3)cc2)cc1] | 470.1 | <0.0005 | 0.71 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 70 | 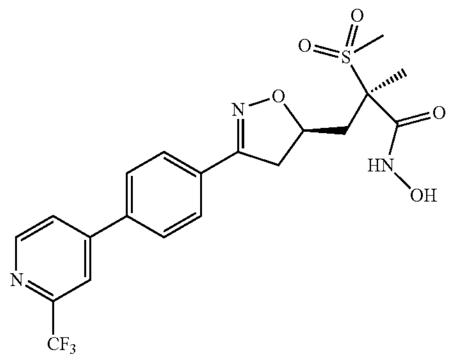 [SMILES: C[C@@](C[C@H]1CC(c2ccc(-c3ccnc(C(F)(F)F)c3)cc2)=NO1)(C(=O)NO)S(C)(=O)=O] | 472.0 | 0.002 | 8 |
| 71 | 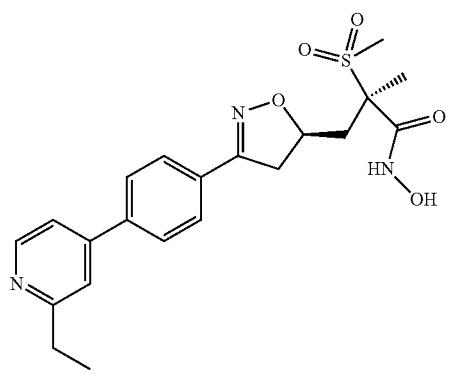 [SMILES: CCc1cc(-c2ccc(C3=NO[C@@H](C[C@](C)(C(=O)NO)S(C)(=O)=O)C3)cc2)ccn1] | 432.1 | 0.006 | 0.71 |
| 72 | 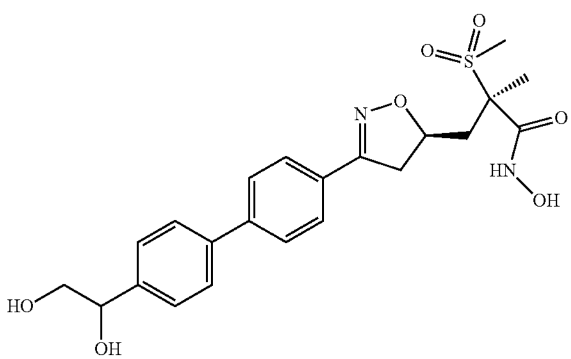 [SMILES: C[C@@](C[C@H]1CC(c2ccc(-c3ccc(C(O)CO)cc3)cc2)=NO1)(C(=O)NO)S(C)(=O)=O] | 463.1 | | 0.35 |
| 73 | 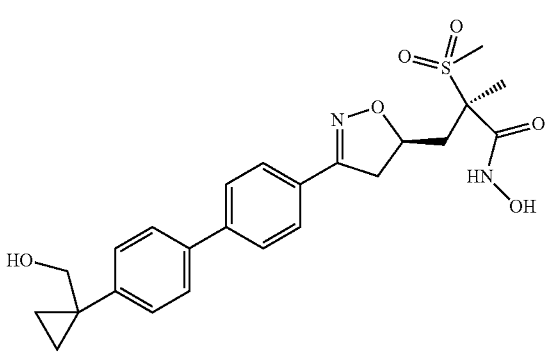 [SMILES: C[C@@](C[C@H]1CC(c2ccc(-c3ccc(C4(CO)CC4)cc3)cc2)=NO1)(C(=O)NO)S(C)(=O)=O] | 473.1 | | 0.25 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 74 | 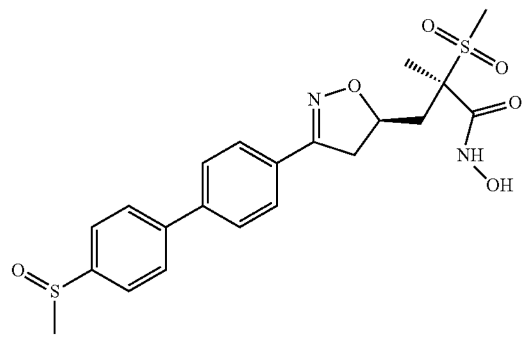 [SMILES: CS(=O)c1ccc(-c2ccc(C3=NO[C@@H](C[C@](C)(C(=O)NO)S(C)(=O)=O)C3)cc2)cc1] | 465.2 | <0.0005 | 0.71 |
| 75 | 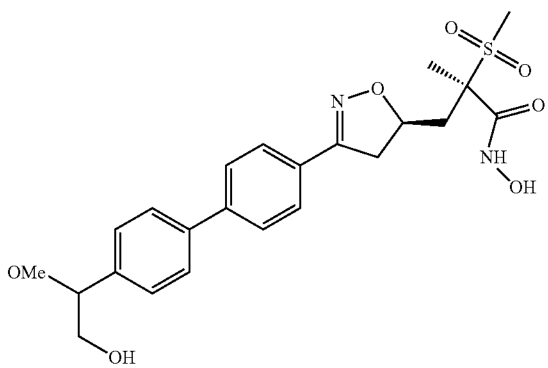 [SMILES: COC(CO)c1ccc(-c2ccc(C3=NO[C@@H](C[C@](C)(C(=O)NO)S(C)(=O)=O)C3)cc2)cc1] | 477.3 | <0.0005 | 0.5 |
| 76 | 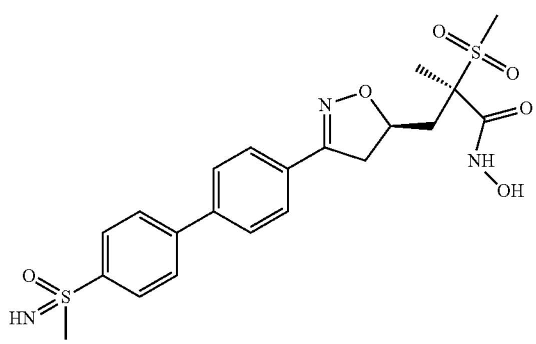 [SMILES: C[C@@](C[C@H]1CC(c2ccc(-c3ccc(S(C)(=N)=O)cc3)cc2)=NO1)(C(=O)NO)S(C)(=O)=O] | 480.2 | <0.0005 | 2 |
| 77 | 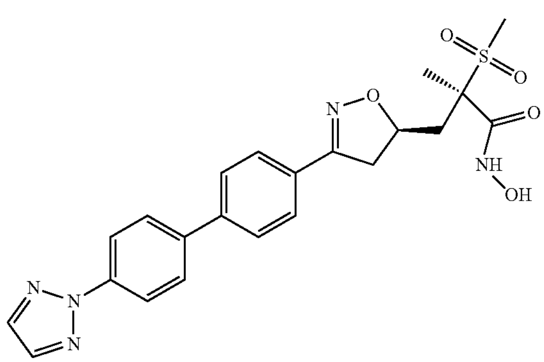 [SMILES: C[C@@](C[C@H]1CC(c2ccc(-c3ccc(-n4nccn4)cc3)cc2)=NO1)(C(=O)NO)S(C)(=O)=O] | 470.2 | <0.0005 | 2 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 78 | 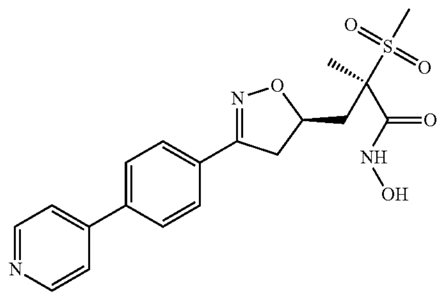 [SMILES: C[C@@](C[C@H]1CC(c2ccc(-c3ccncc3)cc2)=NO1)(C(=O)NO)S(C)(=O)=O] | 404.3 | <0.0005 | 1 |
| 79 | 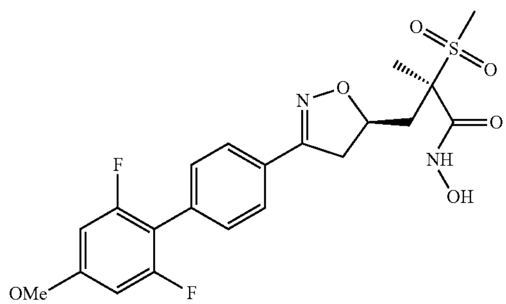 [SMILES: COc1cc(F)c(-c2ccc(C3=NO[C@@H](C[C@](C)(C(=O)NO)S(C)(=O)=O)C3)cc2)c(F)c1] | 469.2 | <0.0005 | 0.35 |
| 80 | 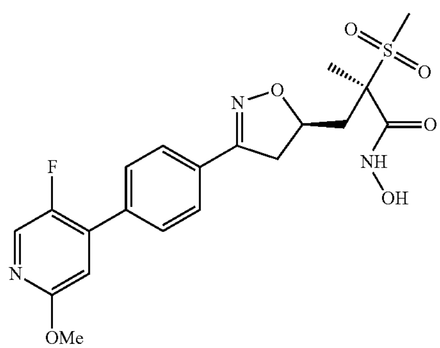 [SMILES: COc1cc(-c2ccc(C3=NO[C@@H](C[C@](C)(C(=O)NO)S(C)(=O)=O)C3)cc2)c(F)cn1] | 452.2 | | 1 |
| 81 | 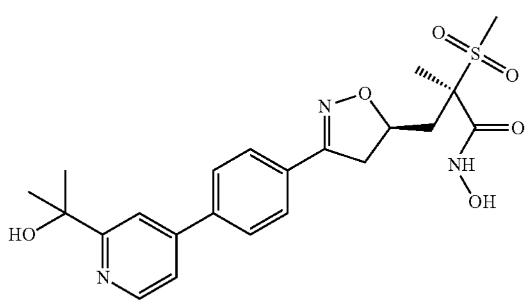 [SMILES: CC(C)(O)c1cc(-c2ccc(C3=NO[C@@H](C[C@](C)(C(=O)NO)S(C)(=O)=O)C3)cc2)ccn1] | 462.2 | 0.002 | 16 |
| 82 | 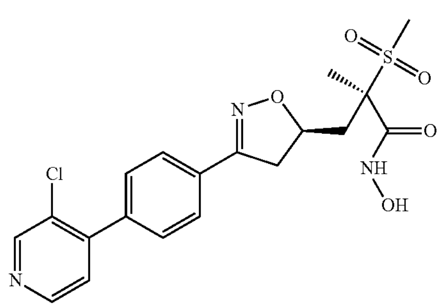 | 438.2 | <0.0005 | 0.35 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 83 | 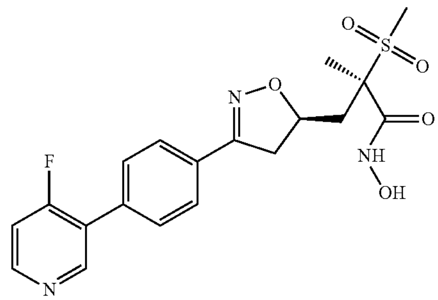 [SMILES: C[C@@](C[C@H]1CC(c2ccc(-c3cnccc3F)cc2)=NO1)(C(=O)NO)S(C)(=O)=O] | 422.2 | <0.0005 | 1 |
| 84 | 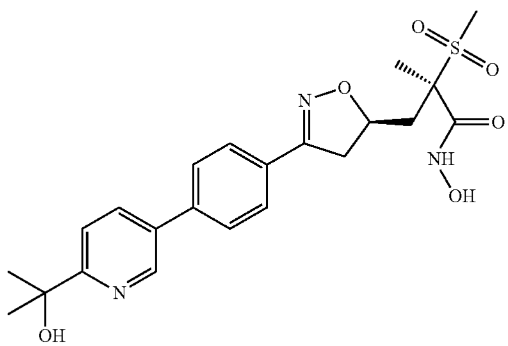 [SMILES: CC(C)(O)c1ccc(-c2ccc(C3=NO[C@@H](C[C@](C)(C(=O)NO)S(C)(=O)=O)C3)cc2)cn1] | 462.3 | <0.0005 | 1 |
| 85 | 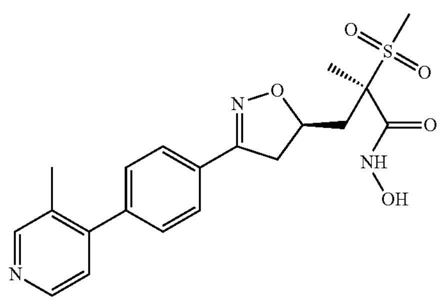 [SMILES: Cc1cnccc1-c1ccc(C2=NO[C@@H](C[C@](C)(C(=O)NO)S(C)(=O)=O)C2)cc1] | 418.2 | <0.0005 | 0.5 |
| 86 | 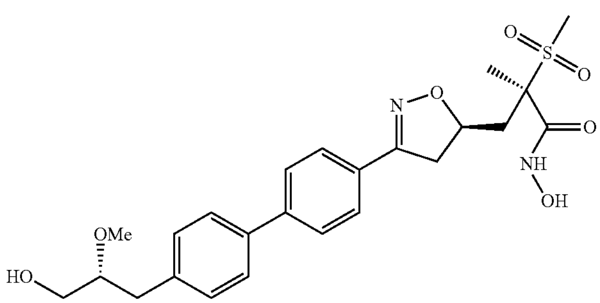 [SMILES: CO[C@@H](CO)Cc1ccc(-c2ccc(C3=NO[C@@H](C[C@](C)(C(=O)NO)S(C)(=O)=O)C3)cc2)cc1] | 491.3 | <0.0005 | 0.35 |
| 87 | 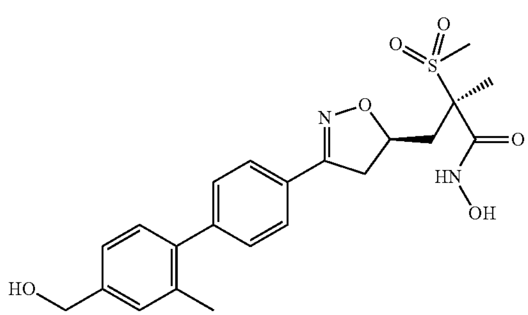 [SMILES: Cc1cc(CO)ccc1-c1ccc(C2=NO[C@@H](C[C@](C)(C(=O)NO)S(C)(=O)=O)C2)cc1] | 447.3 | <0.0005 | 0.25 |

TABLE A-continued
| Cmpd No. | Compound structure | LCMS [M + H]+ | PA LpxC IC50 (nM) | PAO1 MIC (ug/mL) |
|---|---|---|---|---|
| 88 | 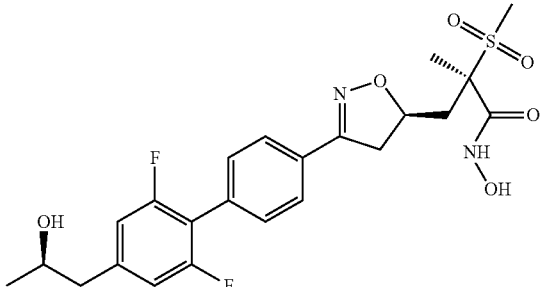 [SMILES: C[C@@H](O)Cc1ccc(-c2ccc(C3=NO[C@@H](C[C@](C)(C(=O)NO)S(C)(=O)=O)C3)cc2)c(F)c1] | 497.2 | <0.0005 | 0.25 |
| 89 | 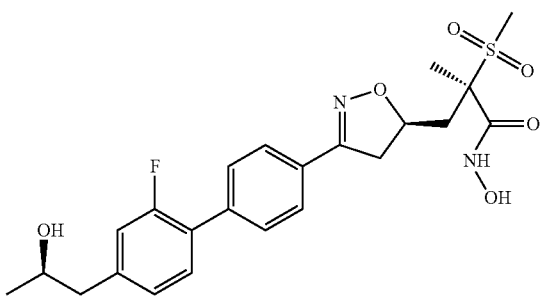 | 479.2 | <0.0005 | 0.71 |
| 90 | 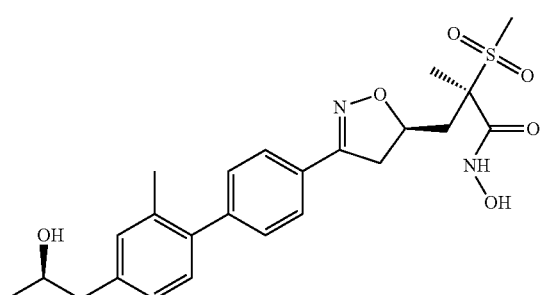 | 475.4 | <0.0005 | 0.5 |
| 91 | 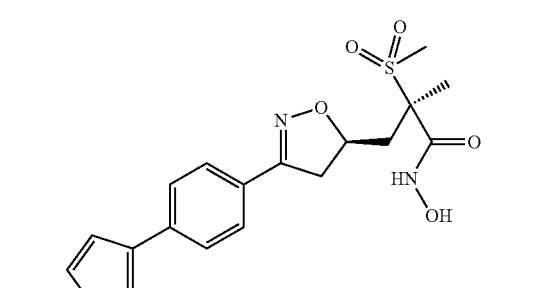 | 409.3 | <0.0005 | 0.125 |
| 92 | 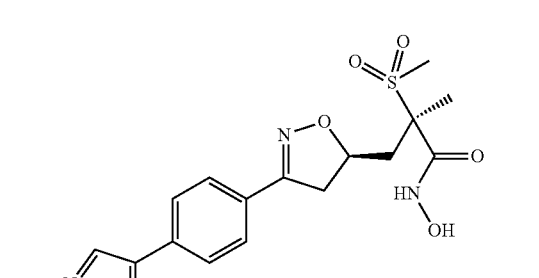 | 410.3 | <0.0005 | 0.35 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 93 | 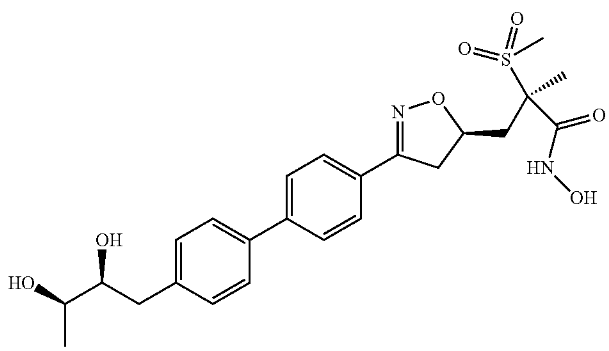 [SMILES: C[C@@H](O)[C@@H](O)Cc1ccc(-c2ccc(C3=NO[C@@H](C[C@](C)(C(=O)NO)S(C)(=O)=O)C3)cc2)cc1] | 491.4 | <0.0005 | 2 |
| 94 | 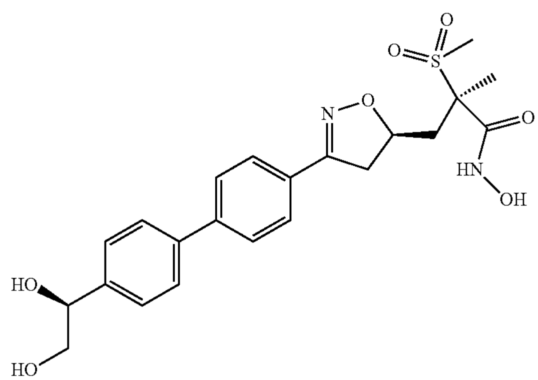 [SMILES: C[C@@](C[C@H]1CC(c2ccc(-c3ccc([C@H](O)CO)cc3)cc2)=NO1)(C(=O)NO)S(C)(=O)=O] | 463.1 | <0.0005 | 0.25 |
| 95 | 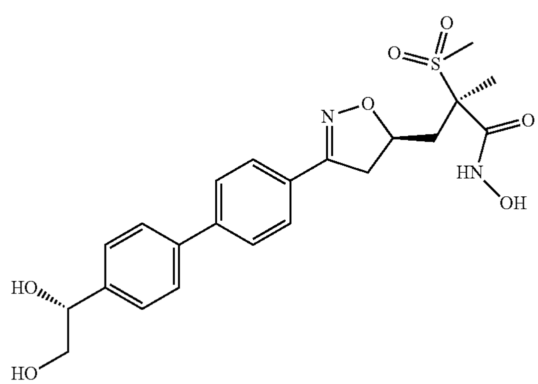 [SMILES: C[C@@](C[C@H]1CC(c2ccc(-c3ccc([C@@H](O)CO)cc3)cc2)=NO1)(C(=O)NO)S(C)(=O)=O] | 463.1 | <0.0001 | 0.25 |
| 96 | 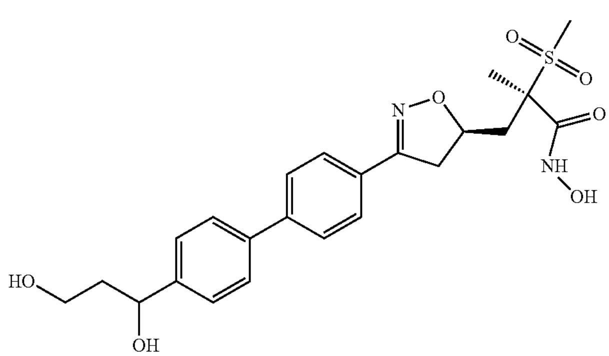 [SMILES: C[C@@](C[C@H]1CC(c2ccc(-c3ccc(C(O)CCO)cc3)cc2)=NO1)(C(=O)NO)S(C)(=O)=O] | 477.2 | <0.0005 | 0.5 |

TABLE A-continued

| Cmpd No. | Compound structure | LCMS [M + H]⁺ | PA LpxC IC$_{50}$ (nM) | PAO1 MIC (ug/mL) |
|---|---|---|---|---|
| 97 | 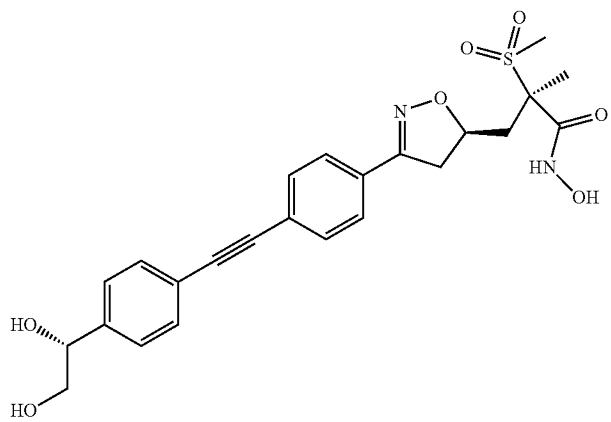 [SMILES: C[C@@](C[C@H]1CC(c2ccc(C#Cc3ccc([C@@H](O)CO)cc3)cc2)=NO1)(C(=O)NO)S(C)(=O)=O] | 487.3 | | 0.71 |
| 98 | 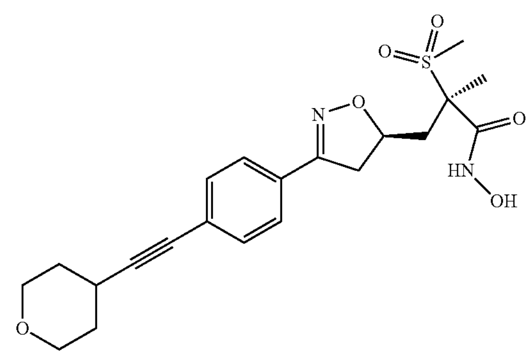 [SMILES: C[C@@](C[C@H]1CC(c2ccc(C#CC3CCOCC3)cc2)=NO1)(C(=O)NO)S(C)(=O)=O] | 487.3 | 0.0006 | 2 |
| 99 | 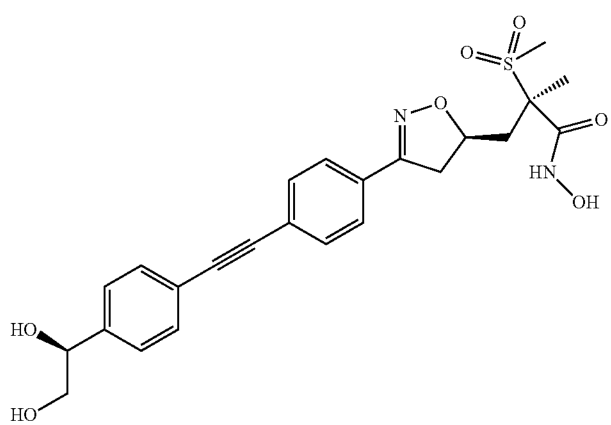 [SMILES: C[C@@](C[C@H]1CC(c2ccc(C#Cc3ccc([C@H](O)CO)cc3)cc2)=NO1)(C(=O)NO)S(C)(=O)=O] | 487.3 | | |
| 100 | 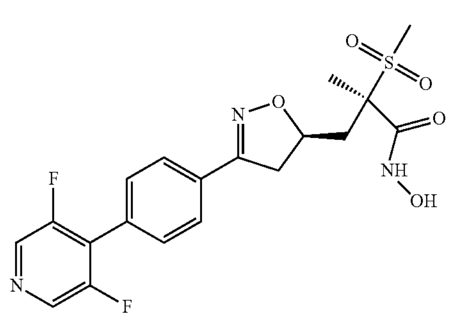 [SMILES: C[C@@](C[C@H]1CC(c2ccc(-c3c(F)cncc3F)cc2)=NO1)(C(=O)NO)S(C)(=O)=O] | 440.2 | <0.0005 | 0.25 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 101 | 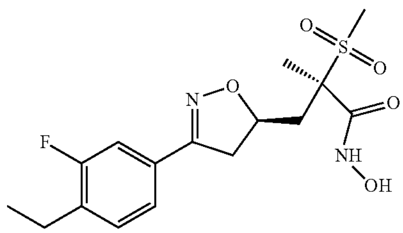 [SMILES: CCc1ccc(C2=NO[C@@H](C[C@](C)(C(=O)NO)S(C)(=O)=O)C2)cc1F] | 373.1 | <0.0005 | 0.35 |
| 102 | 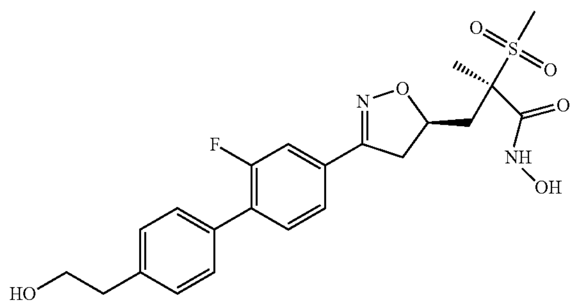 [SMILES: C[C@@](C[C@H]1CC(c2ccc(-c3ccc(CCO)cc3)c(F)c2)=NO1)(C(=O)NO)S(C)(=O)=O] | 465.4 | <0.0005 | 0.18 |
| 103 | 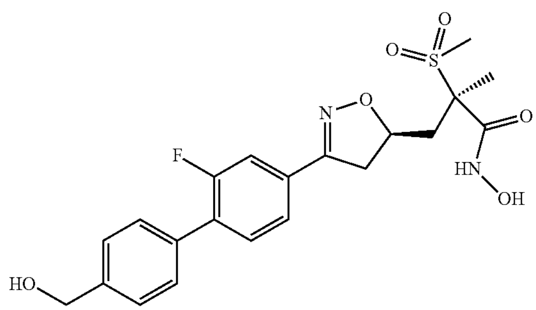 | 451.0 | 0.0006 | 0.18 |
| 104 | 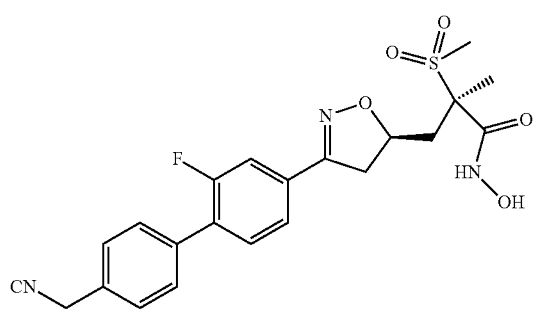 | 460.4 | 0.0005 | 0.125 |
| 105 | 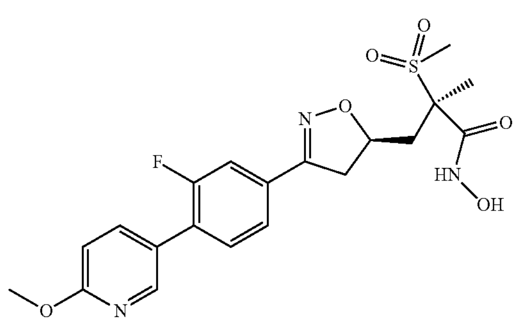 [SMILES: COc1ccc(-c2ccc(C3=NO[C@@H](C[C@](C)(C(=O)NO)S(C)(=O)=O)C3)cc2F)cn1] | 452.4 | 0.001 | |

TABLE A-continued

| Cmpd No. | Compound structure | LCMS [M + H]+ | PA LpxC IC50 (nM) | PAO1 MIC (ug/mL) |
|---|---|---|---|---|
| 107 | 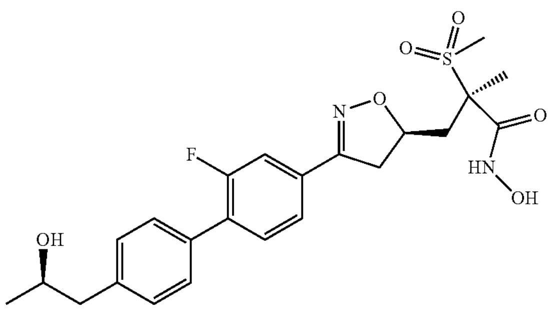 [SMILES: C[C@@H](O)Cc1ccc(-c2ccc(C3=NO[C@@H](C[C@](C)(C(=O)NO)S(C)(=O)=O)C3)cc2F)cc1] | 479.4 | 0.0005 | 0.25 |
| 108 | 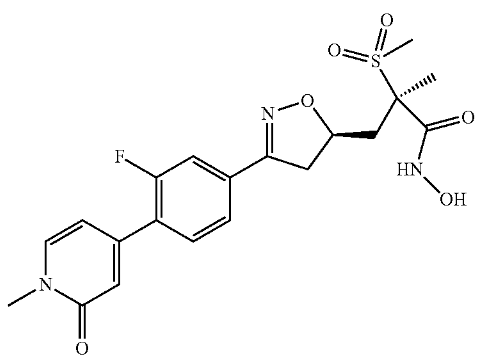 [SMILES: Cn1ccc(-c2ccc(C3=NO[C@@H](C[C@](C)(C(=O)NO)S(C)(=O)=O)C3)cc2F)cc1=O] | 452.4 | 0.002 | 8 |
| 109 | 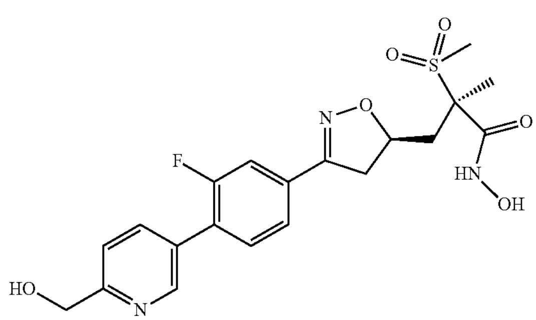 [SMILES: C[C@@](C[C@H]1CC(c2ccc(-c3ccc(CO)nc3)c(F)c2)=NO1)(C(=O)NO)S(C)(=O)=O] | 452.4 | 0.005 | |
| 110 | 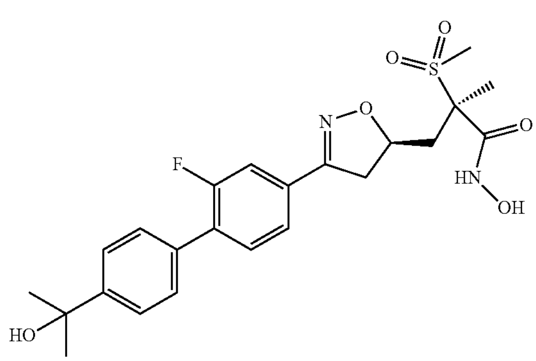 [SMILES: CC(C)(O)c1ccc(-c2ccc(C3=NO[C@@H](C[C@](C)(C(=O)NO)S(C)(=O)=O)C3)cc2F)cc1] | 479.4 | <0.0005 | 0.5 |

TABLE A-continued

| Cmpd No. | Compound structure | LCMS [M + H]+ | PA LpxC IC50 (nM) | PAO1 MIC (ug/mL) |
| --- | --- | --- | --- | --- |
| 111 | 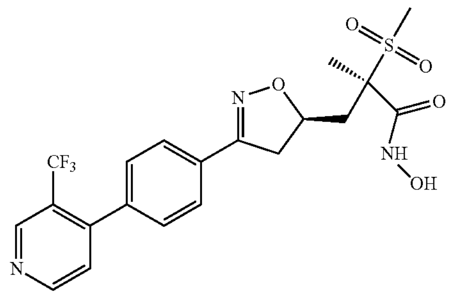 [SMILES: C[C@@](C[C@H]1CC(c2ccc(-c3ccncc3C(F)(F)F)cc2)=NO1)(C(=O)NO)S(C)(=O)=O] | 472.2 | <0.0005 | 1 |
| 112 | 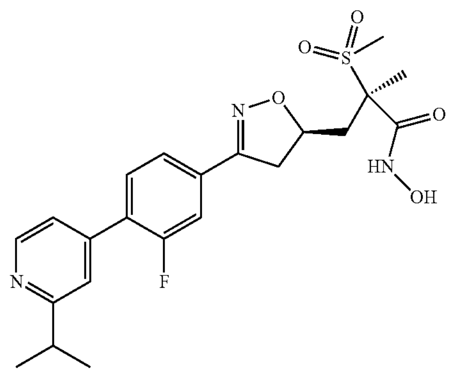 [SMILES: CC(C)c1cc(-c2ccc(C3=NO[C@@H](C[C@](C)(C(=O)NO)S(C)(=O)=O)C3)cc2F)ccn1] | 464.1 | <0.0005 | 1 |
| 113 | 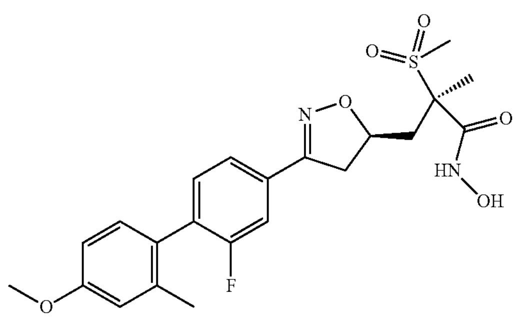 [SMILES: COc1ccc(-c2ccc(C3=NO[C@@H](C[C@](C)(C(=O)NO)S(C)(=O)=O)C3)cc2F)c(C)c1] | 465.1 | <0.0005 | 0.71 |
| 114 | 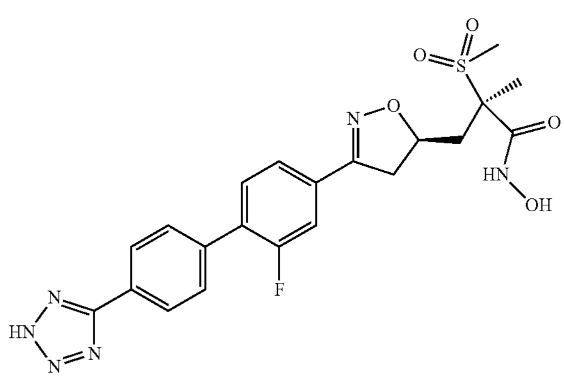 [SMILES: C[C@@](C[C@H]1CC(c2ccc(-c3ccc(-c4nn[nH]n4)cc3)c(F)c2)=NO1)(C(=O)NO)S(C)(=O)=O] | 489.1 | <0.0005 | 32 |

TABLE A-continued

| Cmpd No. | Compound structure | LCMS [M + H]+ | PA LpxC IC$_{50}$ (nM) | PAO1 MIC (ug/mL) |
|---|---|---|---|---|
| 115 | 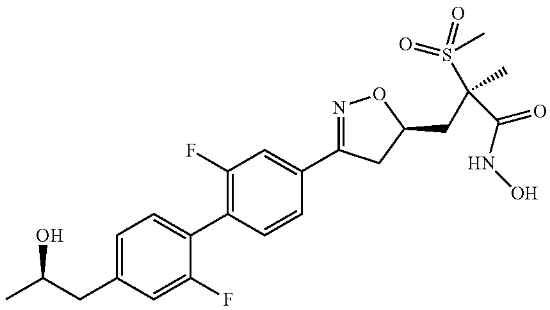 [SMILES: C[C@@H](O)Cc1ccc(-c2ccc(C3=NO[C@@H](C[C@](C)(C(=O)NO)S(C)(=O)=O)C3)cc2F)c(F)c1] | 497.3 | <0.0005 | 1 |
| 116 | 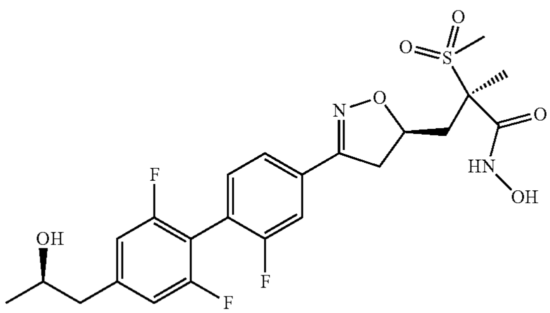 [SMILES: C[C@@H](O)Cc1cc(F)c(-c2ccc(C3=NO[C@@H](C[C@](C)(C(=O)NO)S(C)(=O)=O)C3)cc2F)c(F)c1] | 515.3 | <0.0005 | 0.5 |
| 117 | 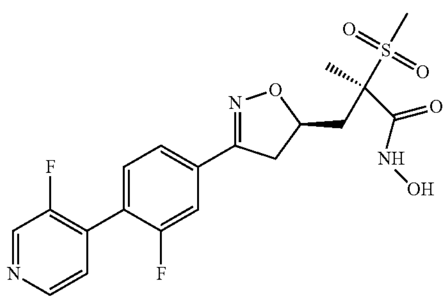 [SMILES: C[C@@](C[C@H]1CC(c2ccc(-c3ccncc3F)c(F)c2)=NO1)(C(=O)NO)S(C)(=O)=O] | 440.2 | <0.0005 | 0.35 |
| 118 | 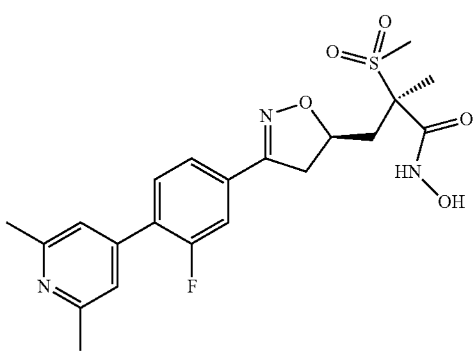 [SMILES: Cc1cc(-c2ccc(C3=NO[C@@H](C[C@](C)(C(=O)NO)S(C)(=O)=O)C3)cc2F)cc(C)n1] | 450.1 | 0.004 | 4 |
| 119 | 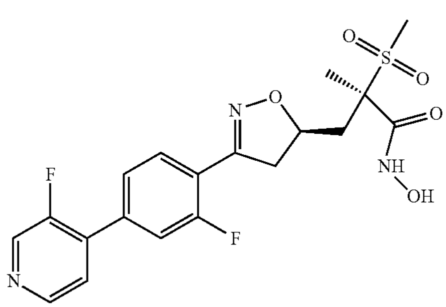 [SMILES: C[C@@](C[C@H]1CC(c2ccc(-c3ccncc3F)cc2F)=NO1)(C(=O)NO)S(C)(=O)=O] | 440.2 | <0.0005 | 0.71 |

TABLE A-continued

| Cmpd No. | Compound structure | LCMS [M + H]+ | PA LpxC IC50 (nM) | PAO1 MIC (ug/mL) |
|---|---|---|---|---|
| 120 | 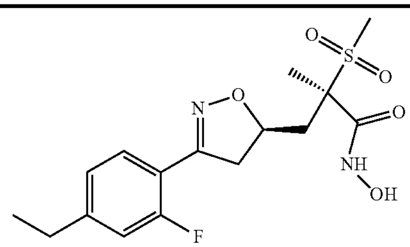 | 373.0 | 0.0006 | 0.5 |
| 121 | 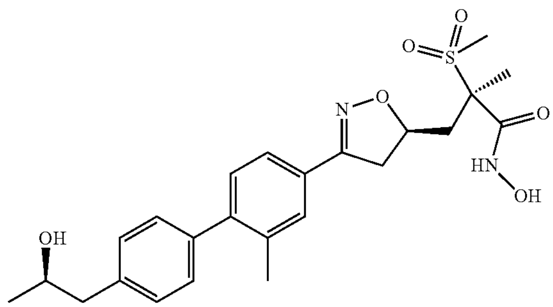 [SMILES: Cc1cc(C2=NO[C@@H](C[C@](C)(C(=O)NO)S(C)(=O)=O)C2)ccc1-c1ccc(C[C@@H](C)O)cc1] | 475.3 | <0.0005 | 0.5 |
| 122 | 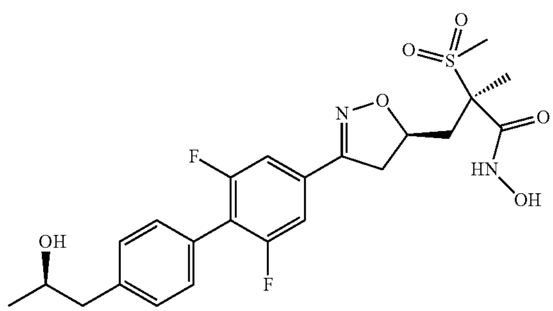 [SMILES: C[C@@H](O)Cc1ccc(-c2c(F)cc(C3=NO[C@@H](C[C@](C)(C(=O)NO)S(C)(=O)=O)C3)cc2F)cc1] | 497.3 | <0.0005 | 0.5 |
| 123 | 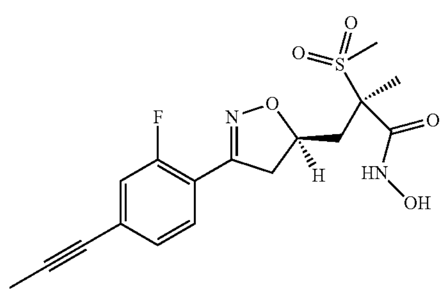 [SMILES: CC#Cc1ccc(C2=NO[C@@H](C[C@](C)(C(=O)NO)S(C)(=O)=O)C2)c(F)c1] | 383.3 | <0.0005 | 0.25 |

Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A compound of formula (I):

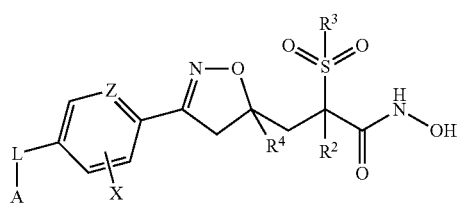

(I)

or a pharmaceutically acceptable salt thereof, wherein:

Z is N or $CR^1$, where 1e is selected from H, halo, $C_{1-4}$ alkyl and $C_{1-4}$ haloalkyl;

$R^2$ and $R^3$ are independently selected from $C_{1-4}$ alkyl and $C_{1-4}$ haloalkyl, $R^4$ is H or $C_{1-4}$ alkyl;

X is selected from H, halo, $C_{1-4}$ alkyl, $C_{1-4}$ haloalkyl, and CN;

L is selected from —$CR^5$=$CR^6$—, —O—, —S—, and a direct bond between A and the ring containing Z;

$R^5$ and $R^6$ are independently selected from H, halo, $C_{1-4}$ alkyl, and $C_{1-4}$ haloalkyl; and A is halo, CN, or an optionally substituted group selected from $C_{1-4}$ alkyl, $C_{3-6}$ cycloalkyl, phenyl, $C_{2-6}$ alkenyl, $C_{2-6}$ alkynyl, 5-6 membered heteroaryl containing up to four heteroatoms selected from N, O and S as ring members, and 4-6 membered heterocyclyl containing up to two heteroatoms selected from N, O and S as ring members, wherein the $C_{1-4}$ alkyl, $C_{3-6}$ cycloalkyl, phenyl, $C_{2-6}$ alkenyl, $C_{2-6}$ alkynyl, 5-6 membered heteroaryl containing up to four heteroatoms selected from N, O and S as ring members, and 4-6 membered heterocyclyl containing up to two heteroatoms selected from N, O and S as ring members are each optionally substituted with up to three groups selected from halo, hydroxy, CN, $R^{10}$, —$(CH_2)_{0-2}OR^{10}$, —$SR^{10}$, —$S(O)R^{10}$, —$SO_2R^{10}$, —$S(O)(NH)R^{10}$, and —$(CH_2)_{0-2}N(R^{10})_2$;

where each $R^{10}$ is independently H or $C_{1-4}$ alkyl optionally substituted with one or two groups selected from amino, hydroxy, $C_{1-4}$ alkoxy, and CN; and —$N(R^{10})_2$ can represent a 5-6 membered heterocyclic ring optionally containing an additional heteroatom selected from N, O and S as a ring member, and optionally substituted with one or two groups selected from oxo, halo, hydroxy, $C_{1-4}$ alkyl, $C_{1-4}$ alkoxy, and amino.

2. The compound of claim 1 or a pharmaceutically acceptable salt thereof, wherein X is H or F.

3. The compound of claim 1 or a pharmaceutically acceptable salt thereof, wherein $R^2$ is methyl.

4. The compound of claim 1, or a pharmaceutically acceptable salt thereof, wherein $R^3$ is methyl.

5. The compound of claim 1, or a pharmaceutically acceptable salt thereof, wherein $R^4$ is H.

6. The compound of claim 1, or a pharmaceutically acceptable salt thereof, wherein Z is CH or CF.

7. The compound of claim 1, or a pharmaceutically acceptable salt thereof, wherein Z is N.

8. The compound of claim 1, or a pharmaceutically acceptable salt thereof, wherein A-L- is a group of the formula

where A is an optionally substituted group selected from $C_{1-4}$ alkyl and $C_{3-6}$ cycloalkyl, wherein A is optionally substituted with up to three groups selected from halo, hydroxy, CN, —OR, and —$N(R^{10})_2$ where each $R^{10}$ is independently H or $C_{1-4}$ alkyl.

9. The compound of claim 8 or a pharmaceutically acceptable salt thereof, wherein A is $C_{1-4}$ alkyl or cyclopropyl and is optionally substituted with F, OH, or OMe.

10. The compound of claim 1, which is of the formula:

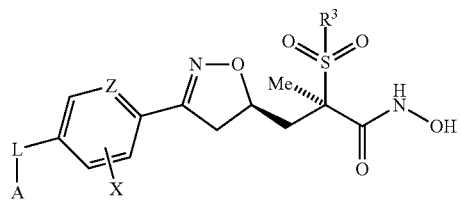

or a pharmaceutically acceptable salt thereof.

11. A pharmaceutical composition, comprising:
the compound according to claim 1, or a pharmaceutically acceptable salt thereof, and
a pharmaceutically acceptable carrier.

12. A pharmaceutical combination comprising:
a compound according to claim 1, or a pharmaceutically acceptable salt thereof,
an antibacterially effective amount of a second therapeutic agent, and
a pharmaceutically acceptable carrier.

13. The pharmaceutical combination composition according to claim 12, wherein the second therapeutic agent is selected from the group consisting of Ampicillin, Piperacillin, Penicillin G, Ticarcillin, Imipenem, Meropenem, Azithromycin, erythromycin, Aztreonam, Cefepime, Cefotaxime, Ceftriaxone, Cefatazidime, Ciprofloxacin, Levofloxacin, Clindamycin, Doxycycline, Gentamycin, Amikacin, Tobramycin, Tetracycline, Tegacyclin, Rifampicin, Vancomycin and Polymyxin.

14. A method of inhibiting a deacetylase enzyme in a Gram-negative bacterium, comprising:
contacting the Gram-negative bacteria with the compound according to claim 1 or a pharmaceutically acceptable salt thereof.

15. A method for treating a subject with a Gram-negative bacterial infection, comprising:
administering to the subject an antibacterially effective amount of the compound according to claim 1, or a pharmaceutically acceptable salt thereof, and a pharmaceutically acceptable carrier.

16. The method of claim 15, wherein the gram negative bacterial infection is an infection comprising at least one bacterium selected from the group consisting of *Pseudomonas, Stenotrophomonas maltophila, Burkholderia, Alcaligenes xylosoxidans, Acinetobacter*, Enterobacteriaceae, *Haemophilus, Moraxella, Bacteroides, Fransicella, Shigella, Proteus, Vibrio, Salmonella, Bordetella, Helicobactor, Legionella, Citrobactor, Serratia, Campylobactor, Yersinia* and *Neisseria*.

17. The method of claim 16, wherein the bacterium is a Enterobacteriaceae which is selected from the group consisting of *Serratia, Proteus, Klebsiella, Enterobacter, Citrobacter, Salmonella, Providencia, Morganella, Cedecea, Yersinia*, and *Edwardsiella* species and *Escherichia coli*.

* * * * *